United States Patent
Pasin et al.

(10) Patent No.: US 11,597,939 B2
(45) Date of Patent: Mar. 7, 2023

(54) BINARY VECTORS AND USES OF SAME

(71) Applicant: Juan Antonio García Álvarez, Madrid (ES)

(72) Inventors: Fabio Pasin, Madrid (ES); Juan Antonio García Álvarez, Madrid (ES); Leonor Cecilia Bedoya Rojas, Madrid (ES); María del Carmen Simón Mateo, Madrid (ES); Diego Vicente Orzáez Calatayud, Valencia (ES); Juan Miguel Bernabé Orts, Valencia (ES)

( * ) Notice: Subject to any disclaimer, the term of this patent is extended or adjusted under 35 U.S.C. 154(b) by 281 days.

(21) Appl. No.: 16/622,037

(22) PCT Filed: Jun. 12, 2018

(86) PCT No.: PCT/ES2018/070421
§ 371 (c)(1),
(2) Date: Apr. 28, 2020

(87) PCT Pub. No.: WO2018/229319
PCT Pub. Date: Dec. 20, 2018

(65) Prior Publication Data
US 2020/0255845 A1    Aug. 13, 2020

(30) Foreign Application Priority Data
Jun. 12, 2017   (ES) ................ ES201730792

(51) Int. Cl.
*C12N 15/82* (2006.01)
(52) U.S. Cl.
CPC ..... *C12N 15/8205* (2013.01); *C12N 15/8241* (2013.01)
(58) Field of Classification Search
None
See application file for complete search history.

(56) References Cited

U.S. PATENT DOCUMENTS

| 2007/0059768 A1* | 3/2007 | Gill | C12N 15/66 |
| | | | 435/7.1 |
| 2008/0184393 A1* | 7/2008 | Zhang | C12N 15/8205 |
| | | | 800/294 |

FOREIGN PATENT DOCUMENTS

| WO | 2017040343 A1 | 3/2017 | |
| WO | WO-2017040343 A1 * | 3/2017 | ........... C07K 14/195 |

OTHER PUBLICATIONS

Hajdukiewicz, Peter, Zora Svab, and Pal Maliga. "The small, versatilepZP family ofAgrobacterium binary vectors for plant transformation." Plant molecular biology 25.6 (1994): 989-994. (Year: 1994).*
Thole et al., The pCLEAN Dual Binary Vector System for Agrobacterium-Mediated Plant Transformation, Plant Physiology, (20071200), vol. 145, pp. 1211-1219.
Komari et al., Binary Vectors and Super-binary Vectors, Methods in Molecular Biology, (20060000), vol. 343, pp. 15-41.
Daley et al., Co-transformation with one Agrobacterium tumefaciens strain containing two binary plasmids as a method for producing marker-free transgenic plants, Plant Cell Reports, (19980000), vol. 17, pp. 489-496, Abstract submitted herewith.
International Search Report and Written Opinion in corresponding International Patent Application No. PCT/ES2018/070421, dated Dec. 20, 2018, 20 Pages with English Translation.

* cited by examiner

*Primary Examiner* — Weihua Fan
(74) *Attorney, Agent, or Firm* — FisherBroyles, LLP; Andrew K. Gonsalves, Esq.

(57) ABSTRACT

The invention relates to binary vectors based on compatible and autonomous origins, specifically based on the pBBR1 and RK2 replication origins. These binary vectors are useful for having a wide range of hosts, for their maintenance in *Agrobacterium* sp. and *Escherichia coli*, and as a new tool for plant synthetic biology as well as a flexible framework for assembly, transfer and characterization of multiple DNA elements. The binary vectors disclosed are small, preferably less than 3.8 kb in size, stable, include an origin compatible with the most commonly used binary T-DNA vectors, comply with current standards for plant synthetic biology, and allow the administration of multiple T-DNA cassettes by means of the multiplexing of the vectors. The present invention also relates to methods for transferring and expressing nucleic acid sequences using said binary vectors, and to the uses of the same.

16 Claims, 16 Drawing Sheets
Specification includes a Sequence Listing.

Fig. 8

BINARY VECTORS AND USES OF SAME

The invention relates in general to the field of molecular biology and to agents useful for the manipulation of eukaryotic organisms. In particular, the present invention provides methods to assemble, transfer, and express DNA sequences using binary vectors, the binary vectors themselves, and uses of the same.

BACKGROUND ART

Plants are plastic organisms that sense and respond to environmental stimuli. These responses or specific plant features might not fit human needs, and can be manipulated by targeted use of plant-interacting microorganisms or by plant genetic transformation. Plant biotechnology uses advanced tools to generate plants with new functions, enhanced agronomic traits, or to produce new products. Synthetic biology applies engineering principles to facilitate the production of organisms with customized functions and for precise control of specific biological functions. Genetic components of complex biological systems are reduced to DNA parts with modular and defined assignments. Once characterized with the aid of computational tools, libraries of parts are assembled to yield pathways and networks with predictable outputs. Methods to analyze dynamic molecular devices have been used to genetically engineer plants with tunable functions.

Assembled DNA constructs are transferred directly to plants, or are introduced into disarmed-pTi *Agrobacterium tumefaciens* strains which serve as shuttle chassis for delivery to plants of constructs maintained in T-DNA binary vectors. From 1986 to 2000, T-DNA binary vectors were generated using diverse replication origins and parts (Murai N., Am. J. Plant Sci. 2013, 4, 932-939). Disadvantages of existing binary vectors, for example the 12-kb pBIN19 (Bevan M., Nucleic Acids Res. 1984, 12, 8711-8721), are their difficult-to-handle size, and their low-copy number, which leads to low yields of DNA plasmids and makes cloning procedures difficult. To improve the low DNA yields and ease cloning procedures, plasmid backbones can be amplified by PCR and used in one-step DNA assembly reactions. Due to the large sizes of many binary vectors, amplification of the plasmid backbones by PCR is not practical. The pPZP and pGreen series of binary vectors include origins with a high copy number that give high plasmid yields (Hajdukiewicz P., et al., Plant Mol. Biol. 1994, 25, 989-994; Helles R., et al, Plant Molecular Biology. 2000, 42, 819-832). Unstable replication origins can lead to variable plasmid losses during replication. The pGreen vector, which is very small (4.6 kb in size), is not autonomous and lacks elements required for stable multiplication in agrobacteria; thus, it can only be used with specific *Agrobacterium* strains (Helles R., et al, Plant Molecular Biology. 2000, 42, 819-832). For certain applications, use of origins with a high copy number is not desirable, since it could promote deletions/alterations of large DNA inserts, of sequences with bacterial toxicity, or of repeated sequence elements. Instability is particularly evident for DNA components used multiple times within constructs. For example, it is not uncommon that a given plant-expressible promoter is used to drive expression of different protein coding regions in a transgenic plant. Other genetic components such as 3' untranslated regions (i.e., sequences that determine transcription termination and polyadenylation addition) and even very similar protein-coding regions can be duplicated or present in several copies within a single T-DNA region. As mentioned above, these repeated sequence elements, which can occur in either inverted or directly repeated orientations, are targets for intramolecular recombination that can lead to DNA deletions and other rearrangements.

The described binary vectors lack features that reduce undesired expression of T-DNA sequences in bacterial hosts. Undesired expression of exogenous sequences can lead to production of toxic products during vector propagation in bacteria, and could increase insert and vector instability. Natural or synthetic transcription terminators are known to insulate against promoters active in bacteria (Chen Y. J., et al, Nat Methods. 2013, 10, 7, 659-664).

In the early series of binary vectors, there is also frequently a lack of a sufficient restriction enzyme sites for cloning desired sequences into the T-DNA cassettes, or the vectors only permit the use of a few selectable markers.

More recent versions of previously described vectors were reported (Murai N., Am. J. Plant Sci. 2013, 4, 932-939). These versions generally adopt the described backbones, modified to include sequences to improve delivery of T-DNA cassettes to eukaryotic cells, and to facilitate insertion of exogenous sequences into the T-DNA cassettes. For decades, the most common approaches for assembling DNA constructs in binary vectors relied on the specificity of restriction endonucleases to create compatible ends that can be joined using DNA ligases. The presence or absence of restriction sites in the vector and insert sequences can limit possible assemblies, particularly those involving multiple inserts. Cloning methods have been developed to overcome these constraints, thus allowing high-throughput assembly of DNA constructs. Recombinase-based technologies such as Gateway, Creator, Echo, and Univector cloning are very efficient and are based on enzymes that specifically recombine insert and vector sequences. Recombinase-based technologies are limited to vectors with appropriate recombination sequences, they allow simultaneous cloning of small number of inserts, and are not always scar-benign, as they leave >20-bp scars between building blocks. New cloning strategies developed in the past decade use Type IIS restriction endonuclease- and overlap-based assembly methods (e.g., Golden Gate and Gibson assembly) to overcome sequence requirements, and allow assembly of multiple inserts in a given reaction. Only a small number of described binary vectors allow generation of T-DNA constructs by high-throughput DNA assembly methods as those based on Type IIS restriction endonucleases and overlaps. Golden Gate is a robust system used by many plant scientists (Patron N. J., et al., New Phytol. 2015, 208, 13-19). Gibson assembly is very versatile, since it requires no domestication of parts, is able to join 2-10 fragments in a predetermined order, and has no sequence restrictions or scars (Gibson D. G., et al., Nat. Methods 2009, 6, 343-345); nonetheless, it has not been widely adopted for building plant constructs. To substantially reduce background of unwanted vector-only colonies in Gibson assembly reactions, the vector should be a PCR product rather than a restriction fragment, and should be DpnI-treated to remove template carryover. The large size of many binary vectors makes backbone linearization by PCR impractical, and small-sized binary vectors are therefore desirable for efficient construct cloning by Gibson assembly and other overlap-based assembly methods.

Multigene transfer is imperative in multiplexed gene editing, and to design and genetically engineer complex traits, circuits and metabolic pathways. In plants, conventional stacking methods require substantial breeding effort, which can be overcome by placing several genes within a single T-DNA, or by simultaneous infection of plant cells with multiple *A. tumefaciens* strains, each harboring a different T-DNA binary vector. A single *A. tumefaciens* strain can deliver two unlinked T-DNA cassettes and transform them in the same eukaryotic cell; simultaneous use of compatible T-DNA binary vectors is nonetheless a seldom-applied strategy in plant biotechnology. Moreover, in most current binary vector systems, selectable markers cannot be removed from transgenic lines at a later time. Delivery of unlinked T-DNA cassettes allows use of a selectable marker during plant regeneration, and subsequent recovery of marker-free progeny.

Binary vector systems are known wherein two T-DNA cassettes were delivered to plants by a single *A. tumefaciens* strain. Specifically, a single binary vector hosting two T-DNA cassettes (Komari T., et al., Plant J. 1996, 10, 165-174), or two T-DNA cassettes hosted in two compatible binary vectors (Daley M., et al., Plant Cell Rep. 1998, 17, 489-496) were delivered to plants by a single *A. tumefaciens* strain. Technical constraints of known systems include limited cloning flexibility due to the large plasmid size (>15 kb), incompatibility with high-throughput methods for construct assembly, or lack of replication independence of the binary vectors used.

Another operational disadvantage of binary vectors is the use of common components in their backbone sequences, which hampers their simultaneous maintenance in a single bacterial cell. As is well known to those skilled in the field of molecular biology, use of origins belonging to identical incompatibility groups impedes vector replication and maintenance in the same cell. Moreover, large sequence repeats can lead to DNA deletions and other rearrangements, particularly when the repeats are part of the plasmid structure. Such rearrangements can lead to partial or complete loss of the T-DNA region, resulting in little or no transfer of the intact, desired foreign sequences into eukaryotic cells.

Another disadvantage of binary vectors are the plasmid mobilization sequences needed to mobilize the vectors into *Agrobacterium* by triparental mating. The presence of mobilization sequences in binary vectors contributes to their size increase and to reducing their biological safety. Moreover, the origin of transfer of certain plasmids can interfere with the desired T-DNA processing and its delivery to eukaryotic cells (Buchanan-Wollaston V., et al, Nature 1987, 328, 172-175). In this sense it is known that plasmids can be transformed into *Agrobacterium* by physical approaches such as electroporation or freeze-thaw methods (Höfgen R. & Willmitzer L., Nucleic Acids Res. 1988, 16, 9877).

In consideration of the hereinabove disadvantages, it would be desirable to design improved binary vectors and binary vector systems without the above-mentioned limitations. There is thus a need for a binary vector of reduced size and with features that render it stable and limit its horizontal transfer. Further, there is a need for a binary vector compatible with advanced, high-throughput DNA cloning methods and that facilitates assembly of multiple components. It is also desirable to provide a binary vector system that incorporates minimal, single, compatible broad-host range replication origins that allow simultaneous maintenance of multiple binary vectors in a single bacterial cell. Consequently, the necessary binary vectors, binary vector systems, compositions, uses and methods comprising the same can be applied to improve the transformation process to integrate full-length T-DNA constructs into the eukaryotic cell or organism, and which are free of any residual sequence of the binary vector backbone. There is thus further a need for a binary vector system that facilitates delivery of multiple T-DNA cassettes to eukaryotic cells. The development of a novel, improved plant transformation system provides significant benefits for cell biologists, for agronomic uses, and for production of pharmaceutical compounds and recombinant proteins.

SUMMARY OF THE INVENTION

The invention resolves the problems described above by generation of the pLX series, a set of T-DNA binary vectors that facilitate the assembly and delivery of multicomponent constructs. The T-DNA binary vectors of the present invention are a new tool for plant synthetic biology as well as a flexible framework for multigene transfer and the characterization of DNA parts. The advantages of the T-DNA binary vectors of the present invention are: (a) a reduced size, preferably less than 3.8 kb; (b) a single, autonomous, broad-host range replication origin for maintenance in bacteria, preferably in *Escherichia coli* and *Agrobacterium tumefaciens*; (c) the use of a replication origin compatible with the most commonly used T-DNA binary vectors; (d) the presence of transcription terminators to reduce undesired expression of T-DNA sequences in bacterial hosts and to promote plasmid stability; (e) the incorporation of T-DNA cassettes with unique rare-cutting recognition sites; (f) consistency with current standards for plant synthetic biology, to allow high-throughput assembly of T-DNA constructs using pre-made DNA elements and Type IIS restriction endonuclease-based cloning methods; (g) the possibility of adopting overlap-dependent methods for high-throughput assembly of T-DNA constructs; (h) the possibility of being amplified and linearized by PCR to improve efficiency of overlap-based cloning; (i) incorporation of a pair of binary vectors with compatible origins, specifically engineered to have no backbone regions with >28 nucleotide identity; and (j) the possibility of delivering multiple T-DNA cassettes by a binary vector system that allows the multiplexing of vectors in a single bacterial cell.

The T-DNA binary vectors of the present invention comprise a minimal replication origin derived from the pBBR1 (pBBR1-based pLX) or RK2 (RK2-based pLX) plasmids, preferably from the pBBR1 plasmid (Antoine R. & Locht C., Mol. Microbiol. 1992, 6, 1785-1799). The size of the pBBR1-based backbone and the RK2-based backbone of the pLX vectors of the invention is substantially smaller than the widely used pBIN19- and pCAMBIA-based vectors, and is equal to pGreen-based vectors, the smallest available binary plasmids (FIG. 2A and FIG. 9). Replication of the pGreen vectors in *A. tumefaciens* requires a co-resident plasmid that supplies the pSa-RepA gene (e.g., pSoup). In contrast, the pLX binary vectors of the present invention facilitate flexible experimental designs, since their replication is autonomous in both *E. coli* and *A. tumefaciens*, and consequently does not require additional factors for their maintenance in bacterial hosts. The pLX binary vectors of the present invention are therefore useful for their autonomous replication in diverse bacteria, and for the presence of T-DNA cassettes.

The pLX binary vectors of the invention also include diverse selectable markers (the npfI, aadA, or aacC1 genes) for their selection in bacterial host cells, a T-DNA cassette with borders from an octopine- or succinamopine-type pTi from *A. tumefaciens*, and a second left border sequence that reduces backbone transfer (FIG. 2A). Bacterial synthetic terminators based on different scaffolds (T1, T2, λT1 and/or λT2) were included to reduce undesired expression of T-DNA sequences in the bacterial hosts and to increase plasmid stability. An AscI rare-cutting recognition site outside the T-DNA cassette was included to modify the pLX vector backbone of the present invention for a given purpose, for example, without limitation, by inserting toxin-antitoxin, counter segregation systems, or virulence gene sequences to improve plasmid stability and/or enhance transformation efficiency, such as, and without limitation, the hok/sok, parD/parE, and virG genes. Additionally, the pLX binary vectors of the present invention facilitate molecular cloning procedures, since the T-DNA cassettes comprise the PmlI and SbfI rare-cutting recognition sites that are useful for standard restriction endonuclease/DNA ligase cloning, and BsaI and BsmBI recognition sites compatible with high-throughput Type IIS restriction endonuclease-based methods, such as Golden Gate and GoldenBraid cloning. The BsaI- and BsmBI-produced overhangs comply with proposed standards for plant synthetic biology and ease assembly of pre-made DNA elements available in public libraries. The T-DNA cassettes also include divergent primer annealing regions with no secondary structures and sequence similarity among them. The mini T-DNA binary vectors of the present invention can thus be easily linearized by PCR, DpnI treated, and used in overlap-dependent cloning methods with high efficiency and no background of unwanted vector-only colonies. The binary pLX vectors of the present invention are therefore a set of mini T-DNA binary plasmids suitable for standard restriction endonuclease/DNA ligase cloning, and for advanced, Type IIS restriction endonuclease- and overlap-based assembly methods, such as and without limitation, Golden Gate/Golden Braid and Gibson assembly.

Given their small size, the pLX vectors might be delivered directly to eukaryotic cells, for example, by cell/protoplast transfection. Alternatively, the pLX vectors can use suitable bacterial strains, preferably *Agrobacterium* sp. strains, as shuttle chassis for transfer of their T-DNA cassette to eukaryotic cells. The pLX vectors can be introduced into bacteria by physical methods (e.g., electroporation, heat shock), and unwanted horizontal transfer of the pLX vector is less likely, since they do not include an origin of conjugative transfer or other plasmid mobilization regions. Transfer of the pLX vector backbone sequences flanking the T-DNA cassettes is predicted to be reduced by the incorporation of double left borders. *Escherichia coli*, *Agrobacterium tumefaciens* and plants have been used in the examples of the present invention, although the binary vectors of the invention are suitable for use in alternative systems such as in prokaryotic chassis other than *E. coli* and *A. tumefaciens*, and to transform eukaryotic organisms other than higher plants, such as algal, fungal, and animal cells.

The binary pLX vectors of the present invention include the pBBR1 origin, which shows no incompatibility with known plasmids. A vector system that uses, without limitation, the pBBR1-based and RK2-based pLX binary vectors of the invention facilitates multiple T-DNA delivery to eukaryotic cells, since it includes vectors with compatible replication origins, diverse selectable markers, and low sequence similarity to reduce homologous recombination events. Simultaneous use of the pBBR1-based and RK2-based pLX vectors as a transformation system, e.g. a two-vector/one-*Agrobacterium* strain system, allows multiple T-DNA and multigene delivery to eukaryotic organisms, such as plants, fungi, and animals.

The use of alternative compatible replication origins might further expand the multigene delivery design to an "N-vector/one-strain" system. This system can be combined by co-infection with multiple *A. tumefaciens* strains to further increase the number of T-DNA cassettes delivered.

The binary vectors disclosed in the present invention have been tested (see examples below) for transient and stable transformation of plants, genome editing, agro-inoculation of a new viral infectious clone, and for delivery of exogenous sequences to plants by viral vectors. The inventors have used a two-vector/one-strain system to deliver multiple T-DNA cassettes to plant germ line cells, and to express in plants the components of a simple buffer gate activated by a chemical inducer.

Applications of the binary pLX vectors of the present invention include, without limitation, their use for assembly of large T-DNA constructs and transcription units; for transient and stable transgene expression; for generation of transgenic plants free of drug-resistance markers; for launching viral infections by agro-inoculation; for exogenous sequence delivery and recombinant protein production using viral vectors; for genome editing; for delivery of clustered regularly interspaced short palindromic repeats (CRISPR)/CRISPR-associated protein (Cas) system components; for delivery of chemically-regulated expression systems; and for delivery of components of genetic circuits.

In this sense, a first aspect of the present invention relates to a binary vector, hereinafter first binary vector of the invention (the pBBR1-based pLX vector), comprising at least three modules: (a) a T-DNA cassette module comprising at least a T-DNA right border and a T-DNA left border; (b) a replication origin module comprising a pBBR1 minimal origin, or a variant functionally equivalent thereof; and (c) at least a selectable marker module.

In a preferred embodiment, the pBBR1-based pLX vector of the invention comprises a T-DNA cassette comprising one T-DNA right border and two T-DNA left borders.

In a further preferred embodiment of the pBBR1-based pLX vector of the invention, the pBBR1 origin comprises the pBBR1-oriV and -rep regions, or a variant functionally equivalent thereof. In a more preferred embodiment, the pBBR1 origin comprises the SEQ ID NO: 105.

In another preferred embodiment, the pBBR1-based pLX vector of the invention comprises a T-DNA cassette which is flanked by at least two transcription terminators, preferably selected from T1 (SEQ ID NO: 108), T2 (SEQ ID NO: 109), λT1 (SEQ ID NO: 110), λT2 (SEQ ID NO: 111), or any combinations thereof.

In a second aspect, the present invention further relates to another binary vector, named as RK2-based pLX vector, comprising at least three modules: (a) a T-DNA cassette module comprising at least a T-DNA right border and a T-DNA left border; (b) a replication origin module comprising an RK2 minimal origin, or a variant functionally equivalent thereof; and (c) at least a selectable marker module.

In an embodiment of the second aspect, the present invention relates to another binary vector that can preferably be used in combination with the pBBR1-based pLX vector of the invention, comprising at least three modules: (a) a T-DNA cassette module comprising at least a T-DNA right border and a T-DNA left border; (b) a replication origin module comprising an origin compatible with the pBBR1 origin, preferably selected form the list consisting of origins of the IncQ, IncW, IncU, pRi, pVS1, IncP-α plasmid incompatibility groups; and (c) at least a selectable marker module.

In a preferred embodiment, the RK2-based pLX vector of the invention comprises a T-DNA cassette comprising one T-DNA right border and two T-DNA left borders.

In a more preferred embodiment, the replication origin module is an origin of the IncP-α plasmid incompatibility group, and more preferably is the RK2 origin. In a further preferred embodiment of the RK2 origin comprises the RK2-oriV and -trfA regions, or a variant functionally equivalent thereof. In a more preferred embodiment the RK2 origin comprises the SEQ ID NO: 106 or SEQ ID NO: 107.

In another preferred embodiment, the RK2-based pLX vector of the invention comprises a T-DNA cassette that is flanked by at least two transcription terminators, preferably, bacterial transcription terminators.

In another preferred embodiment, the selectable marker gene of the RK2-based pLX vector differs from the selectable marker gene of the pBBR1-based pLX vector.

In another preferred embodiment, the backbone of the RK2-based pLX vector has no backbone regions with >28 nucleotide identity to the pBBR1-based pLX vector of the present invention.

In a third aspect, the present invention relates to a binary vector system comprising: (a) a first binary vector being the pBBR1-based pLX binary vector disclosed in the present invention; and (b) a second binary vector selected from the RK2-based pLX vector or a vector that can be used preferably in combination with the first binary vector of the invention, wherein the pBBR1 origin module is replaced by any of the replication origin selected from origins of the plasmid incompatibility groups: IncQ, IncW, IncU, pRi, pVS1, IncP-α; and wherein each of the binary vectors of (a) and (b) has replication and bacterial selection mechanisms enabling a mutual and autonomous coexistence with each other in the same host cell.

In a preferred embodiment of the binary vector system of the invention, the origin module of the second binary vector is an origin of the IncP-α plasmid incompatibility group, and more preferably is the RK2 origin according to the present invention. In a more preferred embodiment, the second binary vector is the RK2-based pLX vector of the present invention.

Another aspect of the present invention relates to a host cell comprising the pBBR1-based pLX vector, the RK2-based pLX vector, or the binary vector system disclosed in the present invention.

Another aspect of the present invention relates to a culture cell comprising the host cell of the present invention.

Another aspect of the present invention relates to a method for delivering at least one nucleotide sequence of interest into at least one plant cell comprising: (a) inserting at least one nucleotide sequence of interest into the first or the second binary vector, or into the binary vector system of the invention; (b) introducing the binary vector or binary vector system of step (a) into at least one bacterial host cell; and (c) contacting the host cell of step (b) with at least one eukaryotic cell.

Another aspect of the present invention relates to a method for in vitro delivering at least one nucleotide sequence of interest into at least one eukaryotic organism, comprising: (a) inserting at least one nucleotide sequence of interest into the binary vector or the binary vector system of the invention; and (b) introducing the binary vector or binary vector system of step (a) into at least one eukaryotic organism.

Another aspect of the present invention relates to a method for obtaining a genetically-engineered plant cell or plant comprising the step of introducing into a plant cell the binary vector, the binary vector system, or the bacterial host cell of the invention. Another aspect of the present invention relates to a genetically-engineered plant cell or plant obtainable by the method for obtaining a genetically-engineered plant cell or plant of the present invention.

Another aspect of the present invention relates to a method for in vitro obtaining a genetically-engineered eukaryotic cell or organism comprising the step of introducing into a eukaryotic cell the binary vector or the binary vector system of the present invention. Another aspect of the present invention relates to a genetically engineered eukaryotic cell or organism obtainable by the method for in vitro obtaining a genetically engineered eukaryotic cell or organism according to the present invention.

As used herein, the term "genetically engineered" refers to a plant cell, plant, eukaryotic cell or organism which has been generated through the aforementioned methods.

The present invention furthermore relates to a genetically modified, preferably transformed, mutant or modified plant system, to a regenerated cell or a regenerated plant therefrom, to their progeny or seeds therefrom generated in accordance with the methods of the invention described hereinabove. In a particular embodiment of the present invention, this transformed plant system is characterized by single or multiple modifications of the plant cell genome, epigenome, transcriptome, or metabolome, and in that it may or may not comprise any sequence segments of the abovementioned vectors, vector system and their T-DNA cassettes.

Another aspect of the present invention relates to a method for transforming eukaryotic cells or eukaryotic organisms comprising the step of introducing into the eukaryotic cell or organism the binary vector, the binary vector system, the host cell, the genetically-engineered plant cell or plant, or the genetically-engineered eukaryotic cell or organism, disclosed in the present invention.

Another aspect of the present invention relates to methods to assemble synthetic, genomic, metagenomic, and/or cDNA sequences of interest into the binary vector or the binary vector system disclosed in the present invention. According to the present invention, a variety of methods can be used for nucleic acid assembly. In a preferred embodiment, the sequences of interest are assembled by use of high-throughput restriction endonuclease-, preferably and without limitations Type IIS restriction endonucleases, or overlap-dependent assembly methods, such as and without limitation, Golden Gate, GoldenBraid or Gibson assembly.

Another aspect of the present invention relates to the in vitro or ex vivo use of the binary vector, the binary vector system, the host cell, or the culture cell of the invention: (a) for site-specific gene knockout; (b) for site-specific genome editing; (c) for DNA sequence-specific interference; (d) for site-specific epigenome editing; (e) for site-specific transcription modulation; or (f) for multiplex genome engineering; and provided the in vitro or ex vivo use does not comprise a process for modifying the germ line genetic identity of human beings.

Another aspect of the present invention relates to a kit comprising the binary vector, the binary vector system, the host cell, or the culture cell of the invention.

Module 1, 2, and 3 refer to the T-DNA cassette, the pBBR1 origin, and the selectable marker, respectively. Each module includes one or several DNA parts, which are flanked by two diverse assembly linkers (diamonds): Linker_1 (SEQ ID NO: 112), Linker_2 (SEQ ID NO: 113), Linker_3 (SEQ ID NO: 114). Parts from the three modules were obtained by PCR or chemical synthesis, and were joined by one-step isothermal DNA assembly to generate the pLX-B2 (SEQ ID NO: 3), pLX-B3 (SEQ ID NO: 4), pLX-B4 (SEQ ID NO: 5) binary vectors.

Figure 2:
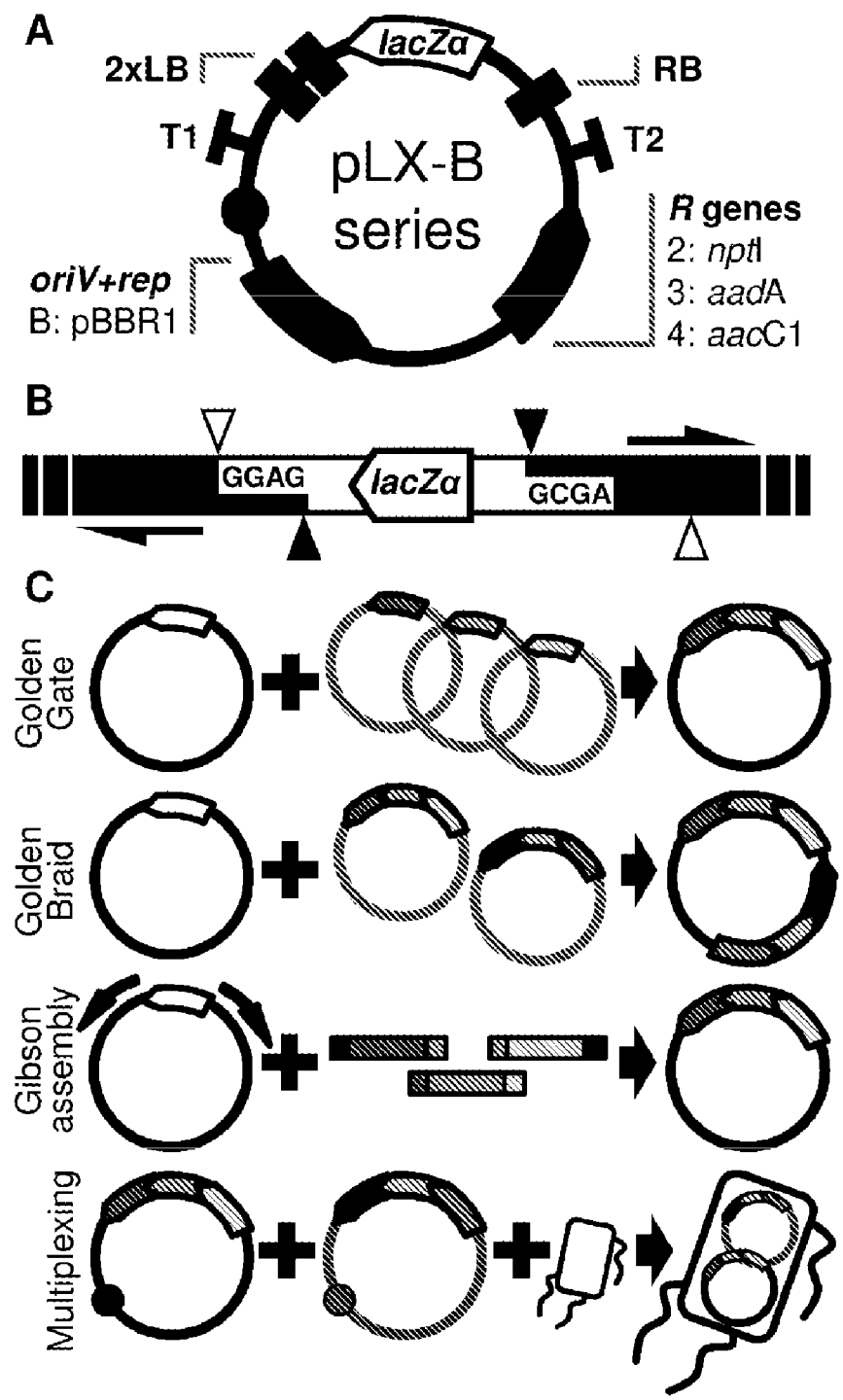

FIG. 2. Novel T-DNA binary vectors of the pLX series and their features (A) Organization of the pBBR1-based pLX plasmids. The binary vectors are composed of three modules, (i) a T-DNA cassette that includes a right border, an *Escherichia coli* reporter gene, two left borders, and is flanked by bacterial transcription terminators (T1 and T2); (ii) the broad host-range pBBR1 origin suitable for plasmid replication in *E. coli* and *Agrobacterium tumefaciens* (oriV+rep); and (iii) a selectable marker such as antibiotic resistance genes. The plasmid vectors are indicated by a letter that reflects their origin module (B, pBBR1-derived origin) and a digit according the R gene: 2, npfI, gene that confers resistance to kanamycin; 3, aadA, gene that confers resistance to spectinomycin/streptomycin; 4, aacC1, gene that confers resistance to gentamicin. (B) Cloning features of a T-DNA cassette of the pLX vectors. The lacZα reporter is flanked by two divergent BsaI recognition sites (solid triangles); the nonpalindromic overhangs generated by BsaI digestion allow assembly of transcription units by one-step digestion-ligation cloning (Golden Gate). Convergent BsmBI sites (open triangles) are included to build multiple transcription unit constructs by Golden Braid assembly. Alternatively, pLX vectors can be linearized by inverse PCR using divergent primers (arrows), DpnI treated, and used to join one or several overlapping inserts by one-step isothermal DNA assembly (Gibson assembly). (C) Diagrams of pLX vector cloning features. Parts or transcription units can be assembled into pLX vectors using the BsaI-based Golden Gate and GoldenBraid standards. Overlapping DNA fragments can be joined into the linearized pLX vectors by Gibson assembly. The pLX vectors can be used for multiple T-DNA delivery by vector multiplexing into *Agrobacterium* cells.

Figure 3:
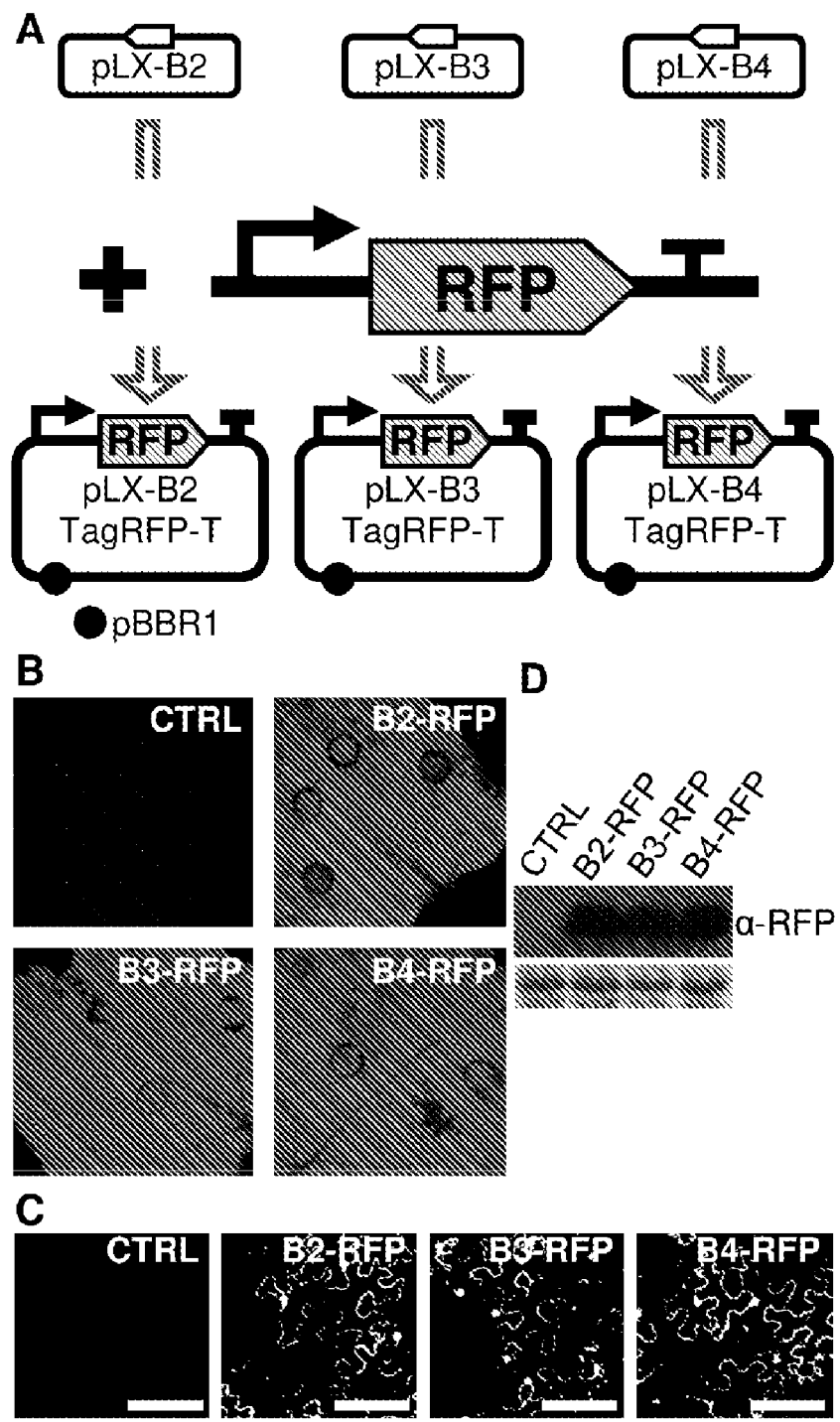

FIG. 3. Transient transgene expression in plants using the pLX vector series (A) Construct scheme of the transgene for transient transformation of *Nicotiana benthamiana* plants. The TagRFP-T gene (RFP) driven by the cauliflower mosaic virus (CaMV) 35S promoter was inserted into different pLX-derived backbones, which were delivered to plants by agro-infiltration. Data were collected at 6 days post-agro-infiltration (dpa); CTRL, an empty control; B2-RFP indicates pLX-B2-TagRFP-T (SEQ ID NO: 13); B3-RFP, pLX-B3-TagRFP-T (SEQ ID NO: 14); B4-RFP, pLX-B4-TagRFP-T (SEQ ID NO: 15). (B) RFP fluorescence of infiltrated leaves was imaged under a fluorescence stereoscope. (C) Cell RFP fluorescence was imaged by confocal microscopy; bars, 100 μm. (D) RFP accumulation was assessed by immunoblot analysis. Ponceau red-stained blot is shown as a loading control.

Figure 4:
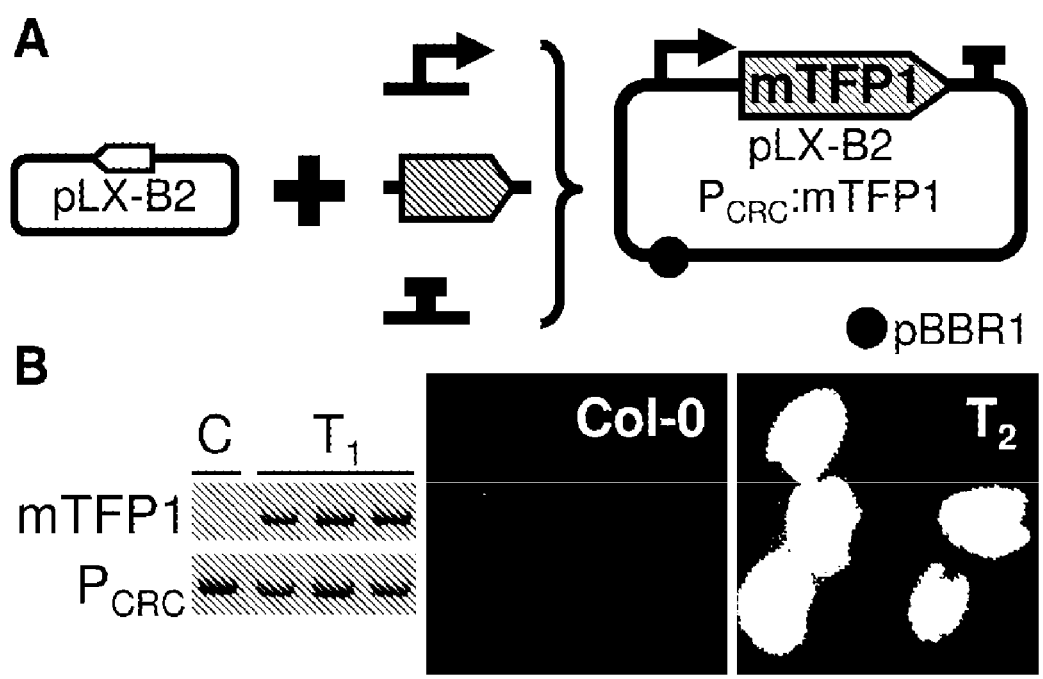

FIG. 4. Stable transgene expression in plants using the pLX vector series (A) A transgene construct for stable transformation of *Arabidopsis thaliana* plants was assembled in pLX-B2-$P_{CRC}$:mTFP1 (SEQ ID NO: 23), and included a cyan fluorescent protein gene (mTFP1) driven by the *A. thaliana* cruciferin C promoter, which is active in seeds ($P_{CRC}$). (B) To confirm stable integration of the transgene, PCR assays of genomic DNA were performed using transgene-specific (mTFP1; 765 bp) or control primers ($P_{CRC}$; 1081 bp). Each lane represents a single plant sample; C, untransformed plant sample; $T_1$, independent lines selected by cyan fluorescence of seed collected from the *Agrobacterium*-treated plants. Fluorescence images of untransformed seeds (Col-0) and those collected from a single $T_1$ plant (T2).

Figure 5:
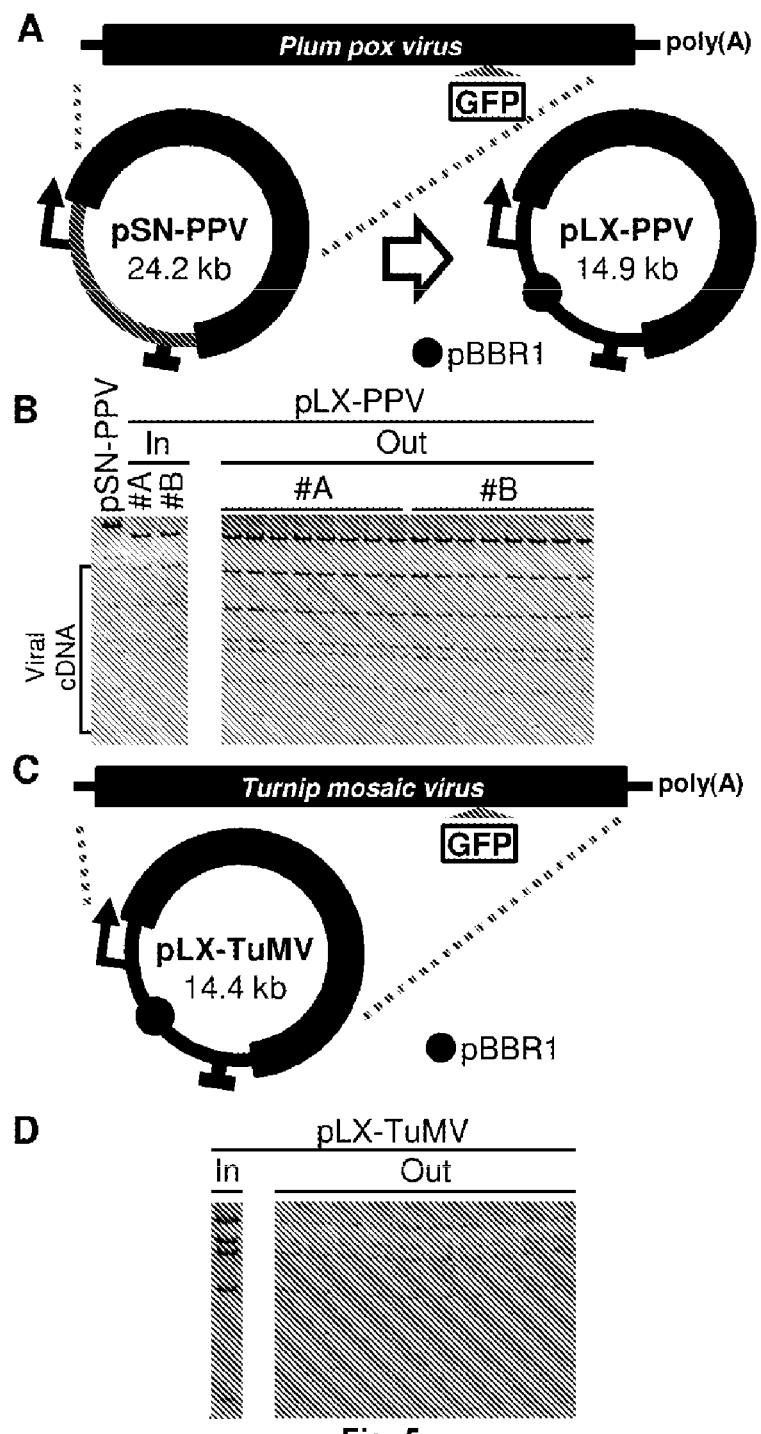

FIG. 5. Stability of the pLX vector series in *Escherichia coli* cells (A) The expression cassette of a GFP-tagged plum pox virus (PPV) cDNA clone was subcloned from a pBIN19-derived vector (pSN-PPV) to a pLX plasmid, to generate the pLX-PPV vector (SEQ ID NO: 21). Schemes are not to scale. (B) Clones # A and # B of the new pLX-PPV vector were transformed in *E. coli* cells to evaluate the plasmid stability, inputs (In). For each transformation, eight individual colonies were picked and subjected to six growth cycles (24 h, 37° C.). The purified plasmids (Out, outputs) were EcoRI-digested and resolved by agarose gel electrophoresis. Fragments derived from the cDNA copy cassette of the PPV genome are indicated (left); upper bands are backbone-specific fragments. (C) To generate the pLX-TuMV vector (SEQ ID NO: 28), the expression cassette of a GFP-tagged turnip mosaic virus (TuMV) cDNA clone was subcloned from a pUC-based vector (p35Tunos-vec01-NAT1) to a pLX-B2-derived plasmid. (D) pLX-TuMV (SEQ ID NO: 28) was transformed into *E. coli* cells to evaluate plasmid stability, input (In). Ten individual colonies were picked and subjected to six growth cycles (24 h, 37° C.). The purified plasmids (Out, outputs) were EcoRI-digested and resolved by agarose gel electrophoresis.

Figure 6:
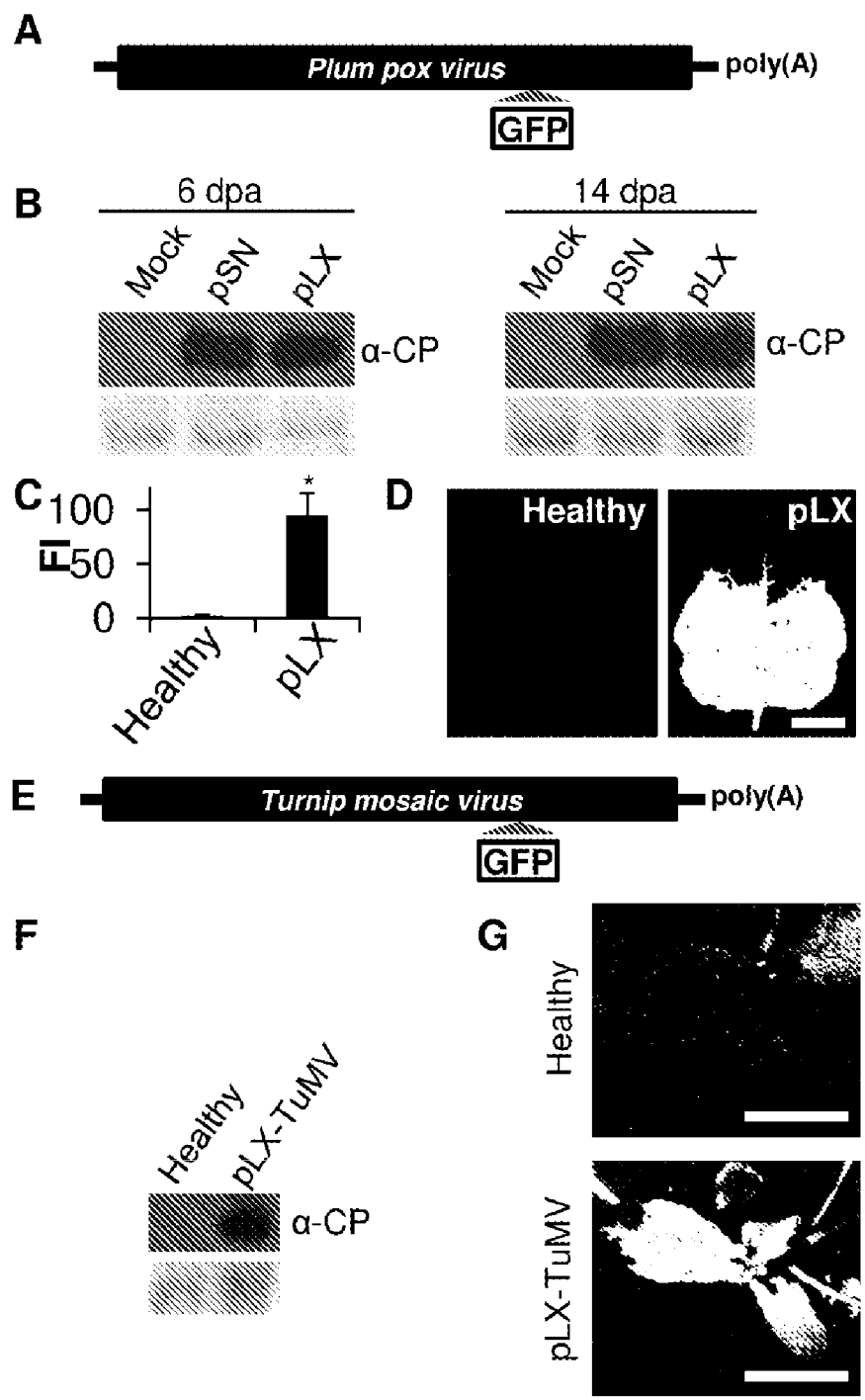

FIG. 6. Viral vector delivery and recombinant protein production in plants using the pLX vector series The pLX-PPV (pLX) (SEQ ID NO: 21) and pSN-PPV (pSN) viral vectors were delivered to *N. benthamiana* plants by agro-infiltration (panels A-D); the pLX-TuMV viral vector was delivered to *A. thaliana* plants by agro-inoculation (panels E-G). (A) Recombinant GFP was expressed in plants using a chimeric PPV clone. (B) Viral accumulation was assessed by anti-PPV coat protein (CP) immunoblot analysis of samples from the agro-infiltrated and upper uninoculated leaves, at 6 and 14 dpa, respectively. Ponceau red-stained blots are shown as loading controls. (C) At 6 dpa, GFP fluorescence intensity (FI) of the agro-infiltrated leaf patches was quantified in a 96-well plate reader. Bar indicates mean±standard deviation (SD, n=4); * p<0.001, Student's t-test. (D) At 14 dpa, the upper uninoculated leaves were imaged on a blue light transilluminator; GFP fluorescence is shown in light gray; scale bar, 2 cm. (E) Recombinant GFP was expressed in plants using a chimeric TuMV clone. (F) The pLX-TuMV (SEQ ID NO: 28) vector was delivered to *A. thaliana* plants by agro-inoculation, and data were collected at 11 days post agro-inoculation. Viral accumulation was assessed by anti-TuMV CP immunoblot analysis of upper uninoculated leaves; the Ponceau red-stained blot is shown as a loading control. (G) Upper uninoculated leaves were imaged; GFP fluorescence is shown in light gray; scale bar, 1 cm.

Figure 7:
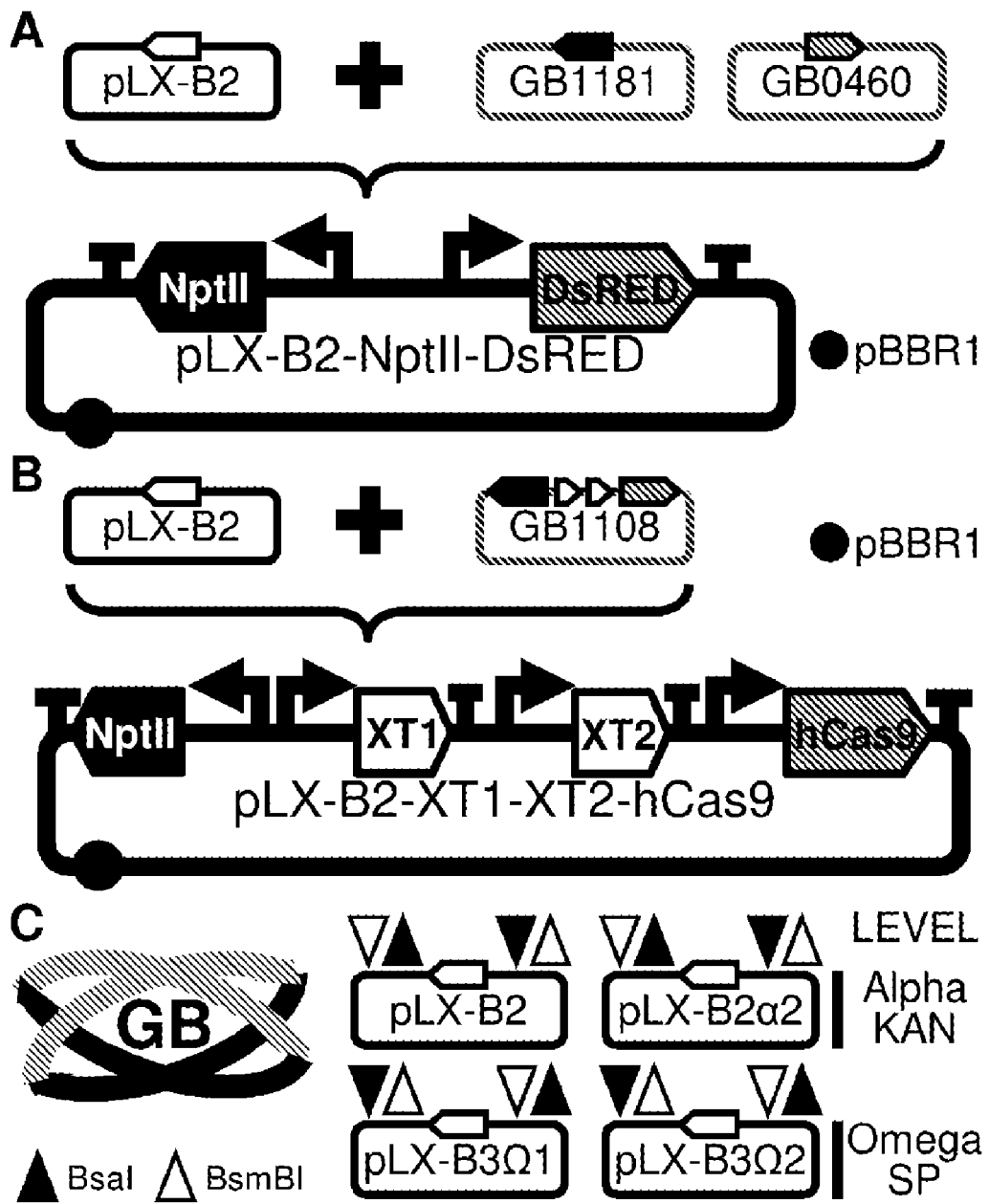

FIG. 7. Assembly of DNA parts into the pLX vectors by using synthetic biology standards (A) Standardized units for delivery to plants of the kanamycin resistance (NptII) and red fluorescent protein (DsRED) genes were assembled into the pLX-B2 vector (SEQ ID NO: 3) to generate the pLX-B2-NptII-DsRED vector (SEQ ID NO: 20). (B) The pLX-B2-XT1-XT2-hCas9 vector (SEQ ID NO: 19) was assembled for delivery of standardized units: a kanamycin resistance gene (NptII), human codon-optimized *Streptococcus pyogenes* Cas9 gene (hCas9), and sgRNA targeting the *N. benthamiana* Niben101Scf04205Ctg025 (XT1) and Niben101Scf04551Ctg021 (XT2) endogenous genes. (C) Scheme of the pLX vectors that incorporate cloning cassettes compatible with the Golden Braid binary assembly. The alpha level kanamycin-resistant plasmids have divergent BsaI and convergent BsmBI sites; the omega level spectinomycin-resistant plasmids have divergent BsmBI and convergent BsaI sites. All plasmids include the pBBR1 origin and the lacZα reporter.

Figure 8:
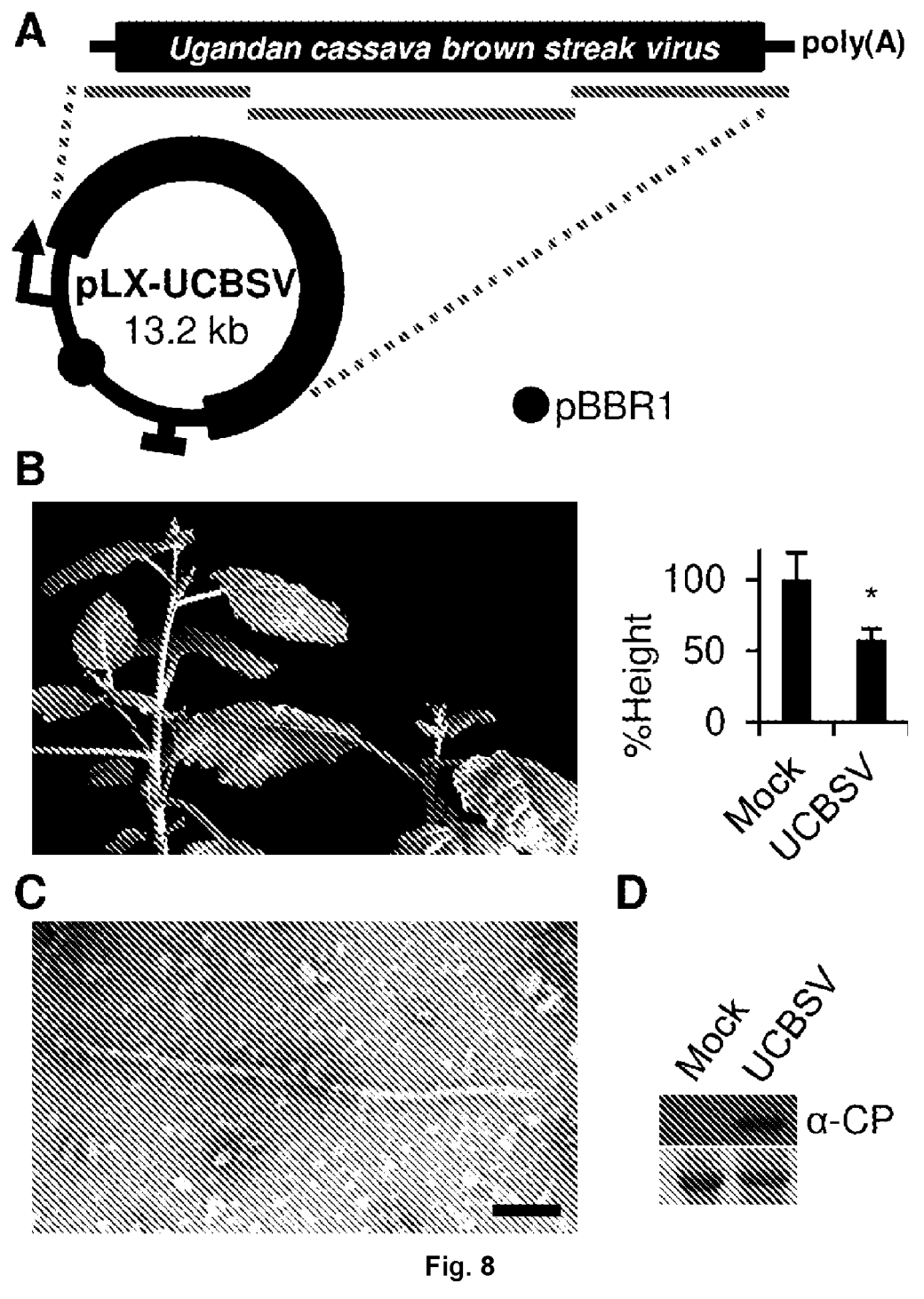

FIG. 8. Assembly of large transcription units by overlap-based cloning methods, and virus agro-inoculation using the pLX vector series (A) Use of a pLX vector to generate an infectious cDNA clone of an RNA virus. Three RT-PCR fragments (gray boxes) spanning the entire Ugandan cassava brown streak virus (UCBSV) genome were cloned in a linearized pLX-B2-based vector by Gibson assembly. The pLX-UCBSV vector (SEQ ID NO: 22) obtained was delivered to N. benthamiana plants by agro-infiltration, and data were collected at 12 dpa. (B) Photographs of mock- and pLX-UCBSV-infiltrated plants (left and right, respectively). The plant relative height is plotted, mean±SD (n=4); * p=0.0059, Student's t-test. (C) Transmission electron micrograph shows particles observed in the infected plant sample; scale bar, 100 nm. (D) Viral accumulation was assessed by anti-UCBSV coat protein (CP) immunoblot analysis of samples from upper uninoculated leaves. The Ponceau red-stained blot is shown as a loading control.

Figure 9:
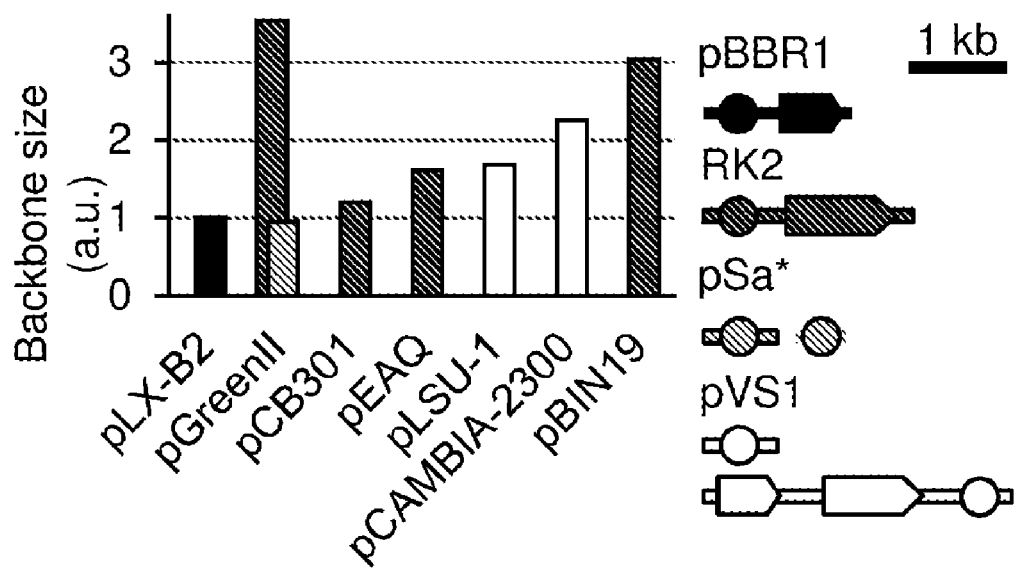

FIG. 9. Relative size comparison of the pLX-B2 backbone and selected T-DNA binary vectors Relative size comparison of the pLX-B2 backbone and selected binary vectors (T-DNA cassette sequences were not considered). Graph bars are filled according to the plasmid replication origins shown at right; the pVS1- and pSa-based binary vectors include a narrow-host-range origin for maintenance in E. coli; *, as the pSa origin in the pGreen-based vectors is not autonomous, the size of the RK2-based pSoup plasmid required for pGreenII maintenance in A. tumefaciens is also included in the graph. Glyphs according to the Synthetic Biology Open Language visual format.

Figure 10:
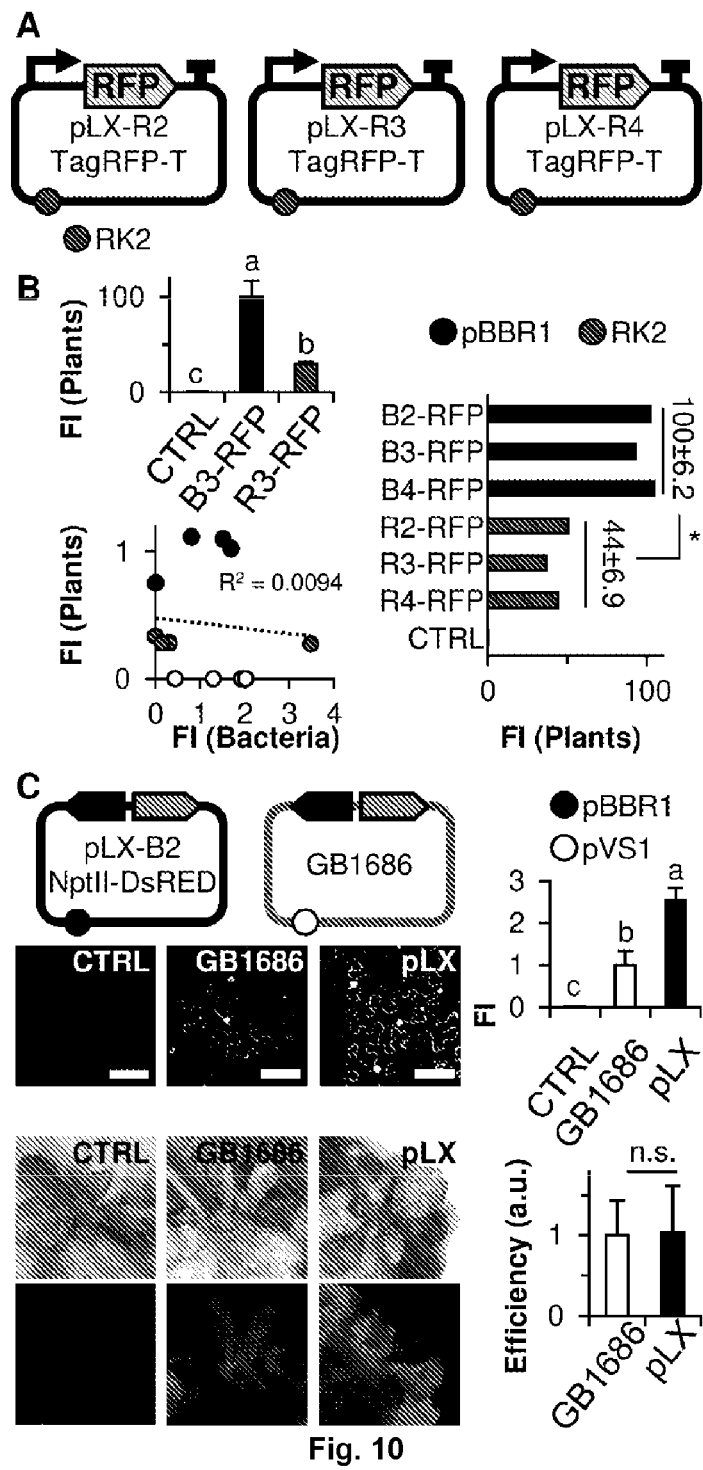

FIG. 10. Comparison in plant expression assays of the pBBR1-based pLX vectors, and T-DNA binary vectors based on the RK2 and pVS1 origins (A) The pBBR1 replication module of pLX vectors was replaced with an RK2 minimal origin to build pLX-R2 (SEQ ID NO: 6), pLX-R3 (SE ID NO: 7) and pLX-R4 (SEQ ID NO: 8) vectors. These were engineered to obtain the pLX-R2-TagRFP-T (SEQ ID NO: 16), pLX-R3-TagRFP-T (SEQ ID NO: 17) and pLX-R4-TagRFP-T (SEQ ID NO: 18) vectors for expression of the TagRFP-T gene (RFP). (B) In transient expression assays, the RFP vectors from FIG. 3 (B2-RFP indicates pLX-B2-TagRFP-T (SEQ ID NO: 13); B3-RFP, pLX-B3-TagRFP-T (SEQ ID NO: 14); B4-RFP, pLX-B4-TagRFP-T (SEQ ID NO: 15)) were compared to RK2-based pLX vectors (R2-RFP indicates pLX-R2-TagRFP-T (SEQ ID NO: 16); R3-RFP, pLX-R3-TagRFP-T (SEQ ID NO: 17); R4-RFP, pLX-R4-TagRFP-T (SEQ ID NO: 18)); CTRL, an empty control. RFP fluorescence intensity (FI) of bacterial suspensions and infiltrated plant samples (at 4 or 6 dpa) was measured in a plate reader. Bar graphs show the FI values for plant samples, mean±SD (n 0.3); letters indicate p<0.05, one-way Anova and Tukey's HSD test; * p=0.00047, Student's t-test. Scatter plot shows linear regression analysis of FI values for plant and bacterial samples; the B3-RFP, R3-RFP, and empty control samples are shown in black, gray and white, respectively. (C) Expression of a DsRED standard cassette was compared in transient and stable expression assays. A pCAMBIA-derived vector (GB1686, SEQ ID NO: 27) and pLX-B2-NptII-DsRED (pLX, SEQ ID NO: 20) were transformed into N. benthamiana plants; CTRL, control. In agro-infiltrated leaf samples, cell DsRED fluorescence was imaged by confocal microscopy (bars, 100 μm) and quantified in a plate reader. FI values were plotted, mean±SD (n=4); letters indicate p<0.05, one-way Anova and Tukey's HSD test. In stable transformation assays, leaf samples were co-cultured with the indicated A. tumefaciens strains and transferred to kanamycin-containing medium. Images show plantlets imaged under an epifluorescence microscope at 40 days post inoculation. The plot shows transformation efficiencies defined as the number of kanamycin-resistant plantlets that showed DsRED fluorescence, mean±SD (n=7); n.s., p=0.91. Vector origins are indicated: pBBR1, solid circle/bars; pVS1, open circle/bars.

Figure 11:
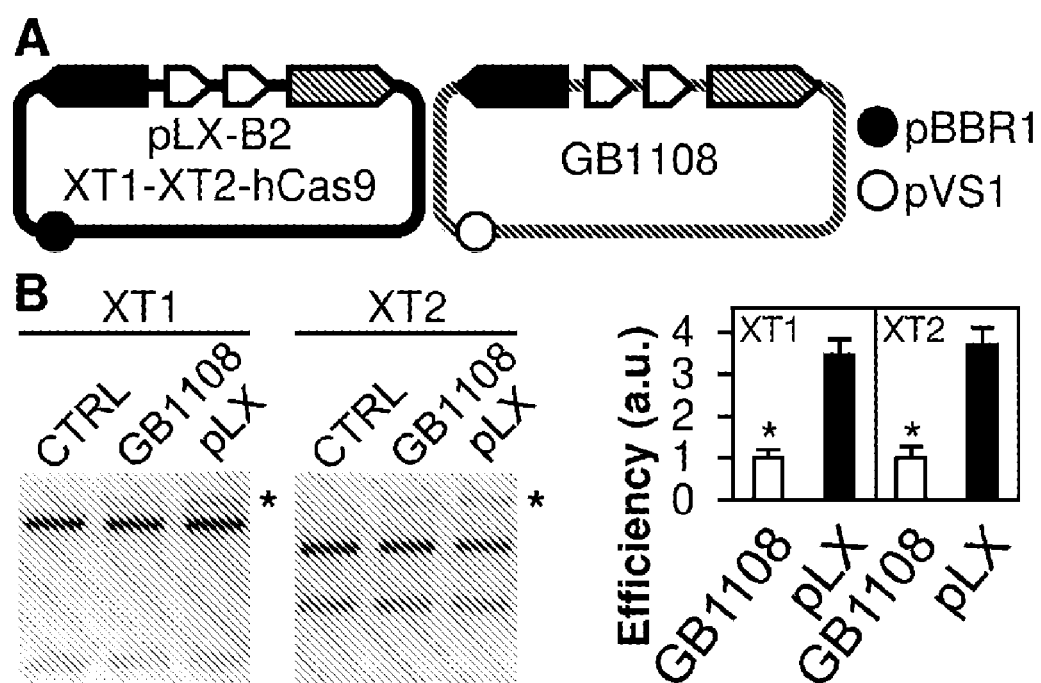

FIG. 11. Delivery of CRISPR/Cas system components, and targeted genome mutagenesis comparison of pBBR1-based pLX vectors and T-DNA binary vectors based on the pVS1 origin Targeted mutagenesis in transient expression assays by using a Golden Braid-based CRISPR/Cas9 system. (A) Nicotiana benthamiana plants were infiltrated with a pCAMBIA-derived vector (GB1108) and the pLX-B2-XT1-XT2-hCas9 (pLX; SEQ ID NO: 19); the vectors bear transcription units for the human codon-optimized Cas9 (hCas9), and sgRNA targeting the Niben101Scf04205Ctg025 (XT1) and Niben101Scf04551Ctg021 (XT2) endogenous genes. (B) Gels show PCR/digestion assays; asterisks mark cleavage-resistant DNA bands; CTRL, hCas9 delivered with no sgRNA sequences. The plot shows mutagenesis efficiencies, which were estimated by quantifying the ratio of uncleaved/cleaved bands; mean±SD (n=4); * p<0.001. Vector origins are indicated: pBBR1, solid circle/bars; pVS1, open circle/bars.

Figure 12:
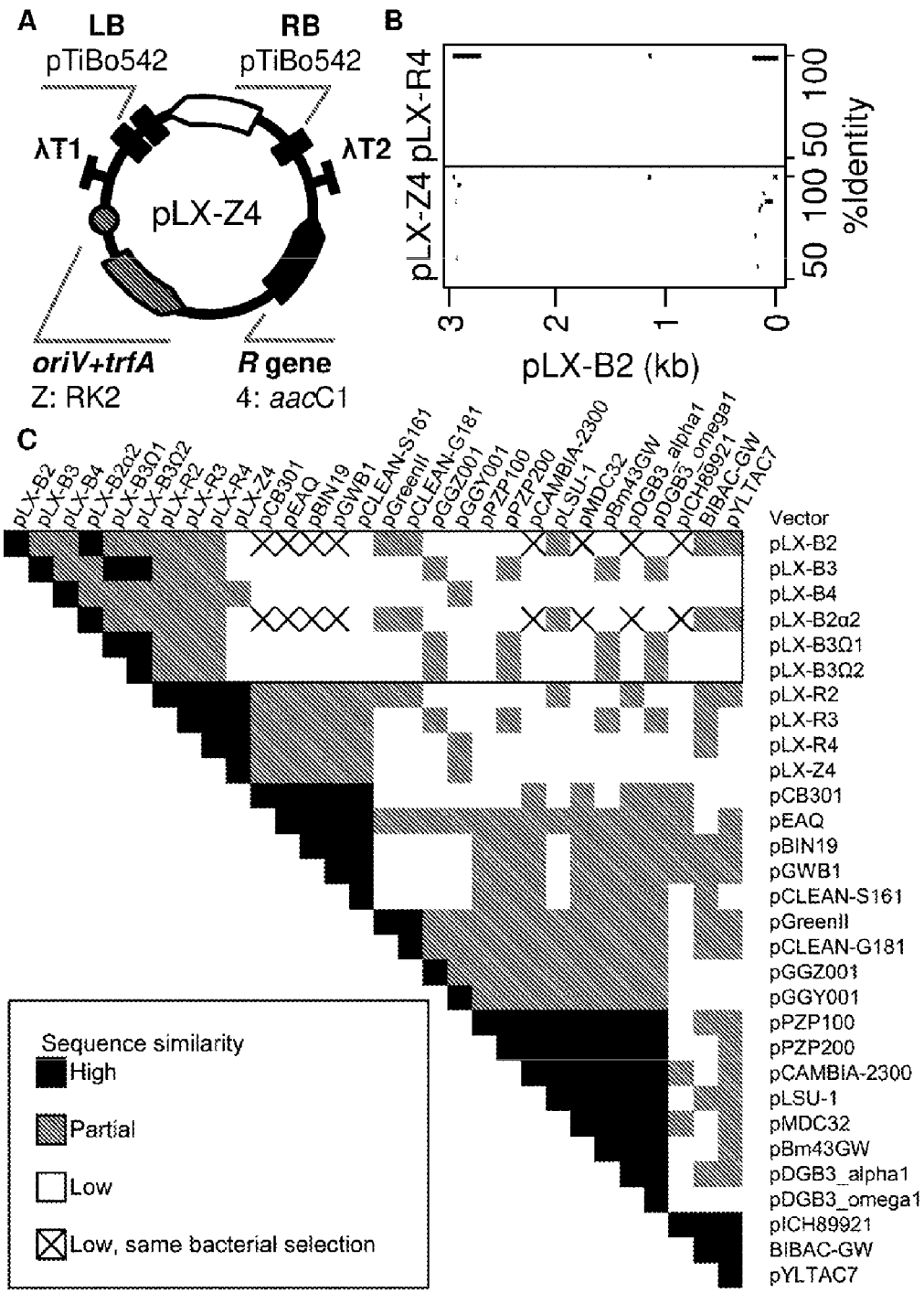

FIG. 12. Sequence similarity of the pLX vectors and reference T-DNA binary vectors (A) Representation of the new pLX binary vector compatible with the pBBR1 origin. pLX-Z4 (SEQ ID NO: 9) shares the pLX modular organization and cloning cassette shown in FIG. 2; it includes T-DNA border sequences from the succinamopine-type pTiBo542 plasmid, a second left border sequence, lambda phage terminators, a gentamicin resistance gene (aacC1), and a 2.2-kb minimal replicon from the broad host-range plasmid RK2. (B) Percent identity plots show significant DNA local alignments between the pBBR1-based pLX-B2 and RK2-based pLX-Z4 (SEQ ID NO: 9), or pLX-R4 (SEQ ID NO: 8) vectors. Cloning cassette sequences were omitted in the comparisons; plots were generated using PipMaker (Schwartz S., et al, Genome Res. 2000, 10, 577-586). (C) Sequence similarity of the new pLX and reference T-DNA binary vectors. The matrix shows outputs obtained by pairwise sequence analysis of the vector backbones. Sequence similarity was classified according to BLASTN total score values: high, >4100; partial, 800-4100; low, <800. Matrix entries of the pBBR1-based pLX vectors are boxed, and crossed entries mark vector pairs that show low sequence similarity but share selection antibiotics.

Figure 13:
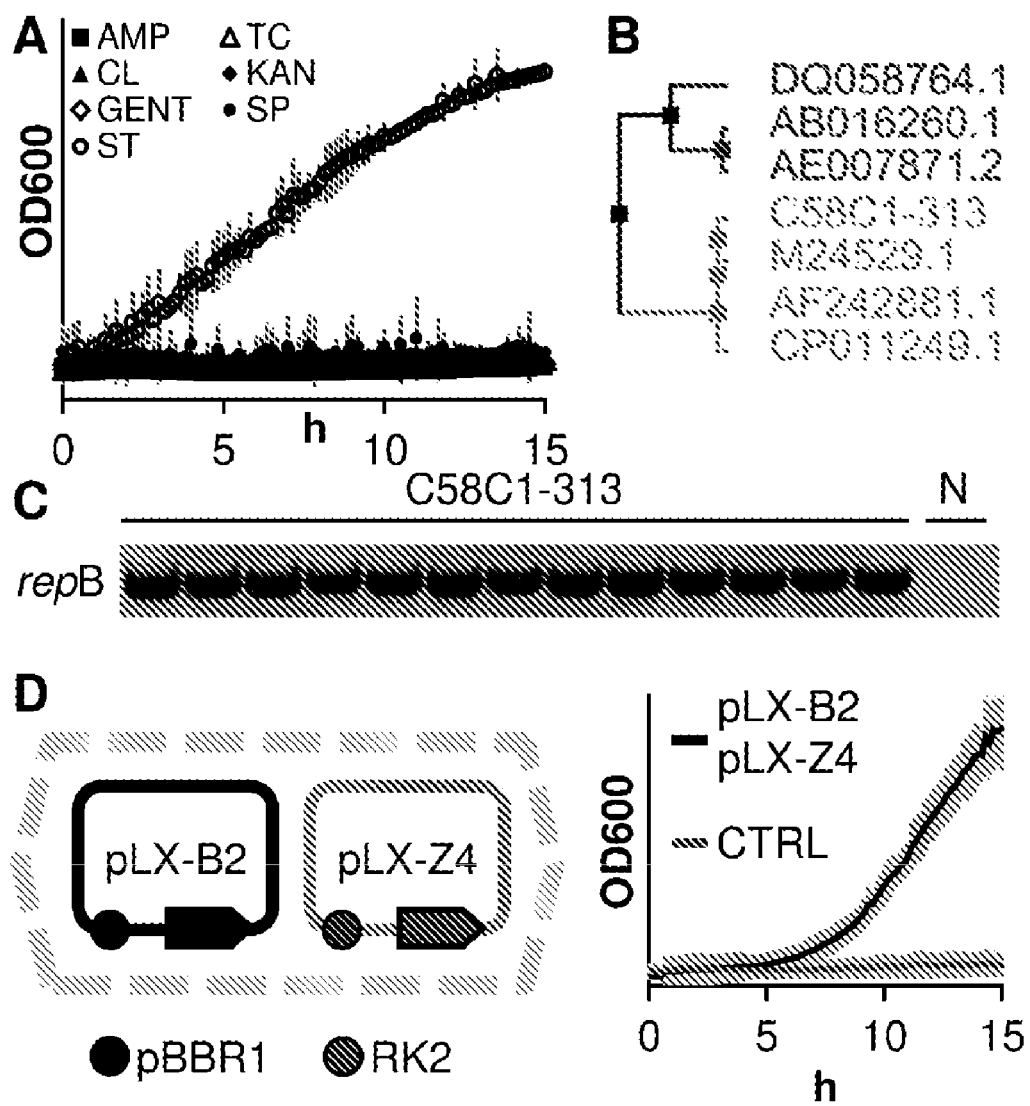

FIG. 13. Characterization of an octopine-type, disarmed strain of A. tumefaciens that shows sensitivity to several antibiotics, and strain usage for vector multiplexing (A) Antibiotic sensitivity of C58C1-313, an A. tumefaciens disarmed strain. Bacteria were inoculated into Luria-Bertani medium supplemented with rifampicin plus indicated antibiotics: AMP (ampicillin), CL (chloramphenicol), GENT (gentamicin), TC (tetracycline), KAN (kanamycin), SP (spectinomycin) and ST (streptomycin). To monitor growth curves, absorbance (OD600) was measured in a plate reader. Plot shows mean±SD (n=6); h, hours. (B) C58C1-313 harbors a pTi of the octopine type. A fragment of pTi repB gene was PCR-amplified from C58C1-313 and sequenced. A phylogenetic tree was built from an alignment of the 607-nt repB sequence from the C58C1-313 strain and deposited Ti plasmid sequences (NCBI: DQ058764.1; AB016260.1; AE007871.2; M24529.1; CP011249.1; AF242881.1). C58C1-313 clusters with the octopine-type pTi accessions. (C) Stability of pTi maintenance in the *A. tumefaciens* strain C58C1-313. C58C1-313 was plated, and the presence of pTi in individual colonies was confirmed by PCR using pTi-specific primers (repB; 724 bp); N, negative control. (D) Diagram of an *A. tumefaciens* strain (dashed hexagon) that simultaneously hosts pLX-B2- and pLX-Z4-derived vectors conferring kanamycin and gentamicin resistance, respectively. Growth curves of *A. tumefaciens* C58C1-313 that harbors no vectors (CTRL, gray), or the pLX-B2– plus pLX-Z4-derived vectors (black). Kanamycin- and gentamicin-supplemented medium was inoculated with the indicated strains, and absorbance measured in a plate reader. The plot shows mean±SD (n=6); h, hours.

Figure 14:
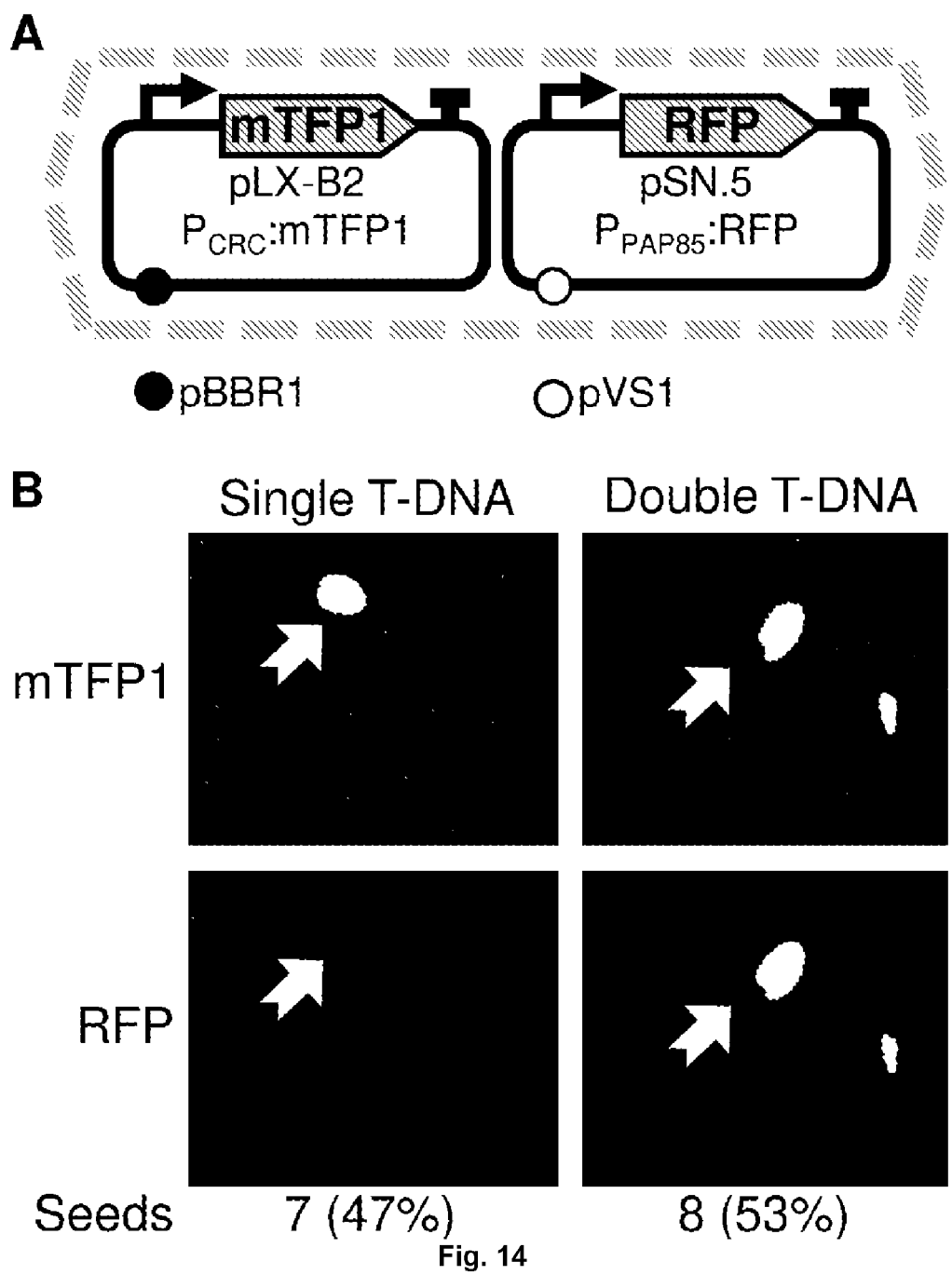

FIG. 14. Usage of the pLX vector series for multiple T-DNA delivery to plants (A) Diagram of an *A. tumefaciens* strain (dashed hexagon) that simultaneously hosts pLX-B2-derived and pCAMBIA-derived vectors conferring kanamycin and spectinomycin resistance, respectively; vector origins are indicated: pBBR1, solid circle; pVS1, open circle. Components of pLX-B2-$P_{CRC}$:mTFP1 are described in FIG. 4; in pSN.5-$P_{PAP85}$:RFP, the TagRFP-T gene (RFP) is driven by the *A. thaliana* PAP85 promoter ($P_{PAP85}$). The $P_{CRC}$ and $P_{PAP85}$ promoters used are active in seeds. (B) *Arabidopsis thaliana* plants were treated with the *A. tumefaciens* pLX-B2-$P_{CRC}$:mTFP1 plus pSN.5-$P_{PAP85}$:RFP strain by floral dipping. The $T_1$ seeds were collected and visualized under a fluorescence stereoscope. Pictures show seeds that express mTFP1 only (Single T-DNA), or mTFP1 plus RFP (Double T-DNA); for each condition, number and percentage of obtained seeds are indicated.

Figure 15:
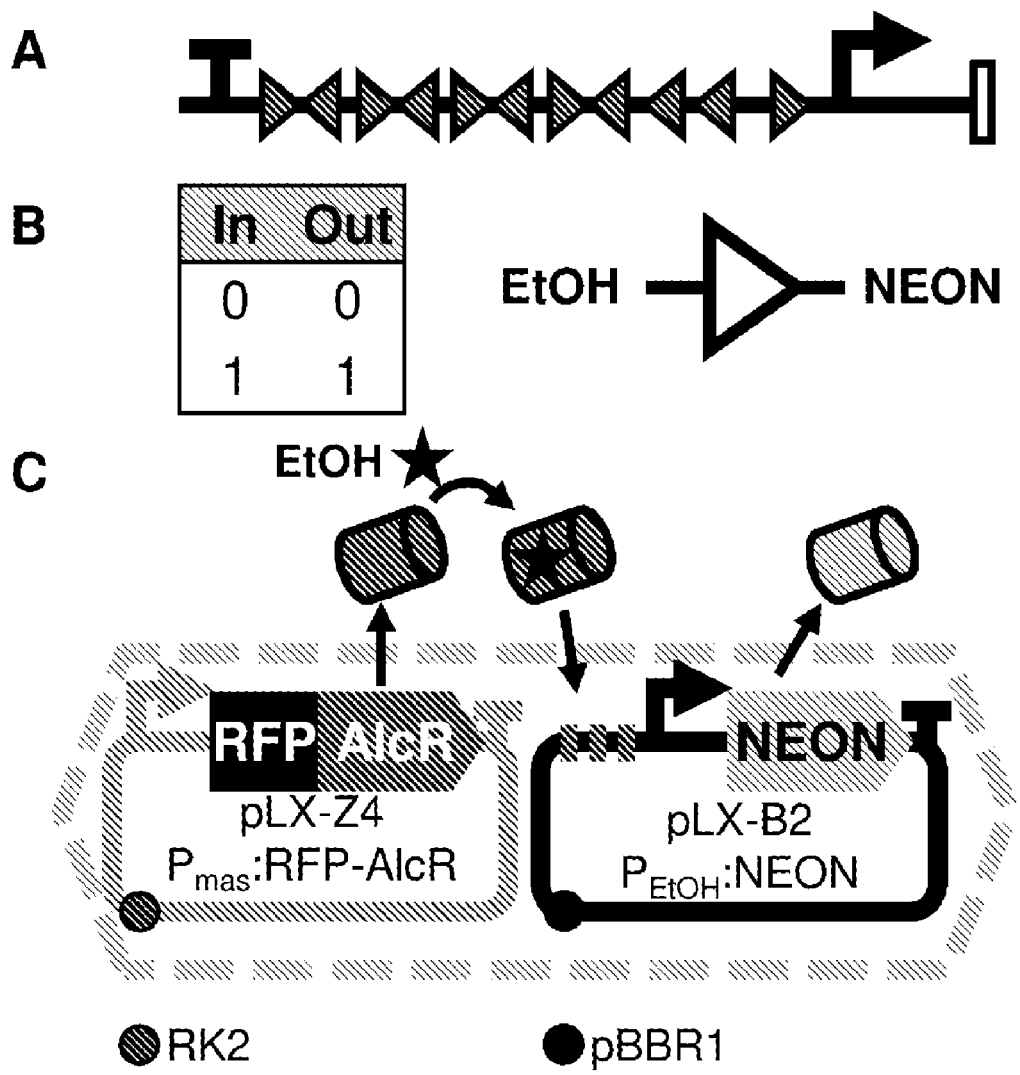

FIG. 15. Experimental design for delivery of synthetic circuit components to plants by multiplexing the pLX vectors (A) Sequence of the $P_{EtOH}$ synthetic promoter (SEQ ID NO: 35). The cauliflower mosaic virus (Ca MV) 35S terminator was included to insulate against promoters that might flank the T-DNA integration sites; AlcR DNA-binding sites (triangles) derived from the *Aspergillus nidulans* alcR, aldA, alcA promoters are placed upstream of a figwort mosaic virus 34S minimal promoter (arrow); open box, starting codon of the coding sequence. (B) Buffer gate truth table. Symbol of a buffer gate that uses ethanol (EtOH) as the input, and mNeonGreen (NEON) fluorescence as the output. (C) Genetic circuit that implements the gate of the previous panel. The dashed hexagon represents a single *A. tumefaciens* strain (R-AlcR+$P_{EtOH}$:NEON) that hosts two compatible T-DNA binary vectors, pLX-Z4-$P_{mas}$:RFP-AlcR (SEQ ID NO: 24) and pLX-B2-$P_{EtOH}$:NEON (SEQ ID NO: 25), which confer gentamicin and kanamycin resistance, respectively. Once delivered to plants, the constitutive mannopine synthase promoter ($P_{mas}$) drives expression of the RFP and AlcR proteins. In the presence of EtOH (star), AlcR binds to and activates an otherwise silent synthetic promoter ($P_{EtOH}$). NEON accumulation results from the activation of the gate.

Figure 16:
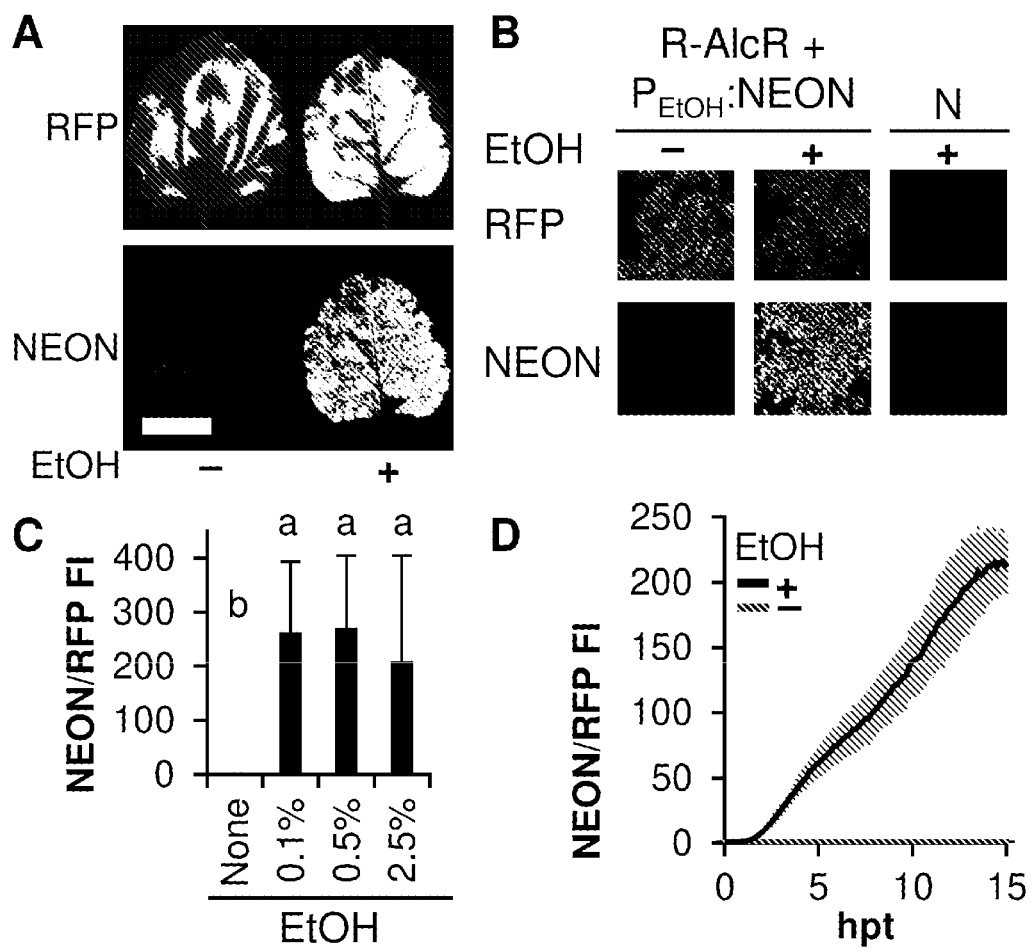

FIG. 16. Gene expression control and delivery of synthetic circuit components to plants by the pLX vectors Evaluation of a buffer gate in plants. (A) *Nicotiana benthamiana* plants were infiltrated with an *Agrobacterium* strain that harbors both pLX-Z4-$P_{mas}$:RFP-AlcR (SEQ ID NO: 24) and pLX-B2-$P_{EtOH}$:NEON (SEQ ID NO: 25) binary vectors (R-AlcR+$P_{EtOH}$:NEON). Plants were treated twice with water or EtOH. At 4 dpa, RFP and NEON fluorescence was imaged by laser scanning of leaves. Scale bar, 3 cm. (B) *Nicotiana benthamiana* leaves were untreated (N), or infiltrated with the *A. tumefaciens* R-AlcR+$P_{EtOH}$:NEON strain. Leaf disks were collected, placed in a 96-well plate and incubated in the presence or absence of EtOH. Cell RFP and NEON fluorescence was imaged by confocal microscopy at 24 h post-treatment (hpt). (C) Leaf disks from agro-infiltrated patches were placed in a 96-well plate and different amounts of inducer were added. Fluorescence intensities (FI) were measured in a plate reader at 22 hpt, and the NEON/RFP FI relative value of the non-inducer condition (None) was set to 1. Bar graph shows mean±SD (n=18). Letters indicate p<0.01, one-way Anova and Tukey's HSD test. (D) Kinetics of the EtOH-responsive buffer gate. Leaf disks from agro-infiltrated patches were treated with water (gray, minus) or 0.1% EtOH (black, plus), and fluorescence intensity was measured in a plate reader. NEON/RFP FI relative value of the water condition was set to 1. The plot shows mean±SD (n=5).

DETAILED DESCRIPTION OF THE INVENTION

In a first aspect, the present invention relates to a binary vector (pBBR1-based pLX vector) comprising at least three modules: (a) a T-DNA cassette module comprising at least sequences of a T-DNA right border and a T-DNA left border; (b) a replication origin module comprising a pBBR1 origin or a variant functionally equivalent thereof; and (c) at least a selectable marker module.

The terms "plasmid" and "vector", as used herein, are interchangeable and refer to an extra-chromosomal element that may carry one or more genes. Plasmids and vectors typically are circular double-stranded DNA molecules. However, plasmids and vectors may be linear or circular nucleic acids, of single- or double-stranded DNA or RNA, and may be derived from any source, in which a number of nucleotide sequences have been joined or recombined into a unique construct that is capable of introducing a promoter fragment and a coding polynucleotide sequence along with any appropriate 3' untranslated sequence into a cell. In the examples, plasmids and vectors may comprise autonomously replicating sequences, genome integrating sequences, and/or phage or nucleotide sequences.

The term "viral vector" refers to a vector that comprises viral genome sequences that can launch viral infections, and are useful for rapid, high-level delivery of exogenous sequences to eukaryotic cells.

The terms "Ti plasmid", "Ri plasmid", "pTi" and "pRi", as used herein, are interchangeable, and refer to a large plasmid contained in the wild-type *Agrobacterium*sp.; pTi comprises a T-DNA (transfer DNA) that is introduced into plants, a virulence region (vir region), etc. T-DNA is a DNA fragment inserted into the genome of a plant cell, and in wild-type *Agrobacterium* sp. comprises genes for the synthesis of opines and plant growth regulators. The vir region is a region that encodes virulence proteins, a protein group required for integration of the T-DNA into plants, and it comprises genes such as virA, virB, virC, virD2, virD3, virG or virJ.

The term "disarmed Ti plasmid" refers to a plasmid produced by removing the T-DNA region from a wild-type Ti plasmid and that encodes virulence proteins, or to a functionally equivalent artificial or natural plasmid, such as and without limitation, the p42a plasmid of *Rhizobium etli* (Lacroix B. & Citovsky V., PLoS Pathog. 2016, 12, 3, e1005502). Thus, a disarmed Ti plasmid lacks the T-DNA region, and is able to mediate the DNA transfer to eukaryotic cells and their subsequent genetic modification.

The term "border sequence", e.g., right border (RB) or left border (LB), refers to a directly repeated nucleic acid sequence defining an end of the T-DNA region. Border sequences may be from a Ti plasmid, or may be other bacterial, plant-derived, or synthetic sequences that function similarly. In a preferred embodiment of the pBBR1-based pLX vector of the invention, the LB and RB are independently selected from the group consisting of a T-DNA border from a nopaline-, an octopine-, a succinamopine-type Ti plasmid, or any combination thereof. In a preferred embodiment, the T-DNA borders are selected from octopine- or succinamopine-type Ti plasmids from *A. tumefaciens*, and include a second left border of the nopaline type.

The terms "binary vector" and "T-DNA binary vector", as used herein, are interchangeable. They refer to a plasmid that has an origin of replication (ori) that permits maintenance of the vector in a wide range of bacteria including *E. coli* and *Agrobacterium* sp., and that comprises a T-DNA cassette, and a marker for selection and maintenance in bacteria. In some embodiments, the binary vector may include a selectable marker for selection in eukaryotic organisms, preferably for selection in plants.

The terms "T-DNA cassette" and "T-DNA cloning cassette", as used herein, are interchangeable and refer to a T-DNA region that comprises at least the RB and LB sequences, and features that allow insertion of a sequence of interest between the RB and LB sequences in a way that the sequence of interest can be transferred to eukaryotic cells.

In a more preferred embodiment, the pBBR1-based pLX binary vector of the present invention is characterized in that the T-DNA cassette comprises one T-DNA right border and two T-DNA left border sequences. In a more preferred embodiment, the right border comprises a nucleotide sequence that is at least 80%, 85%, 90%, 95%, 96%, 97%, 98% or 99% identical to SEQ ID NO: 102 or SEQ ID NO: 115. In a more preferred embodiment, the left border comprises a nucleotide sequence that is at least 80%, 85%, 90%, 95%, 96%, 97%, 98% or 99%, identical to SEQ ID NO: 103, SEQ ID NO: 104 or SEQ ID NO: 116. In a more preferred embodiment, the right border comprises the SEQ ID NO: 102 and the left borders comprise the SEQ ID NO: 103 and SEQ ID NO: 104. In a more preferred embodiment, the right border consists of SEQ ID NO: 102 and the left borders consist of SEQ ID NO: 103 and SEQ ID NO: 104.

In a further preferred embodiment, the pBBR1-based pLX binary vector is characterized in that the T-DNA region also comprises at least two transcription terminators. Transcription terminators useful in the present invention are known in the art (i.e., in Chen Y. J., et al, Nat Methods. 2013, 10, 7, 659-664). In a more preferred embodiment, the transcription terminators comprise a nucleotide sequence that is at least 80%, 85%, 90%, 95%, 96%, 97%, 98% or 99% identical to any of the sequences selected from the list consisting of: SEQ ID NO: 108, 109, 110, 111, or any combinations thereof, more preferably, SEQ ID NO: 108 and 109. In a more preferred embodiment, the transcription terminators are selected from sequences comprising the SEQ ID NO: 108, 109, 110, 111 or any combinations thereof, more preferably, SEQ ID NO: 108 and 109. In a more preferred embodiment, the transcription terminators consist of any of the sequences selected from SEQ ID NO: 108, 109, 110, 111, or any combinations thereof, more preferably, SEQ ID NO: 108 and 109.

"Homology", "identity" or "similarity" refer to the sequence similarity between two nucleic acid or amino acid sequences. Homology can be determined by comparing a position in each sequence, which may be aligned for comparison purposes. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e., structurally related, at positions shared by the amino acid sequences. The degree of homology, identity, and/or similarity can be determined by the use of algorithms, programs and methods, such as and without limitations Clustal, Wilbur-Lipman, GAG, GAP, BLAST, BLASTN, BLASTP, EMBOSS Needle, FASTA, Smith Waterman or BLOSUM.

In a more preferred embodiment, the pBBR1-based pLX vector of the invention is characterized in that the T-DNA borders flank a sequence of interest. The nucleic acid sequence(s) of interest is operatively linked to sequences required for DNA transfer to a target eukaryotic cell.

The term "operatively linked" or "operably associated" refer to a functional linkage between a regulatory sequence and a coding sequence, or a functional linkage between two regulatory sequences. The term "construct" refers to units or components so described that are assembled and operatively linked thus in a relationship that permits them to function in their intended manner. By placing a coding sequence under regulatory control of a promoter or another regulatory sequence means positioning the coding sequence such that the expression of the coding sequence is controlled by the regulatory sequence. The term "transcription unit" refers to a construct including promoter, coding and terminator sequences that are operatively linked to permit the expression or delivery of the sequence of interest in the intended manner.

The sequence of interest, although often a gene sequence, can actually be any nucleic acid sequence whether or not it produces a protein, an RNA, an antisense molecule or regulatory sequence or the like.

A "transgene" refers to a sequence of interest independently of whether this sequence has been introduced exogenously or has been manipulated; in both cases, the sequence defined as "transgene" has not been shown to occur naturally. The terms "endogenous gene", "endogenous sequence", "wild-type gene" or "wild-type sequence" refer to a native gene in its natural location in the genome of an organism.

Sequences of interest or transgenes may include functional elements that affect developmental processes, fertility, abiotic and biotic stress resistance, or that confer new phenotypes, and the like. Other transgenes include sequences useful to produce edible vaccines for humans or animals (e.g., U.S. Pat. Nos. 6,136,320; 6,395,964), to alter fatty acid content or change amino acid composition of crops (e.g., U.S. Pat. No. 6,664,445), to introduce enzymes in pathways to synthesize metabolites such as vitamin A and vitamin E, to increase iron concentration, to control fruit ripening, to reduce allergenic properties of e.g., wheat and nuts, to absorb and store toxic and hazardous substances and to assist contaminated soil cleanup, to alter fiber content of woods, to enhance resistance to diseases, bacteria, fungi, nematodes, herbicides, viruses and insects, or to increase salt tolerance and drought resistance, amongst others.

In a typical vector, the sequence of interest is operatively linked to a promoter. A "promoter" is a sequence of nucleotides from which transcription of a downstream, operatively linked DNA may be initiated. The product of a sequence of interest may be expressed constitutively, after induction, in specific tissues or at certain development stages. Regulatory elements to effect such expression are well known in the art. Many examples of regulatory elements may be found in the Patent Lens document "Promoters used to regulate gene expression" version 1.0, October 2003 (incorporated in its entirety). Other promoters can be identified through a variety of assays. Enhancer elements or other regulatory elements can be included in addition to a promoter. "Minimal promoter" sequences usually require an enhancer element for activity, such as the so-called 35S minimal promoter from cauliflower mosaic virus (CaMV), or the 34S minimal promoter from figwort mosaic virus.

In a more preferred embodiment, the pBBR1-based vector of the invention is characterized in that the T-DNA cassette module also comprises a cloning cassette. More preferably, the T-DNA cloning cassette comprises restriction endonuclease and primer annealing sites; and in a more preferred embodiment, these sites are compatible with high-throughput, Type IIS restriction endonuclease- and/or overlap-based DNA assembly methods, such as and without limitations, Golden Gate, Golden Braid, Modular Cloning (MoClo), one- or two-step Gibson assembly (Gibson D. G., et al, Nat. Methods 2009, 6, 343-345), Sequence and Ligation Independent Cloning (SLIC), GeneArt seamless cloning and assembly (Thermo Fisher Scientific), NEBuilder HiFi DNA assembly (New England BioLabs), Cold Fusion cloning (System Biosciences), or In-fusion cloning (Clontech).

In another preferred embodiment, a T-DNA cloning cassette also comprises a selectable, screenable marker or reporter elements for identifying insertion of the sequence of interest. The marker or reporter element is a gene or an operon that confers a visual phenotype or negative selection, such as, and without limitations, the lacZα, ccdB, sacB, a luciferase or a fluorescent protein gene, or a canthaxanthin biosynthesis operon. Additionally, the screenable marker or reporter element included in the T-DNA cassette can be selected from the list mentioned below for the selectable marker module of the binary vector of the present invention.

In a further preferred embodiment, the replication origin module of the pBBR1-based pLX vector of the invention comprises a pBBR1 origin comprising the pBBR1-oriV and -rep regions, or a variant functionally equivalent thereof. In a further preferred embodiment, the pBBR1 origin comprises a nucleotide sequence that is at least 80%, 85%, 90%, 95%, 96%, 97%, 98% or 99% identical to SEQ ID NO: 105, more preferably the pBBR1 origin comprises the SEQ ID NO: 105, and more preferably the pBBR1 origin consists of SEQ ID NO: 105.

As used herein, the term "functionally equivalent variant" refers to any variant in which the nucleotide sequence encodes an amino acid sequence comprising conservative or non-conservative alterations in the amino acid sequence resulting in silent changes that preserve the functionality of the molecule including, for example, deletions, additions, and substitutions. Such altered molecules may be desirable where they provide certain advantages in their use. As used herein, conservative substitution involves the substitution of one or more amino acids within the sequence of the corresponding peptide with another amino acid having similar polarity and hydrophobicity/hydrophilicity characteristics resulting in a functionally equivalent molecule. Such conservative substitutions include but are not limited to substitutions within the following groups of amino acids: glycine, alanine; valine, isoleucine, leucine; aspartic acid, glutamic acid; asparagine, glutamine; serine, threonine; lysine, arginine; phenylalanine, tyrosine; and methionine, norleucine. The skilled person in the art will understand that mutations in the nucleotide sequence encoding a peptide, which give rise to conservative amino acid substitutions in positions that are non-critical for the functionality of the peptide, are evolutionarily neutral mutations that do not affect its global structure or its functionality.

The term "replication origin" (ori) refers to a cis-acting sequence essential for replication. Origin sequences that permit the plasmid replication or maintenance in a wide range of bacteria have been described (U.S. Pat. Nos. 4,940,838; 5,149,645; 6,165,780; 6,265,638, incorporated in its entirety). In a preferred embodiment, the origin of replication is a wide-host-range origin or a broad-host-range origin, terms that are interchangeable in the present invention. As used herein, "wide-host-range" or "broad-host-range" means that the vector replicates in at least two bacterial species, preferably in *Agrobacterium* sp. and *E. coli*. The host range is conferred by an origin of replication. When a nucleic acid molecule is integrated into the bacterial chromosome or other self-replicating bacterial DNA molecules, an origin is not necessary. Thus, when suitably modified and engineered, these bacteria may be used for transferring nucleic acid sequences into eukaryotic cells, and especially into plant cells.

In another preferred embodiment, the pBBR1-based pLX vector also comprises a selectable or a screenable marker module for identifying host cell transformants, preferably bacterial transformants. Well-known selectable markers are genes that confer resistance to drugs (such as antibiotics selected from the list consisting of: neomycin, ampicillin, carbenicillin, chloramphenicol, kanamycin, tetracycline, gentamicin, spectinomycin, bleomycin, phleomycin, streptomycin, erythromycin, blasticidin, and hygromycin), herbicide resistance genes, and the like. Other selection systems can alternatively be used, including genes encoding resistance to other toxic compounds, such as potassium tellurite resistance genes, genes encoding products required for growth of the cells in positive selection systems. Examples of these "positive selection" systems are abundant (e.g., U.S. Pat. No. 5,994,629). "Negative selection" systems can also be used. Alternatively, a screenable marker or reporter gene may be employed to allow selection of transformed cells based on a visual phenotype, e.g. a β-glucuronidase, a luciferase or a fluorescent protein gene. The selectable marker is also typically operably linked to regulatory elements necessary for gene transcription, e.g., a constitutive or inducible promoter and a terminator sequence. Elements that enhance efficiency of transcription are optionally included. In a preferred embodiment, the selectable marker module comprises a gene that confers resistance to a drug, and is selected from the group consisting of neomycin, ampicillin, carbenicillin, chloramphenicol, kanamycin, tetracycline, gentamicin, spectinomycin, bleomycin, phleomycin, streptomycin, erythromycin, blasticidin and hygromycin resistance genes.

In a more preferred embodiment, the pBBR1-based pLX vector is selected from the list consisting of: SEQ ID NO: 3 (pLX-B2), SEQ ID NO: 4 (pLX-B3), SEQ ID NO: 5 (pLX-B4), SEQ ID NO: 10 (pLX-B2α2), SEQ ID NO: 11 (pLX-B3Ω1), SEQ ID NO: 12 (pLX-B302), SEQ ID NO: 13, SEQ ID NO: 14, SEQ ID NO: 15, SEQ ID NO: 19, SEQ ID NO: 20, SEQ ID NO: 21, SEQ ID NO: 22, SEQ ID NO: 23, SEQ ID NO: 25, and SEQ ID NO: 28.

Furthermore, a pBBR1-based pLX vector of the present invention can be used as a single binary vector, which has autonomous replication, or in a binary vector system, which includes a combination of binary vectors that have replication and bacterial selection mechanisms allowing a mutual and autonomous coexistence with each other.

As used herein, the phrase "binary vector system" refers to binary vectors that are capable of replicating in both *E. coli* and *A. tumefaciens*, and host unlinked T-DNA cassettes. In a binary vector system, vectors are multiplexed and employed for delivery of multiple T-DNA cassettes to eukaryotic cells or organisms, preferably to plants.

In a more preferred embodiment, the binary vectors and vectors of the binary vector system of the present invention have a minimal size between 2 to 20 kb, preferably between 2.5 to 3.8 kb, more preferably have a size below 3.8 kb.

Another aspect of the present invention refers to a binary vector system comprising the pBBR1-based pLX plasmid according to the present disclosure and another binary vector (second binary vector) known in the art and compatible with a first binary vector of the present invention. In a more preferred embodiment of the binary vector system of the present invention, the second binary vector is an RK2-based pLX plasmid as described herein.

Another aspect of the present invention, the RK2-based pLX plasmid, according to the present disclosure refers to a binary vector comprising at least three modules: (a) a T-DNA cassette module comprising at least a T-DNA right border and a T-DNA left border; (b) a replication origin module comprising an origin compatible with the pBBR1 origin, preferably selected from the list consisting of origins of the IncQ, IncW, IncU, pRi, pVS1 and IncP-α plasmid incompatibility groups, wherein more preferably is an origin of the IncP-α plasmid incompatibility group, and wherein more preferably, the replication origin is the RK2 origin, or a variant functionally equivalent thereof; and (c) at least a selectable marker module.

In a preferred embodiment, the RK2-based pLX vector of the invention comprises a T-DNA cassette comprising one T-DNA right border and two T-DNA left borders; preferably comprising the T-DNA border sequences mentioned above. In a more preferred embodiment, the right border comprises the SEQ ID NO: 115 and the left borders comprise the SEQ ID NO: 116 and SEQ ID NO: 104. In a more preferred embodiment, the right border consists of SEQ ID NO: 115, and the left borders consist of the SEQ ID NO: 104 and SEQ ID NO: 116.

In a further preferred embodiment, the RK2-based pLX vector is characterized in that the T-DNA cassette is flanked by at least two transcription terminators, preferably the transcription terminators that are disclosed above. In a more preferred embodiment, the transcription terminators comprise the SEQ ID NO: 110 and 111, more preferably the transcription terminators consist of SEQ ID NO: 110 and 111.

In a more preferred embodiment, the RK2-based pLX vector of the invention is characterized in that the T-DNA borders flank a sequence of interest. The nucleic acid sequence(s) of interest is operatively linked to sequences required for the DNA transfer to a target eukaryotic cell. In a more preferred embodiment, the sequences of interest are mentioned above.

In a more preferred embodiment, the RK2-based vector of the invention is characterized in that the T-DNA cassette module also comprises a cloning cassette; more preferably, the T-DNA cloning cassette comprises the selectable, screenable marker or reporter elements mentioned above. In a further preferred embodiment, the T-DNA cassette comprises restriction endonuclease and primer annealing sites; in a more preferred embodiment, these sites are compatible with high-throughput, Type IIS restriction endonuclease- and overlap-based assembly methods as mentioned above.

In a further preferred embodiment, the replication origin of the RK2-based pLX vector of the invention comprises an RK2 replication origin comprising the RK2-oriV and -trfA regions, or a variant functionally equivalent thereof. In a more preferred embodiment the RK2 origin comprises a nucleotide sequence that is at least 80%, 85%, 90%, 95%, 96%, 97%, 98% or 99% identical to SEQ ID NO: 106 or SEQ ID NO: 107, more preferably the RK2 origin comprises the SEQ ID NO: 106 or SEQ ID NO: 107, and more preferably the RK2 origin consists of SEQ ID NO: 106 or SEQ ID NO: 107.

In another preferred embodiment, the selectable marker module of the RK2-based pLX binary vector comprises a selectable or a screenable marker gene mentioned above.

In a more preferred embodiment, the selectable marker gene of the RK2-based pLX binary vector differs from the selectable marker gene of the pBBR1-based pLX vector, so as to facilitate simultaneous selection of both plasmids.

In a more preferred embodiment, the RK2-based pLX vector is selected from the list consisting of: SEQ ID NO: 6 (pLX-R2), SEQ ID NO: 7 (pLX-R3), SEQ ID NO: 8 (pLX-R4), SEQ ID NO: 9 (pLX-Z4), SEQ ID NO: 16, SEQ ID NO: 17, SEQ ID NO: 18 and SEQ ID NO: 24.

In another preferred embodiment, the backbone of the RK2-based pLX vector has no regions with >28 nucleotide identity to the pBBR1-based pLX vector of the present invention.

Consequently, the binary vector system of the present invention comprises the pBBR1-based pLX plasmid and, preferably, the RK2-based pLX plasmid according to the present disclosure.

Another aspect of the present invention relates to methods to assemble synthetic, genomic, metagenomic, and/or cDNA sequences of interest into the binary vector or the binary vector system disclosed in the present invention.

Another aspect of the present invention is related to a host cell comprising the pBBR1-based pLX vector, the RK2-based pLX vector, or the binary vector system of the present invention.

In accordance with the present invention, the term "host cell" refers to a cell which has been transformed, or is capable of being transformed, by an exogenous DNA sequence, preferably by the binary vector or the binary vector system of the present invention. A host cell can be used, for example, for expression of a nucleic acid of interest, propagation of plasmid vectors and/or delivery of a sequence of interest to eukaryotic cells.

In a preferred embodiment, the host cell of the present invention is a bacterial cell, preferably selected from *Agrobacterium* sp. and *E. coli* cells. In a more preferred embodiment, the host cell is preferably of a species of the Rhizobiaceae family, more preferably is an *Agrobacterium* sp. bacterium, especially preferably an *Agrobacterium* strain that comprises a disarmed Ti plasmid.

Alternatively, genome sequences of *Agrobacterium* sp. and other bacterial species can be compared. Genes that are missing in the latter bacteria and are important for delivery and transformation of T-DNA into eukaryotic cells may be individually picked from the *Agrobacterium* genome and inserted into the desired bacterial genome by any means, or expressed on a plasmid. Similarly, bacteria can be used to transform a eukaryotic organism or cell under a variety of test conditions, such as temperature, pH, nutrient additives and the like. The best conditions can be quickly determined and then tested to transform plant cells or other eukaryotic cells as mentioned above. Furthermore, host bacterial species may naturally interact in specific ways with a number of eukaryotic organisms, such as plants. These bacterial-plant interactions are very different from the way *Agrobacterium* naturally interacts with plants. Thus, tissues and cells that can be transformed by *Agrobacterium* sp. or by the use of other bacteria may be different.

In general, plasmids are transferred through a direct transfer method to the bacteria (host cell) of this invention. By transferring either single or multiple binary vectors as described herein, transformation competent bacteria are generated. These bacteria can be used to transform a eukaryotic cell or organism, such as a yeast, a fungus, a plant, an insect or an animal.

The term "eukaryotic cell" refers to either individual cells or cell aggregates (such as tissues or organs, parts of tissues or organs) and to entire organisms, comprising a yeast, a fungus, an alga, a plant, an insect or an animal.

In a more preferred embodiment, the term "plant cell" refers to individual cells or cell aggregates, organized plant tissues, organs, or entire plants, such as and without limitation, protoplasts, calli, cell cultures, meristems and meristematic tissues, leaves, shoots, roots, flowers, ovules, pollen and pollen tubes, seeds, embryos, hypocotyls, cotyledons, seedlings and mature plants.

Eukaryotic cells may be transformed within the context of this invention. Generally, eukaryotic cells to be transformed are cultured before transformation, or cells may be transformed in situ. In some embodiments, cells are cultured in the presence of additives to render them more susceptible to transformation. Transformants can be easily detected by their phenotypic changes, e.g., growth on a medium including drugs/herbicides/toxic compounds or lacking an essential growth component on which the untransformed cells cannot grow. In other embodiments, cells are transformed without prior culturing.

Briefly, in an exemplary transformation protocol to generate transformed plants, plant cells are transformed by their co-cultivation with a culture of bacteria containing the binary vector or the binary vector system described herein. After co-cultivation for a few days, bacteria are removed, for example by washing and treatment with antibiotics, and plant cells are transferred to post-cultivation medium plates generally containing an antibiotic to inhibit or kill bacterial growth and optionally a selective agent, such as that described in U.S. Pat. No. 5,994,629. Plant cells are further incubated for several days. The expression of the transgene may be tested at this time. After further incubation for several weeks in selective medium, plant cells are transferred to regeneration medium and placed in the light. Shoots obtained are transferred to rooting medium and resulting plants are further propagated.

Alternative methods to transform plant cells include dipping whole flowers into a suspension of bacteria, growing the plants further into seed formation, harvesting the seeds and germinating them in the presence of a selection agent that allows the growth of the transformed seedlings only. Alternatively, germinated seeds may be treated with a selection agent that only the transformed plants tolerate. Alternatively, seeds may be visually selected by detection of fluorescent proteins that only the transformed seeds accumulate.

Cell transformation by *Agrobacterium* is independent of stable transgene integration into host genomes, and the use of transient expression systems or autonomously replicating RNA/DNA units (viral vectors) can bypass the need for gene integration, if desired. In this sense, the terms "infiltration" and "agro-infiltration" refer to a transient transformation method that relies on mechanical introduction of cultures of host cells comprising at least one binary vector, into eukaryotic organisms or their organs, preferably entire plants, seedlings or leaves. Scale-up is achieved, for example, through the use of vacuum infiltration. The term "agro-inoculation" refers to the delivery of viral vectors by *Agrobacterium*-mediated transient transformation.

Plants that are especially desirable to transform include corn, rice, wheat, soybean, alfalfa and other leguminous plants, potato, tomato, tobacco, *Nicotiana benthamiana*, and so on.

Another aspect of the present invention refers to a cell culture comprising the host cells of the present invention.

Another aspect of the present invention relates to a method for delivering at least one nucleotide sequence of interest into at least one plant cell, comprising: (a) inserting the nucleotide sequence of interest into the T-DNA cassette of the pBBR1-based pLX vector, the RK2-based pLX vector, or the binary vector system of the present invention; (b) introducing the pBBR1-based pLX vector, the RK2-based pLX vector, or the binary vector system obtained in step (a) into at least one bacterial host cell according to the present invention; and (c) contacting the host cell of step (b) with a plant cell.

In a preferred embodiment, the method for delivering at least one nucleotide sequence of interest into at least one plant cell is characterized in that the bacterial host cell is an *Agrobacterium* sp. cell, more preferably, the *Agrobacterium* cell comprises a disarmed Ti plasmid.

In addition to the numerous technologies for transforming plants or plant cells, the type of cell, tissue, organ that is contacted with foreign constructs may vary as well. Almost all plant tissues may be transformed during dedifferentiation using appropriate techniques within the skill of the art. One skilled in the field of plant transformation will understand that multiple methodologies are available for the production of transformed plants, and that they may be modified and specialized to accommodate biological differences between various plant species. Regardless of the transformation technique employed, the nucleotide sequence of interest can be incorporated into the binary vector or the binary vector system of the present invention, and adapted to express the nucleotide sequence of interest in a plant cell by including in the vector a plant promoter. In addition to plant promoters, promoters from a variety of sources can be used to efficiently express foreign genes in plant cells. For example, promoters of bacterial origin, such as the octopine synthase promoter, nopaline synthase promoter, and mannopine synthase promoter; promoters of viral origin, such as the 35S and 19S promoters of CaMV, a promoter from sugarcane baciliform virus, and the like may be used. Plant-derived promoters include, but are not limited to, the ribulose-1,5-bisphosphate carboxylase (RuBisCO) small subunit promoter, beta-conglycinin promoter, cruciferin promoter, phaseolin promoter, alcohol dehydrogenase promoter, heat-shock promoters, actin depolymerization factor promoter, and tissue-specific promoters. Promoters may also contain certain enhancer sequence elements that may improve the transcription efficiency. Typical enhancers include, but are not limited to, the alcohol dehydrogenase 1 (ADH1)-intron 1 and ADH1-intron 6. Constitutive promoters may be used. Constitutive promoters direct continuous gene expression in nearly all cell types and at nearly all times (e.g., the actin promoter, ubiquitin promoter, CaMV 35S promoter). Tissue-specific promoters are responsible for gene expression in specific cell, tissue, or organ types. Examples of other promoters that may be used include those that are active during a certain stage of the plant's development, or in specific plant tissues and organs. Examples of such promoters include, but are not limited to, promoters that are root-, pollen-, embryo-, corn silk-, cotton fiber-, seed endosperm-, and phloem-specific promoters. In a further embodiment, the promoter is an inducible promoter. An inducible promoter is "switched on" or increases expression of genes in response to a specific signal, such as physical stimuli (e.g., temperature, heat-shock gene promoters; light, the RuBisCO promoter); hormones (e.g., glucocorticoid); antibiotics (e.g., tetracycline); metabolites or chemical compounds (e.g., ethanol); and stresses (e.g., drought). Other desirable transcription and translation elements that function in plants also may be used, such as, for example, 5' untranslated leader sequences, RNA transcription termination sequences and poly-adenylate addition signal sequences. Any additional element known in the art and functional in plants may be used.

The biological transformation method described herein can be used to introduce one or more sequences of interest (transgene) into eukaryotic cells, wherein the eukaryotic cell is selected from the group consisting of a yeast cell, a fungal cell, a plant cell, an insect cell and an animal cell; preferably, the eukaryotic cell is a plant cell.

Agrobacterium is an extremely advantageous agent for eukaryotic transformation; alternatively, the binary vector or the vector system disclosed in the present invention can be introduced into eukaryotic cells using any physical methods, such as particle or microprojectile bombardment, electroporation, or other forms of direct DNA uptake such as liposome mediated DNA uptake, or the vortexing method. In a preferred embodiment, physical methods for the transformation of plant cells are reviewed in Oard J. H., Biotech. Adv. 1991, 9, 1-11.

The present invention furthermore relates to a transformed plant system, to a regenerated cell or a regenerated plant therefrom, to their progeny or seeds therefrom generated in accordance with the methods described hereinabove.

In a particular embodiment of the present invention, this transformed plant system is characterized by single or multiple modifications of the plant cell genome, epigenome, transcriptome or metabolome, and in that it may or may not comprise any sequence segments of the abovementioned vector, vector system or of their T-DNA cassettes. In this sense, a component of the Clustered regularly interspaced short palindromic repeats (CRISPR)/CRISPR-associated protein (Cas) systems from bacteria and archaea can be used to target specific sequences in eukaryotic and in plant genomes (Murovec J., et al., Plant Biotechnol. J. 2017, doi:10.1111/pbi.12736). This document features a method for modifying the genomic material in a eukaryotic cell, preferably in a plant cell, based on the use of the binary vectors of the invention together with components of the CRISPR/Cas systems; the method provides a relatively simple, effective tool for generating modifications in genomic DNA at selected sites, with no need for transgene integration or maintenance in eukaryotic cell genomes. The CRISPR/Cas systems and their derivatives can be used for, without limitation, targeted mutagenesis, gene targeting, gene replacement, targeted deletion, targeted inversion, targeted translocation, and/or targeted insertion at single or multiple genome site(s). CRISPR/Cas system applications also include epigenetic and transcription regulation, cellular imaging and pathogen targeting. This technology can be used to accelerate the rate of functional genetic studies in eukaryotes, preferably in plants, and to engineer plants with improved characteristics, including enhanced nutritional quality, increased resistance to disease and stress, and heightened production of commercially valuable compounds.

In another aspect, the present invention relates to a method for in vitro delivering at least one nucleotide sequence of interest into at least one eukaryotic cell or organism, comprising: (a) inserting at least one nucleotide sequence of interest into the binary vector or into the binary vector system of the invention; and (b) introducing the binary vector or the binary vector system, of step (a) into at least one eukaryotic cell or organism.

In a preferred embodiment of the method for in vitro delivering at least one nucleotide sequence of interest into at least one eukaryotic cell or organism, the eukaryotic organism is selected from the group consisting of yeasts, fungi, insects and animals.

Another aspect of the present invention relates to a method for transforming eukaryotic cells comprising the step of introducing into the eukaryotic cell the pBBR1-based pLX vector, the RK2-based pLX vector, the binary vector system or the host cell disclosed in the present invention.

Another aspect the present invention relates to a method for obtaining a genetically-engineered plant cell or plant comprising the step of introducing into a plant cell the binary vector, preferably the pBBR1-based pLX vector or the RK2-based pLX vector, the binary vector system, or the bacterial host cell of the invention.

In another aspect, the present invention relates to a genetically-engineered plant cell or plant obtainable by the methods disclosed above.

Another aspect the present invention relates to a method for obtaining in vitro a genetically-engineered eukaryotic cell or organism, comprising the step of introducing into a eukaryotic cell or organism the binary vector, preferably the pBBR1-based or the RK2-based binary vectors, or the binary vector system described herein. In a preferred embodiment, the eukaryotic cell or organism is selected from the group consisting of a yeast, a fungal, an insect and an animal.

In another aspect, the present invention relates to a genetically-engineered eukaryotic cell or organism obtainable by the methods disclosed above.

Another aspect of the present invention relates to the use in vitro or ex vivo of the binary vector, preferably the pBBR1-based pLX binary vector, the RK2-based pLX binary vector, the binary vector system, the bacterial host cell, the culture cells, the genetically-engineered plant cell or plant obtainable by the methods disclosed above, or the genetically-engineered eukaryotic cell or organism obtainable by the methods disclosed above: (a) for site-specific gene knockout; (b) for site-specific genome editing; (c) for DNA sequence-specific interference; (d) for site-specific epigenome editing; (e) for site-specific transcription modulation; or (f) for multiplex genomic engineering; and provided that the use does not comprise a process for modifying the germ line genetic identity of human beings.

In another aspect, the disclosure provides a kit comprising one or more of the components described herein. In some embodiments, the kit comprises the binary vector, the binary vector system, the host cell or the culture cell disclosed herein, and instructions for using the kit. The components or elements may be provided individually or in combinations, and may be provided in any suitable container, such as a vial, a bottle, or a tube. By "kit" as used herein, it refers to a product containing the different reagents necessary to carry out the methods of the invention packaged, allowing transport and storage. Suitable materials for packaging kit components include glass, plastic (polyethylene, polypropylene, polycarbonate, and the like), bottles, vials, paper, envelopes, and the like. Additionally, kits invention may contain instructions for simultaneous, sequential or separate use of the different components found in the kit. Such instructions may be in the form of printed material or in the form of an electronic device capable of storing instructions so that they can be read by a subject, such as electronic storage media (magnetic disks, tapes and the like), optical media (CD-ROM, DVD) and the like. Additionally or alternatively, the media can contain Internet addresses that provide such instructions.

Unless otherwise defined, all technical and scientific terms used herein have the same meaning as commonly understood by one of ordinary skill in the art to which this invention belongs. Methods and materials similar or equivalent to those described herein can be used in the practice of the present invention. Throughout the description and claims the word "comprise", "include" and their variations are not intended to exclude other technical features, additives, components, or steps. Additional objects, advantages and features of the invention will become apparent to those skilled in the art upon examination of the description or may be learned by practice of the invention. The following examples, drawings and sequence listing are provided by way of illustration and are not intended to be limiting of the present invention.

EXAMPLES

The following examples are offered to illustrate, but not to limit, the claimed invention. It is understood that the examples and embodiments described herein are for illustrative purposes only, and persons skilled in the art will recognize various reagents or parameters that can be altered without departing from the spirit of the invention or the scope of the appended claims.

Materials and Methods

DNA Constructs

Unless otherwise indicated, standard molecular cloning methods were used (Sambrook J. & Russel D. W., Molecular cloning: a laboratory manual—3rd edition. Cold Spring Harbor Laboratory Press. 2001). DNA constructs were generated using chemically synthesized and available parts (Table 1). The Ugandan cassava brown streak virus isolate Ke_125 was obtained from DSMZ (PV-0912). Nucleic acids were purified using silica column-based purification kits. Alternatively, genomic DNA from plant samples was extracted following the procedure described by Edwards and collaborators (Edwards K., et al, Nucleic Acids Res. 1991, 19, 1349). PCR reactions were performed with Phusion High-Fidelity DNA polymerase (Fermentas or New England BioLabs), and DpnI-treated to remove plasmid templates, if required. The T-DNA synthetic cassettes T-DNA_1 (SEQ ID NO: 1), for the pLX-B-series and pLX-R series, and T-DNA_2 (SEQ ID NO: 2), for pLX-Z4, were obtained from GeneArt. Overlapping DNA fragments were gel purified and joined using homemade one-step isothermal (Gibson D. G., et al, Nat. Methods. 2009, 6, 343-345) or NEBuilder HiFi (New England BioLabs) DNA assembly master mixes. One-step digestion-ligation reactions were done using Type IIS restriction endonucleases (BsaI or BsmBI, New England BioLabs) and T4 DNA ligase (Promega), as described (Sarrion-Perdigones A., et al, Plant Physiol. 2013, 162, 1618-1631).

Complete details of the plasmids disclosed in the present invention are reported in Table 1.

TABLE 1

| Plasmid name | Origin(s) | Reference |
| --- | --- | --- |
| pSEVA431 | pBBR1 | http://seva.cnb.csic.es/ |
| pSEVA631 | pBBR1 | http://seva.cnb.csic.es/ |
| pSEVA221 | RK2 | http://seva.cnb.csic.es/ |
| pSN.5-TagRFP-T | pVS1 + ColE1 | Pasin F., etal., Plant Methods. 2014, 10, 22 |
| pSN.5-mTFP1 | pVS1 + ColE1 | Pasin F., etal., Plant Methods. 2014, 10, 22 |
| pSN.5-mNeon | pVS1 + ColE1 | Pasin F., etal., Plant Methods. 2014, 10, 22 |
| pGGF003 | pUC | Lannpropoulos A., et al, PLoS One. 2013, 8, e83043 |
| pGGC011 | pUC | Lannpropoulos A., et al, PLoS One. 2013, 8, e83043 |
| p35Tunos-vec01-NAT1 | pUC | Tourifio A., et al, Span. J. Agric. Res. 2008, 6, 48-58 |
| pSN-PPV | RK2 | Pasin F., etal., PLoS Pathog. 2014, 10, e1003985 |
| pSN-PPV-TagRFP-T2A | RK2 | Pasin F., etal., PLoS Pathog. 2014, 10, e1003985 |
| pSN2-ccdB | pVS1 + ColE1 | Pasin F., etal., PLoS Pathog. 2014, 10, e1003985 |
| GB0639 | pVS1 + ColE1 | Vazquez-Vilar M., etal., Plant Methods. 2016, 12, 1-12 |
| GB1108 | pVS1 + ColE1 | Vazquez-Vilar M., etal., Plant Methods. 2016, 12, 1-12 |
| GB1181 | pVS1 + ColE1 | Vazquez-Vilar M., etal., Plant Methods. 2016, 12, 1-12 |
| GB0460 | pSa + pUC | Sarrion-Perdigones A., et al, Plant Physiol. 2013, 162, 1618-1631. |
| pDGB3_alpha1 | pVS1 + ColE1 | Vazquez-Vilar M., et al, Nucleic Acids Res. 2017, 45, 2196-2209 |
| pLX-B2 (SEQ ID NO: 3) | pBBR1 | Present disclosure |
| pLX-B3 (SEQ ID NO: 4) | pBBR1 | Present disclosure |
| pLX-B4 (SEQ ID NO: 5) | pBBR1 | Present disclosure |
| pLX-R2 (SEQ ID NO: 6) | RK2 | Present disclosure |

TABLE 1-continued

| Plasmid name | Origin(s) | Reference |
| --- | --- | --- |
| pLX-R3 (SEQ ID NO: 7) | RK2 | Present disclosure |
| pLX-R4 (SEQ ID NO: 8) | RK2 | Present disclosure |
| pLX-Z4 (SEQ ID NO: 9) | RK2 | Present disclosure |
| pLX-B2α2 (SEQ ID NO: 10) | pBBR1 | Present disclosure |
| pLX-B3Ω1 (SEQ ID NO: 11) | pBBR1 | Present disclosure |
| pLX-B3Ω2 (SEQ ID NO: 12) | pBBR1 | Present disclosure |
| pLX-B2-TagRFP-T (SEQ ID NO: 13) | pBBR1 | Present disclosure |
| pLX-B3-TagRFP-T (SEQ ID NO: 14) | pBBR1 | Present disclosure |
| pLX-B4-TagRFP-T (SEQ ID NO: 15) | pBBR1 | Present disclosure |
| pLX-R2-TagRFP-T (SEQ ID NO: 16) | RK2 | Present disclosure |
| pLX-R3-TagRFP-T (SEQ ID NO: 17) | RK2 | Present disclosure |
| pLX-R4-TagRFP-T (SEQ ID NO: 18) | RK2 | Present disclosure |
| pLX-B2-XT1-XT2-hCas9 (SEQ ID NO: 19) | pBBR1 | Present disclosure |
| pLX-B2-NptII-DsRED (SEQ ID NO: 20) | pBBR1 | Present disclosure |
| pLX-PPV (SEQ ID NO: 21) | pBBR1 | Present disclosure |
| pLX-UCBSV (SEQ ID NO: 22) | pBBR1 | Present disclosure |
| pLX-B2-$P_{CRC}$:mTFP1 (SEQ ID NO: 23) | pBBR1 | Present disclosure |
| pLX-Z4-$P_{mas}$:RFP-AlcR (SEQ ID NO: 24) | RK2 | Present disclosure |
| pLX-B2-$P_{EtOH}$NEON (SEQ ID NO: 25) | pBBR1 | Present disclosure |
| pSN.5-$P_{PAP85}$:RFP (SEQ ID NO: 26) | pVS1 + ColE1 | Present disclosure |
| GB1686 (SEQ ID NO: 27) | pVS1 + ColE1 | Present disclosure |
| pLX-TuMV (SEQ ID NO: 28) | pBBR1 | Present disclosure |

The details of the plasmid of the present invention are the following:

pLX-B2 (SEQ ID NO: 3) is a T-DNA binary vector according to the present invention (pBBR1-based pLX vector) and comprises the replication origin from the pBBR1 plasmid (SEQ ID NO: 105). The following parts were joined by Gibson assembly: (i) pBBR1 origin (SEQ ID NO: 105), amplified from pSEVA631 using the X198_F/X199_R primers (SEQ ID NO: 42/SEQ ID NO: 43); (ii) nptI gene, from pSEVA221 using X192_F/X193_R (SEQ ID NO: 36/SEQ ID NO: 37); (iii) T-DNA_1 synthetic cassette (SEQ ID NO: 1).

pLX-B3 (SEQ ID NO: 4) is a T-DNA binary vector according to the present invention (pBBR1-based pLX vector) and comprises the replication origin from the pBBR1 plasmid (SEQ ID NO: 105). The following parts were joined by Gibson assembly: (i) pBBR1 origin (SEQ ID NO: 105) amplified from pSEVA631 using the X198_F/X199_R primers (SEQ ID NO: 42/SEQ ID NO: 43); (ii) aadA gene, from pSEVA431 using X194_F/X195_R (SEQ ID NO: 38/SEQ ID NO: 39); (iii) T-DNA_1 synthetic cassette (SEQ ID NO: 1).

pLX-B4 (SEQ ID NO: 5) is a T-DNA binary vector according to the present invention (pBBR1-based pLX vector) and comprises the replication origin from the pBBR1 plasmid (SEQ ID NO: 105). The following parts were joined by Gibson assembly: (i) pBBR1 origin (SEQ ID NO: 105), amplified from pSEVA631 using the X198_F/X199_R primers (SEQ ID NO: 42/SEQ ID NO: 43); (ii) aacC1 gene, from pSEVA631 using X196_F/X197_R (SEQ ID NO: 40/SEQ ID NO: 41); (iii) T-DNA_1 synthetic cassette (SEQ ID NO: 1).

pLX-R2 (SEQ ID NO: 6) is a T-DNA binary vector according to the present invention (RK2-based pLX vector) and comprises the replication origin from the RK2 plasmid (SEQ ID NO: 106). The following parts were joined by Gibson assembly: (i) RK2 origin (SEQ ID NO: 106), amplified from pSEVA221 using the X200_F/X201_R primers (SEQ ID NO: 44/SEQ ID NO: 45); (ii) nptI gene, from pSEVA221 using X192_F/X193_R (SEQ ID NO: 36/SEQ ID NO: 37); (iii) T-DNA_1 synthetic cassette (SEQ ID NO: 1).

pLX-R3 (SEQ ID NO: 7) is a T-DNA binary vector according to the present invention (RK2-based pLX vector) and comprises the replication origin from the RK2 plasmid (SEQ ID NO: 106). The following parts were joined by Gibson assembly: (i) RK2 origin (SEQ ID NO: 106), amplified from pSEVA221 using the X200_F/X201_R primers (SEQ ID NO: 44/SEQ ID NO: 45); (ii) aadA gene, from pSEVA431 using X194_F/X195_R (SEQ ID NO: 38/SEQ ID NO: 39); (iii) T-DNA_1 synthetic cassette (SEQ ID NO: 1).

pLX-R4 (SEQ ID NO: 8) is a T-DNA binary vector according to the present invention (RK2-based pLX vector) and comprises the replication origin from the RK2 plasmid (SEQ ID NO: 106). The following parts were joined by Gibson assembly: (i) RK2 origin (SEQ ID NO: 106), amplified from pSEVA221 using the X200_F/X201_R primers (SEQ ID NO: 44/SEQ ID NO: 45); (ii) aacC1 gene, from pSEVA631 using X196_F/X197_R (SEQ ID NO: 40/SEQ ID NO: 41); (iii) T-DNA_1 synthetic cassette (SEQ ID NO: 1).

pLX-Z4 (SEQ ID NO: 9) is a T-DNA binary vector according to the present invention (pLX-R4 derivative with the T-DNA_2 cassette (SEQ ID NO: 2), and no BsmBI sites in RK2-trfA and aacC1 genes) and that comprises the replication origin from the RK2 plasmid (SEQ ID NO: 107). The following parts were joined by Gibson assembly: (i) aacC1_3', amplified from pLX-R4 (SEQ ID NO: 8) using the X295_F/X296_R primers (SEQ ID NO: 73/SEQ ID NO: 74); (ii) aacC1_RK2, from pLX-R4 (SEQ ID NO: 8) using X297_F/X298_R (SEQ ID NO: 75/SEQ ID NO: 76); (iii) RK2_5', from pLX-R4 (SEQ ID NO: 8) using X299_F/X300_R (SEQ ID NO: 77/SEQ ID NO: 78); (iv) T-DNA_2 synthetic cassette (SEQ ID NO: 2).

pLX-B2α2 (SEQ ID NO: 10) is a pLX-B2 derivative with the GoldenBraid alpha2 cloning cassette (Sarrion-Perdigones A., et al, Plant Physiol. 2013, 162, 1618-1631) and comprises the replication origin from the pBBR1 plasmid (SEQ ID NO: 105). The following parts were joined by Gibson assembly: (i) backbone, amplified from pLX-B2 (SEQ ID NO: 3) using the X210_R/X321_F primers (SEQ ID NO: 46/SEQ ID NO: 89); (ii) lacZα cloning cassette, amplified using X322_F/X323_R (SEQ ID NO: 90/SEQ ID NO: 91).

pLX-B3Ω1 (SEQ ID NO: 11) is a pLX-B3 derivative with the GoldenBraid omega1 cloning cassette (Sarrion-Perdigones A., et al, Plant Physiol. 2013, 162, 1618-1631) and comprises the replication origin from the pBBR1 plasmid (SEQ ID NO: 105). The following parts were joined by Gibson assembly: (i) backbone, amplified from pLX-B3 (SEQ ID NO: 4) using the X324_R/X325_F primers (SEQ ID NO: 92/SEQ ID NO: 93); (ii) lacZα cloning cassette, amplified using X326_F/X327_R (SEQ ID NO: 94/SEQ ID NO: 95).

pLX-B3Ω2 (SEQ ID NO: 12) is a pLX-B3 derivative with the GoldenBraid omega2 cloning cassette (Sarrion-Perdigones A., et al, Plant Physiol. 2013, 162, 1618-1631) and comprises the replication origin from the pBBR1 plasmid (SEQ ID NO: 105). The following parts were joined by Gibson assembly: (i) backbone, amplified from pLX-B3 (SEQ ID NO: 4) using the X324_R/X325_F primers (SEQ ID NO: 92/SEQ ID NO: 93); (ii) lacZα cloning cassette, amplified using X328_F/X329_R (SEQ ID NO: 96/SEQ ID NO: 34).

pLX-B2-TagRFP-T (SEQ ID NO: 13) is a pLX-B2 derivative with the CaMV 35S promoter, TagRFP-T and nopaline synthase terminator transcription unit ($P_{35S}$:RFP:$T_{nos}$). The following parts were joined by Gibson assembly: (i) backbone, amplified from pLX-B2 (SEQ ID NO: 3) using the X210_R/X211_F primers (SEQ ID NO: 46/SEQ ID NO: 47); (ii) $P_{35S}$:RFP:$T_{nos}$, from pSN.5-TagRFP-T using X218_F/X219_R (SEQ ID NO: 51/SEQ ID NO: 52).

pLX-B3-TagRFP-T (SEQ ID NO: 14) is a pLX-B3 derivative with $P_{35S}$:RFP:$T_{nos}$. The following parts were joined by Gibson assembly: (i) backbone, amplified from pLX-B3 (SEQ ID NO: 4) using the X210_R/X211_F primers (SEQ ID NO: 46/SEQ ID NO: 47); (ii) $P_{35S}$:RFP:$T_{nos}$, from pSN.5-TagRFP-T using X218_F/X219_R (SEQ ID NO: 51/SEQ ID NO: 52).

pLX-B4-TagRFP-T (SEQ ID NO: 15) is a pLX-B4 derivative with $P_{35S}$:RFP:$T_{nos}$. The following parts were joined by Gibson assembly: (i) backbone, amplified from pLX-B4 (SEQ ID NO: 5) using the X210_R/X211_F primers (SEQ ID NO: 46/SEQ ID NO: 47); (ii) $P_{35S}$:RFP:$T_{nos}$, from pSN.5-TagRFP-T using X218_F/X219_R (SEQ ID NO: 51/SEQ ID NO: 52).

pLX-R2-TagRFP-T (SEQ ID NO: 16) is a pLX-R2 derivative with $P_{35S}$:RFP:$T_{nos}$. The following parts were joined by Gibson assembly: (i) backbone, amplified from pLX-R2 (SEQ ID NO: 6) using the X210_R/X211_F primers (SEQ ID NO: 46/SEQ ID NO: 47); (ii) $P_{35S}$:RFP:$T_{nos}$, from pSN.5-TagRFP-T using X218_F/X219_R (SEQ ID NO: 51/SEQ ID NO: 52).

pLX-R3-TagRFP-T (SEQ ID NO: 17) is a pLX-R3 derivative with $P_{35S}$:RFP:$T_{nos}$. The following parts were joined by Gibson assembly: (i) backbone, amplified from pLX-R3 (SEQ ID NO: 7) using the X210_R/X211_F primers (SEQ ID NO: 46/SEQ ID NO: 47); (ii) $P_{35S}$:RFP:$T_{nos}$, from pSN.5-TagRFP-T using X218_F/X219_R (SEQ ID NO: 51/SEQ ID NO: 52).

pLX-R4-TagRFP-T (SEQ ID NO: 18) is a pLX-R4 derivative with $P_{35S}$:RFP:$T_{nos}$. The following parts were joined by Gibson assembly: (i) backbone, amplified from pLX-R4 (SEQ ID NO: 8) using the X210_R/X211_F primers (SEQ ID NO: 46/SEQ ID NO: 47); (ii) $P_{35S}$:RFP:$T_{nos}$, from pSN.5-TagRFP-T using X218_F/X219_R (SEQ ID NO: 51/SEQ ID NO: 52).

pLX-B2-XT1-XT2-hCas9 (SEQ ID NO: 19) is a pLX-B2 derivative with the XT1 sgRNA, XT2 sgRNA, and hCas9 transcription units. Transcription units were transferred from the GB1108 vector to pLX-B2 performing a restriction-ligation reaction that included BsmBI (New England BioLabs) and T4 DNA ligase (Promega). The reaction mixture was subjected to 30 cycles of 7 min each (3 min at 37° C. and 4 min at 16° C.). Clones were selected onto kanamycin medium plates, and by restriction enzyme assays.

pLX-B2-NptII-DsRED (SEQ ID NO: 20) is a pLX-B2 derivative with the $P_{nos}$: NptII:$T_{nos}$ and $P_{35S}$:DsRED:$T_{35S}$ transcription units. Transcription units were transferred from the GB0460 and GB1181 vectors to pLX-B2 performing a restriction-ligation reaction that included BsaI (New England BioLabs) and T4 DNA ligase (Promega). The reaction mixture was subjected to 30 cycles of 7 min each (3 min at 37° C. and 4 min at 16° C.). Clones were selected onto kanamycin medium plates, and by restriction enzyme assays.

pLX-PPV (SEQ ID NO: 21) is a pLX-B2 derivative with a GFP-tagged plum pox virus cDNA clone cassette ($P_{35S}$:PPV:$T_{nos}$). ScaI/XbaI-digested pSN-PPV was mixed with ScaI/NheI-digested pLX-B2. The fragments were ligated using T4 DNA ligase (New England BioLabs).

pLX-UCBSV (SEQ ID NO: 22) is a pLX-B2 derivative with a cDNA clone cassette of Ugandan cassava brown streak virus ($P_{35S}$:UCBSV:$T_{nos}$). Total RNA purified from plants infected with the UCBSV isolate Ke_125 (PV-0912, DSMZ) was used in a cDNA synthesis reaction. This included X122_R (SEQ ID NO: 32), X123_R (SEQ ID NO: 33), random primers and commercial kit components (High Capacity cDNA reverse transcription kit, Applied Biosystems). The cDNA sample was used in PCR reactions: (i) 5UTR-P3, using the X240_F/X241_R primers (SEQ ID NO: 59/SEQ ID NO: 60); (ii) P3-NIB, using X242_F/X243_R (SEQ ID NO: 61/SEQ ID NO: 62); (iii) NIB-3UTR, using X244_F/X245_R (SEQ ID NO: 63/SEQ ID NO: 64). The pLX-B2 backbone with $P_{35S}$ and $T_{nos}$ was amplified from pLX-PPV using X238_R/X239_F (SEQ ID NO: 57/SEQ ID NO: 58). The RT- and PCR fragments were joined by Gibson assembly. The sequence of the UCBSV cDNA clone was determined by Sanger sequencing using the 1989_F (SEQ ID NO: 29), X241_R (SEQ ID NO: 60), X244_F (SEQ ID NO: 63), X245_R (SEQ ID NO: 64), X253_R (SEQ ID NO: 65), X254_F (SEQ ID NO: 66), X255_R (SEQ ID NO: 67), X256_F (SEQ ID NO: 68), X257_F (SEQ ID NO: 69), X258_F (SEQ ID NO: 70), X259_R (SEQ ID NO: 71), X260_R (SEQ ID NO: 72) primers.

pLX-B2-$P_{CRC}$:mTFP1 (SEQ ID NO: 23) is a pLX-B2 derivative with a transcription unit ($P_{CRC}$:mTFP1:$T_{CRC}$) including an *A. thaliana* seed promoter of the cruciferin C gene (AT4G28520), a cyan fluorescent protein (mTFP1) and AT4G28520 terminator. The following parts were joined by Gibson assembly: (i) backbone, amplified from pLX-B2 using the X210_R/X211_F primers (SEQ ID NO: 46/SEQ ID NO: 47); (ii) $P_{CRC}$, from *A. thaliana* Col-0 genomic DNA using X220_F/X221_R (SEQ ID NO: 53/SEQ ID NO: 54); (iii) mTFP1, from pSN.5-mTFP1 using X212_F/X213_R (SEQ ID NO: 48/SEQ ID NO: 49); (iv) $T_{CRC}$, from *A. thaliana* Col-0 genomic DNA using X222_F/X223_R (SEQ ID NO: 55/SEQ ID NO: 56).

pLX-Z4-$P_{mas}$:RFP-AlcR (SEQ ID NO: 24) is a pLX-Z4 derivative with the TagRFP-T, Thosea asigna virus 2A peptide (Donnelly M. L. L., et al., J. Gen. Virol. 2001, 82, 1027-1041), *A. nidulans* AlcR coding sequences flanked by the mannopine synthase promoter and terminator ($P_{mas}$:RFP-2A-AlcR:$T_{mas}$). The following parts were joined by Gibson assembly: (i) backbone, amplified from pLX-Z4 using X210_R/X211_F primers (SEQ ID NO: 46/SEQ ID NO: 47); (ii) $P_{mas}$, from pGGF003 using X301_F/X302_R (SEQ ID NO: 79/SEQ ID NO: 80); (iii) RFP-2A, from pSN-PPV-TagRFP-T2A using X216_F/X303_R (SEQ ID NO: 50/SEQ ID NO: 81); (iv) AlcR_5', from pGGC011 using X304_F/X305_R (SEQ ID NO: 82/SEQ ID NO: 83); (v) AlcR_3', from pGGC011 using X306_F/X307_R (SEQ ID NO: 84/SEQ ID NO: 85); (vi) $T_{mas}$, from pGGF003 using X308_F/X309_R (SEQ ID NO: 86/SEQ ID NO: 87).

pLX-B2-$P_{EtOH}$:NEON (SEQ ID NO: 25) is a pLX-B2 derivative with the mNeonGreen sequence under an ethanol-responsive synthetic promoter ($P_{EtOH}$:NEON:$T_{nos}$). The following parts were joined by Gibson assembly: (i) backbone, amplified from pLX-B2 using the X210_R/X211_F primers (SEQ ID NO: 46/SEQ ID NO: 47); (ii) NEON:$T_{nos}$, from pSN.5-mNeon using X310_F/X219_R (SEQ ID NO: 88/SEQ ID NO: 52); (iii) $P_{EtOH}$ synthetic fragment (SEQ ID NO: 35).

pSN.5-$P_{PAP85}$:RFP (SEQ ID NO: 26) is a pSN2-ccdB derivative with the *A. thaliana* AT3G22640 seed promoter, RFP and nopaline synthase terminator transcription unit ($P_{PAP85}$:RFP:$T_{nos}$). To generate the pSN.5-$P_{PAP85}$:RFP vector the following parts were joined by Gibson assembly: (i) backbone, XbaI/PmII-digested pSN2-ccdB; (ii) $P_{PAP85}$, from *A. thaliana* Col-0 genomic DNA using X228_F/X229_R (SEQ ID NO: 98/SEQ ID NO: 99); (iii) RFP:$T_{nos}$, from pSN.5-TagRFP-T using X216_F/X80_R (SEQ ID NO: 50/SEQ ID NO: 97).

GB1686 (SEQ ID NO: 27) is a pDGB3_alpha1 derivative with the $P_{nos}$: NptII:$T_{nos}$ and $P_{35S}$:DsRED:$T_{35S}$ transcription units. Transcription units were transferred from the GB0460 and GB1181 vectors to pDGB3_alpha1 performing a restriction-ligation reaction that included BsaI (New England BioLabs) and T4 DNA ligase (Promega). The reaction mixture was subjected to 30 cycles of 7 min each (3 min at 37° C. and 4 min at 16° C.). Clones were selected onto kanamycin medium plates, and by restriction enzyme assays.

pLX-TuMV (SEQ ID NO: 28) is a pLX-B2 derivative with the $P_{35S}$:TuMV:$T_{nos}$ cassette from p35Tunos-vec01-NAT1. To generate the pLX-TuMV vector the following parts were joined by Gibson assembly: (i) backbone, amplified from pLX-PPV using X333_R/X334_F primers (SEQ ID NO: 100/SEQ ID NO: 101); (ii) XmaI/SalI-digested p35Tunos-vec01-NAT1.

The primers were synthesized by Sigma-Aldrich, and their sequences are listed in Table 2.

TABLE 2

Table 2. List of the primers, and assembly linkers

| ID | Sequence | SEQ ID NO: |
|---|---|---|
| 1989_F | GATTGATGTGATTTCTCCACTGACG | 29 |
| 2050_F | GCCATTGTCCGAAATCTCACG | 30 |
| 2051_R | CTGGAAATGCGATTCTCTTAGC | 31 |
| X122_R | CGTCAATCGTTAGAGC | 32 |
| X123_R | CGACCTTGCACTTCA | 33 |
| X329_R | CGCATCCTTGTCCGGTCTCCAGCGAGAGACGTCACTCATTAG | 34 |
| X192_F | CGACTTGCGACATGCGGTCCTTTGCAATCAACTATTAGAAAAATTCATCC | 36 |
| X193_R | AACCGCATAACCGCCAATCCGATCTTGTGTCTCAAAATCTCTGATGTTAC | 37 |
| X194_F | CGACTTGCGACATGCGGTCCTTTGTTATTTGCCGACTACCTTGGTGA | 38 |
| X195_R | AACCGCATAACCGCCAATCCGATCGAACCTTGACCGAACGCAGC | 39 |

TABLE 2-continued Table 2. List of the primers, and assembly linkers

| ID | Sequence | SEQ ID NO: |
|---|---|---|
| X196_F | CGACTTGCGACATGCGGTCCTTTGCAATTTACCCAACAACTCCGC | 40 |
| X197_R | AACCGCATAACCGCCAATCCGATCTTGACATAAGCCTGTTCGGTTC | 41 |
| X198_F | GATCGGATTGGCGGTTATGCGGTTCTACCGGCGCGGCAG | 42 |
| X199_R | GGAAGACCACCGAACTGATGATGGCCCCCTACGGGCTTGCTCTC | 43 |
| X200_F | GATCGGATTGGCGGTTATGCGGTTGCGATGCAGGTGGCTGCTGA | 44 |
| X201_R | GGAAGACCACCGAACTGATGATGGGTAGAAAAGATCAAAGGATCTTCTTG | 45 |
| X210_R | TGAGACGGTTTCGACCAGG | 46 |
| X211_F | GTCAGGAGACGGGACAAGGA | 47 |
| X212_F | ATGGTTTCTAAAGGTGAAGAGAC | 48 |
| X213_R | TTATGCTCCTTTATCGTCGTC | 49 |
| X216_F | ATGGTTTCAAAGGGAGAAGAG | 50 |
| X218_F | GTAGCCTGGTCGAAACCGTCTCACCAGTACGCACGATTCAAGG | 51 |
| X219_R | CGCATCCTTGTCCCGTCTCCTGACGAGATCGAGTAACATAGATGACACC | 52 |
| X220_F | GTAGCCTGGTCGAAACCGTCTCATAACGAACGCTCATGCTAAG | 53 |
| X221_R | TTGTAGTCTCTTCACCTTTAGAAACCATTTTCTTTTTGTTTGTTGTGAG | 54 |
| X222_F | GGATGACGACGATAAAGGAGCATAATGCACTGGAGGTCAAGGAAG | 55 |
| X223_R | CGCATCCTTGTCCCGTCTCCTGACATAGCTCGATAGAATCATTTGCT | 56 |
| X238_R | GTCATATTTATTTTCCTCTCCAAATGAAATGAACTTCC | 57 |
| X239_F | GAAATACACCTTATAAAGTACAAAAAAAAAAAAAAAAAAAAAATGC | 58 |
| X240_F | GTTCATTTCATTTGGAGAGGAAAAATAAATATGACATAAGAATACATAA | 59 |
| X241_R | CTCTTCCTTTCGACCTTGCACTTCA | 60 |
| X242_F | TTGAAGTGCAAGGTCGAAAGGAAGAG | 61 |
| X243_R | AAAGAAGTATCAAACCTACTACCATCACAATC | 62 |
| X244_F | GATTGTGATGGTAGTAGGTTTGATACTTCTT | 63 |
| X245_R | TTTTTTTTTTTTTGTACTTTTATAAGGTGTATTTCTACACCAAACAAAGGATATGG | 64 |
| X253_R | CTTTCGTAACAGCTTGCTTTCTCA | 65 |
| X254_F | CTTTGGTTTAGACAAGCAATGTGTG | 66 |
| X255_R | CCACTATTATTTCCACGATGCTTC | 67 |
| X256_F | CAGAGGTGAAGTCTATTCTTGGCAT | 68 |
| X257_F | AGTTTGGTGGAGTTTTGGATAGC | 69 |
| X258_F | ATACACACGCTTGAGATAATGGATG | 70 |
| X259_R | ATCGCCACTGATACAATTCAAAAG | 71 |
| X260_R | AGGACCAAAATTCTCATAAGTCTCTCT | 72 |
| X295_F | CAATTTACCCAACAACTCCGC | 73 |
| X296_R | TGAGTTCGGCGATGTAGCCACCT | 74 |
| X297_F | GGTGGCTACATCGCCGAACTCA | 75 |
| X298_R | CGTTCGCGTCGGCTAGAACAGGAG | 76 |
| X299_F | TGTTCTAGCCGACGCGAACGCT | 77 |

TABLE 2-continued

Table 2. List of the primers, and assembly linkers

| ID | Sequence | SEQ ID NO: |
|---|---|---|
| X300_R | GTAGAAAAGATCAAAGGATCTTCTTG | 78 |
| X301_F | GTAGCCTGGTCGAAACCGTCTCATTTTTCAAATCAGTGCGCAAGA | 79 |
| X302_R | CAGCTCTTCTCCCTTTGAAACCATTGTTGTTACCCGATTTGGTG | 80 |
| X303_R | TGGCCCTGGATTTTCCTCAA | 81 |
| X304_F | TTGAGGAAAATCCAGGGCCAATGGCAGATACACGCCGAC | 82 |
| X305_R | TCCAGCACAGATTGCGTGAGAGAA | 83 |
| X306_F | CTCTCACGCAATCTGTGCTGGATG | 84 |
| X307_R | AGCTACAAGAAGCTGTCAACTTTCCCA | 85 |
| X308_F | GGAAAGTTGACAGCTTCTTGTAGCTCTTGGACTCCCATGTTGG | 86 |
| X309_R | GCATCCTTGTCCCGTCTCCTGACGATAATTTATTTGAAAATTCATAAG | 87 |
| X310_F | CAACATTACAATTACTATTTACAATTACAATGGTGAGCAAGGGAGAGGAG | 88 |
| X321_F | GAGACGGGACAAGGATGCG | 89 |
| X322_F | CCTGGTCGAAACCGTCTCAGTCAGGAGAGAGACCAAAAGCAAAAC | 90 |
| X323_R | CGCATCCTTGTCCCGTCTCCAGCGAGAGACCTCACTCATTAG | 91 |
| X324_R | TGAGACCGTTTCGACCAGG | 92 |
| X325_F | GAGACCGGACAAGGATGCG | 93 |
| X326_F | CCTGGTCGAAACGGTCTCAGGAGAGAGACGAAAAGCAAAAC | 94 |
| X327_R | CGCATCCTTGTCCGGTCTCCTGACAGCGAGAGACGTCACTCATTAG | 95 |
| X328_F | CCTGGTCGAAACGGTCTCAGTCAGGAGAGAGACGAAAAGCAAAAC | 96 |
| X80_R | CTCAATGCTGCTGCCTTCATCTGGATATGAGCTTCAC | 97 |
| X228_F | CCTCGAGTACGTAGGATCCATTTAAATTCCTTCAAGAGAGCAAACCATT | 98 |
| X229_R | ATCAGCTCTTCTCCCTTTGAAACCATTTTTTCTTGTTGTTTTGTTG | 99 |
| X333_R | CGTGTCGTGCTCCACCATGTTCACGAAGATT | 100 |
| X334_F | AAAAAAAAAAATCGGTTCCCCCTAGAGCAGATCGTTCAAACATTTGGCA | 101 |
| Linker_1 | CCATCATCAGTTCGGTGGTCTTCC | 112 |
| Linker_2 | CGACTTGCGACATGCGGTCCTTTG | 113 |
| Linker_3 | GATCGGATTGGCGGTTATGCGGTT | 114 |

Bacterial Growth Conditions

The *E. coli* DH10B strain was used for cloning and plasmid propagation. To increase plasmid miniprep yields, 10 mL cultures were grown in 50 mL tubes at 30 or 37° C. Overnight cultures were pelleted by centrifugation and processed using commercial minicolumn kits (FavorPrep Plasmid Extraction Mini Kit, Favorgen; Wizard Plus SV Minipreps, Promega). Double volumes of resuspension (50 mM Tris-HCl pH 7.5, 10 mM EDTA, 100 µg/mL RNase A), lysis (0.2 M NaOH, 1% SDS) and neutralization (4.09 M guanidine hydrochloride, 0.759 M potassium acetate, 2.12 M glacial acetic acid) kit solutions were used to improve clearing of bacterial lysates and final plasmid yields. Bacteria were grown in Luria-Bertani medium and antibiotics used at final concentrations of 100 mg/L ampicillin, 15 mg/L chloramphenicol, 20 mg/L gentamicin, 50 mg/L kanamycin, 50 mg/L rifampicin, 100 mg/L spectinomycin, 100 mg/L streptomycin, and 10 mg/L tetracycline. Growth curves were measured in 96-well plates, by recording OD600 absorbance values at 10-minute intervals in a plate reader (Infinite M200, Tecan). Maintenance of pTi in the *A. tumefaciens* C58C1-313 strain was evaluated by PCR amplification of a repB fragment using the 2050_F/2051_R primers (SEQ ID NO: 30/SEQ ID NO: 31).

Plant Transformation and Agro-Inoculation

The T-DNA binary vectors (See Table 1) were transformed into *A. tumefaciens* cells by the freeze-thawing or electroporation methods. In transient expression and agro-inoculation assays, *A. tumefaciens* suspensions were mechanically infiltrated into *N. benthamiana* and *A. thaliana* leaves as described (Pasin F., et al., Plant Methods. 2014, 10, 22). The floral dip method was used to stably transform germ line cells of *A. thaliana* (Clough S. J. & Bent A. F., Plant J. 1998, 16, 735-743). Stable transformation of *N. benthamiana* leaf disks was carried as described (Horsch R. B. & Klee H. J., Proc. Natl. Acad. Sci. USA 1986, 83, 4428-4432).

Protein Detection

Plant samples that express fluorescent proteins were visualized under an epifluorescence stereoscope, confocal microscope, or imaged in a laser scanner (Pasin F., et al., Plant Methods. 2014, 10, 22). Fluorescence was measured by placing leaf discs in 96-well flat-bottom plates; in kinetics studies, plates were sealed with optical adhesive films (4311971, Applied Biosystems). The fluorescence signal was acquired in filter-based (VICTOR X5, PerkinElmer) or monochromator-based plate readers (Infinite M200, Tecan), as reported (Pasin F., et al., Plant Methods. 2014, 10, 22). Total protein extracts were resolved by SDS-PAGE, and immunodetection was done using rabbit anti-tRFP (AB234, Evrogen), anti-UCBSV CP (AS-0912, DSMZ), anti-PPV CP and anti-TuMV CP sera as the primary antibodies. For the electron microscopy, plant extracts were incubated with collodion-coated carbon-stabilized copper grids, which were negative stained with 2% uranyl acetate. Grids were observed in a transmission electron microscope (JEM 1011, Jeol).

Targeted Genome Mutagenesis

The CRISPR/Cas constructs were transiently expressed in *N. benthamiana* leaves. To estimate the mutagenesis efficiency, PCR/restriction enzyme assays were done as described (Vazquez-Vilar M., et al., Plant Methods. 2016, 12, 1-12). Briefly, genomic DNA was purified from infiltrated leave samples and used in PCR reactions to amplify DNA fragments spanning the sites targeted by the CRISPR/Cas constructs. The resulting PCR products were purified, and used in DNA digestion reactions that included restriction enzymes whose target sequences overlap predicted editing sites. Intensities of cleaved and cleavage-resistant bands were estimated using the ImageJ software (https://imagej.nih.gov/ij/).

Example 1. Construction of T-DNA Binary Vectors by Assembly of Modular Parts, and Cloning Features of a pBBR1-Based pLX Vector In the design of new T-DNA binary vectors, the inventors chose basic principles: (a) reduced size; (b) stability; (c) a broad-host-range replication origin for maintenance in *E. coli* and *A. tumefaciens*; (d) an origin compatible with the most commonly used T-DNA binary vectors; (e) consistency with current standards for plant synthetic biology; and (f) the possibility to adopt overlap-dependent cloning methods for construct assembly.

Figure 1:
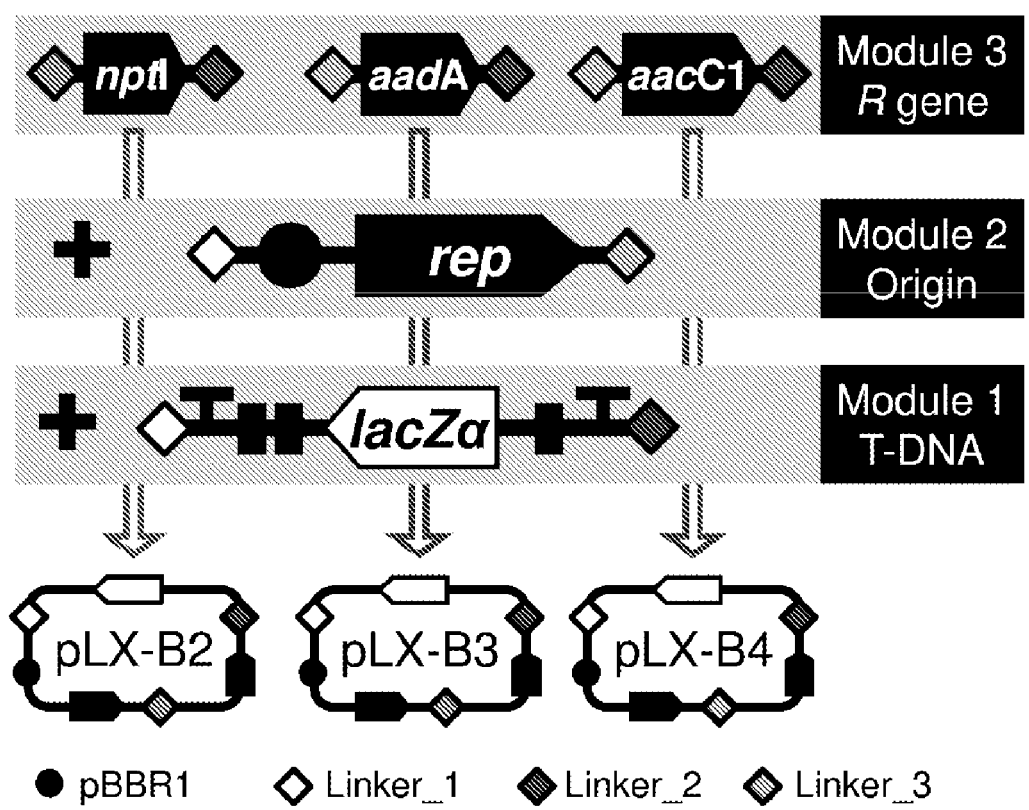
FIG. 1. Construction of T-DNA binary vectors by assembly of modular parts

Therefore, to construct the pLX binary vectors of the present invention, modular parts were assembled by overlap-based cloning methods. Sequences of synthetic orthogonal overlapping junctions known as assembly linker were designed to allow combinatorial assembly of DNA modules (Table 2). Module 1, 2, and 3 refer to the T-DNA cassette, the pBBR1 origin and a selectable marker (resistance (R) genes such as nptI, aadA, and aacC1), respectively (FIG. 1). Each module includes one or several DNA parts, which are flanked by two diverse assembly linkers that are shown as diamonds in FIG. 1. Parts from the three modules were obtained by PCR or chemical synthesis, and were joined by one-step isothermal DNA assembly to generate the pLX-B2 (SEQ ID NO: 3), pLX-B3 (SEQ ID NO: 4) and pLX-B4 (SEQ ID NO: 5) binary vectors (FIG. 1, Table 3). Details for the generation of the pLX-B2, pLX-B3 and pLX-B4 plasmid are disclosed above.

TABLE 3

Binary T-DNA vectors of the present invention

| Vector | Size bp | Origin | T-DNA* | Bacterial selection | Cassette | Cloning features[§] | | | |
|---|---|---|---|---|---|---|---|---|---|
| | | | | | | Golden Gate | Golden Braid | Gibson assembly | Multiplexing |
| pLX-B2 | 3287 | pBBR1 | octopine | KAN | alpha1 | ■ | ■ | ■ | ■ |
| pLX-B3 | 3349 | pBBR1 | octopine | SP | alpha1 | ■ | — | ■ | n.t. |
| pLX-B4 | 3165 | pBBR1 | octopine | GENT | alpha1 | ■ | — | ■ | n.t. |
| pLX-B2α2 | 3287 | pBBR1 | octopine | KAN | alpha2 | ■ | ■ | ■ | n.t. |
| pLX-B3Ω1 | 3349 | pBBR1 | octopine | SP | omega1 | — | ■ | ■ | n.t. |
| pLX-B3Ω2 | 3349 | pBBR1 | octopine | SP | omega2 | — | ■ | ■ | n.t. |
| pLX-Z4 | 3740 | RK2 | succinamopine | GENT | alpha1 | ■ | — | ■ | ■ |

*pTi type of right and left border source, all vectors include a second left border of the nopaline type;
[§]cloning cassette nomenclature according to GoldenBraid standards (Sarrion-Perdigones A., et al.. Plant Physiol. 2013, 162, 1618-1631): solid square, suitable; open square, not suitable; n.t., not tested.

The pLX binary vectors of the present invention facilitate flexible experimental designs since their replication is autonomous in both *E. coli* and *A. tumefaciens*. Additional features of the pLX binary vectors include diverse selectable markers, a T-DNA with borders from an octopine-type pTi and a second left border sequence that was shown to reduce the backbone transfer (FIG. 2A). Bacterial synthetic terminators based on different scaffolds (T1, SEQ ID NO: 108; and T2, SEQ ID NO: 109) were included to increase plasmid stability.

For cloning purposes, the T-DNA cassette hosts the *E. coli* lacZα reporter gene flanked by Type IIS restriction endonuclease sites (FIG. 2B). Sequences of BsaI- or BsmBI-produced overhangs comply with the syntax proposed for plant synthetic biology; the pLX vectors are thus suitable for assembly of single and multiple eukaryotic transcription units from libraries of standard DNA parts. Parts or transcription units can be assembled from plasmid libraries into the pLX vectors using the BsaI-based Golden Gate, and GoldenBraid standards (FIG. 2C). The T-DNA cassette hosts divergent primer annealing regions with no sequence similarity and secondary structures (arrows, FIG. 2B). These allow linearization of the small pLX backbones by inverse PCR, and subsequent use in the cloning of multiple overlapping fragments by Gibson assembly (FIG. 2C). The pLX vectors with compatible replicons can be multiplexed into *Agrobacterium* cells for multiple T-DNA delivery (Multiplexing; FIG. 2C). Therefore, the binary vectors of the present invention comprise features that make them compatible with Type IIS restriction endonuclease- and overlap-based assembly methods, and with the delivery of multiple T-DNA cassettes by the multiplexing of binary vectors with compatible origins (Table 3).

Example 2. Transgene Expression in Plants Using the pLX Vector Series

To demonstrate that the binary vectors of the present invention can be used to deliver DNA constructs to eukaryotic cells, specifically to plant cells by *Agrobacterium* tumefaciens-mediated transformation, a transcription unit ($P_{35S}$: RFP:$T_{nos}$) that comprises sequences of the cauliflower mosaic virus 35S promoter, the red fluorescent protein (RFP, as a reporter; FIG. 3A), and the nopaline synthase terminator was assembled into the pLX vectors of the present invention to obtain pLX-B2-TagRFP-T (SEQ ID NO: 13), pLX-B3-TagRFP-T (SEQ ID NO: 14) and pLX-B4-TagRFP-T (SEQ ID NO: 15)(FIG. 3A). Details for the generation of the vectors are disclosed above. Transient expression of RFP in *Nicotiana benthamiana* leaves was evaluated by *A. tumefaciens*-mediated delivery. At 6 dpa, leaves infiltrated with pLX-B2-TagRFP-T (SEQ ID NO: 13), pLX-B3-TagRFP-T (SEQ ID NO: 14) and pLX-B4-TagRFP-T (SEQ ID NO: 15) showed bright RFP fluorescence, which was absent in the control sample (FIG. 3B). Consistent with genuine plant expression, confocal images showed that the RFP fluorescent protein signal distributes in the cytosol and nucleoplasm of plant cells (FIG. 3C). The RFP accumulation in leaf samples was confirmed by immunoblot analysis of total protein extracts (FIG. 3D).

For some applications, stable integration of T-DNA cassettes into eukaryotic cell genomes is desirable. To prove the suitability of the pLX vectors to mediate stable transgene integration into plant genomes, the inventors used *Arabidopsis thaliana* as a model plant and the pLX-B2-$P_{CRC}$: mTFP1 vector (SEQ ID NO: 23) (FIG. 4A). Details for its synthesis are disclosed above.

The construct was inserted in *A. tumefaciens* and transformed into plants by floral dipping. Consistent with mTFP1 expression, bright cyan fluorescence was detectable in seed collected from the *Agrobacterium*-treated plants ($T_1$ seeds). The mTFP1-expressing seeds were selected under an epifluorescence stereoscope, and sown to soil. The stable transgene integration in germ-line cells was confirmed by PCR analysis of the Ti plants: the promoter of the endogenous cruciferin C gene was amplified ($P_{CRC}$) from transformed and untransformed plants, whereas the mTFP1 sequence could be amplified only from plants derived from the cyan fluorescent seeds. Diverse fluorescence phenotypes of the T2 seeds were consistent with the transgene integration into the plant genome and its segregation across generations (FIG. 4B).

The present invention shows that T-DNA cassettes from the pLX vectors can be delivered to plants, and the pLX vectors can be used to transiently express or stably integrate transgenes into eukaryotic cell genomes. The inventors generated transgenic plants that are "marker-free", since they do not include genes that confer resistance to antibiotics, herbicides, or other chemical compounds used in transgenic plant selection.

Example 3. Stable Maintenance of T-DNA Cassettes in the pLX Binary Plasmid Series of the Invention cDNA copies of RNA virus genomes can be inserted into plasmids to generate viral infectious clones; these often show instability problems and sequence deletions that arise during the clone propagation in bacteria. To test the stability of the pLX binary vectors of the present invention in challenging conditions, the inventors transferred the entire cDNA sequence of potyvirus genomes into a pLX vector. The vectors generated were propagated in *Escherichia coli*, and the bacteria were subjected to several growth cycles. Vector stability was evaluated by restriction enzyme digestion assays.

The whole cDNA sequence of an RNA virus was obtained from a pBIN19-based vector, pSN-PPV (Pasin F., et al, PLoS Pathog. 2014, 10, e1003985), which contains the cauliflower mosaic virus 35S promoter, a cDNA copy of the plum pox virus (PPV) genome and the nopaline synthase terminator ($P_{35S}$:PPV:$T_{nos}$) sequences. As disclosed above, the inventors generated pLX-PPV (SEQ ID NO: 21), a pLX-B2 derivative with the $P_{35S}$:PPV:$T_{nos}$ cassette from pSN-PPV (FIG. 5A). The pLX-PPV vector obtained (SEQ ID NO: 21) has the pBBR1 origin (SEQ ID NO: 105), and is 38% and 9.3 kb smaller than pSN-PPV. Purified plasmids from two independent clones of pLX-PPV (In, # A and # B) were EcoRI digested and resolved by agarose gel (FIG. 5B). Compared to the pSN-PPV digestion profile, pLX-PPV clones showed all the bands corresponding to the viral cDNA cassette of pSN-PPV. High molecular weight DNA bands were consistent with differences in the pSN-PPV and pLX-PPV backbones, pBIN19 and pLX-B2, respectively. The new pLX-PPV # A and # B clones (pLX-PPV, In) were transformed in *E. coli* cells to evaluate the plasmid stability. For each transformation, eight individual colonies were picked and subjected to six growth cycles (24 h, 37° C.). Purified plasmids were digested with EcoRI and resolved by agarose gel electrophoresis (pLX-PPV, Out; FIG. 5B). The pLX-PPV plasmid showed no instability, since digestion profiles of the input and output plasmids were identical.

To further confirm the results, the entire cDNA sequence from a different RNA virus was obtained from a pUC-based vector, p35Tunos-vec01-NAT1, which contains the cauliflower mosaic virus 35S promoter, a cDNA copy of the turnip mosaic virus (TuMV) genome and the nopaline synthase terminator ($P_{35S}$:TuMV:$T_{nos}$) sequences (Touriño A., et al, Span. J. Agric. Res. 2008, 6, 48-58). The p35Tunos-vec01-NAT1 vector cannot replicate in *A. tumefaciens*, and does not include T-DNA borders for its transformation to plants. The inventors generated pLX-TuMV (SEQ ID NO: 28), a pLX-B2 derivative with the $P_{35S}$:TuMV:$T_{nos}$ cassette from p35Tunos-vec01-NAT1 (FIG. 5C). The pLX-TuMV vector (SEQ ID NO: 28) obtained as disclosed above, is only slightly larger (3%, and 0.4 kb) than p35Tunos-vec01-NAT1, but includes the pBBR1 origin (SEQ ID NO: 105) and T-DNA borders suitable for its delivery to plants by *Agrobacterium*-mediated transformation. The new pLX-TuMV vector (SEQ ID NO: 28) (pLX-TuMV, In) was transformed in *E. coli* cells to evaluate the plasmid stability. For each transformation, ten individual colonies were picked and subjected to six growth cycles (24 h, 37° C.). Purified plasmids were digested with EcoRI and resolved by agarose gel electrophoresis (pLX-TuMV, Out; FIG. 5D). In agreement with the pLX-PPV results, the newly generated pLX-TuMV plasmid showed no instability, since digestion profiles of the input and output plasmids were identical.

The present example shows that pLX vectors of the present invention can host >10 kb T-DNA cassettes, and that they can be used to generate clones that contain viral genome sequences. cDNA copies of RNA virus genomes have been reported to cause plasmid instability and loss of partial or entire insert sequences. In contrast, the pLX vectors that host cDNA genome copies of plant RNA viruses showed no instability when propagated in the bacterium *E. coli*.

Example 4. Viral Agro-Inoculation and Delivery of Exogenous Sequences to Plants Using pLX-Based Viral Vectors The pLX-PPV (SEQ ID NO: 21) and pLX-TuMV (SEQ ID NO: 28) binary vectors from Example 3, if properly expressed in plants, would initiate an infection of a chimeric PPV or TuMV, respectively. These chimeric viruses would host in their genome the GFP coding sequence (FIG. 6A, 6E), and GFP fluorescence could be measured and visualized to confirm exogenous sequence expression in plants by viral expression vectors.

An *A. tumefaciens* strain hosting pLX-PPV (pLX) (SEQ ID NO: 21) was infiltrated to *N. benthamiana* plants; a pSN-PPV strain (pSN) (Pasin F., et al., PLoS Pathog. 2014, 10, e1003985) was used as a positive control. The PPV infection and viral accumulation were confirmed by coat protein immunoblot analyses of samples from the agro-infiltrated and upper uninoculated leaves (6 dpa and 14 dpa, respectively; FIG. 6B). The accumulation of recombinant GFP in infected plant samples was confirmed by measuring the fluorescence intensity (FIG. 6C), and by imaging of upper uninoculated leaves (FIG. 6D). To further confirm the results, an *A. tumefaciens* strain hosting pLX-TuMV (SEQ ID NO: 28) was agro-inoculated to *A. thaliana* plants. In agreement with the pLX-PPV results, the TuMV infection and viral accumulation in upper uninoculated leaf samples were confirmed by immunoblot analysis of the TuMV coat protein (FIG. 6F). Bright green fluorescence signal was detectable in inoculated plants (FIG. 6G), confirming the accumulation of recombinant GFP.

Therefore, the present example shows that the pLX binary vectors of the present invention can be used to engineer viral infectious clones and viral vectors. These can be delivered by agro-inoculation, and used to introduce exogenous sequences and express recombinant proteins into plants.

Example 5. Assembly of Transcription Units into the pLX Vectors of the Invention Using Plant Synthetic Biology Standards To demonstrate pLX vector compatibility with plant synthetic biology standards, DNA parts from public libraries were assembled into the pLX binary vectors of the present invention.

The GB1181 and GB0460 plasmids that contain standardized units for plant delivery of the kanamycin resistance (NptII) and red fluorescent protein (DsRED) genes, respectively, were obtained from a public repository (https://gbcloning.upv.es/). As disclosed above, the inventors assembled the standardized units into the pLX-B2 vector (SEQ ID NO: 3) to generate pLX-B2-NptII-DsRED (SEQ ID NO: 20) (FIG. 7A). The pLX-B2-NptII-DsRED vector (SEQ ID NO: 20) obtained is a pLX-B2 derivative with the pBBR1 origin (SEQ ID NO: 105) and two transcription units for plant expression of NptII and DsRED.

To further confirm the results, the inventors transferred the GB1108 (https://gbcloning.upv.es/) standardized units into the pLX-B2 vector (SEQ I NO: 3) to generate pLX-B2-XT1-XT2-hCas9 (SEQ ID NO: 19) (FIG. 7B). The pLX-B2-XT1-XT2-hCas9 vector (SEQ ID NO: 19) obtained is a pLX-B2 derivative with the pBBR1 origin (SEQ ID NO: 105) and four transcription units for plant expression of NptII, a human codon-optimized *Streptococcus pyogenes* Cas9 gene (hCas9), and single-guide RNA targeting the *N. benthamiana* Niben101Scf04205Ctg025 (XT1) and Niben101Scf04551Ctg021 (XT2) endogenous genes. Details for the generation of pLX-B2-XT1-XT2-hCas9 vector are disclosed above. To improve flexibility of the binary vectors of the present invention and facilitate the reuse of assembled DNA parts, the inventors generated the pLX-B2α2 (SEQ ID NO: 10), pLX-B3Ω1 (SEQ ID NO: 11) and pLX-B3Ω2 vectors (SEQ ID NO: 12) including the GoldenBraid cloning cassettes (Sarrion-Perdigones A., et al, Plant Physiol. 2013, 162, 1618-1631) (FIG. 7C, Table 3). The pLX-B2α2 (SEQ ID NO: 10) vector is a pLX-B2 derivative with the alpha2 cloning cassette; pLX-B3Ω1 (SEQ ID NO: 11) is a pLX-B3 derivative with the omega1 cloning cassette; and pLX-B3Ω2 (SEQ ID NO: 12) is a pLX-B3 derivative with the omega2 cloning cassette; details for their generation are disclosed above. The pLX-B2α2, pLX-B3Ω1 and pLX-B3Ω2 vectors include the replication origin from the pBBR1 plasmid (SEQ ID NO: 105) and, together with the pLX-B2 plasmid of the present invention, comprise a minimal set of two alpha and two omega level cloning cassettes with convergent and divergent BsaI and BsmBI sites (Table 3). Following the GoldenBraid standards (Sarrion-Perdigones A., et al, Plant Physiol. 2013, 162, 1618-1631), these cloning cassettes allow reuse of assembled parts and building of large multigenic constructs.

Therefore, based on the pLX binary vectors described in the present invention, the inventors generated the pLX-B2α2 (SEQ ID NO: 10), pLX-B3Ω1 (SEQ ID NO: 11) and pLX-B3Ω2 (SEQ ID NO: 12) vectors (Table 3) that include cloning cassettes facilitating combinatorial assembly of pre-made DNA elements and transcription units into multigene constructs.

Example 6. Direct Cloning and Assembly of Large T-DNA Constructs into the pLX Vector Series without Intermediate Plasmids This example demonstrates that the pLX binary vectors of the present invention can be used to assemble large T-DNA constructs with no intermediate subcloning steps.

The inventors sought to use the vectors of the present invention to generate an infectious clone of the Ugandan cassava brown streak virus (UCBSV), a plant virus, since: (a) the UCBSV genome is a large RNA molecule of 9.1 kb; (b) a cDNA copy of UCBSV genome is not available in public parts libraries; (c) the cDNA copy of UCBSV genome would contain several Type IIS restriction endonuclease sites, whose removal is required for parts domestication and Golden Gate/GoldenBraid cloning; (d) mutagenesis of the UCBSV genome sequence (e.g., to remove BsaI/BsmBI sites) is not desirable, as its effects on virus viability are unknown; (e) correct assembly of the UCBSV genome into a pLX vector can be easily evaluated in plants; (f) UCBSV is a major threat to the staple food crop cassava, and an UCBSV infectious clone would have commercial applications as it facilitates screens for plant genetic resistance.

The inventors generated the pLX-UCBSV vector (SEQ ID NO: 22), a pLX-B2 derivative with a Ugandan cassava brown streak virus cDNA clone cassette ($P_{35S}$:UCBSV:$T_{nos}$), by one-step assembly of three RT-PCR fragments that spanned the entire 9.1-kb UCBSV genome (FIG. 8A). Details for the generation of the pLX-UCBSV vector are disclosed above.

An *A. tumefaciens* strain that contains pLX-UCBSV (SEQ ID NO: 22) was infiltrated to *N. benthamiana* plants.

At 12 dpa, the agro-inoculated plants showed reduced height (FIG. 8B). In upper uninoculated leaves, the inventors detected filamentous particles typical of potyvirid virions (FIG. 8C), and confirmed accumulation of the UCBSV coat protein by immunoblot analysis (FIG. 8D). These results demonstrated that a cDNA copy of UCBSV was assembled into a pLX vectors to obtain pLX-UCBSV (SEQ ID NO: 22), which is an infectious clone of UCBSV that can be delivered to plants by *Agrobacterium*-mediated inoculation.

Thus, the inventors assembled large T-DNA constructs into the pLX binary vectors of the present invention and this assembly did not require the use of restriction enzymes, parts domestication, intermediate plasmids and subcloning steps.

Example 7. Comparison of a pBBR1-Based pLX Vector of the Present Invention Versus RK2 and pVS1 Binary Vectors Briefly, vectors that use the replicon from the RK2 plasmid include pBIN19, and its smaller derivatives pEAQ and pCB301 (FIG. 9). Due to its reduced size, pCB301 is classified as a mini binary vector. The pVS1 origin is used in the pPZP series, and its derivatives of the pCAMBIA and pLSU series. The pCAMBIA vectors are among those most commonly used by plant scientists (http://www.cambia.org/daisy/cambia/585.html). A pSa minimal replicon includes the ori and RepA regions. These were split and used in the pGreen/pSoup dual-plasmid system: pGreen is a T-DNA binary vector that hosts the pSa-ori sequence, and its replication in *A. tumefaciens* is not autonomous since it lacks the pSa-RepA gene. The pGreen maintenance in *A. tumefaciens* requires the simultaneous presence of the helper plasmid pSoup, which provides the pSa-RepA gene and allows replication of the pGreen binary vector (FIG. 9). On the one hand, removal of the RepA gene allowed pGreen size to be kept to a minimum, and on the other, it sacrificed plasmid replication autonomy and promoted instability under non-selective conditions.

To demonstrate that the pLX-binary vectors of the present invention can be classified as mini binary vectors and additionally are useful for driving high transient expression in plants, the inventors compared the pLX binary vectors to the binary vectors mentioned above, which are known in the art.

Firstly, backbone sizes of pLX-B2 (SEQ ID NO: 3) and of the mentioned binary vectors known in the art were compared (FIG. 9). The pBBR1-based backbone of the pLX vectors of the present invention is substantially smaller than the widely used pBIN- and pCAMBIA-based vectors (pBIN19, pCAMBIA-2300; FIG. 9). The pLX-B2 (SEQ ID NO: 3) backbone size equals to those of the pGreen-based vectors, which are not autonomous and require pSoup for their replication in *A. tumefaciens*. In contrast, the pLX vectors facilitate flexible experimental designs since their replication is autonomous in both *E. coli* and *A. tumefaciens*.

pLX-B2 (SEQ ID NO: 3) can be classified as a mini binary vector since its size is below the one of pCB301, an RK2-based vector. Although larger than pBBR1, the RK2 replicon is relatively small and has previously been used to generate autonomous, mini binary vectors. To compare the performance of the pBBR1 and RK2 replicons, the inventors replaced the pBBR1 replication module (SEQ ID NO: 105) of the pLX vectors by an RK2 minimal origin (SEQ ID NO: 106) to build pLX-R2 (SEQ ID NO: 6), pLX-R3 (SEQ ID NO: 7) and pLX-R4 (SEQ ID NO: 8). A transcription unit ($P_{35S}$:RFP:$T_{nos}$) that contains sequences of the cauliflower mosaic virus 35S promoter, RFP, and nopaline synthase terminator was inserted into the pLX-R2, pLX-R3 and pLX-R4 vectors to obtain pLX-R2-TagRFP-T (SEQ ID NO: 16), pLX-R3-TagRFP-T (SEQ ID NO: 17) and pLX-R4-TagRFP-T (SEQ ID NO: 18), respectively (FIG. 10A). Details for the generation of these vectors are disclosed above.

Transient expression of RFP in *N. benthamiana* leaves was evaluated by *A. tumefaciens*-mediated delivery of the pLX vectors including the pBBR1 (FIG. 3A) or RK2 origins (FIG. 10A). Compared to RK2, the use of the pBBR1-based pLX vectors led to significantly higher RFP accumulation in plant transient expression assays (FIG. 10B). The result was independent of the resistance genes used for plasmid selection, and did not correlate significantly with the *A. tumefaciens* fluorescence that might derive from undesired RFP accumulation in bacteria (FIG. 10B).

The pCAMBIA plasmids have the pVS1 origin, and among the most commonly used T-DNA binary vectors. To compare the pLX and pCAMBIA vectors, the inventors assembled standardized units for plant delivery of the kanamycin resistance (NptII) and red fluorescent protein (DsRED) genes into the pLX-B2 (SEQ ID NO: 3) and pCAMBIA-derived vectors to obtain pLX-B2-NptII-DsRED (SEQ ID NO: 20) and GB1686 (SEQ ID NO: 27), respectively (FIG. 7A, 10C). *Agrobacterium* strains that contain pLX-B2-NptII-DsRED (pLX) (SEQ ID NO: 20) or GB1686 (SEQ ID NO: 27) were used in transient and stable transformation of *N. benthamiana* plants. Compared to GB1686, the pLX-B2 backbone significantly enhanced the DsRED accumulation in transient expression assays. In stable transformation assays, a similar number of kanamycin-resistant plantlets that showed DsRED fluorescence were obtained (FIG. 10C). The result indicates that the pLX- and pCAMBIA-based vectors tested have equal stable transformation efficiencies (FIG. 10C).

Therefore, whereas stable transformation efficiencies of the present invention and commercially available vectors are similar, transient expression yields obtained by the use of the pBBR1-based binary vectors of the present invention are higher than those obtained by use of the RK2- and pVS1-based binary vectors.

Example 8. CRISPR/Cas Delivery and High Efficiency of Plant Genome Editing Using the pLX Vector Series of the Present Invention To demonstrate that the binary vectors of the present invention can be used for CRISPR/Cas construct delivery and targeted genome mutagenesis, transient expression of components of a CRISPR/Cas system was evaluated. The pLX-B2-XT1-XT2-hCas9 (pLX) (SEQ ID NO: 19) vector and GB1108, a pCAMBIA-derived vector that has the pVS1 origin and comprises transcription units identical to those of pLX-B2-XT1-XT2-hCas9 (SEQ ID NO: 19) were delivered to *N. benthamiana* leaves by *A. tumefaciens* (FIG. 7C, 11A). The hCas9 gene was delivered with no sgRNA sequences as a control (CTRL). In infiltrated samples, BsmBI- and SpeI-site loss was predicted to occur in the XT1 and XT2 edited loci, respectively. The mutagenesis was confirmed by the appearance of cleavage-resistant bands in PCR/digestion assays (FIG. 11B). Compared to pDGB3, and consistent with the DsRED transient expression results, the pLX vector showed greater mutagenesis efficiency (FIG. 11B).

Therefore, genome mutagenesis obtained by the binary vectors of the present invention is higher than that obtained by use of a pVS1-based binary vector.

Example 9. Multiplexing of T-DNA Binary Vectors Using the pLX Vector Series of the Present Invention To demonstrate that the vectors generated in Example 1 can be multiplexed with compatible T-DNA binary vectors into A. tumefaciens cells and delivered to plants, the inventors designed the pLX-Z4 plasmid (SEQ ID NO: 9). pLX-Z4 is a novel T-DNA vector of low sequence similarity, and compatible with the pLX-B2 (SEQ ID NO: 3) and pLX-B3 (SEQ ID NO: 4) plasmids (FIG. 12, Table 3). pLX-B4 (SEQ ID NO: 5) and pLX-Z4 (SEQ ID NO: 9) are not compatible, since their selection relies on the same antibiotic, gentamicin. Additional features of pLX-Z4 (SEQ ID NO: 9) include small size, autonomous replication, and compatibility with Type IIS endonuclease-based and overlap-dependent cloning. The pLX-Z4 obtained as disclosed above is an improved pLX-R4 derivative with the T-DNA_2 cassette (SEQ ID NO: 2), and no BsmBI sites in the RK2-trfA and aacC1 genes. It incorporates the RK2 replication origin (SEQ ID NO: 107), lambda phage terminators (λ T1, SEQ ID NO: 110; and λ T2, SEQ ID NO: 111), and T-DNA border sequences from a succinamopine-type pTi, pTiBo542, and a second left border sequence (FIG. 12A). For cloning purposes, the pLX-Z4 T-DNA cassette includes the lacZα reporter, divergent BsaI and convergent BsmBI sites, and primer annealing regions with no sequence similarity and secondary structures and that allow the backbone linearization by inverse PCR. pLX-B2 (SEQ ID NO: 3) shows minimal sequence similarity with the pLX-Z4 backbone (SEQ ID NO: 9) (FIG. 12B). More extensive sequence analyses predicted that the pBBR1-based pLX vectors described in Examples 1 and 5 could be multiplexed with pLX-Z4, and a wide array of binary vectors commonly used by plant scientists (FIG. 12C).

To facilitate vector multiplexing, the inventors characterized a disarmed A. tumefaciens strain (C58C1-313) that is sensitive to antibiotics commonly used in the plasmid selection: C58C1-313 growth is inhibited by the presence of ampicillin, chloramphenicol, gentamicin, tetracycline, kanamycin, or spectinomycin (FIG. 13A). A pTi-repB fragment was amplified from the C58C1-313 cells using the 2050_F (SEQ ID NO: 30)/2051_R (SEQ ID NO: 31) primers, and sequenced. Phylogenetic analysis showed that C58C1-313 hosts an octopine-type Ti plasmid, which is stably retained (FIG. 13B, C). Thus, C58C1-313 is a disarmed A. tumefaciens strain of the octopine type that is suitable for the simultaneous use of multiple plasmids, since it shows sensitivity to several antibiotics. To confirm the results, the C58C1-313 strain was sequentially transformed with the pLX-B2 and pLX-Z4 derivatives disclosed in the present invention, which include, respectively, the pBBR1 origin (SEQ ID NO: 105) and the kanamycin resistance gene or the RK2 origin (SEQ ID NO: 107) and the gentamicin resistance gene (FIG. 13D). A C58C1-313 strain that simultaneously hosts the pLX-B2 and pLX-Z4 derivatives showed resistance to kanamycin and gentamicin, and grew in a medium supplemented with these antibiotics (FIG. 13D). In the same conditions, growth of C58C1-313, a strain that harbors no vectors, was inhibited (CTRL; FIG. 13O).

In Example 2, the pLX-B2-P$_{CRC}$:mTFP1 vector (SEQ ID NO: 23) including the pBBR1 origin (SEQ ID NO: 105), and kanamycin resistance was used to drive seed expression of the cyan fluorescent mTFP1. Under epifluorescence stereoscopes, cyan and red fluorescence can be imaged with no signal overlap. The inventors generated the pSN.5-P$_{PAP85}$:RFP vector (SEQ ID NO: 26) (FIG. 14A), a pCAMBIA derivative with the pVS1 origin, spectinomycin resistance and a transcription unit (P$_{PAP85}$:RFP:T$_{nos}$) that contains an A. thaliana seed-specific promoter from a seed storage protein gene (PAP85; AT3G22640), RFP and nopaline synthase terminator sequences. Details for the generation of the pSN.5-P$_{PAP85}$:RFP vector are disclosed above.

To show that vectors of the present invention (Example 1) can be multiplexed with commercially available binary vectors, the inventors used a two-vector/one-strain system to transform A. thaliana. The pLX-B2-P$_{CRC}$:mTFP1 (SEQ ID NO: 23) and pSN.5-P$_{PAP85}$:RFP (SEQ ID NO: 26) T-DNA binary vectors were inserted in A. tumefaciens C58C1-313 (FIG. 14A), and transformed into plants by floral dipping. Consistent with the Example 2 results and the mTFP1 expression, cyan fluorescence was detectable in seed collected from the Agrobacterium-treated plants (FIG. 14B); 53% of the mTFP1-expressing seeds also showed red fluorescence derived by RFP expression (FIG. 14B).

These results indicate that the binary vectors of the present invention can be multiplexed with compatible vectors, and used in a two-vector/one-strain system to deliver multiple and diverse T-DNA cassettes to plant cells.

Example 10. Gene Expression Control and Delivery of Synthetic Circuit Components to Plants by Multiplexing of Binary Vectors The inventors used a chemical expression switch to test whether the binary vectors of the present invention and the multiplexing strategy described in Example 9 could be applied to deliver synthetic circuit components to plants and to regulate gene expression. Ethanol was chosen as a chemical inducer of the expression switch because of its potential in fundamental research and commercial biotechnology applications.

P$_{EtOH}$ (SEQ ID NO: 35), a novel synthetic promoter that is activated by Aspergillus nidulans AlcR in the presence of ethanol, was designed. The P$_{EtOH}$ promoter (SEQ ID NO: 35) includes multiple AlcR DNA-binding sites derived from the A. nidulans alcM, alcR, aldA, alcA promoters, and a figwort mosaic virus 34S minimal promoter (FIG. 15A). An ethanol-responsive buffer gate was designed to sense ethanol as the input, and to produce a bright green fluorescent protein (NEON, output; FIG. 15B). To evaluate the two-vector/one-bacterial strain system for the delivery of synthetic circuit components, the gate elements were distributed into the gentamicin-selectable pLX-Z4-P$_{mas}$:RFP-AlcR (SEQ ID NO: 24) and the kanamycin-selectable pLX-B2-P$_{EtOH}$:NEON (SEQ ID NO: 25) vectors, which have the RK2 and pBBR1 origins respectively (FIG. 15C). pLX-Z4-P$_{mas}$:RFP-AlcR (SEQ ID NO: 24) codes for RFP (used as an expression control) and the A. nidulans AlcR transcription factor under the mannopine synthase promoter (P$_{mas}$), which directs constitutive expression in plants; whereas pLX-B2-P$_{EtOH}$:NEON (SEQ ID NO: 25) encodes the NEON sequence under P$_{EtOH}$, a synthetic promoter activated by AlcR in the presence of the inducer (FIG. 15C). Details for the vector generation are disclosed above.

The plasmids were introduced sequentially into A. tumefaciens C58C1-313, and selected using a gentamicin plus kanamycin medium to obtain the R-AlcR+P$_{EtOH}$:NEON strain. The R-AlcR+P$_{EtOH}$:NEON strain was infiltrated into N. benthamiana leaves, and plants were treated with water or ethanol. As anticipated, while the RFP fluorescence was visible in both conditions, the NEON fluorescence was significantly increased in the presence of the gate inducer (FIG. 16A). Circuit modeling requires quantitative characterization of genetic parts. To test whether the two-vector/one-strain expression system is compatible with medium-throughput analyses, leaf disks were collected from the R-AlcR+$P_{EtOH}$:NEON-infiltrated leaves, and placed in 96-well plates to evaluated the gate responses. At 24 h post-treatment (hpt), the gate function was maintained in leaf disks, since the NEON fluorescence was detected only in the presence of the gate input (FIG. 16B). Quantification of the output fluorescence intensity in intact leaf disks showed appropriate gate responsiveness and sensitivity, since 0.1% ethanol was sufficient to trigger >200-fold induction (FIG. 16C). NEON detection requires no lysis or substrate addition steps, which allowed measuring the gate kinetics in a continuous-read assay. In the conditions tested and compared to the water control, the ratio of NEON/RFP fluorescence intensity was significantly increased at 1.5 hpt and reached a plateau at 15 hpt (FIG. 16D).

The results show that the pBBR1-based and RK2-based pLX binary vectors of the present invention can be used to control gene expression in plants, and be coupled in a two-plasmid/one-strain system to allow multiple T-DNA delivery from *A. tumefaciens*. The binary vector system of the present invention is suitable for delivery of genetic circuit components, and their quantitative characterization in a medium-throughput scale.

The invention claimed is:

1. A binary vector comprising a nucleotide sequence selected from the group consisting of SEQ ID NO:3, SEQ ID NO:4, SEQ ID NO: 5, SEQ ID N0:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:28.

2. A binary vector system comprising:
(a) a first binary vector according to claim 1; and
(b) one or more additional binary vector(s).

3. A host cell comprising one or more binary vector(s) according to claim 1.

4. A host cell according to claim 3, wherein the host cell is a cell of a species of the phylum Proteobacteria.

5. A method for delivering at least one nucleotide sequence of interest in at least one host cell, or one eukaryotic cell or organism comprising: (a) introducing at least one nucleotide sequence of interest in at least one binary vector according to claim 1; and (b) contacting with or introducing into at least one host cell, or one eukaryotic cell or organism a linear or circular version of the binary vector(s) of step (a).

6. A host cell, eukaryotic cell or organism, regenerated cell, regenerated organism, progeny or seed obtainable by the method according to claim 5.

7. A method for delivering at least one nucleotide sequence of interest in at least one eukaryotic cell or organism comprising: (a) introducing at least one nucleotide sequence of interest in at least one binary vector according to claim 1; and (b) introducing the binary vector(s) of step (a) into a host cell; and (c) contacting with or introducing into at least one eukaryotic cell or organism the host cell of step (b).

8. A eukaryotic cell or organism, regenerated cell, regenerated organism, progeny or seed obtainable by the method according to claim 7.

9. A method according to claim 7, wherein the host cell is a cell of a species of the phylum Proteobacteria.

10. A method according to claim 9, wherein the eukaryotic cell or organism is a plant cell or plant.

11. A plant cell or plant, regenerated plant cell, regenerated plant, progeny or seed obtainable by the method according to claim 10.

12. A kit comprising: (a) the binary vector according to claim 1; and (b) instructions for using the kit.

13. A kit comprising: (a) the host cell according to claim 3; and (b) instructions for using the kit.

14. A method for obtaining a binary vector comprising at least one nucleotide sequence of interest, said method comprising assembling at least one nucleotide sequence of interest into at least one binary vector according to claim 1.

15. A binary vector obtained from the method according to claim 14.

16. A host cell comprising one or more binary vector(s) according to claim 15.

* * * * *

SEQUENCE LISTING

```
<160> NUMBER OF SEQ ID NOS: 116

<210> SEQ ID NO 1
<211> LENGTH: 814
<212> TYPE: DNA
<213> ORGANISM: Artificial Sequence
<220> FEATURE:
<223> OTHER INFORMATION: T-DNA_1 synthetic construct
<220> FEATURE:
<221> NAME/KEY: terminator
<222> LOCATION: (25)..(72)
<223> OTHER INFORMATION: Bacterial transcription terminator
<220> FEATURE:
<221> NAME/KEY: misc_feature
<222> LOCATION: (73)..(221)
<223> OTHER INFORMATION: T-DNA border
<220> FEATURE:
<221> NAME/KEY: primer_bind
<222> LOCATION: (241)..(259)
<223> OTHER INFORMATION: Annealing region of the X210_R primer
<220> FEATURE:
<221> NAME/KEY: misc_binding
<222> LOCATION: (253)..(258)
<223> OTHER INFORMATION: BsmBI site
<220> FEATURE:
<221> NAME/KEY: misc_binding
<222> LOCATION: (265)..(270)
<223> OTHER INFORMATION: BsaI site
<220> FEATURE:
<221> NAME/KEY: gene
<222> LOCATION: (299)..(475)
<223> OTHER INFORMATION: LacZ alpha
<220> FEATURE:
<221> NAME/KEY: misc_binding
<222> LOCATION: (580)..(585)
<223> OTHER INFORMATION: BsaI site
<220> FEATURE:
<221> NAME/KEY: primer_bind
<222> LOCATION: (591)..(610)
<223> OTHER INFORMATION: Annealing region of the X211_F primer
<220> FEATURE:
<221> NAME/KEY: misc_binding
<222> LOCATION: (596)..(601)
<223> OTHER INFORMATION: BsmBI site
<220> FEATURE:
<221> NAME/KEY: misc_feature
<222> LOCATION: (629)..(740)
<223> OTHER INFORMATION: T-DNA border
<220> FEATURE:
<221> NAME/KEY: terminator
<222> LOCATION: (741)..(781)
<223> OTHER INFORMATION: Bacterial transcription terminator

<400> SEQUENCE: 1
ccatcatcag ttcggtggtc ttccgacgaa caataaggcc gcaaatcgcg gccttttta        60 ttgataacaa aaccggctca gttctgcgta gaaaccaaca tgcaagctcc accgggtgca     120
```

| | |
|---|---|
| aagcggcagc ggcggcagga tatattcaat tgtaaatggc ttcatgtccg ggaaatctac | 180 |
| tggtggcagg atatattgtg gtgtaaacaa tggagaaaaa gattaattaa gtactagtag | 240 |
| cctggtcgaa accgtctcag gagagagacc aaaagcaaaa acccgccgaa gcgggttact | 300 |
| agcgccattc gccattcaga gagcggagct gctgcgacgg acgatcggta cgcgcctctt | 360 |
| cgctattacg ccaactggcg aaaggtggat gtgctgcaag gcgattaagt tgggtaacgc | 420 |
| cagggttttc ccagtcacga cgttgtagta ccacggcaag gctatctgta atcattgttg | 480 |
| tactccggtt aggacggatt gggaactggc taactcaaaa tccacacatt atacgagccg | 540 |
| gaagcataaa gtgtaaagcc tggggtgcct aatgagtgag gtctctcgct gtcaggagac | 600 |
| gggacaagga tgcgagctag cctgcaggaa ttgttgattt tgtgatgact gatggcagga | 660 |
| tatatgcggt tgtaattcat ttttattgtc taaatttctg tatttgtttg tttgttcggt | 720 |
| tgtaaatttt tttggaagaa caagaaaaga aaaacaccc gttagggtgt ttttagttag | 780 |
| tgtggcgcgc cgacttgcga catgcggtcc tttg | 814 |

<210> SEQ ID NO 2
<211> LENGTH: 750
<212> TYPE: DNA
<213> ORGANISM: Artificial Sequence
<220> FEATURE:
<223> OTHER INFORMATION: T-DNA_2 synthetic construct
<220> FEATURE:
<221> NAME/KEY: terminator
<222> LOCATION: (37)..(68)
<223> OTHER INFORMATION: Bacterial transcription terminator
<220> FEATURE:
<221> NAME/KEY: misc_feature
<222> LOCATION: (69)..(156)
<223> OTHER INFORMATION: T-DNA border
<220> FEATURE:
<221> NAME/KEY: primer_bind
<222> LOCATION: (169)..(187)
<223> OTHER INFORMATION: Annealing region of the X210_R primer
<220> FEATURE:
<221> NAME/KEY: misc_binding
<222> LOCATION: (181)..(186)
<223> OTHER INFORMATION: BsmBI site
<220> FEATURE:
<221> NAME/KEY: misc_binding
<222> LOCATION: (193)..(198)
<223> OTHER INFORMATION: BsaI site
<220> FEATURE:
<221> NAME/KEY: gene
<222> LOCATION: (227)..(403)
<223> OTHER INFORMATION: LacZ alpha
<220> FEATURE:
<221> NAME/KEY: misc_binding
<222> LOCATION: (508)..(513)
<223> OTHER INFORMATION: BsaI site
<220> FEATURE:
<221> NAME/KEY: primer_bind
<222> LOCATION: (519)..(538)
<223> OTHER INFORMATION: Annealing region of the X211_F primer
<220> FEATURE:
<221> NAME/KEY: misc_binding
<222> LOCATION: (524)..(529)
<223> OTHER INFORMATION: BsmBI site
<220> FEATURE:
<221> NAME/KEY: misc_feature
<222> LOCATION: (551)..(666)
<223> OTHER INFORMATION: T-DNA border
<220> FEATURE:
<221> NAME/KEY: terminator
<222> LOCATION: (667)..(719)
<223> OTHER INFORMATION: Bacterial transcription terminator

<400> SEQUENCE: 2

| | |
|---|---|
| aaaaggatct caagaagatc ctttgatctt ttctacaggc ctgctggtaa tcgcaggcct | 60 |

| | |
|---|---|
| ttttattttg gcaggatata ttgtggtgta aacacttacc gcacctctgc agcagcggca | 120 |
| ggatatatgg cagtgtaaac tccattttcg aacgcgttaa ttaagtagcc tggtcgaaac | 180 |
| cgtctcagga gagagaccaa aagcaaaaac ccgccgaagc gggttactag cgccattcgc | 240 |
| cattcagaga gcggagctgc tgcgacggac gatcggtacg cgcctcttcg ctattacgcc | 300 |
| aactggcgaa aggtggatgt gctgcaaggc gattaagttg ggtaacgcca gggttttccc | 360 |
| agtcacgacg ttgtagtacc acggcaaggc tatctgtaat cattgttgta ctccggttag | 420 |
| gacggattgg gaactggcta actcaaaatc cacacattat acgagccgga agcataaagt | 480 |
| gtaaagcctg gggtgcctaa tgagtgaggt ctctcgctgt caggagacgg gacaaggatg | 540 |
| cgcctgcagg ttgttgatga tgtgatgact gatggcagga tatatgtggt tgtaattcat | 600 |
| ttctaccgtg taatttactg tattttttg tttgttcgtt cgtttgtaaa aatatttttt | 660 |
| ggaagcaaaa aattagcgca agaagacaaa aatcaccttg cgctaatgct ctgttacagg | 720 |
| cgcgccaatt tacccaacaa ctccgcggcc | 750 |

<210> SEQ ID NO 3
<211> LENGTH: 3287
<212> TYPE: DNA
<213> ORGANISM: Artificial Sequence
<220> FEATURE:
<223> OTHER INFORMATION: pLX-B2 plasmid

<400> SEQUENCE: 3

| | |
|---|---|
| ccatcatcag ttcggtggtc ttccgacgaa caataaggcc gcaaatcgcg gcctttttta | 60 |
| ttgataacaa aaccggctca gttctgcgta gaaaccaaca tgcaagctcc accgggtgca | 120 |
| aagcggcagc ggcggcagga tatattcaat tgtaaatggc ttcatgtccg ggaaatctac | 180 |
| tggtggcagg atatattgtg gtgtaaacaa tggagaaaaa gattaattaa gtactagtag | 240 |
| cctggtcgaa accgtctcag gagagagacc aaaagcaaaa acccgccgaa gcgggttact | 300 |
| agcgccattc gccattcaga gagcggagct gctgcgacgg acgatcggta cgcgcctctt | 360 |
| cgctattacg ccaactggcg aaaggtggat gtgctgcaag gcgattaagt tgggtaacgc | 420 |
| cagggttttc ccagtcacga cgttgtagta ccacggcaag gctatctgta atcattgttg | 480 |
| tactccggtt aggacggatt gggaactggc taactcaaaa tccacacatt atacgagccg | 540 |
| gaagcataaa gtgtaaagcc tggggtgcct aatgagtgag gtctctcgct gtcaggagac | 600 |
| gggacaagga tgcgagctag cctgcaggaa ttgttgattt tgtgatgact gatggcagga | 660 |
| tatatgcggt tgtaattcat ttttattgtc taaatttctg tatttgtttg tttgttcggt | 720 |
| tgtaaatttt tttggaagaa caagaaaaga aaaacacccc gttagggtgt ttttagttag | 780 |
| tgtggcgcgc cgacttgcga catgcggtcc tttgcaatca actattagaa aaattcatcc | 840 |
| agcatcagat gaaattgcag tttgttcata tccggattat caatgccata tttctgaaac | 900 |
| agacgttttt gcaggctcgg gctaaattcg cccaggcagt tccacagaat ggccagatcc | 960 |
| tgataacgat ccgcaatgcc cacacggccc acatcaatgc agccaatcag tttgccttca | 1020 |
| tcgaaaatca ggttatccag gctaaaatcc ccgtgggtca ccacgctatc cgggctaaac | 1080 |
| ggcagcagtt tatgcatttc tttccacacc tgttccaccg ccagccgtt acgttcatca | 1140 |
| tcaaaatcgc tcgcatccac caggccgttg ttcatacggc tctgcgcctg gccagacga | 1200 |
| aacacacgat cgctgttaaa cgggcagttg cacaccggaa tgctatgcag acgacgcaga | 1260 |
| aacacggcca gcgcatccac aatgttttcg ccgctatccg gatattcttc cagcacctga | 1320 |

| | |
|---|---|
| aacgcggttt tgcccggaat cgcggtggtc agcagccacg catcatccgg ggtgcgaata | 1380 |
| aaatgtttaa tggtcggcag cggcataaat tcggtcagcc agttcagacg caccatttca | 1440 |
| tcggtcacat cgttcgccac gctgcctttg ccatgtttca gaaacagttc cggcgcatcc | 1500 |
| ggtttgccat acagacgata aatggtcgcg ccgctctgac ccacgttatc acgcgcccat | 1560 |
| ttatagccat acagatccgc atccatgttg ctgttcagac gcggacggct acagctcgtt | 1620 |
| tcacgctgaa tatggctcat aacacccctt gtattactgt ttatgtaagc agacagtttt | 1680 |
| attgttcatg atgatatatt tttatcttgt gcaatgtaac atcagagatt ttgagacaca | 1740 |
| agatcggatt ggcggttatg cggttctacc ggcgcggcag cgttacccgt gtcggcggct | 1800 |
| ccaacggctc gccatcgtcc agaaaacacg gctcatcggg catcggcagg cgctgctgcc | 1860 |
| cgcgccgttc ccattcctcc gtttcggtca aggctggcag gtctggttcc atgcccggaa | 1920 |
| tgccgggctg gctgggcggc tcctcgccgg ggccggtcgg tagttgctgc tcgcccggat | 1980 |
| acagggtcgg gatgcggcgc aggtcgccat gccccaacag cgattcgtcc tggtcgtcgt | 2040 |
| gatcaaccac cacggcggca ctgaacaccg acaggcgcaa ctggtcgcgg ggctggcccc | 2100 |
| acgccacgcg gtcattgacc acgtaggccg acacggtgcc ggggccgttg agcttcacga | 2160 |
| cggagatcca gcgctcggcc accaagtcct tgactgcgta ttggaccgtc cgcaaagaac | 2220 |
| gtccgatgag cttggaaagt gtcttctggc tgaccaccac ggcgttctgg tggcccatct | 2280 |
| gcgccacgag gtgatgcagc agcattgccg ccgtgggttt cctcgcaata agcccggccc | 2340 |
| acgcctcatg cgctttgcgt tccgtttgca cccagtgacc gggcttgttc ttggcttgaa | 2400 |
| tgccgatttc tctggactgc gtggccatgc ttatctccat gcggtagggg tgccgcacgg | 2460 |
| ttgcggcacc atgcgcaatc agctgcaact tttcggcagc gcgacaacaa ttatgcgttg | 2520 |
| cgtaaaagtg gcagtcaatt acagattttc tttaacctac gcaatgagct attgcggggg | 2580 |
| gtgccgcaat gagctgttgc gtaccccct tttttaagtt gttgattttt aagtctttcg | 2640 |
| catttcgccc tatatctagt tctttggtgc ccaaagaagg gcacccctgc ggggttcccc | 2700 |
| cacgccttcg gcgcggctcc ccctccggca aaaagtggcc cctccggggc ttgttgatcg | 2760 |
| actgcgcggc cttcggcctt gcccaaggtg gcgctgcccc cttggaaccc cgcactcgc | 2820 |
| cgccgtgagg ctcgggggc aggcgggcgg gcttcgccct tcgactgccc ccactcgcat | 2880 |
| aggcttgggt cgttccaggc gcgtcaaggc caagccgctg cgcggtcgct gcgcgagcct | 2940 |
| tgaccgcct tccacttggt gtccaaccgg caagcgaagc gcgcaggccg caggccggag | 3000 |
| gcttttcccc agagaaaatt aaaaaaattg atggggcaag gccgcaggcc gcgcagttgg | 3060 |
| agccggtggg tatgtggtcg aaggctgggt agccggtggg caatccctgt ggtcaagctc | 3120 |
| gtgggcaggc gcagcctgtc catcagcttg tccagcaggg ttgtccacgg gccgagcgaa | 3180 |
| gcgagccagc cggtggccgc tcgcggccat cgtccacata tccacgggct ggcaagggag | 3240 |
| cgcagcgacc gcgcagggcg aagcccggag agcaagcccg taggggg | 3287 |

<210> SEQ ID NO 4
<211> LENGTH: 3349
<212> TYPE: DNA
<213> ORGANISM: Artificial Sequence
<220> FEATURE:
<223> OTHER INFORMATION: pLX-B3 plasmid

<400> SEQUENCE: 4

| | |
|---|---|
| ccatcatcag ttcggtggtc ttccgacgaa caataaggcc gcaaatcgcg gccttttta | 60 |
| ttgataacaa aaccggctca gttctgcgta gaaaccaaca tgcaagctcc accgggtgca | 120 |

```
aagcggcagc ggcggcagga tatattcaat tgtaaatggc ttcatgtccg ggaaatctac    180
tggtggcagg atatattgtg gtgtaaacaa tggagaaaaa gattaattaa gtactagtag    240
cctggtcgaa accgtctcag gagagagacc aaaagcaaaa acccgccgaa gcgggttact    300
agcgccattc gccattcaga gagcggagct gctgcgacgg acgatcggta cgcgcctctt    360
cgctattacg ccaactggcg aaaggtggat gtgctgcaag gcgattaagt tgggtaacgc    420
cagggttttc ccagtcacga cgttgtagta ccacggcaag gctatctgta atcattgttg    480
tactccggtt aggacggatt gggaactggc taactcaaaa tccacacatt atacgagccg    540
gaagcataaa gtgtaaagcc tggggtgcct aatgagtgag gtctctcgct gtcaggagac    600
gggacaagga tgcgagctag cctgcaggaa ttgttgattt tgtgatgact gatggcagga    660
tatatgcggt tgtaattcat ttttattgtc taaatttctg tatttgtttg tttgttcggt    720
tgtaaatttt tttggaagaa caagaaaaga aaaacacccc gttagggtgt ttttagttag    780
tgtggcgcgc cgacttgcga catgcggtcc tttgttattt gccgactacc ttggtgatct    840
cgcctttcac gtagtggaca aattcttcca actgatctgc gcgcgaggcc aagcgatctt    900
cttcttgtcc aagataagcc tgtctagctt caagtatgac gggctgatac tgggccggca    960
ggcgctccat tgcccagtcg gcagcgacat ccttcggcgc gattttgccg gttactgcgc   1020
tgtaccaaat gcgggacaac gtaagcacta catttcgctc atcgccagcc cagtcgggcg   1080
gcgagttcca tagcgttaag gtttcattta gcgcctcaaa tagatcctgt tcaggaaccg   1140
gatcaaagag ttcctccgcc gctggaccta ccaaggcaac gctatgttct cttgcttttg   1200
tcagcaagat agccagatca atgtcgatcg tggctggctc gaagatacct gcaagaatgt   1260
cattgcgctg ccattctcca aattgcagtt cgcgcttagc tggataacgc cacggaatga   1320
tgtcgtcgtg cacaacaatg gtgacttcta cagcgcggag aatctcgctc tctccagggg   1380
aagccgaagt ttccaaaagg tcgttgatca aagctcgccg cgttgtttca tcaagcctta   1440
cggtcaccgt aaccagcaaa tcaatatcac tgtgtggctt caggccgcca tccactgcgg   1500
agccgtacaa atgtacggcc agcaacgtcg gttcgagatg gcgctcgatg acgccaacta   1560
cctctgatag ttgagtcgat acttcggcga tcaccgcttc cctcatgatg tttaactttg   1620
ttttagggcg actgccctgc tgcgtaacat cgttgctgct ccataacatc aaacatcgac   1680
ccacggcgta acgcgcttgc tgcttggatg cccgaggcat agactgtacc ccaaaaaaac   1740
agtcataaca agccatgaaa accgccactg cgccgttacc accgctgcgt tcggtcaagg   1800
ttcgatcgga ttggcggtta tgcggttcta ccggcgcggc agcgttaccc gtgtcggcgg   1860
ctccaacggc tcgccatcgt ccagaaaaca cggctcatcg gcatcggca ggcgctgctg    1920
cccgcgccgt tccattcct ccgtttcggt caaggctgg aggtctggtt ccatgcccgg     1980
aatgccgggc tggctgggcg gctcctcgcc ggggccggtc ggtagttgct gctcgcccgg   2040
atacagggtc gggatgcggc gcaggtcgcc atgcccaac agcgattcgt cctggtcgtc    2100
gtgatcaacc accacggcgg cactgaacac cgacaggcgc aactggtcgc ggggctggcc   2160
ccacgccacg cggtcattga ccacgtaggc cgacacggtg ccggggccgt tgagcttcac   2220
gacggagatc cagcgctcgg ccaccaagtc cttgactgcg tattggaccg tccgcaaaga   2280
acgtccgatg agcttggaaa gtgtcttctg gctgaccacc acggcgttct ggtggcccat   2340
ctgcgccacg aggtgatgca gcagcattgc cgccgtgggt ttcctcgcaa taagcccggc   2400
ccacgcctca tgcgctttgc gttccgtttg cacccagtga ccgggcttgt tcttggcttg   2460
```

| | |
|---|---|
| aatgccgatt tctctggact gcgtggccat gcttatctcc atgcggtagg ggtgccgcac | 2520 |
| ggttgcggca ccatgcgcaa tcagctgcaa cttttcggca gcgcgacaac aattatgcgt | 2580 |
| tgcgtaaaag tggcagtcaa ttacagattt tctttaacct acgcaatgag ctattgcggg | 2640 |
| gggtgccgca atgagctgtt gcgtaccccc cttttttaag ttgttgattt ttaagtcttt | 2700 |
| cgcatttcgc cctatatcta gttctttggt gcccaaagaa gggcacccct gcggggttcc | 2760 |
| cccacgcctt cggcgcggct cccccctccgg caaaaagtgg cccctccggg gcttgttgat | 2820 |
| cgactgcgcg gccttcggcc ttgcccaagg tggcgctgcc cccttggaac ccccgcactc | 2880 |
| gccgccgtga ggctcggggg gcaggcgggc gggcttcgcc cttcgactgc ccccactcgc | 2940 |
| ataggcttgg gtcgttccag gcgcgtcaag gccaagccgc tgcgcggtcg ctgcgcgagc | 3000 |
| cttgacccgc cttccacttg gtgtccaacc ggcaagcgaa gcgcgcaggc cgcaggccgg | 3060 |
| aggcttttcc ccagagaaaa ttaaaaaaat tgatggggca aggccgcagg ccgcgcagtt | 3120 |
| ggagccggtg ggtatgtggt cgaaggctgg gtagccggtg ggcaatccct gtggtcaagc | 3180 |
| tcgtgggcag gcgcagcctg tccatcagct tgtccagcag ggttgtccac gggccgagcg | 3240 |
| aagcgagcca gccggtggcc gctcgcggcc atcgtccaca tatccacggg ctggcaaggg | 3300 |
| agcgcagcga ccgcgcaggg cgaagcccgg agagcaagcc cgtaggggg | 3349 |

<210> SEQ ID NO 5
<211> LENGTH: 3165
<212> TYPE: DNA
<213> ORGANISM: Artificial Sequence
<220> FEATURE:
<223> OTHER INFORMATION: pLX-B4 plasmid

<400> SEQUENCE: 5

| | |
|---|---|
| ccatcatcag ttcggtggtc ttccgacgaa caataaggcc gcaaatcgcg gccttttta | 60 |
| ttgataacaa aaccggctca gttctgcgta gaaaccaaca tgcaagctcc accgggtgca | 120 |
| aagcggcagc ggcggcagga tatattcaat tgtaaatggc ttcatgtccg ggaaatctac | 180 |
| tggtggcagg atatattgtg gtgtaaacaa tggagaaaaa gattaattaa gtactagtag | 240 |
| cctggtcgaa accgtctcag gagagagacc aaaagcaaaa acccgccgaa gcgggttact | 300 |
| agcgccattc gccattcaga gagcggagct gctgcgacgg acgatcggta cgcgcctctt | 360 |
| cgctattacg ccaactggcg aaaggtggat gtgctgcaag gcgattaagt tgggtaacgc | 420 |
| cagggttttc ccagtcacga cgttgtagta ccacggcaag gctatctgta atcattgttg | 480 |
| tactccggtt aggacggatt gggaactggc taactcaaaa tccacacatt atacgagccg | 540 |
| gaagcataaa gtgtaaagcc tggggtgcct aatgagtgag gtctctcgct gtcaggagac | 600 |
| gggacaagga tgcgagctag cctgcaggaa ttgttgattt tgtgatgact gatggcagga | 660 |
| tatatgcggt tgtaattcat ttttattgtc taaatttctg tatttgtttg tttgttcggt | 720 |
| tgtaaattt tttggaagaa caagaaaaga aaaacaccc gttagggtgt tttagttag | 780 |
| tgtggcgcgc cgacttgcga catgcggtcc tttgcaattt acccaacaac tccgcggccg | 840 |
| ggaagccgat ctcggcttga acgaattgtt aggtggcggt acttgggtcg atatcaaagt | 900 |
| gcatcacttc ttcccgtatg cccaactttg tatagagagc cactgcggga tcgtcaccgt | 960 |
| aatctgcttg cacgtagatc acataagcac caagcgcgtt ggcctcatgc ttgaggagat | 1020 |
| tgatgagcgc ggtggcaatg ccctgcctcc ggtgctctcc ggagactgcg agatcataga | 1080 |
| tatagatctc actacgcggc tgctcaaact tgggcagaac gtaagccgcg agagcgccaa | 1140 |
| caaccgcttc ttggtcgaag gcagcaagcg cgatgaatgt cttactacgg agcaagttcc | 1200 |

```
cgaggtaatc ggagtccggc tgatgttggg agtaggtggc tacgtctccg aactcacgac   1260
cgaaaagatc aagagcagcc cgcatggatt tgacttggtc agggccgagc ctacatgtgc   1320
gaatgatgcc catacttgag ccacctaact ttgttttagg gcgactgccc tgctgcgtaa   1380
catcgttgct gctgcgtaac atcgttgctg ctccataaca tcaaacatcg acccacggcg   1440
taacgcgctt gctgcttgga tgcccgaggc ataggctgta caaaaaaaca gtcataacaa   1500
gccatgaaaa ccgccactgc gccgttacca ccgctgcgtt cggtcaaggt tctgaccag    1560 ttgcgtgagc gcatacgcta cttgcattac agtttacgaa ccgaacaggc ttatgtcaag   1620
atcggattgg cggttatgcg gttctaccgg cgcggcagcg ttacccgtgt cggcggctcc   1680
aacggctcgc catcgtccag aaaacacggc tcatcgggca tcggcaggcg ctgctgcccg   1740
cgccgttccc attcctccgt ttcggtcaag gctggcaggt ctggttccat gcccggaatg   1800
ccgggctggc tgggcggctc ctcgccgggg ccggtcggta gttgctgctc gcccggatac   1860
agggtcggga tgcggcgcag gtcgccatgc cccaacagcg attcgtcctg gtcgtcgtga   1920
tcaaccacca cggcggcact gaacaccgac aggcgcaact ggtcgcgggg ctggcccac    1980 gccacgcggt cattgaccac gtaggccgac acggtgccgg ggccgttgag cttcacgacg   2040
gagatccagc gctcggccac caagtccttg actgcgtatt ggaccgtccg caaagaacgt   2100
ccgatgagct tggaaagtgt cttctggctg accaccacgg cgttctggtg gcccatctgc   2160
gccacgaggt gatgcagcag cattgccgcc gtgggtttcc tcgcaataag cccggcccac   2220
gcctcatgcg ctttgcgttc cgtttgcacc cagtgaccgg gcttgttctt ggcttgaatg   2280
ccgatttctc tggactgcgt ggccatgctt atctccatgc ggtaggggtg ccgcacggtt   2340
gcggcaccat gcgcaatcag ctgcaacttt tcggcagcgc gacaacaatt atgcgttgcg   2400
taaaagtggc agtcaattac agattttctt taacctacgc aatgagctat gcggggggt    2460 gccgcaatga gctgttgcgt acccccctttt tttaagttgt tgattttttaa gtctttcgca   2520 tttcgcccta tatctagttc tttggtgccc aaagaagggc accctgcgg ggttccccca    2580 cgccttcggc gcggctcccc ctccggcaaa aagtggcccc tccggggctt gttgatcgac   2640
tgcgcggcct tcggccttgc ccaaggtggc gctgccccct tggaacccc gcactcgccg    2700 ccgtgaggct cggggggcag gcgggcgggc ttcgcccttc gactgccccc actcgcatag   2760
gcttgggtcg ttccaggcgc gtcaaggcca agccgctgcg cggtcgctgc gcgagccttg   2820
acccgccttc cacttggtgt ccaaccggca agcgaagcgc gcaggccgca ggccggaggc   2880
tttctcccag agaaaattaa aaaaattgat ggggcaaggc cgcaggccgc gcagttggag   2940
ccggtgggta tgtggtcgaa ggctgggtag ccggtgggca atccctgtgg tcaagctcgt   3000
gggcaggcgc agcctgtcca tcagcttgtc cagcagggtt gtccacgggc cgagcgaagc   3060
gagccagccg gtggccgctc gcggccatcg tccacatatc cacgggctgg caagggagcg   3120
cagcgaccgc gcagggcgaa gcccggagag caagcccgta ggggg                   3165
```

<210> SEQ ID NO 6
<211> LENGTH: 3987
<212> TYPE: DNA
<213> ORGANISM: Artificial Sequence
<220> FEATURE:
<223> OTHER INFORMATION: pLX-R2 plasmid

<400> SEQUENCE: 6

```
ccatcatcag ttcggtggtc ttccgacgaa caataaggcc gcaaatcgcg gccttttttta    60
```

-continued

| | |
|---|---|
| ttgataacaa aaccggctca gttctgcgta gaaaccaaca tgcaagctcc accgggtgca | 120 |
| aagcggcagc ggcggcagga tatattcaat tgtaaatggc ttcatgtccg ggaaatctac | 180 |
| tggtggcagg atatattgtg gtgtaaacaa tggagaaaaa gattaattaa gtactagtag | 240 |
| cctggtcgaa accgtctcag gagagagacc aaaagcaaaa acccgccgaa gcgggttact | 300 |
| agcgccattc gccattcaga gagcggagct gctgcgacgg acgatcggta cgcgcctctt | 360 |
| cgctattacg ccaactggcg aaaggtggat gtgctgcaag gcgattaagt tgggtaacgc | 420 |
| cagggttttc ccagtcacga cgttgtagta ccacggcaag gctatctgta atcattgttg | 480 |
| tactccggtt aggacggatt gggaactggc taactcaaaa tccacacatt atacgagccg | 540 |
| gaagcataaa gtgtaaagcc tggggtgcct aatgagtgag gtctctcgct gtcaggagac | 600 |
| gggacaagga tgcgagctag cctgcaggaa ttgttgattt tgtgatgact gatggcagga | 660 |
| tatatgcggt tgtaattcat ttttattgtc taaatttctg tatttgtttg tttgttcggt | 720 |
| tgtaaatttt tttggaagaa caagaaaaga aaaacaccc gttagggtgt ttttagttag | 780 |
| tgtggcgcgc cgacttgcga catgcggtcc tttgcaatca actattagaa aaattcatcc | 840 |
| agcatcagat gaaattgcag tttgttcata tccggattat caatgccata tttctgaaac | 900 |
| agacgttttt gcaggctcgg gctaaattcg cccaggcagt tccacagaat ggccagatcc | 960 |
| tgataacgat ccgcaatgcc cacacggccc acatcaatgc agccaatcag tttgccttca | 1020 |
| tcgaaaatca ggttatccag gctaaaatcg ccgtgggtca ccacgctatc cgggctaaac | 1080 |
| ggcagcagtt tatgcatttc tttccacacc tgttccaccg gccagccgtt acgttcatca | 1140 |
| tcaaaatcgc tcgcatccac caggccgttg ttcatacggc tctgcgcctg gccagacga | 1200 |
| aacacacgat cgctgttaaa cgggcagttg cacaccggaa tgctatgcag acgacgcaga | 1260 |
| aacacggcca gcgcatccac aatgttttcg ccgctatccg gatattcttc cagcacctga | 1320 |
| aacgcggttt tgcccggaat cgcggtggtc agcagccacg catcatccgg ggtgcgaata | 1380 |
| aaatgtttaa tggtcggcag cggcataaat tcggtcagcc agttcagacg caccatttca | 1440 |
| tcggtcacat cgttcgccac gctgcctttg ccatgtttca gaaacagttc cggcgcatcc | 1500 |
| ggtttgccat acagacgata aatggtcgcg ccgctctgac ccacgttatc acgcgcccat | 1560 |
| ttatagccat acagatccgc atccatgttg ctgttcagac gcggacggct acagctcgtt | 1620 |
| tcacgctgaa tatggctcat aacacccctt gtattactgt ttatgtaagc agacagtttt | 1680 |
| attgttcatg atgatatatt tttatcttgt gcaatgtaac atcagagatt ttgagacaca | 1740 |
| agatcggatt ggcggttatg cggttgcgat gcaggtggct gctgaacccc cagccggaac | 1800 |
| tgaccccaca aggccctagc gtttgcaatg caccaggtca tcattgaccc aggcgtgttc | 1860 |
| caccaggccg ctgcctcgca actcttcgca ggcttcgccg acctgctcgc gccacttctt | 1920 |
| cacgcgggtg gaatccgatc cgcacatgag gcggaaggtt tccagcttga gcgggtacgg | 1980 |
| ctcccggtgc gagctgaaat agtcgaacat ccgtcgggcc gtcggcgaca gcttgcggta | 2040 |
| cttctcccat atgaatttcg tgtagtggtc gccagcaaac agcacgacga tttcctcgtc | 2100 |
| gatcaggacc tggcaacggg acgttttctt gccacggtcc aggacgcgga agcggtgcag | 2160 |
| cagcgacacc gattccaggt gcccaacgcg gtcggacgtg aagcccatcg ccgtcgcctg | 2220 |
| taggcgcgac aggcattcct cggccttcgt gtaataccgg ccattgatcg accagcccag | 2280 |
| gtcctggcaa agctcgtaga acgtgaaggt gatcggctcg ccgatagggg tgcgcttcgc | 2340 |
| gtactccaac acctgctgcc acaccagttc gtcatcgtcg gcccgcagct cgacgccggt | 2400 |
| gtaggtgatc ttcacgtcct tgttgacgtg gaaaatgacc ttgttttgca gcgcctcgcg | 2460 |

```
cgggatttc  ttgttgcgcg  tggtgaacag  ggcagagcgg  gccgtgtcgt  ttggcatcgc   2520
tcgcatcgtg  tccggccacg  gcgcaatatc  gaacaaggaa  agctgcattt  ccttgatctg   2580
ctgcttcgtg  tgtttcagca  acgcggcctg  cttggcttcg  ctgacctgtt  ttgccaggtc   2640
ctcgccggcg  gttttcgct   tcttggtcgt  catagttcct  cgcgtgtcga  tggtcatcga   2700
cttcgccaaa  cctgccgcct  cctgttcgag  acgacgcgaa  cgctccacgg  cggccgatgg   2760
cgcgggcagg  gcaggggag   ccagttgcac  gctgtcgcgc  tcgatcttgg  ccgtagcttg   2820
ctggactatc  gagccgacgg  actggaaggt  ttcgcggggc  gcacgcatga  cggtgcggct   2880
tgcgatggtt  tcggcatcct  cggcggaaaa  ccccgcgtcg  atcagttctt  gcctgtatgc   2940
cttccggtca  aacgtccgat  tcattcaccc  tccttgcggg  attgccccgg  aattaattcc   3000
ccggatcgat  ccgtcgatct  tgatcccctg  cgccatcaga  tccttggcgg  caagaaagcc   3060
atccagttta  ctttgcaggg  cttcccaacc  ttaccagagg  gcgcccagc   tggcaattcc   3120
ggttcgcttg  ctgtccataa  aaccgccag   tctagctatc  gccatgtaag  cccactgcaa   3180
gctacctgct  ttctctttgc  gcttgcgttt  tccttgtcc   agatagccca  gtagctgaca   3240
ttcatccggg  gtcagcaccg  tttctgcgga  ctggctttct  acgtggctgc  cattttggg    3300
gtgaggccgt  tcgcggccga  ggggcgcagc  cctgggggg   atgggaggcc  cgcgttagcg   3360
ggccgggagg  gttcgagaag  ggggggcacc  cccccttcggc  gtgcgcggtc  acgcgcacag   3420
ggcgcagccc  tggttaaaaa  caaggtttat  aaatattggt  ttaaaagcag  gttaaaagac   3480
aggttagcgg  tggccgaaaa  acgggcgaa   acccttgcaa  atgctggatt  ttctgcctgt   3540
ggacagcccc  tcaaatgtca  ataggtgcgc  ccctcatctg  tcagcactct  gccctcaag    3600
tgtcaaggat  cgcgcccctc  atctgtcagt  agtcgcgccc  ctcaagtgtc  aataccgcag   3660
ggcacttatc  cccaggcttg  tccacatcat  ctgtgggaaa  ctcgcgtaaa  atcaggcgtt   3720
ttcgccgatt  tgcgaggctg  gccagctcca  cgtcgccggc  cgaaatcgag  cctgcccctc   3780
atctgtcaac  gccgcgccgg  gtgagtcggc  ccctcaagtg  tcaacgtccg  ccctcatct    3840
gtcagtgagg  gccaagtttt  ccgcgaggta  tccacaacgc  cggcggccct  acatggctct   3900
gctgtagtga  gtgggttgcg  ctccggcagc  ggtcctgatc  ccccgcagaa  aaaaggatc    3960
tcaagaagat  cctttgatct  tttctac                                         3987
```

<210> SEQ ID NO 7
<211> LENGTH: 4049
<212> TYPE: DNA
<213> ORGANISM: Artificial Sequence
<220> FEATURE:
<223> OTHER INFORMATION: pLX-R3 plasmid

<400> SEQUENCE: 7

```
ccatcatcag  ttcggtggtc  ttccgacgaa  caataaggcc  gcaaatcgcg  gcctttttta    60
ttgataacaa  aaccggctca  gttctgcgta  gaaaccaaca  tgcaagctcc  accgggtgca   120
aagcggcagc  ggcggcagga  tatattcaat  tgtaaatggc  ttcatgtccg  ggaaatctac   180
tggtggcagg  atatattgtg  gtgtaaacaa  tggagaaaaa  gattaattaa  gtactagtag   240
cctggtcgaa  accgtctcag  gagagagacc  aaaagcaaaa  acccgccgaa  gcgggttact   300
agcgccattc  gccattcaga  gagcggagct  gctgcgacgg  acgatcggta  cgcgcctctt   360
cgctattacg  ccaactggcg  aaaggtggat  gtgctgcaag  gcgattaagt  tgggtaacgc   420
cagggttttc  ccagtcacga  cgttgtagta  ccacggcaag  gctatctgta  atcattgttg   480
```

```
tactccggtt aggacggatt gggaactggc taactcaaaa tccacacatt atacgagccg    540
gaagcataaa gtgtaaagcc tggggtgcct aatgagtgag gtctctcgct gtcaggagac    600
gggacaagga tgcgagctag cctgcaggaa ttgttgattt tgtgatgact gatggcagga    660
tatatgcggt tgtaattcat ttttattgtc taaatttctg tatttgtttg tttgttcggt    720
tgtaaatttt tttggaagaa caagaaaaga aaaacaccc gttagggtgt ttttagttag     780
tgtggcgcgc cgacttgcga catgcggtcc tttgttattt gccgactacc ttggtgatct    840
cgcctttcac gtagtggaca aattcttcca actgatctgc gcgcgaggcc aagcgatctt    900
cttcttgtcc aagataagcc tgtctagctt caagtatgac gggctgatac tgggccggca    960
ggcgctccat tgcccagtcg gcagcgacat ccttcggcgc gattttgccg gttactgcgc   1020
tgtaccaaat gcgggacaac gtaagcacta catttcgctc atcgccagcc cagtcgggcg   1080
gcgagttcca tagcgttaag gtttcattta gcgcctcaaa tagatcctgt tcaggaaccg   1140
gatcaaagag ttcctccgcc gctggaccta ccaaggcaac gctatgttct cttgcttttg   1200
tcagcaagat agccagatca atgtcgatcg tggctggctc gaagatacct gcaagaatgt   1260
cattgcgctg ccattctcca aattgcagtt cgcgcttagc tggataacgc cacggaatga   1320
tgtcgtcgtg cacaacaatg gtgacttcta cagcgcggaa atctcgctc tctccagggg    1380 aagccgaagt ttccaaaagg tcgttgatca aagctcgccg cgttgtttca tcaagcctta   1440
cggtcaccgt aaccagcaaa tcaatatcac tgtgtggctt caggccgcca tccactgcgg   1500
agccgtacaa atgtacggcc agcaacgtcg gttcgagatg gcgctcgatg acgccaacta   1560
cctctgatag ttgagtcgat acttcggcga tcaccgcttc cctcatgatg tttaactttg   1620
ttttagggcg actgccctgc tgcgtaacat cgttgctgct ccataacatc aaacatcgac   1680
ccacggcgta acgcgcttgc tgcttggatg cccgaggcat agactgtacc ccaaaaaaac   1740
agtcataaca agccatgaaa accgccactg cgccgttacc accgctgcgt tcggtcaagg   1800
ttcgatcgga ttggcggtta tgcggttgcg atgcaggtgg ctgctgaacc cccagccgga   1860
actgacccca caaggcccta gcgtttgcaa tgcaccaggt catcattgac ccaggcgtgt   1920
tccaccaggc cgctgcctcg caactcttcg caggcttcgc cgacctgctc gcgccacttc   1980
ttcacgcggg tggaatccga tccgcacatg aggcggaagg tttccagctt gagcgggtac   2040
ggctcccggt gcgagctgaa atagtcgaac atccgtcggg ccgtcggcga cagcttgcgg   2100
tacttctccc atatgaattt cgtgtagtgg tcgccagcaa acagcacgac gatttcctcg   2160
tcgatcagga cctggcaacg ggacgttttc ttgccacggt ccaggacgcg gaagcggtgc   2220
agcagcgaca ccgattccag gtgcccaacg cggtcggacg tgaagcccat cgccgtcgcc   2280
tgtaggcgcg acaggcattc ctcggccttc gtgtaatacc ggccattgat cgaccagccc   2340
aggtcctggc aaagctcgta gaacgtgaag gtgatcggct cgccgatagg ggtgcgcttc   2400
gcgtactcca acacctgctg ccacaccagt tcgtcatcgt cggcccgcag ctcgacgccg   2460
gtgtaggtga tcttcacgtc cttgttgacg tggaaaatga ccttgttttg cagcgcctcg   2520
cgcgggattt tcttgttgcg cgtggtgaac agggcagagc gggccgtgtc gtttggcatc   2580
gctcgcatcg tgtccggcca cggcgcaata tcgaacaagg aaagctgcat ttccttgatc   2640
tgctgcttcg tgtgtttcag caacgcggcc tgcttggctt cgctgacctg ttttgccagg   2700
tcctcgccgg cggttttcg cttcttggtc gtcatagttc ctcgcgtgtc gatggtcatc    2760
gacttcgcca aacctgccgc ctcctgttcg agacgacgcg aacgctccac ggcggccgat   2820
ggcgcgggca gggcaggggg agccagttgc acgctgtcgc gctcgatctt ggccgtagct   2880
```

| | | | | |
|---|---|---|---|---|
| tgctggacta | tcgagccgac | ggactggaag | gtttcgcggg | gcgcacgcat | gacggtgcgg | 2940 |
| cttgcgatgg | tttcggcatc | ctcggcggaa | accccgcgt | cgatcagttc | ttgcctgtat | 3000 |
| gccttccggt | caaacgtccg | attcattcac | cctccttgcg | ggattgcccc | ggaattaatt | 3060 |
| ccccggatcg | atccgtcgat | cttgatcccc | tgcgccatca | gatccttggc | ggcaagaaag | 3120 |
| ccatccagtt | tactttgcag | ggcttcccaa | ccttaccaga | gggcgcccca | gctggcaatt | 3180 |
| ccggttcgct | tgctgtccat | aaaaccgccc | agtctagcta | tcgccatgta | agcccactgc | 3240 |
| aagctacctg | ctttctcttt | gcgcttgcgt | tttcccttgt | ccagatagcc | cagtagctga | 3300 |
| cattcatccg | gggtcagcac | cgtttctgcg | gactggcttt | ctacgtggct | gccattttg | 3360 |
| gggtgaggcc | gttcgcggcc | gaggggcgca | gccctgggg | ggatgggagg | cccgcgttag | 3420 |
| cgggccggga | gggttcgaga | aggggggggca | ccccccttcg | gcgtgcgcgg | tcacgcgcac | 3480 |
| agggcgcagc | cctggttaaa | acaaggtttt | ataaatattg | gtttaaaagc | aggttaaaag | 3540 |
| acaggttagc | ggtggccgaa | aaacgggcgg | aaacccttgc | aaatgctgga | ttttctgcct | 3600 |
| gtggacagcc | cctcaaatgt | caataggtgc | gcccctcatc | tgtcagcact | ctgcccctca | 3660 |
| agtgtcaagg | atcgcgcccc | tcatctgtca | gtagtcgcgc | ccctcaagtg | tcaataccgc | 3720 |
| agggcactta | tccccaggct | tgtccacatc | atctgtggga | aactcgcgta | aaatcaggcg | 3780 |
| ttttcgccga | tttgcgaggc | tggccagctc | cacgtcgccg | gccgaaatcg | agcctgcccc | 3840 |
| tcatctgtca | acgccgcgcc | gggtgagtcg | gccctcaag | tgtcaacgtc | cgcccctcat | 3900 |
| ctgtcagtga | gggccaagtt | ttccgcgagg | tatccacaac | gccggcggcc | ctacatggct | 3960 |
| ctgctgtagt | gagtgggttg | cgctccggca | gcggtcctga | tcccccgcag | aaaaaaagga | 4020 |
| tctcaagaag | atcctttgat | cttttctac | | | | 4049 |

<210> SEQ ID NO 8
<211> LENGTH: 3865
<212> TYPE: DNA
<213> ORGANISM: Artificial Sequence
<220> FEATURE:
<223> OTHER INFORMATION: pLX-R4 plasmid

<400> SEQUENCE: 8

| | | | | |
|---|---|---|---|---|
| ccatcatcag | ttcggtggtc | ttccgacgaa | caataaggcc | gcaaatcgcg | gcctttttta | 60 |
| ttgataacaa | aaccggctca | gttctgcgta | gaaaccaaca | tgcaagctcc | accgggtgca | 120 |
| aagcggcagc | ggcggcagga | tatattcaat | tgtaaatggc | ttcatgtccg | ggaaatctac | 180 |
| tggtggcagg | atatattgtg | gtgtaaacaa | tggagaaaaa | gattaattaa | gtactagtag | 240 |
| cctggtcgaa | accgtctcag | gagagagacc | aaaagcaaaa | accgccgaa | gcgggttact | 300 |
| agcgccattc | gccattcaga | gagcggagct | gctgcgacgg | acgatcggta | cgcgcctctt | 360 |
| cgctattacg | ccaactggcg | aaaggtggat | gtgctgcaag | gcgattaagt | tgggtaacgc | 420 |
| cagggttttc | ccagtcacga | cgttgtagta | ccacggcaag | gctatctgta | atcattgttg | 480 |
| tactccggtt | aggacggatt | gggaactggc | taactcaaaa | tccacacatt | atacgagccg | 540 |
| gaagcataaa | gtgtaaagcc | tggggtgcct | aatgagtgag | gtctctcgct | gtcaggagac | 600 |
| gggacaagga | tgcgagctag | cctgcaggaa | ttgttgattt | tgtgatgact | gatggcagga | 660 |
| tatatgcggt | tgtaattcat | ttttattgtc | taaatttctg | tatttgtttg | tttgttcggt | 720 |
| tgtaaatttt | tttggaagaa | caagaaaaga | aaaacaccc | gttagggtgt | ttttagttag | 780 |
| tgtggcgcgc | cgacttgcga | catgcggtcc | tttgcaattt | acccaacaac | tccgcggccg | 840 |

```
ggaagccgat ctcggcttga acgaattgtt aggtggcggt acttgggtcg atatcaaagt    900
gcatcacttc ttcccgtatg cccaactttg tatagagagc cactgcggga tcgtcaccgt    960
aatctgcttg cacgtagatc acataagcac caagcgcgtt ggcctcatgc ttgaggagat   1020
tgatgagcgc ggtggcaatg ccctgcctcc ggtgctctcc ggagactgcg agatcataga   1080
tatagatctc actacgcggc tgctcaaact tgggcagaac gtaagccgcg agagcgccaa   1140
caaccgcttc ttggtcgaag gcagcaagcg cgatgaatgt cttactacgg agcaagttcc   1200
cgaggtaatc ggagtccggc tgatgttggg agtaggtggc tacgtctccg aactcacgac   1260
cgaaaagatc aagagcagcc cgcatggatt tgacttggtc agggccgagc ctacatgtgc   1320
gaatgatgcc catacttgag ccacctaact ttgttttagg gcgactgccc tgctgcgtaa   1380
catcgttgct gctgcgtaac atcgttgctg ctccataaca tcaaacatcg acccacggcg   1440
taacgcgctt gctgcttgga tgcccgaggc ataggctgta caaaaaaaca gtcataacaa   1500
gccatgaaaa ccgccactgc gccgttacca ccgctgcgtt cggtcaaggt tctggaccag   1560
ttgcgtgagc gcatacgcta cttgcattac agtttacgaa ccgaacaggc ttatgtcaag   1620
atcggattgg cggttatgcg gttgcgatgc aggtggctgc tgaaccccca gccggaactg   1680
accccacaag gccctagcgt ttgcaatgca ccaggtcatc attgacccag gcgtgttcca   1740
ccaggccgct gcctcgcaac tcttcgcagg cttcgccgac ctgctcgcgc cacttcttca   1800
cgcgggtgga atccgatccg cacatgaggc ggaaggtttc cagcttgagc gggtacggct   1860
cccggtgcga gctgaaatag tcgaacatcc gtcgggccgt cggcgacagc ttgcggtact   1920
tctcccatat gaatttcgtg tagtggtcgc cagcaaacag cacgacgatt tcctcgtcga   1980
tcaggacctg gcaacgggac gttttcttgc cacggtccag gacgcggaag cggtgcagca   2040
gcgacaccga ttccaggtgc ccaacgcggt cggacgtgaa gcccatcgcc gtcgcctgta   2100
ggcgcgacag gcattcctcg gccttcgtgt aataccggcc attgatcgac cagcccaggt   2160
cctggcaaag ctcgtagaac gtgaaggtga tcggctcgcc gataggggtg cgcttcgcgt   2220
actccaacac ctgctgccac accagttcgt catcgtcggc ccgcagctcg acgccggtgt   2280
aggtgatctt cacgtccttg ttgacgtgga aaatgacctt gttttgcagc gcctcgcgcg   2340
ggatttctct gttgcgcgtg gtgaacaggg cagagcgggc cgtgtcgttt ggcatcgctc   2400
gcatcgtgtc cggccacggc gcaatatcga acaaggaaag ctgcatttcc ttgatctgct   2460
gcttcgtgtg tttcagcaac gcggcctgct tggcttcgct gacctgtttt gccaggtcct   2520
cgccggcggt ttttgcttc ttggtcgtca tagttcctcg cgtgtcgatg gtcatcgact   2580
tcgccaaacc tgccgcctcc tgttcgagac gacgcgaacg ctccacggcg gccgatggcg   2640
cgggcaggga aggggagcc agttgcacgc tgtcgcgctc gatcttggcc gtagcttgct   2700
ggactatcga gccgacggac tggaaggttt cgcggggcgc acgcatgacg gtgcggcttg   2760
cgatggtttc ggcatcctcg gcggaaaacc ccgcgtcgat cagttcttgc ctgtatgcct   2820
tccggtcaaa cgtccgattc attcaccctc cttgcgggat tgccccggaa ttaattcccc   2880
ggatcgatcc gtcgatcttg atccctgcg ccatcagatc cttggcggca agaaagccat   2940
ccagtttact ttgcagggct tcccaacctt accagagggc gccccagctg gcaattccgg   3000
ttcgcttgct gtccataaaa ccgcccagtc tagctatcgc catgtaagcc cactgcaagc   3060
tacctgcttt ctctttgcgc ttgcgttttc ccttgtccag atagcccagt agctgacatt   3120
catccggggt cagcaccgtt tctgcggact ggctttctac gtggctgcca ttttggggt    3180
gaggccgttc gcggccgagg ggcgcagccc ctgggggat gggaggcccg cgttagcggg   3240
```

```
ccgggagggt tcgagaaggg ggggcacccc ccttcggcgt gcgcggtcac gcgcacaggg      3300
cgcagccctg gttaaaaaca aggtttataa atattggttt aaaagcaggt taaaagacag      3360
gttagcggtg gccgaaaaac gggcggaaac ccttgcaaat gctggatttt ctgcctgtgg      3420
acagcccctc aaatgtcaat aggtgcgccc ctcatctgtc agcactctgc ccctcaagtg      3480
tcaaggatcg cgcccctcat ctgtcagtag tcgcgcccct caagtgtcaa taccgcaggg      3540
cacttatccc caggcttgtc cacatcatct gtgggaaact cgcgtaaaat caggcgtttt      3600
cgccgatttg cgaggctggc cagctccacg tcgccggccg aaatcgagcc tgcccctcat      3660
ctgtcaacgc cgcgccgggt gagtcggccc tcaagtgtc aacgtccgcc cctcatctgt       3720
cagtgagggc caagttttcc gcgaggtatc cacaacgccg gcggccctac atggctctgc      3780
tgtagtgagt gggttgcgct ccggcagcgg tcctgatccc ccgcagaaaa aaggatctc      3840 aagaagatcc tttgatcttt tctac                                            3865
```

<210> SEQ ID NO 9
<211> LENGTH: 3740
<212> TYPE: DNA
<213> ORGANISM: Artificial Sequence
<220> FEATURE:
<223> OTHER INFORMATION: pLX-Z4 plasmid

<400> SEQUENCE: 9

```
caagaagatc ctttgatctt ttctacaggc ctgctggtaa tcgcaggcct ttttattttg        60
gcaggatata ttgtggtgta aacacttacc gcacctctgc agcagcggca ggatatatgg       120
cagtgtaaac tccattttcg aacgcgttaa ttaagtagcc tggtcgaaac cgtctcagga       180
gagagaccaa aagcaaaaac ccgccgaagc gggttactag cgccattcgc cattcagaga       240
gcggagctgc tgcgacggac gatcggtacg cgcctcttcg ctattacgcc aactggcgaa       300
aggtggatgt gctgcaaggc gattaagttg ggtaacgcca gggttttccc agtcacgacg       360
ttgtagtacc acggcaaggc tatctgtaat cattgttgta ctccggttag gacggattgg       420
gaactggcta actcaaaatc cacacattat acgagccgga agcataaagt gtaaagcctg       480
gggtgcctaa tgagtgaggt ctctcgctgt caggagacgg gacaaggatg cgcctgcagg       540
ttgttgatga tgtgatgact gatggcagga tatatgtggt tgtaattcat ttctaccgtg       600
taatttactg tatttttttg tttgttcgtt cgtttgtaaa atatttttt ggaagcaaaa        660 aattagcgca agaagacaaa aatcaccttg cgctaatgct ctgttacagg cgcgccaatt       720
tacccaacaa ctccgcggcc gggaagccga tctcggcttg aacgaattgt taggtggcgg       780
tacttgggtc gatatcaaag tgcatcactt cttcccgtat gcccaacttt gtatagagag       840
ccactgcggg atcgtcaccg taatctgctt gcacgtagat cacataagca caagcgcgt       900 tggcctcatg cttgaggaga ttgatgagcg cggtggcaat gccctgcctc cggtgctctc       960
cggagactgc gagatcatag atatagatct cactacgcgg ctgctcaaac ttgggcagaa      1020
cgtaagccgc gagagcgcca caaccgcttc ttggtcgaa ggcagcaagc gcgatgaatg       1080
tcttactacg gagcaagttc ccgaggtaat cggagtccgg ctgatgttgg gagtaggtgg      1140
ctacatcgcc gaactcacga ccgaaaagat caagagcagc ccgcatggat ttgacttggt      1200
cagggccgag cctacatgtg cgaatgatgc ccatacttga gccacctaac tttgtttag       1260 ggcgactgcc ctgctgcgta acatcgttgc tgctgcgtaa catcgttgct gctccataac      1320
atcaaacatc gacccacggc gtaacgcgct tgctgcttgg atgcccgagg cataggctgt      1380
```

-continued

```
acaaaaaaac agtcataaca agccatgaaa accgccactg cgccgttacc accgctgcgt    1440
tcggtcaagg ttctggacca gttgcgtgag cgcatacgct acttgcatta cagtttacga    1500
accgaacagg cttatgtcaa gatcggattg gcggttatgc ggttgcgatg caggtggctg    1560
ctgaaccccc agccggaact gaccccacaa ggccctagcg tttgcaatgc accaggtcat    1620
cattgaccca ggcgtgttcc accaggccgc tgcctcgcaa ctcttcgcag gcttcgccga    1680
cctgctcgcg ccacttcttc acgcgggtgg aatccgatcc gcacatgagg cggaaggttt    1740
ccagcttgag cgggtacggc tcccggtgcg agctgaaata gtcgaacatc cgtcgggccg    1800
tcggcgacag cttgcggtac ttctcccata tgaatttcgt gtagtggtcg ccagcaaaca    1860
gcacgacgat ttcctcgtcg atcaggacct ggcaacggga cgttttcttg ccacggtcca    1920
ggacgcggaa gcggtgcagc agcgacaccg attccaggtg cccaacgcgg tcggacgtga    1980
agcccatcgc cgtcgcctgt aggcgcgaca ggcattcctc ggccttcgtg taataccggc    2040
cattgatcga ccagcccagg tcctggcaaa gctcgtagaa cgtgaaggtg atcggctcgc    2100 cgatagggt gcgcttcgcg tactccaaca cctgctgcca caccagttcg tcatcgtcgg    2160
cccgcagctc gacgccggtg taggtgatct tcacgtcctt gttgacgtgg aaaatgacct    2220
tgttttgcag cgcctcgcgc gggatttttct tgttgcgcgt ggtgaacagg gcagagcggg    2280
ccgtgtcgtt tggcatcgct cgcatcgtgt ccggccacgg cgcaatatcg aacaaggaaa    2340
gctgcatttc cttgatctgc tgcttcgtgt gtttcagcaa cgcggcctgc ttggcttcgc    2400
tgacctgttt tgccaggtcc tcgccggcgg ttttttcgctt cttggtcgtc atagttcctc    2460
gcgtgtcgat ggtcatcgac ttcgccaaac ctgccgcctc ctgttctagc cgacgcgaac    2520
gctccacggc ggccgatggc gcgggcaggg caggggagc cagttgcacg ctgtcgcgct    2580
cgatcttggc cgtagcttgc tggactatcg agccgacgga ctggaaggtt tcgcggggcg    2640
cacgcatgac ggtgcggctt gcgatggttt cggcatcctc ggcggaaaac cccgcgtcga    2700
tcagttcttg cctgtatgcc ttccggtcaa acgtccgatt cattcaccct ccttgcggga    2760
ttgccccgga attaattccc cggatcgatc cgtcgatctt gatcccctgc gccatcagat    2820
ccttggcggc aagaaagcca tccagtttac tttgcagggc ttcccaacct taccagaggg    2880
cgccccagct ggcaattccg gttcgcttgc tgtccataaa accgcccagt ctagctatcg    2940
ccatgtaagc ccactgcaag ctacctgctt tctctttgcg cttgcgtttt ccttgtcca    3000 gatagcccag tagctgacat tcatccgggg tcagcaccgt ttctgcggac tggctttcta    3060
cgtggctgcc attttgggg tgaggccgtt cgcggccgag gggcgcagcc cctgggggga    3120
tgggaggccc gcgttagcgg gccgggaggg ttcgagaagg ggggcaccc ccttcggcg     3180 tgcgcggtca cgcgcacagg gcgcagccct ggttaaaaac aaggtttata aatattggtt    3240
taaaagcagg ttaaaagaca ggttagcggt ggccgaaaaa cgggcggaaa cccttgcaaa    3300
tgctggattt tctgcctgtg gacagcccct caaatgtcaa taggtgcgcc cctcatctgt    3360
cagcactctg cccctcaagt gtcaaggatc gcgcccctca tctgtcagta gtcgcgcccc    3420
tcaagtgtca ataccgcagg gcacttatcc ccaggcttgt ccacatcatc tgtgggaaac    3480
tcgcgtaaaa tcaggcgttt tcgccgattt gcgaggctgg ccagctccac gtcgccggcc    3540
gaaatcgagc ctgcccctca tctgtcaacg ccgcgccggg tgagtcggcc cctcaagtgt    3600
caacgtccgc ccctcatctg tcagtgaggg ccaagttttc cgcgaggtat ccacaacgcc    3660
ggcggcccta catggctctg ctgtagtgag tgggttgcgc tccggcagcg gtcctgatcc    3720
cccgcagaaa aaaggatct                                                3740
```

<210> SEQ ID NO 10
<211> LENGTH: 3287
<212> TYPE: DNA
<213> ORGANISM: Artificial Sequence
<220> FEATURE:
<223> OTHER INFORMATION: pLX-B2alpha2 plasmid

<400> SEQUENCE: 10

| | | | | | |
|---|---|---|---|---|---|
| ccatcatcag | ttcggtggtc | ttccgacgaa | caataaggcc | gcaaatcgcg | gccttttta | 60 |
| ttgataacaa | aaccggctca | gttctgcgta | gaaaccaaca | tgcaagctcc | accgggtgca | 120 |
| aagcggcagc | ggcggcagga | tatattcaat | tgtaaatggc | ttcatgtccg | ggaaatctac | 180 |
| tggtggcagg | atatattgtg | gtgtaaacaa | tggagaaaaa | gattaattaa | gtactagtag | 240 |
| cctggtcgaa | accgtctcag | tcaggagaga | gaccaaaagc | aaaaacccgc | cgaagcgggt | 300 |
| tactagcgcc | attcgccatt | cagagagcgg | agctgctgcg | acggacgatc | ggtacgcgcc | 360 |
| tcttcgctat | tacgccaact | ggcgaaaggt | ggatgtgctg | caaggcgatt | aagttgggta | 420 |
| acgccagggt | tttcccagtc | acgacgttgt | agtaccacgg | caaggctatc | tgtaatcatt | 480 |
| gttgtactcc | ggttaggacg | gattgggaac | tggctaactc | aaaatccaca | cattatacga | 540 |
| gccggaagca | taaagtgtaa | agcctgggt | gcctaatgag | tgaggtctct | cgctggagac | 600 |
| gggacaagga | tgcgagctag | cctgcaggaa | ttgttgattt | tgtgatgact | gatggcagga | 660 |
| tatatgcggt | tgtaattcat | ttttattgtc | taaatttctg | tatttgtttg | tttgttcggt | 720 |
| tgtaaatttt | tttggaagaa | caagaaaaga | aaaacacccc | gttagggtgt | ttttagttag | 780 |
| tgtggcgcgc | cgacttgcga | catgcggtcc | tttgcaatca | actattagaa | aaattcatcc | 840 |
| agcatcagat | gaaattgcag | tttgttcata | tccggattat | caatgccata | tttctgaaac | 900 |
| agacgttttt | gcaggctcgg | gctaaattcg | cccaggcagt | tccacagaat | ggccagatcc | 960 |
| tgataacgat | ccgcaatgcc | cacacggccc | acatcaatgc | agccaatcag | tttgccttca | 1020 |
| tcgaaaatca | ggttatccag | gctaaaatcg | ccgtgggtca | ccacgctatc | cgggctaaac | 1080 |
| ggcagcagtt | tatgcatttc | tttccacacc | tgttccaccg | gccagccgtt | acgttcatca | 1140 |
| tcaaaatcgc | tcgcatccac | caggccgttg | ttcatacggc | tctgcgcctg | gccagacga | 1200 |
| aacacacgat | cgctgttaaa | cgggcagttg | cacaccggaa | tgctatgcag | acgacgcaga | 1260 |
| aacacggcca | gcgcatccac | aatgttttcg | ccgctatccg | gatattcttc | cagcacctga | 1320 |
| aacgcggttt | tgcccggaat | cgcggtggtc | agcagccacg | catcatccgg | ggtgcgaata | 1380 |
| aaatgtttaa | tggtcggcag | cggcataaat | tcggtcagcc | agttcagacg | caccatttca | 1440 |
| tcggtcacat | cgttcgccac | gctgcctttg | ccatgtttca | gaaacagttc | cggcgcatcc | 1500 |
| ggtttgccat | acagacgata | aatggtcgcg | ccgctctgac | ccacgttatc | acgcgcccat | 1560 |
| ttatagccat | acagatccgc | atccatgttg | ctgttcagac | gcggacggct | acagctcgtt | 1620 |
| tcacgctgaa | tatggctcat | aacacccctt | gtattactgt | ttatgtaagc | agacagtttt | 1680 |
| attgttcatg | atgatatatt | tttatcttgt | gcaatgtaac | atcagagatt | ttgagacaca | 1740 |
| agatcggatt | ggcggttatg | cggttctacc | ggcgcggcag | cgttacccgt | gtcggcggct | 1800 |
| ccaacggctc | gccatcgtcc | agaaaacacg | gctcatcggg | catcggcagg | cgctgctgcc | 1860 |
| cgcgccgttc | ccattcctcc | gtttcggtca | aggctggcag | gtctggttcc | atgcccggaa | 1920 |
| tgccgggctg | gctgggcggc | tcctcgccgg | ggccggtcgg | tagttgctgc | tcgcccggat | 1980 |
| acagggtcgg | gatgcggcgc | aggtcgccat | gccccaacag | cgattcgtcc | tggtcgtcgt | 2040 |

-continued

```
gatcaaccac cacggcggca ctgaacaccg acaggcgcaa ctggtcgcgg ggctggcccc      2100
acgccacgcg gtcattgacc acgtaggccg cacggtgcc ggggccgttg agcttcacga       2160
cggagatcca gcgctcggcc accaagtcct tgactgcgta ttggaccgtc cgcaaagaac      2220
gtccgatgag cttggaaagt gtcttctggc tgaccaccac ggcgttctgg tggcccatct      2280
gcgccacgag gtgatgcagc agcattgccg ccgtgggttt cctcgcaata agcccggccc      2340
acgcctcatg cgctttgcgt tccgtttgca cccagtgacc gggcttgttc ttggcttgaa      2400
tgccgatttc tctggactgc gtggccatgc ttatctccat gcggtagggg tgccgcacgg      2460
ttgcggcacc atgcgcaatc agctgcaact tttcggcagc gcgacaacaa ttatgcgttg      2520
cgtaaaagtg gcagtcaatt acagattttc tttaacctac gcaatgagct attgcggggg      2580
gtgccgcaat gagctgttgc gtaccccccct tttttaagtt gttgattttt aagtctttcg     2640
catttcgccc tatatctagt tctttggtgc ccaaagaagg gcaccctgc ggggttcccc       2700 cacgccttcg gcgcggctcc ccctccggca aaagtggcc cctccggggc ttgttgatcg       2760
actgcgcggc cttcggcctt gcccaaggtg gcgctgcccc cttggaaccc cgcactcgc       2820 cgccgtgagg ctcggggggc aggcgggcgg gcttcgccct tcgactgccc ccactcgcat      2880
aggcttgggt cgttccaggc gcgtcaaggc caagccgctg cgcggtcgct gcgcgagcct      2940
tgacccgcct tccacttggt gtccaaccgg caagcgaagc gcgcaggccg caggccggag      3000
gcttttcccc agagaaaatt aaaaaaattg atggggcaag gccgcaggcc gcgcagttgg      3060
agccggtggg tatgtggtcg aaggctgggt agccggtggg caatccctgt ggtcaagctc     3120
gtgggcaggc gcagcctgtc catcagcttg tccagcaggg ttgtccacgg gccgagcgaa      3180
gcgagccagc cggtggccgc tcgcggccat cgtccacata tccacgggct ggcaagggag     3240
cgcagcgacc gcgcagggcg aagcccggag agcaagcccg taggggg                   3287
```

<210> SEQ ID NO 11
<211> LENGTH: 3349
<212> TYPE: DNA
<213> ORGANISM: Artificial Sequence
<220> FEATURE:
<223> OTHER INFORMATION: pLX-B3omega1 plasmid

<400> SEQUENCE: 11

```
ccatcatcag ttcggtggtc ttccgacgaa caataaggcc gcaaatcgcg gcctttttta       60
ttgataacaa aaccggctca gttctgcgta gaaaccaaca tgcaagctcc accgggtgca      120
aagcggcagc ggcggcagga tatattcaat tgtaaatggc ttcatgtccg ggaaatctac      180
tggtggcagg atatattgtg gtgtaaacaa tggagaaaaa gattaattaa gtactagtag      240
cctggtcgaa acggtctcag gagagagacg aaaagcaaaa acccgccgaa gcgggttact     300
agcgccattc gccattcaga gagcggagct gctgcgacgg acgatcggta cgcgcctctt      360
cgctattacg ccaactggcg aaaggtggat gtgctgcaag gcgattaagt tgggtaacgc      420
cagggttttc ccagtcacga cgttgtagta ccacggcaag gctatctgta atcattgttg      480
tactccggtt aggacggatt gggaactggc taactcaaaa tccacacatt atacgagccg     540
gaagcataaa gtgtaaagcc tggggtgcct aatgagtgac gtctctcgct gtcaggagac      600
cggacaagga tgcgagctag cctgcaggaa ttgttgattt tgtgatgact gatggcagga      660
tatatgcggt tgtaattcat ttttattgtc taaatttctg tatttgtttg tttgttcggt      720
tgtaaatttt tttggaagaa caagaaaaga aaaacaccc gttagggtgt tttagttag       780 tgtggcgcgc cgacttgcga catgcggtcc tttgttattt gccgactacc ttggtgatct      840
```

```
cgcctttcac gtagtggaca aattcttcca actgatctgc gcgcgaggcc aagcgatctt     900
cttcttgtcc aagataagcc tgtctagctt caagtatgac gggctgatac tgggccggca     960
ggcgctccat tgcccagtcg gcagcgacat ccttcggcgc gattttgccg gttactgcgc    1020
tgtaccaaat gcgggacaac gtaagcacta catttcgctc atcgccagcc cagtcgggcg    1080
gcgagttcca tagcgttaag gtttcattta gcgcctcaaa tagatcctgt tcaggaaccg    1140
gatcaaagag ttcctccgcc gctggaccta ccaaggcaac gctatgttct cttgcttttg    1200
tcagcaagat agccagatca atgtcgatcg tggctggctc gaagatacct gcaagaatgt    1260
cattgcgctg ccattctcca aattgcagtt cgcgcttagc tggataacgc cacggaatga    1320
tgtcgtcgtg cacaacaatg gtgacttcta cagcgcggag aatctcgctc tctccagggg    1380
aagccgaagt ttccaaaagg tcgttgatca aagctcgccg cgttgtttca tcaagcctta    1440
cggtcaccgt aaccagcaaa tcaatatcac tgtgtggctt caggccgcca tccactgcgg    1500
agccgtacaa atgtacggcc agcaacgtcg gttcgagatg cgctcgatgc acgccaacta    1560
cctctgatag ttgagtcgat acttcggcga tcaccgcttc cctcatgatg tttaactttg    1620
ttttagggcg actgccctgc tgcgtaacat cgttgctgct ccataacatc aaacatcgac    1680
ccacggcgta acgcgcttgc tgcttggatg cccgaggcat agactgtacc caaaaaaac    1740
agtcataaca agccatgaaa accgccactg cgccgttacc accgctgcgt tcggtcaagg    1800
ttcgatcgga ttggcggtta tgcggttcta ccggcgcggc agcgttaccc gtgtcggcgg    1860
ctccaacggc tcgccatcgt ccagaaaaca cggctcatcg gcatcggca ggcgctgctg    1920
cccgcgccgt tcccattcct ccgtttcggt caaggctggc aggtctggtt ccatgcccgg    1980
aatgccgggc tggctgggcg gctcctcgcc ggggccggtc ggtagttgct gctcgcccgg    2040
atacagggtc gggatgcggc gcaggtcgcc atgcccaac agcgattcgt cctggtcgtc    2100
gtgatcaacc accacggcgg cactgaacac cgacaggcgc aactggtcgc ggggctggcc    2160
ccacgccacg cggtcattga ccacgtaggc cgacacggtg ccggggccgt tgagcttcac    2220
gacggagatc cagcgctcgg ccaccaagtc cttgactgcg tattggaccg tccgcaaaga    2280
acgtccgatg agcttggaaa gtgtcttctg gctgaccacc acggcgttct ggtggcccat    2340
ctgcgccacg aggtgatgca gcagcattgc cgccgtgggt ttcctcgcaa taagcccggc    2400
ccacgcctca tgcgctttgc gttccgtttg cacccagtga ccgggcttgt tcttggcttg    2460
aatgccgatt tctctggact gcgtggccat gcttatctcc atgcggtagg ggtgccgcac    2520
ggttgcggca ccatgcgcaa tcagctgcaa ctttccggca gcgcgacaac aattatgcgt    2580
tgcgtaaaag tggcagtcaa ttacagattt tctttaacct acgcaatgag ctattgcggg    2640
gggtgccgca atgagctgtt gcgtaccccc cttttttaag ttgttgattt ttaagtcttt    2700
cgcatttcgc cctatatcta gttctttggt gcccaaagaa gggcacccct gcggggttcc    2760
cccacgcctt cggcgcggct ccccctccgg caaaaagtgg cccctccggg gcttgttgat    2820
cgactgcgcg gccttcggcc ttgcccaagg tggcgctgcc cccttggaac cccgcactc    2880
gccgccgtga ggctcggggg gcaggcgggc gggcttcgcc cttcgactgc ccccactcgc    2940
ataggcttgg gtcgttccag gcgcgtcaag gccaagccgc tgcgcggtcg ctgcgcgagc    3000
cttgacccgc cttccacttg tgtccaacc ggcaagcgaa gcgcgcaggc cgcaggccgg    3060
aggcttttcc ccagagaaaa ttaaaaaaat tgatggggca aggccgcagg ccgcgcagtt    3120
ggagccggtg ggtatgtggt cgaaggctgg gtagccggtg ggcaatccct gtggtcaagc    3180
```

```
tcgtgggcag gcgcagcctg tccatcagct tgtccagcag ggttgtccac gggccgagcg    3240
aagcgagcca gccggtggcc gctcgcggcc atcgtccaca tatccacggg ctggcaaggg    3300
agcgcagcga ccgcgcaggg cgaagcccgg agagcaagcc cgtaggggg               3349

<210> SEQ ID NO 12
<211> LENGTH: 3349
<212> TYPE: DNA
<213> ORGANISM: Artificial Sequence
<220> FEATURE:
<223> OTHER INFORMATION: pLX-B3omega2 plasmid

<400> SEQUENCE: 12
ccatcatcag ttcggtggtc ttccgacgaa caataaggcc gcaaatcgcg gccttttta     60 ttgataacaa aaccggctca gttctgcgta gaaaccaaca tgcaagctcc accgggtgca   120
aagcggcagc ggcggcagga tatattcaat tgtaaatggc ttcatgtccg ggaaatctac   180
tggtggcagg atatattgtg gtgtaaacaa tggagaaaaa gattaattaa gtactagtag   240
cctggtcgaa acggtctcag tcaggagaga acgaaaagc aaaaacccgc cgaagcgggt    300
tactagcgcc attcgccatt cagagagcgg agctgctgcg acggacgatc ggtacgcgcc   360
tcttcgctat tacgccaact ggcgaaaggt ggatgtgctg caaggcgatt aagttgggta   420
acgccagggt tttcccagtc acgacgttgt agtaccacgg caaggctatc tgtaatcatt   480
gttgtactcc ggttaggacg gattgggaac tggctaactc aaaatccaca cattatacga   540
gccggaagca taaagtgtaa agcctgggt gcctaatgag tgacgtctct cgctggagac    600
cggacaagga tgcgagctag cctgcaggaa ttgttgattt tgtgatgact gatggcagga   660
tatatgcggt tgtaattcat ttttattgtc taaatttctg tatttgtttg tttgttcggt   720
tgtaaatttt tttggaagaa caagaaaaga aaaacaccc gttagggtgt ttttagttag    780
tgtggcgcgc cgacttgcga catgcggtcc tttgttattt gccgactacc ttggtgatct   840
cgcctttcac gtagtggaca aattcttcca actgatctgc gcgcgaggcc aagcgatctt   900
cttcttgtcc aagataagcc tgtctagctt caagtatgac gggctgatac tgggccggca   960
ggcgctccat tgcccagtcg gcagcgacat ccttcggcgc gattttgccg gttactgcgc  1020
tgtaccaaat gcgggacaac gtaagcacta catttcgctc atcgccagcc cagtcgggcg  1080
gcgagttcca tagcgttaag gtttcattta gcgcctcaaa tagatcctgt tcaggaaccg  1140
gatcaaagag ttcctccgcc gctggaccta ccaaggcaac gctatgttct cttgcttttg  1200
tcagcaagat agccagatca atgtcgatcg tggctggctc gaagatacct gcaagaatgt  1260
cattgcgctg ccattctcca aattgcagtt cgcgcttagc tggataacgc cacggaatga  1320
tgtcgtcgtg cacaacaatg gtgacttcta cagcgcggag aatctcgctc tctccagggg  1380
aagccgaagt ttccaaaagg tcgttgatca agctcgccg cgttgtttca tcaagcctta   1440
cggtcaccgt aaccagcaaa tcaatatcac tgtgtggctt caggccgcca tccactgcgg  1500
agccgtacaa atgtacggcc agcaacgtcg gttcgagatg cgctcgatg acgccaacta    1560 cctctgatag ttgagtcgat acttcggcga tcaccgcttc cctcatgatg tttaactttg  1620
ttttagggcg actgccctgc tgcgtaacat cgttgctgct ccataacatc aaacatcgac  1680
ccacggcgta acgcgcttgc tgcttggatg cccgaggcat agactgtacc ccaaaaaaac  1740
agtcataaca agccatgaaa accgccactg cgccgttacc accgctgcgt tcggtcaagg  1800
ttcgatcgga ttggcggtta tgcggttcta ccggcgcggc agcgttaccc gtgtcggcgg  1860
ctccaacggc tcgccatcgt ccagaaaaca cggctcatcg ggcatcggca ggcgctgctg  1920
```

```
cccgcgccgt tcccattcct ccgtttcggt caaggctggc aggtctggtt ccatgcccgg    1980
aatgccgggc tggctgggcg gctcctcgcc ggggccggtc ggtagttgct gctcgcccgg    2040
atacagggtc gggatgcggc gcaggtcgcc atgccccaac agcgattcgt cctggtcgtc    2100
gtgatcaacc accacggcgg cactgaacac cgacaggcgc aactggtcgc ggggctggcc    2160
ccacgccacg cggtcattga ccacgtaggc cgacacggtg ccggggccgt tgagcttcac    2220
gacggagatc cagcgctcgg ccaccaagtc cttgactgcg tattggaccg tccgcaaaga    2280
acgtccgatg agcttggaaa gtgtcttctg gctgaccacc acggcgttct ggtggcccat    2340
ctgcgccacg aggtgatgca gcagcattgc cgccgtgggt ttcctcgcaa taagcccggc    2400
ccacgcctca tgcgctttgc gttccgtttg cacccagtga ccgggcttgt tcttggcttg    2460
aatgccgatt tctctggact gcgtggccat gcttatctcc atgcggtagg ggtgccgcac    2520
ggttgcggca ccatgcgcaa tcagctgcaa cttttcggca gcgcgacaac aattatgcgt    2580
tgcgtaaaag tggcagtcaa ttacagattt tctttaacct acgcaatgag ctattgcggg    2640
gggtgccgca atgagctgtt gcgtaccccc cttttttaag ttgttgattt ttaagtcttt    2700
cgcatttcgc cctatatcta gttctttggt gcccaaagaa gggcacccct gcggggttcc    2760
cccacgcctt cggcgcggct ccccctccgg caaaaagtgg cccctccggg gcttgttgat    2820
cgactgcgcg gccttcggcc ttgcccaagg tggcgctgcc cccttggaac cccgcactc    2880
gccgccgtga ggctcggggg gcaggcgggc gggcttcgcc cttcgactgc ccccactcgc    2940
ataggcttgg gtcgttccag gcgcgtcaag gccaagccgc tgcgcggtcg ctgcgcgagc    3000
cttgacccgc cttccacttg gtgtccaacc ggcaagcgaa gcgcgcaggc cgcaggccgg    3060
aggcttttcc ccagagaaaa ttaaaaaaat tgatggggca aggccgcagg ccgcgcagtt    3120
ggagccggtg ggtatgtggt cgaaggctgg gtagccggtg ggcaatccct gtggtcaagc    3180
tcgtgggcag gcgcagcctg tccatcagct tgtccagcag ggttgtccac gggccgagcg    3240
aagcgagcca gccggtggcc gctcgcggcc atcgtccaca tatccacggg ctggcaaggg    3300
agcgcagcga ccgcgcaggg cgaagcccgg agagcaagcc cgtaggggg              3349
```

<210> SEQ ID NO 13
<211> LENGTH: 5485
<212> TYPE: DNA
<213> ORGANISM: Artificial Sequence
<220> FEATURE:
<223> OTHER INFORMATION: pLX-B2-TagRFP-T plasmid

<400> SEQUENCE: 13

```
ccatcatcag ttcggtggtc ttccgacgaa caataaggcc gcaaatcgcg gccttttta      60
ttgataacaa aaccggctca gttctgcgta gaaaccaaca tgcaagctcc accgggtgca    120
aagcggcagc ggcggcagga tatattcaat tgtaaatggc ttcatgtccg gaaatctac    180
tggtggcagg atatattgtg gtgtaaacaa tggagaaaaa gattaattaa gtactagtag    240
cctggtcgaa accgtctcac cagtacgcac gattcaaggc ttgcttcaca aaccaaggca    300
agtaatagag attggagtct ctaaaaaggt agttcccact gaatcaaagg ccatggagtc    360
aaagattcaa atagaggacc taacagaact cgccgtaaag actggcgaac agttcataca    420
gagtctctta cgactcaatg acaagaagaa aatcttcgtc aacatggtgg agcacgacac    480
acttgtctac tccaaaaata tcaaagatac agtctcagaa gaccaaaggg caattgagac    540
ttttcaacaa agggtaatat ccggaaacct cctcggattc cattgcccag ctatctgtca    600
```

```
ctttattgtg aagatagtgg aaaaggaagg tggctcctac aaatgccatc attgcgataa      660
aggaaaggcc atcgttgaag atgcctctgc cgacagtggt cccaaagatg gacccccacc      720
cacgaggagc atcgtggaaa aagaagacgt tccaaccacg tcttcaaagc aagtggattg      780
atgtgataac atggtggagc acgacacact tgtctactcc aaaatatca aagatacagt       840 ctcagaagac caaagggcaa ttgagacttt tcaacaaagg gtaatatccg gaaacctcct      900
cggattccat tgcccagcta tctgtcactt tattgtgaag atagtggaaa aggaaggtgg      960
ctcctacaaa tgccatcatt gcgataaagg aaaggccatc gttgaagatc ctctgccgac     1020
agtggtccca agatggaccc ccacccacg aggagcatcg tggaaaaaga agacgttcca      1080
accacgtctt caaagcaagt ggattgatgt gatatctcca ctgacgtaag ggatgacgca     1140
caatcccact atccttcgca agacccttcc tctatataag gaagttcatt tcatttggag     1200
aggaaaatat aaaaactcaa cacaacatac aaaattttaa gcaatcaaat caatctcaag     1260
ctatcaaaat ttttcaaatc tcacttgaaa gatcaaaaat caacaaagaa atcccttaa      1320 tttctctacc aaatttactg caagtcaaga tggtttcaaa gggagaagag ctgattaagg     1380
agaacatgca catgaagctg tacatggagg gcaccgtgaa caaccaccac ttcaagtgca     1440
catccgaggg cgaaggcaag ccctacgagg gcacccagac catgagaatc aaggtggtcg     1500
agggcggccc tctccccttc gccttcgaca tcctggctac cagcttcatg tacggcagca     1560
gaaccttcat caaccacacc cagggcatcc ccgacttctt taagcagtcc ttccctgagg     1620
gcttcacatg ggagagagtc accacatacg aagacggggg cgtgctgacc gctacccagg     1680
acaccagcct ccaggacggc tgcctcatct acaacgtcaa gatcagaggg gtgaacttcc     1740
catccaacgg ccctgtgatg cagaagaaaa cactcggctg ggaggccaac accgagatgc     1800
tgtaccccgc tgacgcggc ctggaaggca gaacagacat ggccctgaag ctcgtgggcg       1860
ggggccacct gatctgcaac ttcaagacca catacagatc caagaaaccc gctaagaacc     1920
tcaagatgcc cggcgtctac tatgtggacc acagactgga aagaatcaag gaggccgaca     1980
aagagaccta cgtcgagcag cacgaggtgg ctgtggccag atactgcgac ctccctagca     2040
aactggggca caaacttaac taatcgatca cgtgaagctc atatccagat gaaggcagca     2100
gcattgagaa atgttcaaaa tcgtttattt ggcttggatg gaaacgtcgg aacacaagaa     2160
gaggacacag agagacacac cgctggtgat gttaatcgca acatgcacaa cctcctcggt     2220
gtgaggggag tgtagtggtc tcggtatcta tcataaactc tacctgggtg agagtctaat     2280
catccagttg ttttttagatt cctgttagca tccttttctc cgctttaata gcagtacatt    2340
cagtgaggtt ttacctccat atgttctagt ctgttattgt cgaacacagg cccttgtatc     2400
tgatgtagcg agtgcttcac tccattcggg ttatagttct tgtgcaagag acaaaaaaaa     2460 aaaaaaaaa aaaaaaaaa aaaaaaaaa aaaaaaaaa aaaaaaaaa aaaaaaaaa          2520 atgcatgcct gcagatcgtt caaacatttg gcaataaagt ttcttaagat tgaatcctgt     2580
tgccggtctt gcgatgatta tcatctaatt tctgttgaat tacgttaagc atgtaataat     2640
taacatgtaa tgcatgacgt tatttatgag atgggttttt atgattagag tcccgcaatt     2700
atacatttaa tacgcgatag aaaacaaaat atagcgcgca aactaggata aattatcgcg     2760
cgcggtgtca tctatgttac tcgatctcgt caggagacgg gacaaggatg cgagctagcc     2820
tgcaggaatt gttgattttg tgatgactga tggcaggata tatgcggttg taattcattt     2880
ttattgtcta aatttctgta tttgtttgtt tgttcggttg taaattttttt tggaagaaca     2940 agaaaagaaa aaacacccgt tagggtgttt ttagttagtg tggcgcgccg acttgcgaca     3000
```

```
tgcggtcctt tgcaatcaac tattagaaaa attcatccag catcagatga aattgcagtt    3060
tgttcatatc cggattatca atgccatatt tctgaaacag acgttttgc aggctcgggc    3120 taaattcgcc caggcagttc cacagaatgg ccagatcctg ataacgatcc gcaatgccca    3180
cacggcccac atcaatgcag ccaatcagtt tgccttcatc gaaaatcagg ttatccaggc    3240
taaaatcgcc gtgggtcacc acgctatccg ggctaaacgg cagcagttta tgcatttctt    3300
tccacacctg ttccaccggc cagccgttac gttcatcatc aaaatcgctc gcatccacca    3360
ggccgttgtt catacggctc tgcgcctggg ccagacgaaa cacgatcg ctgttaaacg    3420 ggcagttgca caccggaatg ctatgcagac gacgcagaaa cacggccagc gcatccacaa    3480
tgttttcgcc gctatccgga tattcttcca gcacctgaaa cgcggttttg cccggaatcg    3540
cggtggtcag cagccacgca tcatccgggg tgcgaataaa atgtttaatg gtcggcagcg    3600
gcataaattc ggtcagccag ttcagacgca ccatttcatc ggtcacatcg ttcgccacgc    3660
tgcctttgcc atgtttcaga aacagttccg gcgcatccgg tttgccatac agacgataaa    3720
tggtcgcgcc gctctgaccc acgttatcac gcgcccattt atagccatac agatccgcat    3780
ccatgttgct gttcagacgc ggacggctac agctcgtttc acgctgaata tggctcataa    3840
caccccttgt attactgttt atgtaagcag acagttttat tgttcatgat gatatatttt    3900
tatcttgtgc aatgtaacat cagagatttt gagacacaag atcggattgg cggttatgcg    3960
gttctaccgg cgcggcagcg ttacccgtgt cggcggctcc aacggctcgc catcgtccag    4020
aaaacacggc tcatcgggca tcggcaggcg ctgctgcccg cgccgttccc attcctccgt    4080
ttcggtcaag gctggcaggt ctggttccat gcccggaatg ccgggctggc tgggcggctc    4140
ctcgccgggg ccggtcggta gttgctgctc gcccggatac agggtcggga tgcggcgcag    4200
gtcgccatgc cccaacagcg attcgtcctg gtcgtcgtga tcaaccacca cggcggcact    4260
gaacaccgac aggcgcaact ggtcgcgggg ctggccccac gccacgcggt cattgaccac    4320
gtaggccgac acggtgccgg ggccgttgag cttcacgacg gagatccagc gctcggccac    4380
caagtccttg actgcgtatt ggaccgtccg caaagaacgt ccgatgagct tggaaagtgt    4440
cttctggctg accaccacgg cgttctggtg gcccatctgc gccacgaggt gatgcagcag    4500
cattgccgcc gtgggtttcc tcgcaataag cccggcccac gcctcatgcg ctttgcgttc    4560
cgtttgcacc cagtgaccgg gcttgttctt ggcttgaatg ccgatttctc tggactgcgt    4620
ggccatgctt atctccatgc ggtaggggtg ccgcacggtt gcggcaccat gcgcaatcag    4680
ctgcaacttt tcggcagcgc gacaacaatt atgcgttgcg taaaagtggc agtcaattac    4740 agatttctt taacctacgc aatgagctat tgcgggggggt gccgcaatga gctgttgcgt    4800
accccctttt tttaagttgt tgattttttaa gtctttcgca tttcgcccta tatctagttc    4860
tttggtgccc aaagaagggc accctgcgg ggttccccca cgccttcggc gcggctcccc    4920
ctccggcaaa aagtggcccc tccgggcttt gttgatcgac tgcgcggcct tcggccttgc    4980
ccaaggtggc gctgccccct tggaaccccc gcactcgccg ccgtgaggct cggggggcag    5040
gcgggcgggc ttcgcccttc gactgccccc actcgcatag gcttgggtcg ttccaggcgc    5100
gtcaaggcca agccgctgcg cggtcgctgc gcgagccttg acccgccttc cacttggtgt    5160
ccaaccggca agcgaagcgc gcaggccgca ggccggaggc ttttcccag agaaaattaa    5220 aaaaattgat gggcaaggc cgcaggccgc gcagttggag ccggtgggta tgtggtcgaa    5280
ggctgggtag ccggtgggca atccctgtgg tcaagctcgt gggcaggcgc agcctgtcca    5340
```

```
tcagcttgtc cagcagggtt gtccacgggc cgagcgaagc gagccagccg gtggccgctc    5400
gcggccatcg tccacatatc cacgggctgg caagggagcg cagcgaccgc gcagggcgaa    5460
gcccggagag caagcccgta ggggg                                         5485

<210> SEQ ID NO 14
<211> LENGTH: 5547
<212> TYPE: DNA
<213> ORGANISM: Artificial Sequence
<220> FEATURE:
<223> OTHER INFORMATION: pLX-B3-TagRFP-T plasmid

<400> SEQUENCE: 14
ccatcatcag ttcggtggtc ttccgacgaa caataaggcc gcaaatcgcg gccttttta      60 ttgataacaa aaccggctca gttctgcgta gaaaccaaca tgcaagctcc accgggtgca    120
aagcggcagc ggcggcagga tatattcaat tgtaaatggc ttcatgtccg ggaaatctac    180
tggtggcagg atatattgtg gtgtaaacaa tggagaaaaa gattaattaa gtactagtag    240
cctggtcgaa accgtctcac cagtacgcac gattcaaggc ttgcttcaca aaccaaggca    300
agtaatagag attggagtct ctaaaaaggt agttcccact gaatcaaagg ccatggagtc    360
aaagattcaa atagaggacc taacagaact cgccgtaaag actggcgaac agttcataca    420
gagtctctta cgactcaatg acaagaagaa aatcttcgtc aacatggtgg agcacgacac    480
acttgtctac tccaaaaata tcaaagatac agtctcagaa gaccaaaggg caattgagac    540
ttttcaacaa agggtaatat ccggaaacct cctcggattc cattgcccag ctatctgtca    600
ctttattgtg aagatagtgg aaaaggaagg tggctcctac aaatgccatc attgcgataa    660
aggaaaggcc atcgttgaag atgcctctgc cgacagtggt cccaaagatg accccccacc    720
cacgaggagc atcgtggaaa aagaagacgt tccaaccacg tcttcaaagc aagtggattg    780
atgtgataac atggtggagc acgacacact tgtctactcc aaaaatatca agatacagt     840 ctcagaagac caaagggcaa ttgagacttt tcaacaaagg gtaatatccg gaaacctcct    900
cggattccat tgcccagcta tctgtcactt tattgtgaag atagtggaaa aggaaggtgg    960
ctcctacaaa tgccatcatt gcgataaagg aaaggccatc gttgaagatc tctgccgac    1020 agtggtccca agatggaccc cacccacg aggagcatcg tggaaaaaga agacgttcca    1080
accacgtctt caaagcaagt ggattgatgt gatatctcca ctgacgtaag ggatgacgca    1140
caatcccact atccttcgca agacccttcc tctatataag gaagttcatt tcatttggag    1200
aggaaaatat aaaaactcaa cacaacatac aaaattttaa gcaatcaaat caatctcaag    1260
ctatcaaaat ttttcaaatc tcacttgaaa gatcaaaaat caacaaagaa aatcccttaa    1320
tttctctacc aaatttactg caagtcaaga tggtttcaaa gggagaagag ctgattaagg    1380
agaacatgca catgaagctg tacatggagg gcaccgtgaa caaccaccac ttcaagtgca    1440
catccgaggg cgaaggcaag ccctacgagg gcacccagac catgagaatc aaggtggtcg    1500
agggcggccc tctcccttc gccttcgaca tcctggctac cagcttcatg tacggcagca    1560
gaaccttcat caaccacacc cagggcatcc ccgacttctt taagcagtcc ttccctgagg    1620
gcttcacatg ggagagagtc accacatacg aagacggggg cgtgctgacc gctacccagg    1680
acaccagcct ccaggacggc tgcctcatct acaacgtcaa gatcagaggg gtgaacttcc    1740
catccaacgg ccctgtgatg cagaagaaaa cactcggctg ggaggccaac accgagatgc    1800
tgtaccccgc tgacgcggc ctggaaggca aacagacat ggccctgaag ctcgtgggcg    1860
ggggccacct gatctgcaac ttcaagacca catacagatc caagaaaccc gctaagaacc    1920
```

```
tcaagatgcc cggcgtctac tatgtggacc acagactgga aagaatcaag gaggccgaca    1980
aagagaccta cgtcgagcag cacgaggtgg ctgtggccag atactgcgac ctccctagca    2040
aactggggca caaacttaac taatcgatca cgtgaagctc atatccagat gaaggcagca    2100
gcattgagaa atgttcaaaa tcgtttattt ggcttggatg gaaacgtcgg aacacaagaa    2160
gaggacacag agagacacac cgctggtgat gttaatcgca acatgcacaa cctcctcggt    2220
gtgaggggag tgtagtggtc tcggtatcta tcataaactc tacctgggtg agagtctaat    2280
catccagttg tttttagatt cctgttagca tcctttctc cgctttaata gcagtacatt    2340
cagtgaggtt ttacctccat atgttctagt ctgttattgt cgaacacagg cccttgtatc    2400
tgatgtagcg agtgcttcac tccattcggg ttatagttct tgtgcaagag acaaaaaaaa    2460
aaaaaaaaaa aaaaaaaaaa aaaaaaaaaa aaaaaaaaaa aaaaaaaaaa aaaaaaaaaa    2520
atgcatgcct gcagatcgtt caaacatttg gcataaagt ttcttaagat tgaatcctgt     2580
tgccggtctt gcgatgatta tcatctaatt tctgttgaat tacgttaagc atgtaataat    2640
taacatgtaa tgcatgacgt tatttatgag atgggttttt atgattagag tcccgcaatt    2700
atacatttaa tacgcgatag aaaacaaaat atagcgcgca aactaggata aattatcgcg    2760
cgcggtgtca tctatgttac tcgatctcgt caggagacgg gacaaggatg cgagctagcc    2820
tgcaggaatt gttgattttg tgatgactga tggcaggata tatgcggttg taattcattt    2880
ttattgtcta aatttctgta tttgtttgtt tgttcggttg taaattttt tggaagaaca     2940 agaaaagaaa aaacacccgt tagggtgttt ttagttagtg tggcgcgccg acttgcgaca    3000
tgcggtcctt tgttatttgc cgactacctt ggtgatctcg cctttcacgt agtggacaaa    3060
ttcttccaac tgatctgcgc gcgaggccaa gcgatcttct tcttgtccaa gataagcctg    3120
tctagcttca agtatgacgg gctgatactg gccggcagg cgctccattg cccagtcggc     3180
agcgacatcc ttcggcgcga ttttgccggt tactgcgctg taccaaatgc gggacaacgt    3240
aagcactaca tttcgctcat cgccagccca gtcgggcggc gagttccata gcgttaaggt    3300
ttcatttagc gcctcaaata gatcctgttc aggaaccgga tcaaagagtt cctccgccgc    3360
tggacctacc aaggcaacgc tatgttctct tgcttttgtc agcaagatag ccagatcaat    3420
gtcgatcgtg gctggctcga agatacctgc aagaatgtca ttgcgctgcc attctccaaa    3480
ttgcagttcg cgcttagctg gataacgcca cggaatgatg tcgtcgtgca caacaatggt    3540
gacttctaca gcgcggagaa tctcgctctc tccaggggaa gccgaagttt ccaaaaggtc    3600
gttgatcaaa gctcgccgcg ttgtttcatc aagccttacg gtcaccgtaa ccagcaaatc    3660
aatatcactg tgtggcttca ggccgccatc cactgcggag ccgtacaaat gtacggccag    3720
caacgtcggt tcgagatggc gctcgatgac gccaactacc tctgatagtt gagtcgatac    3780
ttcggcgatc accgcttccc tcatgatgtt taactttgtt ttagggcgac tgccctgctg    3840
cgtaacatcg ttgctgctcc ataacatcaa acatcgaccc acggcgtaac gcgcttgctg    3900
cttggatgcc cgaggcatag actgtacccc aaaaaaacag tcataacaag ccatgaaaac    3960
cgccactgcg ccgttaccac cgctgcgttc ggtcaaggtt cgatcggatt ggcggttatg    4020
cggttctacc ggcgcggcag cgttaccgt gtcggcggct ccaacggctc gccatcgtcc     4080
agaaaacacg gctcatcggg catcggcagg cgctgctgcc cgcgccgttc ccattcctcc    4140
gtttcggtca aggctggcag gtctggtcc atgcccggaa tgccgggctg ctgggcggc     4200 tcctcgccgg ggccggtcgg tagttgctgc tcgcccggat acagggtcgg gatgcggcgc    4260
```

```
aggtcgccat gccccaacag cgattcgtcc tggtcgtcgt gatcaaccac cacggcggca    4320
ctgaacaccg acaggcgcaa ctggtcgcgg ggctggcccc acgccacgcg gtcattgacc    4380
acgtaggccg acacggtgcc ggggccgttg agcttcacga cggagatcca gcgctcggcc    4440
accaagtcct tgactgcgta ttggaccgtc cgcaaagaac gtccgatgag cttggaaagt    4500
gtcttctggc tgaccaccac ggcgttctgg tggcccatct gcgccacgag gtgatgcagc    4560
agcattgccg ccgtgggttt cctcgcaata agcccggccc acgcctcatg cgctttgcgt    4620
tccgtttgca cccagtgacc gggcttgttc ttggcttgaa tgccgatttc tctggactgc    4680
gtggccatgc ttatctccat gcggtagggg tgccgcacgg ttgcggcacc atgcgcaatc    4740
agctgcaact tttcggcagc gcgacaacaa ttatgcgttg cgtaaaagtg gcagtcaatt    4800
acagattttc tttaacctac gcaatgagct attgcggggg gtgccgcaat gagctgttgc    4860 gtaccccccct tttttaagtt gttgattttt aagtctttcg catttcgccc tatatctagt    4920
tctttggtgc ccaaagaagg gcaccccctgc ggggttcccc cacgccttcg gcgcggctcc    4980
ccctccggca aaaagtggcc cctccggggc ttgttgatcg actgcgcggc cttcggcctt    5040
gcccaaggtg gcgctgcccc cttggaaccc ccgcactcgc cgccgtgagg ctcgggggc    5100 aggcgggcgg gcttcgccct tcgactgccc ccactcgcat aggcttgggt cgttccaggc    5160
gcgtcaaggc caagccgctg cgcggtcgct gcgcgagcct tgacccgcct tccacttggt    5220
gtccaaccgg caagcgaagc gcgcaggccg caggccggag gcttttcccc agagaaaatt    5280
aaaaaaattg atggggcaag gccgcaggcc gcgcagttgg agccggtggg tatgtggtcg    5340
aaggctgggt agccggtggg caatccctgt ggtcaagctc gtgggcaggc gcagcctgtc    5400
catcagcttg tccagcaggg ttgtccacgg gccgagcgaa gcgagccagc cggtggccgc    5460
tcgcggccat cgtccacata tccacgggct ggcaagggag cgcagcgacc gcgcagggcg    5520
aagcccggag agcaagcccg taggggg                                        5547
```

<210> SEQ ID NO 15
<211> LENGTH: 5363
<212> TYPE: DNA
<213> ORGANISM: Artificial Sequence
<220> FEATURE:
<223> OTHER INFORMATION: pLX-B4-TagRFP-T plasmid

<400> SEQUENCE: 15

```
ccatcatcag ttcggtggtc ttccgacgaa caataaggcc gcaaatcgcg gccttttta     60 ttgataacaa aaccggctca gttctgcgta gaaaccaaca tgcaagctcc accgggtgca    120
aagcggcagc ggcggcagga tatattcaat tgtaaatggc ttcatgtccg ggaaatctac    180
tggtggcagg atatattgtg gtgtaaacaa tggagaaaaa gattaattaa gtactagtag    240
cctggtcgaa accgtctcac cagtacgcac gattcaaggc ttgcttcaca aaccaaggca    300
agtaatagag attggagtct ctaaaaaggt agttcccact gaatcaaagg ccatggagtc    360
aaagattcaa atagaggacc taacagaact cgccgtaaag actggcgaac agttcataca    420
gagtctctta cgactcaatg acaagaagaa aatcttcgtc aacatggtgg agcacgacac    480
acttgtctac tccaaaaata tcaaagatac agtctcagaa gaccaaaggg caattgagac    540
ttttcaacaa agggtaatat ccggaaacct cctcggattc cattgcccag ctatctgtca    600
ctttattgtg aagatagtgg aaaaggaagg tggctcctac aaatgccatc attgcgataa    660
aggaaaggcc atcgttgaag atgcctctgc cgacagtggt cccaaagatg acccccacc     720 cacgaggagc atcgtggaaa aagaagacgt tccaaccacg tcttcaaagc aagtggattg    780
```

```
atgtgataac atggtggagc acgacacact tgtctactcc aaaaatatca aagatacagt    840
ctcagaagac caaagggcaa ttgagacttt tcaacaaagg gtaatatccg gaaacctcct    900
cggattccat tgcccagcta tctgtcactt tattgtgaag atagtggaaa aggaaggtgg    960
ctcctacaaa tgccatcatt gcgataaagg aaaggccatc gttgaagatc ctctgccgac   1020
agtggtccca aagatggacc cccacccacg aggagcatcg tggaaaaaga agacgttcca   1080
accacgtctt caaagcaagt ggattgatgt gatatctcca ctgacgtaag ggatgacgca   1140
caatcccact atccttcgca agacccttcc tctatataag gaagttcatt tcatttggag   1200
aggaaaatat aaaaactcaa cacaacatac aaaattttaa gcaatcaaat caatctcaag   1260
ctatcaaaat ttttcaaatc tcacttgaaa gatcaaaaat caacaaagaa aatcccttaa   1320
tttctctacc aaatttactg caagtcaaga tggtttcaaa gggagaagag ctgattaagg   1380
agaacatgca catgaagctg tacatggagg gcaccgtgaa caaccaccac ttcaagtgca   1440
catccgaggg cgaaggcaag ccctacgagg gcacccagac catgagaatc aaggtggtcg   1500
agggcggccc tctcccccttc gccttcgaca tcctggctac cagcttcatg tacggcagca   1560
gaaccttcat caaccacacc cagggcatcc ccgacttctt taagcagtcc ttccctgagg   1620
gcttcacatg ggagagagtc accacatacg aagacggggg cgtgctgacc gctacccagg   1680
acaccagcct ccaggacggc tgcctcatct acaacgtcaa gatcagaggg gtgaacttcc   1740
catccaacgg ccctgtgatg cagaagaaaa cactcggctg ggaggccaac accgagatgc   1800
tgtaccccgc tgacgcggc ctggaaggca gaacagacat ggccctgaag ctcgtgggcg   1860
ggggccacct gatctgcaac ttcaagacca catacagatc caagaaaccc gctaagaacc   1920
tcaagatgcc cggcgtctac tatgtggacc acagactgga aagaatcaag gaggccgaca   1980
aagagaccta cgtcgagcag cacgaggtgg ctgtggccag atactgcgac ctccctagca   2040
aactggggca caaacttaac taatcgatca cgtgaagctc atatccagat gaaggcagca   2100
gcattgagaa atgttcaaaa tcgttttattt ggcttggatg gaaacgtcgg aacacaagaa   2160
gaggacacag agagacacac cgctggtgat gttaatcgca acatgcacaa cctcctcggt   2220
gtgaggggag tgtagtggtc tcggtatcta tcataaactc tacctgggtg agagtctaat   2280
catccagttg ttttagatt cctgttagca tcctttctc cgctttaata gcagtacatt   2340
cagtgaggtt ttacctccat atgttctagt ctgttattgt cgaacacagg cccttgtatc   2400
tgatgtagcg agtgcttcac tccattcggg ttatagttct tgtgcaagag acaaaaaaaa   2460
aaaaaaaaa aaaaaaaaa aaaaaaaaa aaaaaaaaa aaaaaaaaa aaaaaaaaa   2520
atgcatgcct gcagatcgtt caaacatttg gcaataaagt ttcttaagat tgaatcctgt   2580
tgccggtctt gcgatgatta tcatctaatt tctgttgaat tacgttaagc atgtaataat   2640
taacatgtaa tgcatgacgt tatttatgag atgggttttt atgattagag tcccgcaatt   2700
atacatttaa tacgcgatag aaaacaaaat atagcgcgca aactaggata aattatcgcg   2760
cgcggtgtca tctatgttac tcgatctcgt caggagacgg gacaaggatg cgagctagcc   2820
tgcaggaatt gttgattttg tgatgactga tggcaggata tatgcggttg taattcattt   2880
ttattgtcta aatttctgta tttgtttgtt tgttcggttg taaattttttt tggaagaaca   2940
agaaaagaaa aaacacccgt tagggtgttt ttagttagtg tggcgcgccg acttgcgaca   3000
tgcggtcctt tgcaatttac ccaacaactc cgcggccggg aagccgatct cggcttgaac   3060
gaattgttag gtggcggtac ttgggtcgat atcaaagtgc atcacttctt cccgtatgcc   3120
```

```
caactttgta tagagagcca ctgcgggatc gtcaccgtaa tctgcttgca cgtagatcac    3180
ataagcacca agcgcgttgg cctcatgctt gaggagattg atgagcgcgg tggcaatgcc    3240
ctgcctccgg tgctctccgg agactgcgag atcatagata tagatctcac tacgcggctg    3300
ctcaaacttg ggcagaacgt aagccgcgag agcgccaaca accgcttctt ggtcgaaggc    3360
agcaagcgcg atgaatgtct tactacggag caagttcccg aggtaatcgg agtccggctg    3420
atgttgggag taggtggcta cgtctccgaa ctcacgaccg aaaagatcaa gagcagcccg    3480
catggatttg acttggtcag ggccgagcct acatgtgcga atgatgccca tacttgagcc    3540
acctaacttt gttttagggc gactgccctg ctgcgtaaca tcgttgctgc tgcgtaacat    3600
cgttgctgct ccataacatc aaacatcgac ccacggcgta acgcgcttgc tgcttggatg    3660
cccgaggcat aggctgtaca aaaaaacagt cataacaagc catgaaaacc gccactgcgc    3720
cgttaccacc gctgcgttcg gtcaaggttc tggaccagtt gcgtgagcgc atacgctact    3780
tgcattacag tttacgaacc gaacaggctt atgtcaagat cggattggcg gttatgcggt    3840
tctaccggcg cggcagcgtt acccgtgtcg gcggctccaa cggctcgcca tcgtccagaa    3900
aacacggctc atcgggcatc ggcaggcgct gctgcccgcg ccgttcccat tcctccgttt    3960
cggtcaaggc tggcaggtct ggttccatgc ccggaatgcc gggctggctg gcggctcct     4020
cgccggggcc ggtcggtagt tgctgctcgc ccggatacag ggtcgggatg cggcgcaggt    4080
cgccatgccc aacagcgat tcgtcctggt cgtcgtgatc aaccaccacg gcggcactga     4140
acaccgacag gcgcaactgg tcgcggggct ggccccacgc cacgcggtca ttgaccacgt    4200
aggccgcacac ggtgccgggg ccgttgagct tcacgacgga gatccagcgc tcggccacca  4260
agtccttgac tgcgtattgg accgtccgca agaacgtcc gatgagcttg aaagtgtct     4320
tctggctgac caccacggcg ttctggtggc ccatctgcgc cacgaggtga tgcagcagca    4380
ttgccgccgt gggtttcctc gcaataagcc cggcccacgc ctcatgcgct ttgcgttccg    4440
tttgcaccca gtgaccgggc ttgttcttgg cttgaatgcc gatttctctg gactgcgtgg    4500
ccatgcttat ctccatgcgg taggggtgcc gcacggttgc ggcaccatgc gcaatcagct    4560
gcaacttttc ggcagcgcga caacaattat gcgttgcgta aaagtggcag tcaattacag    4620
attttcttta acctacgcaa tgagctattg cgggggggtgc cgcaatgagc tgttgcgtac    4680
ccccctttttt taagttgttg attttttaagt ctttcgcatt tcgccctata tctagttctt   4740
tggtgcccaa agaagggcac ccctgcgggg ttcccccacg ccttcggcgc ggctcccct     4800
ccggcaaaaa gtggcccctc cggggcttgt tgatcgactg cgcggccttc ggccttgccc    4860
aaggtggcgc tgcccccttg aaccccccgc actcgccgcc gtgaggctcg gggggcaggc    4920
gggcgggctt cgcccttcga ctgcccccac tcgcataggc ttgggtcgtt ccaggcgcgt    4980
caaggccaag ccgctgcgcg gtcgctgcgc gagccttgac ccgccttcca cttggtgtcc    5040
aaccggcaag cgaagcgcgc aggccgcagg ccggaggctt ttccccagag aaaattaaaa    5100
aaattgatgg ggcaaggccg caggccgcgc agttggagcc ggtgggtatg tggtcgaagg    5160
ctgggtagcc ggtgggcaat ccctgtggtc aagctcgtgg gcaggcgcag cctgtccatc    5220
agcttgtcca gcagggttgt ccacgggccg agcgaagcga gccagccggt ggccgctcgc    5280
ggccatcgtc cacatatcca cgggctggca agggagcgca gcgaccgcgc agggcgaagc    5340
ccggagagca agcccgtagg ggg                                           5363

<210> SEQ ID NO 16
<211> LENGTH: 6185
```

<212> TYPE: DNA
<213> ORGANISM: Artificial Sequence
<220> FEATURE:
<223> OTHER INFORMATION: pLX-R2-TagRFP-T plasmid

<400> SEQUENCE: 16

```
ccatcatcag ttcggtggtc ttccgacgaa caataaggcc gcaaatcgcg gccttttta     60
ttgataacaa aaccggctca gttctgcgta gaaaccaaca tgcaagctcc accgggtgca    120
aagcggcagc ggcggcagga tatattcaat tgtaaatggc ttcatgtccg ggaaatctac    180
tggtggcagg atatattgtg gtgtaaacaa tggagaaaaa gattaattaa gtactagtag    240
cctggtcgaa accgtctcac cagtacgcac gattcaaggc ttgcttcaca aaccaaggca    300
agtaatagag attggagtct ctaaaaaggt agttcccact gaatcaaagg ccatggagtc    360
aaagattcaa atagaggacc taacagaact cgccgtaaag actggcgaac agttcataca    420
gagtctctta cgactcaatg acaagaagaa aatcttcgtc aacatggtgg agcacgacac    480
acttgtctac tccaaaaata tcaaagatac agtctcagaa gaccaaaggg caattgagac    540
ttttcaacaa agggtaatat ccggaaacct cctcggattc cattgcccag ctatctgtca    600
ctttattgtg aagatagtgg aaaggaagg tggctcctac aaatgccatc attgcgataa    660
aggaaaggcc atcgttgaag atgcctctgc cgacagtggt cccaaagatg accccaccc    720
cacgaggagc atcgtggaaa aagaagacgt tccaaccacg tcttcaaagc aagtggattg    780
atgtgataac atggtggagc acgacacact tgtctactcc aaaaatatca agatacagt    840
ctcagaagac caaagggcaa ttgagacttt tcaacaaagg gtaatatccg gaaacctcct    900
cggattccat tgcccagcta tctgtcactt tattgtgaag atagtggaaa ggaaggtgg    960
ctcctacaaa tgccatcatt gcgataaagg aaaggccatc gttgaagatc ctctgccgac   1020
agtggtccca aagatggacc cccacccacg aggagcatcg tggaaaaaga gacgttcca   1080
accacgtctt caaagcaagt ggattgatgt gatatctcca ctgacgtaag ggatgacgca   1140
caatcccact atccttcgca agacccttcc tctatataag gaagttcatt tcatttggag   1200
aggaaaatat aaaaactcaa cacaacatac aaaattttaa gcaatcaaat caatctcaag   1260
ctatcaaaat ttttcaaatc tcacttgaaa gatcaaaaat caacaaagaa atcccttaa   1320
tttctctacc aaatttactg caagtcaaga tggtttcaaa gggagaagag ctgattaagg   1380
agaacatgca catgaagctg tacatggagg gcaccgtgaa caaccaccac ttcaagtgca   1440
catccgaggg cgaaggcaag ccctacgagg gcacccagac catgagaatc aaggtggtcg   1500
agggcggccc tctccccttc gccttcgaca tcctggctac cagcttcatg tacggcagca   1560
gaaccttcat caaccacacc cagggcatcc ccgacttctt taagcagtcc ttccctgagg   1620
gcttcacatg ggagagagtc accacatacg aagacgggg cgtgctgacc gctacccagg   1680
acaccagcct ccaggacggc tgcctcatct acaacgtcaa gatcagaggg gtgaacttcc   1740
catccaacgg ccctgtgatg cagaagaaaa cactcggctg gaggccaac accgagatgc   1800
tgtaccccgc tgacggcggc ctggaaggca gaacagacat ggcctgaag ctcgtgggcg   1860
ggggccacct gatctgcaac ttcaagacca catacagatc caagaaaccc gctaagaacc   1920
tcaagatgcc cggcgtctac tatgtggacc acagactgga aagaatcaag gaggccgaca   1980
aagagaccta cgtcgagcag cacgaggtgg ctgtggccag atactgcgac ctccctagca   2040
aactggggca caaacttaac taatcgatca cgtgaagctc atatccagat gaaggcagca   2100
gcattgagaa atgttcaaaa tcgttttatt ggcttggatg gaaacgtcgg aacacaagaa   2160
```

```
gaggacacag agagacacac cgctggtgat gttaatcgca acatgcacaa cctcctcggt    2220
gtgaggggag tgtagtggtc tcggtatcta tcataaactc tacctgggtg agagtctaat    2280
catccagttg ttttttagatt cctgttagca tccttttctc cgctttaata gcagtacatt    2340
cagtgaggtt ttacctccat atgttctagt ctgttattgt cgaacacagg cccttgtatc    2400
tgatgtagcg agtgcttcac tccattcggg ttatagttct tgtgcaagag acaaaaaaaa    2460
aaaaaaaaaa aaaaaaaaaa aaaaaaaaaa aaaaaaaaaa aaaaaaaaaa aaaaaaaaaa    2520
atgcatgcct gcagatcgtt caaacatttg gcaataaagt ttcttaagat tgaatcctgt    2580
tgccggtctt gcgatgatta tcatctaatt tctgttgaat tacgttaagc atgtaataat    2640
taacatgtaa tgcatgacgt tatttatgag atgggttttt atgattagag tcccgcaatt    2700
atacatttaa tacgcgatag aaaacaaaat atagcgcgca aactaggata aattatcgcg    2760
cgcggtgtca tctatgttac tcgatctcgt caggagacgg gacaaggatg cgagctagcc    2820
tgcaggaatt gttgattttg tgatgactga tggcaggata tatgcggttg taattcattt    2880
ttattgtcta aatttctgta tttgtttgtt tgttcggttg taaattttttt tggaagaaca    2940 agaaaagaaa aaacacccgt tagggtgttt ttagttagtg tggcgcgccg acttgcgaca    3000
tgcggtcctt tgcaatcaac tattagaaaa attcatccag catcagatga aattgcagtt    3060
tgttcatatc cggattatca atgccatatt tctgaaacag acgttttttgc aggctcgggc    3120 taaattcgcc caggcagttc cacagaatgg ccagatcctg ataacgatcc gcaatgccca    3180
cacggcccac atcaatgcag ccaatcagtt tgccttcatc gaaaatcagg ttatccaggc    3240
taaaatcgcc gtgggtcacc acgctatccg ggctaaacgg cagcagttta tgcatttctt    3300
tccacacctg ttccaccggc cagccgttac gttcatcatc aaaatcgctc gcatccacca    3360
ggccgttgtt catacggctc tgcgcctggg ccagacgaaa cacacgatcg ctgttaaacg    3420
ggcagttgca caccggaatg ctatgcagac gacgcagaaa cacggccagc gcatccacaa    3480
tgttttcgcc gctatccgga tattcttcca gcacctgaaa gcggttttg cccggaatcg    3540 cggtggtcag cagccacgca tcatccgggg tgcgaataaa atgtttaatg gtcggcagcg    3600
gcataaattc ggtcagccag ttcagacgca ccatttcatc ggtcacatcg ttcgccacgc    3660
tgcctttgcc atgtttcaga aacagttccg gcgcatccgg tttgccatac agacgataaa    3720
tggtcgcgcc gctctgaccc acgttatcac gcgcccattt atagccatac agatccgcat    3780
ccatgttgct gttcagacgc ggacggctac agctcgtttc acgctgaata tggctcataa    3840 cacccttgt attactgttt atgtaagcag acagttttat tgttcatgat gatatatttt    3900
tatcttgtgc aatgtaacat cagagatttt gagacacaag atcggattgg cggttatgcg    3960
gttgcgatgc aggtggctgc tgaaccccca gccggaactg accccacaag gccctagcgt    4020
ttgcaatgca ccaggtcatc attgacccag gcgtgttcca ccaggccgct gcctcgcaac    4080
tcttcgcagg cttcgccgac ctgctcgcgc cacttcttca cgcgggtgga atccgatccg    4140
cacatgaggc ggaaggtttc cagcttgagc gggtacggct cccggtgcga gctgaaatag    4200
tcgaacatcc gtcgggccgt cggcgacagc ttgcggtact tctcccatat gaatttcgtg    4260
tagtggtcgc cagcaaacag cacgacgatt tcctcgtcga tcaggacctg gcaacgggac    4320
gttttcttgc cacggtccag gacgcggaag cggtgcagca gcgacaccga ttccaggtgc    4380
ccaacgcggt cggacgtgaa gcccatcgcc gtcgcctgta ggcgcgacag gcattcctcg    4440
gccttcgtgt aataccggcc attgatcgac cagcccaggt cctggcaaag ctcgtagaac    4500
gtgaaggtga tcggctcgcc gataggggtg cgcttcgcgt actccaacac ctgctgccac    4560
```

```
accagttcgt catcgtcggc ccgcagctcg acgccggtgt aggtgatctt cacgtccttg    4620
ttgacgtgga aaatgacctt gttttgcagc gcctcgcgcg ggattttctt gttgcgcgtg    4680
gtgaacaggg cagagcgggc cgtgtcgttt ggcatcgctc gcatcgtgtc cggccacggc    4740
gcaatatcga acaaggaaag ctgcatttcc ttgatctgct gcttcgtgtg tttcagcaac    4800
gcggcctgct tggcttcgct gacctgtttt gccaggtcct cgccggcggt ttttcgcttc    4860
ttggtcgtca tagttcctcg cgtgtcgatg gtcatcgact cgccaaacc tgccgcctcc    4920 tgttcgagac gacgcgaacg ctccacggcg gccgatggcg cgggcagggc agggggagcc    4980
agttgcacgc tgtcgcgctc gatcttggcc gtagcttgct ggactatcga ccgacggac    5040 tggaaggttt cgcggggcgc acgcatgacg gtgcggcttg cgatggtttc ggcatcctcg    5100
gcggaaaacc ccgcgtcgat cagttcttgc ctgtatgcct tccggtcaaa cgtccgattc    5160
attcaccctc cttgcgggat tgccccggaa ttaattcccc ggatcgatcc gtcgatcttg    5220 atccctgcg ccatcagatc cttggcggca agaaagccat ccagtttact ttgcagggct    5280
tcccaacctt accagagggc gccccagctg gcaattccgg ttcgcttgct gtccataaaa    5340
ccgcccagtc tagctatcgc catgtaagcc cactgcaagc tacctgcttt ctctttgcgc    5400
ttgcgttttc ccttgtccag atagcccagt agctgacatt catccggggt cagcaccgtt    5460
tctgcggact ggctttctac gtggctgcca tttttggggt gaggccgttc gcggccgagg    5520
ggcgcagccc ctgggggat gggaggcccg cgttagcggg ccgggagggt tcgagaaggg    5580
ggggcacccc ccttcggcgt gcgcggtcac gcgcacaggg cgcagccctg gttaaaaaca    5640
aggtttataa atattggttt aaaagcaggt taaagacag gttagcggtg gccgaaaaac    5700
gggcggaaac ccttgcaaat gctggatttt ctgcctgtgg acagccctc aaatgtcaat    5760 aggtgcgccc ctcatctgtc agcactctgc ccctcaagtg tcaaggatcg cgcccctcat    5820
ctgtcagtag tcgcgcccct caagtgtcaa taccgcaggg cacttatccc caggcttgtc    5880
cacatcatct gtgggaaact cgcgtaaaat caggcgtttt cgccgatttg cgaggctggc    5940
cagctccacg tcgccggccg aaatcgagcc tgcccctcat ctgtcaacgc cgcgccgggt    6000
gagtcggccc ctcaagtgtc aacgtccgcc cctcatctgt cagtgagggc caagttttcc    6060
gcgaggtatc cacaacgccg gcggccctac atggctctgc tgtagtgagt gggttgcgct    6120
ccggcagcgg tcctgatccc ccgcagaaaa aaggatctc aagaagatcc tttgatcttt    6180
tctac                                                                6185
```

<210> SEQ ID NO 17  
<211> LENGTH: 6247  
<212> TYPE: DNA  
<213> ORGANISM: Artificial Sequence  
<220> FEATURE:  
<223> OTHER INFORMATION: pLX-R3-TagRFP-T plasmid

<400> SEQUENCE: 17

```
ccatcatcag ttcggtggtc ttccgacgaa caataaggcc gcaaatcgcg gccttttta      60 ttgataacaa aaccggctca gttctgcgta gaaaccaaca tgcaagctcc accgggtgca    120
aagcggcagc ggcggcagga tatattcaat tgtaaatggc ttcatgtccg ggaaatctac    180
tggtggcagg atatattgtg gtgtaaacaa tggagaaaaa gattaattaa gtactagtag    240
cctggtcgaa accgtctcac cagtacgcac gattcaaggc ttgcttcaca aaccaaggca    300
agtaatagag attggagtct ctaaaaaggt agttcccact gaatcaaagg ccatggagtc    360
```

```
aaagattcaa atagaggacc taacagaact cgccgtaaag actggcgaac agttcataca    420
gagtctctta cgactcaatg acaagaagaa aatcttcgtc aacatggtgg agcacgacac    480
acttgtctac tccaaaaata tcaaagatac agtctcagaa gaccaaaggg caattgagac    540
ttttcaacaa agggtaatat ccggaaacct cctcggattc cattgcccag ctatctgtca    600
ctttattgtg aagatagtgg aaaaggaagg tggctcctac aaatgccatc attgcgataa    660
aggaaaggcc atcgttgaag atgcctctgc cgacagtggt cccaaagatg acccccacc    720
cacgaggagc atcgtggaaa aagaagacgt tccaaccacg tcttcaaagc aagtggattg    780
atgtgataac atggtggagc acgacacact tgtctactcc aaaaatatca agatacagt    840
ctcagaagac caagggcaa ttgagacttt tcaacaaagg gtaatatccg gaaacctcct    900
cggattccat tgcccagcta tctgtcactt tattgtgaag atagtggaaa aggaaggtgg    960
ctcctacaaa tgccatcatt gcgataaagg aaaggccatc gttgaagatc ctctgccgac   1020
agtggtccca agatggacc cccacccacg aggagcatcg tggaaaaaga agacgttcca   1080
accacgtctt caaagcaagt ggattgatgt gatatctcca ctgacgtaag ggatgacgca   1140
caatcccact atccttcgca agacccttcc tctatataag gaagttcatt tcatttggag   1200
aggaaaatat aaaaactcaa cacaacatac aaaattttaa gcaatcaaat caatctcaag   1260
ctatcaaaat ttttcaaatc tcacttgaaa gatcaaaaat caacaaagaa aatcccttaa   1320
tttctctacc aaatttactg caagtcaaga tggtttcaaa gggagaagag ctgattaagg   1380
agaacatgca catgaagctg tacatggagg caccgtgaa caaccaccac ttcaagtgca   1440
catccgaggg cgaaggcaag ccctacgagg cacccagac catgagaatc aaggtggtcg   1500
agggcggccc tctccccttc gccttcgaca tcctggctac cagcttcatg tacggcagca   1560
gaaccttcat caaccacacc cagggcatcc ccgacttctt taagcagtcc ttccctgagg   1620
gcttcacatg ggagagagtc accacatacg aagacgggg cgtgctgacc gctacccagg   1680
acaccagcct ccaggacggc tgcctcatct acaacgtcaa gatcagaggg gtgaacttcc   1740
catccaacgg ccctgtgatg cagaagaaaa cactcggctg ggaggccaac accgagatgc   1800
tgtaccccgc tgacggcggc ctggaaggca gaacagacat ggccctgaag ctcgtgggcg   1860
ggggccacct gatctgcaac ttcaagacca catacagatc caagaaaccc gctaagaacc   1920
tcaagatgcc cggcgtctac tatgtggacc acagactgga agaatcaag gaggccgaca   1980
aagagaccta cgtcgagcag cacgaggtgg ctgtggccag atactgcgac ctccctagca   2040
aactggggca caaacttaac taatcgatca cgtgaagctc atatccagat gaaggcagca   2100
gcattgagaa atgttcaaaa tcgtttattt ggcttggatg gaaacgtcgg aacacaagaa   2160
gaggacacag agagacacac cgctggtgat gttaatcgca acatgcacaa cctcctcggt   2220
gtgaggggag tgtagtggtc tcggtatcta tcataaactc tacctgggtg agagtctaat   2280
catccagttg tttttagatt cctgttagca tccttttctc cgctttaata gcagtacatt   2340
cagtgaggtt ttacctccat atgttctagt ctgttattgt cgaacacagg cccttgtatc   2400
tgatgtagcg agtgcttcac tccattcggg ttatagttct tgtgcaagag acaaaaaaaa   2460
aaaaaaaaaa aaaaaaaaa aaaaaaaaa aaaaaaaaa aaaaaaaaa aaaaaaaaa       2520
atgcatgcct gcagatcgtt caaacatttg gcaataaagt ttcttaagat tgaatcctgt   2580
tgccggtctt gcgatgatta tcatctaatt tctgttgaat tacgttaagc atgtaataat   2640
taacatgtaa tgcatgacgt tatttatgag atgggttttt atgattagag tcccgcaatt   2700
atacatttaa tacgcgatag aaaacaaaat atagcgcgca aactaggata aattatcgcg   2760
```

```
cgcggtgtca tctatgttac tcgatctcgt caggagacgg gacaaggatg cgagctagcc    2820
tgcaggaatt gttgattttg tgatgactga tggcaggata tatgcggttg taattcattt    2880
ttattgtcta aatttctgta tttgtttgtt tgttcggttg taaattttttt tggaagaaca    2940 agaaaagaaa aaacacccgt tagggtgttt ttagttagtg tggcgcgccg acttgcgaca    3000
tgcggtcctt tgttatttgc cgactacctt ggtgatctcg cctttcacgt agtggacaaa    3060
ttcttccaac tgatctgcgc gcgaggccaa gcgatcttct tcttgtccaa gataagcctg    3120
tctagcttca agtatgacgg gctgatactg ggccggcagg cgctccattg cccagtcggc    3180
agcgacatcc ttcggcgcga ttttgccggt tactgcgctg taccaaatgc gggacaacgt    3240
aagcactaca tttcgctcat cgccagccca gtcgggcggc gagttccata gcgttaaggt    3300
ttcatttagc gcctcaaata gatcctgttc aggaaccgga tcaaagagtt cctccgccgc    3360
tggacctacc aaggcaacgc tatgttctct tgcttttgtc agcaagatag ccagatcaat    3420
gtcgatcgtg gctggctcga agatacctgc aagaatgtca ttgcgctgcc attctccaaa    3480
ttgcagttcg cgcttagctg gataacgcca cggaatgatg tcgtcgtgca caacaatggt    3540
gacttctaca gcgcggagaa tctcgctctc tccaggggaa gccgaagttt ccaaaaggtc    3600
gttgatcaaa gctcgccgcg ttgtttcatc aagccttacg gtcaccgtaa ccagcaaatc    3660
aatatcactg tgtggcttca ggccgccatc cactgcggag ccgtacaaat gtacggccag    3720
caacgtcggt tcgagatggc gctcgatgac gccaactacc tctgatagtt gagtcgatac    3780
ttcggcgatc accgcttccc tcatgatgtt aactttgtt ttagggcgac tgccctgctg    3840
cgtaacatcg ttgctgctcc ataacatcaa acatcgaccc acggcgtaac gcgcttgctg    3900
cttggatgcc cgaggcatag actgtacccc aaaaaaacag tcataacaag ccatgaaaac    3960
cgccactgcg ccgttaccac cgctgcgttc ggtcaaggtt cgatcggatt ggcggttatg    4020
cggttgcgat gcaggtggct gctgaacccc cagccggaac tgaccccaca aggccctagc    4080
gtttgcaatg caccaggtca tcattgaccc aggcgtgttc caccaggccg ctgcctcgca    4140
actcttcgca ggcttcgccg acctgctcgc gccacttctt cacgcgggtg gaatccgatc    4200
cgcacatgag gcggaaggtt tccagcttga gcgggtacgg ctcccggtgc gagctgaaat    4260
agtcgaacat ccgtcgggcc gtcggcgaca gcttgcggta cttctcccat atgaatttcg    4320
tgtagtggtc gccagcaaac agcacgacga tttcctcgtc gatcaggacc tggcaacggg    4380
acgttttctt gccacggtcc aggacgcgga agcggtgcag cagcgacacc gattccaggt    4440
gcccaacgcg gtcggacgtg aagcccatcg ccgtcgcctg taggcgcgac aggcattcct    4500
cggccttcgt gtaataccgg ccattgatcg accagcccag gtcctggcaa agctcgtaga    4560
acgtgaaggt gatcggctcg ccgataggg tgcgcttcgc gtactccaac acctgctgcc    4620
acaccagttc gtcatcgtcg gcccgcagct cgacgccggt gtaggtgatc ttcacgtcct    4680
tgttgacgtg gaaaatgacc ttgttttgca gcgcctcgcg cgggattttc ttgttgcgcg    4740
tggtgaacag ggcagagcgg gccgtgtcgt ttggcatcgc tcgcatcgtg tccggccacg    4800
gcgcaatatc gaacaaggaa agctgcattt ccttgatctg ctgcttcgtg tgtttcagca    4860
acgcggcctg cttggcttcg ctgacctgtt ttgccaggtc ctcgccggcg ttttttcgct    4920
tcttggtcgt catagttcct ccgcgtgtcga tggtcatcga cttcgccaaa cctgccgcct    4980
cctgttcgag acgacgcgaa cgctccacgg cggccgatgg cgcgggcagg caggggagg    5040 ccagttgcac gctgtcgcgc tcgatcttgg ccgtagcttg ctggactatc gagccgacgg    5100
```

```
actggaaggt tcgcggggc gcacgcatga cggtgcggct tgcgatggtt tcggcatcct    5160
cggcggaaaa ccccgcgtcg atcagttctt gcctgtatgc cttccggtca aacgtccgat    5220
tcattcaccc tccttgcggg attgccccgg aattaattcc ccggatcgat ccgtcgatct    5280
tgatcccctg cgccatcaga tccttggcgg caagaaagcc atccagttta ctttgcaggg    5340
cttcccaacc ttaccagagg gcgccccagc tggcaattcc ggttcgcttg ctgtccataa    5400
aaccgcccag tctagctatc gccatgtaag cccactgcaa gctacctgct ttctctttgc    5460
gcttgcgttt tcccttgtcc agatagccca gtagctgaca ttcatccggg gtcagcaccg    5520
tttctgcgga ctggctttct acgtggctgc cattttgggg gtgaggccgt tcgcggccga    5580
ggggcgcagc ccctggggg atgggaggcc cgcgttagcg ggccgggagg gttcgagaag    5640
gggggcacc ccccttcggc gtgcgcggtc acgcgcacag ggcgcagccc tggttaaaaa    5700
caaggtttat aaatattggt ttaaaagcag gttaaaagac aggttagcgg tggccgaaaa    5760
acgggcggaa acccttgcaa atgctggatt ttctgcctgt ggacagcccc tcaaatgtca    5820
ataggtgcgc ccctcatctg tcagcactct gcccctcaag tgtcaaggat cgcgcccctc    5880
atctgtcagt agtcgcgccc tcaagtgtc aataccgcag ggcacttatc cccaggcttg    5940
tccacatcat ctgtgggaaa ctcgcgtaaa atcaggcgtt ttcgccgatt tgcgaggctg    6000
gccagctcca cgtcgccggc cgaaatcgag cctgcccctc atctgtcaac gccgcgccgg    6060
gtgagtcggc ccctcaagtg tcaacgtccg cccctcatct gtcagtgagg gccaagtttt    6120
ccgcgaggta ccacaacgc cggcggccct acatggctct gctgtagtga gtgggttgcg    6180
ctccggcagc ggtcctgatc ccccgcagaa aaaaggatc tcaagaagat cctttgatct    6240
tttctac                                                               6247
```

<210> SEQ ID NO 18
<211> LENGTH: 6063
<212> TYPE: DNA
<213> ORGANISM: Artificial Sequence
<220> FEATURE:
<223> OTHER INFORMATION: pLX-R4-TagRFP-T plasmid

<400> SEQUENCE: 18

```
ccatcatcag ttcggtggtc ttccgacgaa caataaggcc gcaaatcgcg gcctttttta     60
ttgataacaa aaccggctca gttctgcgta gaaaccaaca tgcaagctcc accgggtgca    120
aagcggcagc ggcggcagga tatattcaat tgtaaatggc ttcatgtccg ggaaatctac    180
tggtggcagg atatattgtg gtgtaaacaa tggagaaaaa gattaattaa gtactagtag    240
cctggtcgaa accgtctcac cagtacgcac gattcaaggc ttgcttcaca aaccaaggca    300
agtaatagag attggagtct ctaaaaaggt agttcccact gaatcaaagg ccatggagtc    360
aaagattcaa atagaggacc taacagaact cgccgtaaag actggcgaac agttcataca    420
gagtctctta cgactcaatg acaagaagaa aatcttcgtc aacatggtgg agcacgacac    480
acttgtctac tccaaaaata tcaaagatac agtctcagaa gaccaaaggg caattgagac    540
ttttcaacaa agggtaatat ccggaaacct cctcggattc cattgcccag ctatctgtca    600
ctttattgtg aagatagtgg aaaaggaagg tggctcctac aaatgccatc attgcgataa    660
aggaaaggcc atcgttgaag atgcctctgc cgacagtggt cccaaagatg acccccacc    720
cacgaggagc atcgtggaaa aagaagacgt tccaaccacg tcttcaaagc aagtggattg    780
atgtgataac atggtggagc acgacacact tgtctactcc aaaaatatca agatacagt    840
ctcagaagac caaagggcaa ttgagacttt tcaacaaagg gtaatatccg gaaacctcct    900
```

-continued

```
cggattccat tgcccagcta tctgtcactt tattgtgaag atagtggaaa aggaaggtgg    960
ctcctacaaa tgccatcatt gcgataaagg aaaggccatc gttgaagatc ctctgccgac   1020
agtggtccca agatggacc cccacccacg aggagcatcg tggaaaaaga agacgttcca    1080
accacgtctt caaagcaagt ggattgatgt gatatctcca ctgacgtaag ggatgacgca   1140
caatcccact atccttcgca agacccttcc tctatataag gaagttcatt tcatttggag   1200
aggaaaatat aaaaactcaa cacaacatac aaaattttaa gcaatcaaat caatctcaag   1260
ctatcaaaat ttttcaaatc tcacttgaaa gatcaaaaat caacaaagaa aatcccttaa   1320
tttctctacc aaatttactg caagtcaaga tggtttcaaa gggagaagag ctgattaagg   1380
agaacatgca catgaagctg tacatggagg gcaccgtgaa caaccaccac ttcaagtgca   1440
catccgaggg cgaaggcaag ccctacgagg gcacccagac catgagaatc aaggtggtcg   1500
agggcggccc tctccccttc gccttcgaca tcctggctac cagcttcatg tacggcagca   1560
gaaccttcat caaccacacc cagggcatcc ccgacttctt taagcagtcc ttccctgagg   1620
gcttcacatg ggagagagtc accacatacg aagacggggg cgtgctgacc gctacccagg   1680
acaccagcct ccaggacggc tgcctcatct acaacgtcaa gatcagaggg gtgaacttcc   1740
catccaacgg ccctgtgatg cagaagaaaa cactcggctg ggaggccaac accgagatgc   1800
tgtaccccgc tgacggcggc ctggaaggca gaacagacat ggccctgaag ctcgtgggcg   1860
ggggccacct gatctgcaac ttcaagacca catacagatc caagaaaccc gctaagaacc   1920
tcaagatgcc cggcgtctac tatgtggacc acagactgga aagaatcaag gaggccgaca   1980
aagagaccta cgtcgagcag cacgaggtgg ctgtggccag atactgcgac ctccctagca   2040
aactggggca caaacttaac taatcgatca cgtgaagctc atatccagat gaaggcagca   2100
gcattgagaa atgttcaaaa tcgtttattt ggcttggatg gaaacgtcgg aacacaagaa   2160
gaggacacag agagacacac cgctggtgat gttaatcgca acatgcacaa cctcctcggt   2220
gtgaggggag tgtagtggtc tcggtatcta tcataaactc tacctgggtg agagtctaat   2280
catccagttg ttttttagatt cctgttagca tccttttctc cgctttaata gcagtacatt   2340
cagtgaggtt ttacctccat atgttctagt ctgttattgt cgaacacagg cccttgtatc   2400
tgatgtagcg agtgcttcac tccattcggg ttatagttct tgtgcaagag acaaaaaaaa   2460
aaaaaaaaaa aaaaaaaaaa aaaaaaaaaa aaaaaaaaaa aaaaaaaaaa aaaaaaaaaa   2520
atgcatgcct gcagatcgtt caaacatttg gcaataaagt ttcttaagat tgaatcctgt   2580
tgccggtctt gcgatgatta tcatctaatt tctgttgaat tacgttaagc atgtaataat   2640
taacatgtaa tgcatgacgt tatttatgag atgggttttt atgattagag tcccgcaatt   2700
atacatttaa tacgcgatag aaaacaaaat atagcgcgca aactaggata aattatcgcg   2760
cgcggtgtca tctatgttac tcgatctcgt caggagacgg gacaaggatg cgagctagcc   2820
tgcaggaatt gttgattttg tgatgactga tggcaggata tatgcggttg taattcattt   2880
ttattgtcta aatttctgta tttgtttgtt tgttcggttg taaatttttt tggaagaaca   2940
agaaaagaaa aaacacccgt tagggtgttt ttagttagtg tggcgcgccg acttgcgaca   3000
tgcggtcctt tgcaatttac ccaacaactc cgcggccggg aagccgatct cggcttgaac   3060
gaattgttag gtggcggtac ttgggtcgat atcaaagtgc atcacttctt cccgtatgcc   3120
caactttgta tagagagcca ctgcgggatc gtcaccgtaa tctgcttgca cgtagatcac   3180
ataagcacca agcgcgttgg cctcatgctt gaggagattg atgagcgcgg tggcaatgcc   3240
```

-continued

```
ctgcctccgg tgctctccgg agactgcgag atcatagata tagatctcac tacgcggctg    3300
ctcaaacttg ggcagaacgt aagccgcgag agcgccaaca accgcttctt ggtcgaaggc    3360
agcaagcgcg atgaatgtct tactacggag caagttcccg aggtaatcgg agtccggctg    3420
atgttgggag taggtggcta cgtctcccga actcacgaccg aaaagatcaa gagcagcccg    3480
catggatttg acttggtcag ggccgagcct acatgtgcga atgatgccca tacttgagcc    3540
acctaacttt gttttagggc gactgccctg ctgcgtaaca tcgttgctgc tgcgtaacat    3600
cgttgctgct ccataacatc aaacatcgac ccacggcgta acgcgcttgc tgcttggatg    3660
cccgaggcat aggctgtaca aaaaaacagt cataacaagc catgaaaacc gccactgcgc    3720
cgttaccacc gctgcgttcg gtcaaggttc tggaccagtt gcgtgagcgc atacgctact    3780
tgcattacag tttacgaacc gaacaggctt atgtcaagat cggattggcg gttatgcggt    3840
tgcgatgcag gtggctgctg aacccccagc cggaactgac cccacaaggc cctagcgttt    3900
gcaatgcacc aggtcatcat tgacccaggc gtgttccacc aggccgctgc ctcgcaactc    3960
ttcgcaggct tcgccgacct gctcgcgcca cttcttcacg cgggtggaat ccgatccgca    4020
catgaggcgg aaggtttcca gcttgagcgg gtacggctcc cggtgcgagc tgaaatagtc    4080
gaacatccgt cgggccgtcg gcgacagctt gcggtacttc tcccatatga atttcgtgta    4140
gtggtcgcca gcaaacagca cgacgatttc ctcgtcgatc aggacctgga acgggacgt    4200 tttcttgcca cggtccagga gcggaagcg gtgcagcagc gacaccgatt ccaggtgccc    4260
aacgcggtcg gacgtgaagc ccatcgccgt cgcctgtagg cgcgacaggc attcctcggc    4320
cttcgtgtaa taccggccat tgatcgacca gcccaggtcc tggcaaagct cgtagaacgt    4380
gaaggtgatc ggctcgccga taggggtgcg cttcgcgtac tccaacacct gctgccacac    4440
cagttcgtca tcgtcggccc gcagctcgac gccggtgtag gtgatcttca cgtccttgtt    4500
gacgtggaaa atgaccttgt tttgcagcgc ctcgcgcggg attttcttgt tgcgcgtggt    4560
gaacagggca gagcgggccg tgtcgtttgg catcgctcgc atcgtgtccg gccacgcgc    4620 aatatcgaac aaggaaagct gcatttcctt gatctgctgc ttcgtgtgtt tcagcaacgc    4680
ggcctgcttg gcttcgctga cctgttttgc caggtcctcg ccggcggttt ttcgcttctt    4740
ggtcgtcata gttcctcgcg tgtcgatggt catcgacttc gccaaacctg ccgcctcctg    4800
ttcgagacga cgcgaacgct ccacggcggc cgatggcgcg ggcagggcag ggggagccag    4860
ttgcacgctg tcgcgctcga tcttggccgt agcttgctgg actatcgagc cgacggactg    4920
gaaggtttcg cggggcgcac gcatgacggt gcggcttgcg atggtttcgg catcctcggc    4980
ggaaaacccc gcgtcgatca gttcttgcct gtatgccttc cggtcaaacg tccgattcat    5040
tcaccctcct tgcgggattg ccccggaatt aattccccgg atcgatccgt cgatcttgat    5100
cccctgcgcc atcagatcct tggcggcaag aaagccatcc agtttacttt gcagggcttc    5160
ccaaccttac cagagggcgc cccagctggc aattccggtt cgcttgctgt ccataaaacc    5220
gcccagtcta gctatcgcca tgtaagccca ctgcaagcta cctgctttct ctttgcgctt    5280
gcgttttccc ttgtccagat agcccagtag ctgacattca tccggggtca gcaccgtttc    5340
tgcggactgg ctttctacgt ggctgccatt tttggggtga ggccgttcgc ggccgagggg    5400
cgcagcccct gggggggatgg gaggcccgcg ttagcgggcc gggagggttc gagaagggg    5460 ggcacccccc ttcggcgtgc gcggtcacgc gcacagggcg cagccctggt taaaaacaag    5520
gtttataaat attggtttaa aagcaggtta aagacaggt tagcggtggc cgaaaaacgg    5580
gcggaaaccc ttgcaaatgc tggatttctct gcctgtggac agcccctcaa atgtcaatag    5640
```

-continued

| | |
|---|---|
| gtgcgccct catctgtcag cactctgccc ctcaagtgtc aaggatcgcg cccctcatct | 5700 |
| gtcagtagtc gcgcccctca agtgtcaata ccgcagggca cttatcccca ggcttgtcca | 5760 |
| catcatctgt gggaaactcg cgtaaaatca ggcgttttcg ccgatttgcg aggctggcca | 5820 |
| gctccacgtc gccggccgaa atcgagcctg cccctcatct gtcaacgccg cgccgggtga | 5880 |
| gtcggcccct caagtgtcaa cgtccgcccc tcatctgtca gtgagggcca agttttccgc | 5940 |
| gaggtatcca caacgccggc ggccctacat ggctctgctg tagtgagtgg gttgcgctcc | 6000 |
| ggcagcggtc ctgatccccc gcagaaaaaa aggatctcaa gaagatcctt tgatcttttc | 6060 |
| tac | 6063 |

<210> SEQ ID NO 19
<211> LENGTH: 10749
<212> TYPE: DNA
<213> ORGANISM: Artificial Sequence
<220> FEATURE:
<223> OTHER INFORMATION: pLX-B2-XT1-XT2-hCas9 plasmid

<400> SEQUENCE: 19

| | |
|---|---|
| ccatcatcag ttcggtggtc ttccgacgaa caataaggcc gcaaatcgcg gccttttta | 60 |
| ttgataacaa aaccggctca gttctgcgta gaaaccaaca tgcaagctcc accgggtgca | 120 |
| aagcggcagc ggcggcagga tatattcaat tgtaaatggc ttcatgtccg ggaaatctac | 180 |
| tggtggcagg atatattgtg gtgtaaacaa tggagaaaaa gattaattaa gtactagtag | 240 |
| cctggtcgaa accgtctcag gagagcgatc agcttgcatg ccggtcgatc tagtaacata | 300 |
| gatgacaccg cgcgcgataa tttatcctag tttgcgcgct atattttgtt ttctatcgcg | 360 |
| tattaaatgt ataattgcgg gactctaatc ataaaaaccc atctcataaa taacgtcatg | 420 |
| cattacatgt taattattac atgcttaacg taattcaaca gaaattatat gataatcatg | 480 |
| gcaagaccgg caacaggatt caatcttaag aaactttatt gccaaatgtt tgaacgatct | 540 |
| gcttgactct agctagagtc gaacccccag agtcccgctc agaagaactc gtcaagaagg | 600 |
| cgatagaagg ctatgcgctg cgaatcggga gcggcgatac cgtaaagcac gaggaagcgg | 660 |
| tcagcccatt cgccgccaag ctcttcagca atatcacggg tagccaacgc tatgtcctga | 720 |
| tagcggtccg ccacacccag ccggccacag tcgatgaatc cagaaaagcg gccattttcc | 780 |
| accatgatat tcggcaagca ggcgtcgccg tgggtcacga cgagatcctc gccgtcgggc | 840 |
| atccgcgcct tgagcctggc gaacagttcg gctggcgcga gcccctgatg ctcttcgtcc | 900 |
| agatcatcct gatcgacaag accggcttcc atccgagtac gtgctcgctc gatgcggtgt | 960 |
| ttcgcttggt ggtcgaatgg gcaggtagcc ggatcaagcg tatgcagccg ccgcattgca | 1020 |
| tcagccatga tggatacttt ctcggcagga gcaaggtgag atgacaggag atcctgcccc | 1080 |
| ggcacttcgc ccaatagcag ccagtcccct tcccgcttca gtgacaacgt cgagcacagct | 1140 |
| gcgcaaggaa cgcccgtcgt ggccagccac gatagccgcg ctgcctcgtc ttggagttca | 1200 |
| ttcagggcac cggacaggtc ggtcttgaca aaaagaaccg ggcgcccctg cgctgacagc | 1260 |
| cggaacacgg cggcatcaga gcagccgatt gtctgttgtg cccagtcata gccgaatagc | 1320 |
| ctctccaccc aagcggccgg agaacctgcg tgcaatccat cttgttcaat catgcctcga | 1380 |
| tcgagttgag agtgaatatg agactctaat tggataccga ggggaattta tggaacgtca | 1440 |
| gtggagcatt tttgacaaga atatttgct agctgatagt gaccttaggc gacttttgaa | 1500 |
| cgcgcaataa tggtttctga cgtatgtgct tagctcatta aactccagaa acccgcggct | 1560 |

```
gagtggctcc ttcaacgttg cggttctgtc agttccaaac gtaaaacggc ttgtcccgcg    1620
tcatcggcgg gggtcataac gtgactccct taattctcat gtatctccgt caggagcatc    1680
ttcattctta agatatgaag ataatcttca aaggcccct gggaatctga agaagagaa      1740 gcaggcccat ttatatggga aagaacaata gtatttctta tataggccca tttaagttga    1800
aaacaatctt caaaagtccc acatcgctta gataagaaaa cgaagctgag tttatataca    1860
gctagagtcg aagtagtgat tgaaaacacc gtcttcggag agttttagag ctagaaatag    1920
caagttaaaa taaggctagt ccgttatcaa cttgaaaaag tggcaccgag tcggtgcttt    1980
ttttctagac ccagctttct tgtacaaagt tggcattacg ctgtcaggag catcttcatt    2040
cttaagatat gaagataatc ttcaaaaggc ccctgggaat ctgaaagaag agaagcaggc    2100
ccatttatat gggaaagaac aatagtattt cttatatagg cccatttaag ttgaaaacaa    2160
tcttcaaaag tcccacatcg cttagataag aaaacgaagc tgagtttata tacagctaga    2220
gtcgaagtag tgattgaaaa ttgggaaaaa actaggtttt agagctagaa atagcaagtt    2280
aaaataaggc tagtccgtta tcaacttgaa aaagtggcac cgagtcggtg ctttttttct    2340
agacccagct ttcttgtaca aagttggcat tacgctgtca ggagactaga gccaagctga    2400
tctcctttgc cccggagatc accatggacg actttctcta tctctacgat ctaggaagaa    2460
agttcgacgg agaaggtgac gataccatgt tcaccaccga taatgagaag attagcctct    2520
tcaatttcag aaagaatgct gacccacaga tggttagaga ggcctacgcg gcaggtctga    2580
tcaagacgat ctaccgagt aataatctcc aggagatcaa ataccttccc aagaaggtta    2640
aagatgcagt caaaagattc aggactaact gcatcaagaa cacagagaaa gatatatttc    2700
tcaagatcag aagtactatt ccagtatgga cgattcaagg cttgcttcat aaaccaaggc    2760
aagtaataga gattggagtc tctaagaaag tagttcctac tgaatcaaag gccatggagt    2820
caaaaattca gatcgaggat ctaacagaac tcgccgtgaa gactggcgaa cagttcatac    2880
agagtctttt acgactcaat gacaagaaga aatcttcgt caacatggtg gagcacgaca    2940
ctctcgtcta ctccaagaat atcaaagata cagtctcaga agaccaaagg gctattgaga    3000
cttttcaaca aagggtaata tcgggaaacc tcctcggatt ccattgccca gctatctgtc    3060
acttcatcaa aaggacagta gaaaggaag gtggcaccta caaatgccat cattgcgata    3120
aaggaaaggc tatcgttcaa gatgcctctg ccgacagtgg tcccaaagat gaccccac     3180 ccacgaggag catcgtggaa aaagaagacg ttccaaccac gtcttcaaag caagtggatt    3240
gatgtgatat ctccactgac gtaagggatg acgcacaatc ccactatcct tcgcaagacc    3300
cttcctctat ataaggaagt tcatttcatt tggagaggac tccggtattt ttacaacaat    3360
accacaacaa aacaaacaac aaacaacatt acaatttact attctagtcg aaatggacaa    3420
gaagtactcc attgggctcg atatcggcac aaacagcgtc ggctgggccg tcattacgga    3480
cgagtacaag gtgccgagca aaaaattcaa agttctgggc aataccgatc gccacagcat    3540
aaagaagaac ctcattggcg ccctcctgtt cgactccggg aaacggccg aagccacgcg    3600 gctcaaaaga acagcacggc gcagatatac ccgcagaaag aatcggatct gctacctgca    3660
ggagatcttt agtaatgaga tggctaaggt ggatgactct ttcttccata ggctggagga    3720 gtccttttg gtggaggagg ataaaaagca cgagcgccac ccaatctttg caatatcgt    3780 ggacgaggtg gcgtaccatg aaaagtaccc aaccatatat catctgagga agaagcttgt    3840
agacagtact gataaggctg acttgcggtt gatctatctc gcgctggcgc atatgatcaa    3900
atttcgggga cacttcctca tcgagggga cctgaaccca gacaacagcg atgtcgacaa    3960
```

```
actctttatc caactggttc agacttacaa tcagcttttc gaagagaacc cgatcaacgc    4020
atccggagtt gacgccaaag caatcctgag cgctaggctg tccaaatccc ggcggctcga    4080
aaacctcatc gcacagctcc ctggggagaa gaagaacggc ctgtttggta atcttatcgc    4140
cctgtcactc gggctgaccc ccaactttaa atctaacttc gacctggccg aagatgccaa    4200
gcttcaactg agcaaagaca cctacgatga tgatctcgac aatctgctgg cccagatcgg    4260
cgaccagtac gcagaccttt ttttggcggc aaagaacctg tcagacgcca ttctgctgag    4320
tgatattctg cgagtgaaca cggagatcac caaagctccg ctgagcgcta gtatgatcaa    4380
gcgctatgat gagcaccacc aagacttgac tttgctgaag gcccttgtca gacagcaact    4440
gcctgagaag tacaaggaaa ttttcttcga tcagtctaaa aatggctacg ccggatacat    4500
tgacggcgga gcaagccagg aggaatttta caaatttatt aagcccatct tggaaaaaat    4560
ggacggcacc gaggagctgc tggtaaagct taacagagaa gatctgttgc gcaaacagcg    4620
cactttcgac aatggaagca tcccccacca gattcacctg ggcgaactgc acgctatcct    4680
caggcggcaa gaggatttct accccttttt gaaagataac agggaaaaga ttgagaaaat    4740
cctcacattt cggatacccct actatgtagg ccccctcgcc cggggaaatt ccagattcgc    4800
gtggatgact cgcaaatcag aagagactat cactccctgg aacttcgagg aagtcgtgga    4860
taagggggcc tctgcccagt ccttcatcga aaggatgact aactttgata aaaatctgcc    4920
taacgaaaag gtgcttccta acactctctc tgctgtacgag tacttcacag tttataacga    4980
gctcaccaag gtcaaatacg tcacagaagg gatgagaaag ccagcattcc tgtctggaga    5040
gcagaagaaa gctatcgtgg acctcctctt caagacgaac cggaaagtta ccgtgaaaca    5100
gctcaaagaa gattatttca aaagattga atgtttcgac tctgttgaaa tcagcggagt    5160
ggaggatcgc ttcaacgcat ccctgggaac gtatcacgat ctcctgaaaa tcattaaaga    5220
caaggacttc ctggacaatg aggagaacga ggacattctt gaggacattg tcctcacccct    5280 tacgttgttt gaagatagg atgattga agaacgcttg aaaacttacg ctcatctctt    5340
cgacgacaaa gtcatgaaac agctcaagag gcgccgatat acaggatggg ggcggctgtc    5400
aagaaaactg atcaatggga tccgagacaa gcagagtgga aagacaatcc tggatttttct    5460 taagtccgat ggatttgcca accggaactt catgcagttg atccatgatg actctctcac    5520
ctttaaggag gacatccaga aagcacaagt ttctggccag ggggacagtc tccacgagca    5580
catcgctaat cttgcaggta gcccagctat caaaaaggga atactgcaga ccgttaaggt    5640
cgtggatgaa ctcgtcaaag taatgggaag gcataagccc gagaatatcg ttatcgagat    5700
ggcccgagag aaccaaacta cccagaaggg acagaagaac agtagggaaa ggatgaagag    5760
gattgaagag ggtataaaag aactggggtc ccaaatcctt aaggaacacc cagttgaaaa    5820
cacccagctt cagaatgaga agctctacct gtactacctg cagaacggca gggacatgta    5880
cgtggatcag gaactggaca tcaatcggct ctccgactac gacgtggatc atatcgtgcc    5940
ccagtctttt ctcaaagatg attctattga taataaagtg ttgacaagat ccgataaaaa    6000
tagagggaag agtgataacg tcccctcaga agaagttgtc aagaaaatga aaaattattg    6060
gcggcagctg ctgaacgcca aactgatcac acaacgaag ttcgataatc tgactaaggc    6120
tgaacgaggt ggcctgtctg agttggataa agccggcttc atcaaaaggc agcttgttga    6180
gacacgccag atcaccaagc acgtggccca aattctcgat tcacgcatga acaccaagta    6240
cgatgaaaat gacaaactga ttcgagaggt gaaagttatt actctgaagt ctaagctggt    6300
```

```
ttcagatttc agaaaggact ttcagtttta aaggtgaga gagatcaaca attaccacca   6360
tgcgcatgat gcctacctga atgcagtggt aggcactgca cttatcaaaa aatatcccaa   6420
gcttgaatct gaatttgttt acggagacta taaagtgtac gatgttagga aaatgatcgc   6480
aaagtctgag caggaaatag gcaaggccac cgctaagtac ttcttttaca gcaatattat   6540
gaatttttc aagaccgaga ttacactggc caatggagag attcggaagc gaccacttat   6600
cgaaacaaac ggagaaacag gagaaatcgt gtgggacaag ggtagggatt tcgcgacagt   6660
ccggaaggtc ctgtccatgc cgcaggtgaa catcgttaaa aagaccgaag tacagaccgg   6720
aggcttctcc aaggaaagta tcctcccgaa aggaacagc gacaagctga tcgcacgcaa   6780
aaaagattgg gaccccaaga aatacggcgg attcgattct cctacagtcg cttacagtgt   6840
actggttgtg gccaaagtgg agaaagggaa gtctaaaaaa ctcaaaagcg tcaaggaact   6900
gctgggcatc acaatcatgg agcgatcaag cttcgaaaaa aaccccatcg actttctcga   6960
ggcgaaagga tataagagg tcaaaaaaga cctcatcatt aagcttccca agtactctct   7020
ctttgagctt gaaaacggcc ggaaacgaat gctcgctagt gcgggcgagc tgcagaaagg   7080
taacgagctg gcactgccct ctaaatacgt taatttcttg tatctggcca gccactatga   7140
aaagctcaaa ggatctcccg aagataatga gcagaagcag ctgttcgtgg aacaacacaa   7200
acactacctt gatgagatca tcgagcaaat aagcgaattc tccaaaagag tgatcctcgc   7260
cgacgctaac ctcgataagg tgcttctctgc ttacaataag cacagggata gcccatcag   7320
ggagcaggca gaaaacatta tccacttgtt tactctgacc aacttgggcg cgcctgcagc   7380
cttcaagtac ttcgacacca ccatagacag aaagcggtac acctctacaa aggaggtcct   7440
ggacgccaca ctgattcatc agtcaattac ggggctctat gaaacaagaa tcgacctctc   7500
tcagctcggt ggagacagca gggctgaccc caagaagaag aggaaggtgt gagcttggaa   7560
tggatcttcg atcccgatcg ttcaaacatt tggcaataaa gtttcttaag attgaatcct   7620
gttgccggtc ttgcgacgat tatcatataa tttctgttga attacgttaa gcatgtaata   7680
attaacatgt aatgcatgac gttatttatg agatgggttt ttatgattag agtcccgcaa   7740
ttatacattt aatacgcgat agaaaacaaa atatagcgcg caaactagga taaattatcg   7800
cgcdcggtgt catctatgtt actagatcgg gaattgccaa gctaattctt gaagacgaaa   7860
gggcctcgtg atacgcctat ttttataggt taatgtcatg ataataatgg tttcttagac   7920
gtcaggtggc acttttcggg gaaatgtgcg cggaaccccct atttgtttat ttttctaaat   7980
acattcaaat atgtatccgc tcatgagaca ataaccctga taaatgcttc aataatggga   8040
ccgactcgcg ctgtcaggag acgggacaag gatgcgagct agcctgcagg aattgttgat   8100
tttgtgatga ctgatggcag gatatatgcg gttgtaattc attttttattg tctaaatttc   8160
tgtatttgtt tgtttgttcg gttgtaaatt ttttttggaag aacaagaaaa gaaaaaacac   8220
ccgttagggt gttttttagtt agtgtggcgc gccgacttgc gacatgcggt cctttgcaat   8280
caactattag aaaaattcat ccagcatcag atgaaattgc agtttgttca tatccggatt   8340
atcaatgcca tatttctgaa acagacgttt ttgcaggctc gggctaaatt cgcccaggca   8400
gttccacaga atggcagat cctgataacg atccgcaatg cccacacggc ccacatcaat   8460
gcagccaatc agtttgcctt catcgaaaat caggttatcc aggctaaaat cgccgtgggt   8520
caccacgcta tccgggctaa acggcagcag tttatgcatt tctttccaca cctgttccac   8580
cggcagccg ttacgttcat catcaaaatc gctcgcatcc accaggccgt tgttcatacg   8640
gctctgcgcc tgggccagac gaaacacacg atcgctgtta acgggcagt tgcacaccgg   8700
```

```
aatgctatgc agacgacgca gaaacacggc cagcgcatcc acaatgtttt cgccgctatc    8760
cggatattct tccagcacct gaaacgcggt tttgcccgga atcgcggtgg tcagcagcca    8820
cgcatcatcc ggggtgcgaa taaaatgttt aatggtcggc agcggcataa attcggtcag    8880
ccagttcaga cgcaccattt catcggtcac atcgttcgcc acgctgcctt tgccatgttt    8940
cagaaacagt tccggcgcat ccggtttgcc atacagacga taaatggtcg cgccgctctg    9000
acccacgtta tcacgcgccc atttatagcc atacagatcc gcatccatgt tgctgttcag    9060
acgcggacgg ctacagctcg tttcacgctg aatatggctc ataacacccc ttgtattact    9120
gtttatgtaa gcagacagtt ttattgttca tgatgatata ttttatctt gtgcaatgta    9180 acatcagaga ttttgagaca caagatcgga ttggcggtta tgcggttcta ccggcgcggc    9240
agcgttaccc gtgtcggcgg ctccaacggc tcgccatcgt ccagaaaaca cggctcatcg    9300
ggcatcggca ggcgctgctg cccgcgccgt tcccattcct ccgtttcggt caaggctggc    9360
aggtctggtt ccatgcccgg aatgccgggc tggctgggcg gctcctcgcc ggggccggtc    9420
ggtagttgct gctcgcccgg atacagggtc gggatgcggc gcaggtcgcc atgccccaac    9480
agcgattcgt cctggtcgtc gtgatcaacc accacggcgg cactgaacac cgacaggcgc    9540
aactggtcgc ggggctggcc ccacgccacg cggtcattga ccacgtaggc cgacacggtg    9600
ccggggccgt tgagcttcac gacggagatc cagcgctcgg ccaccaagtc cttgactgcg    9660
tattggaccg tccgcaaaga acgtccgatg agcttggaaa gtgtcttctg gctgaccacc    9720
acggcgttct ggtggcccat ctgcgccacg aggtgatgca gcagcattgc cgccgtgggt    9780
ttcctcgcaa taagcccggc ccacgcctca tgcgctttgc gttccgtttg cacccagtga    9840
ccgggcttgt tcttggcttg aatgccgatt tctctggact gcgtggccat gcttatctcc    9900
atgcggtagg ggtgccgcac ggttgcggca ccatgcgcaa tcagctgcaa cttttcggca    9960
gcgcgacaac aattatgcgt tgcgtaaaag tggcagtcaa ttacagattt tctttaacct   10020
acgcaatgag ctattgcggg gggtgccgca atgagctgtt gcgtaccccc cttttttaag   10080
ttgttgattt ttaagtcttt cgcatttcgc cctatatcta gttctttggt gcccaaagaa   10140
gggcacccct gcggggttcc cccacgcctt cggcgcggct cccccctccgg caaaaagtgg   10200 cccctccggg gcttgttgat cgactgcgcg gccttcggcc ttgcccaagg tggcgctgcc   10260
cccttggaac ccccgcactc gccgccgtga ggctcggggg gcaggcgggc gggcttcgcc   10320
cttcgactgc ccccactcgc ataggcttgg gtcgttccag gcgcgtcaag gccaagccgc   10380
tgcgcggtcg ctgcgcgagc cttgacccgc cttccacttg gtgtccaacc ggcaagcgaa   10440
gcgcgcaggc gcaggccgg aggcttttcc ccagagaaaa ttaaaaaaat tgatggggca   10500
aggccgcagg ccgcgcagtt ggagccggtg ggtatgtggt cgaaggctgg gtagccggtg   10560
ggcaatccct gtggtcaagc tcgtgggcag gcgcagcctg tccatcagct tgtccagcag   10620
ggttgtccac gggccgagcg aagcgagcca gccgtggcc gctcgcggcc atcgtccaca   10680
tatccacggg ctggcaaggg agcgcagcga ccgcgcaggg cgaagcccgg agagcaagcc   10740
cgtaggggg                                                          10749
```

<210> SEQ ID NO 20
<211> LENGTH: 6637
<212> TYPE: DNA
<213> ORGANISM: Artificial Sequence
<220> FEATURE:
<223> OTHER INFORMATION: pLX-B2-NptII-DsRED plasmid

<400> SEQUENCE: 20

```
ccatcatcag ttcggtggtc ttccgacgaa caataaggcc gcaaatcgcg gccttttta       60
ttgataacaa aaccggctca gttctgcgta gaaaccaaca tgcaagctcc accgggtgca     120
aagcggcagc ggcggcagga tatattcaat tgtaaatggc ttcatgtccg ggaaatctac     180
tggtggcagg atatattgtg gtgtaaacaa tggagaaaaa gattaattaa gtactagtag     240
cctggtcgaa accgtctcag gagagcgatc agcttgcatg ccggtcgatc tagtaacata     300
gatgacaccg cgcgcgataa tttatcctag tttgcgcgct atattttgtt ttctatcgcg     360
tattaaatgt ataattgcgg gactctaatc ataaaaaccc atctcataaa taacgtcatg     420
cattacatgt taattattac atgcttaacg taattcaaca gaaattatat gataatcatg     480
gcaagaccgg caacaggatt caatcttaag aaactttatt gccaaatgtt tgaacgatct     540
gcttgactct agctagagtc cgaaccccag agtcccgctc agaagaactc gtcaagaagg     600
cgatagaagg ctatgcgctg cgaatcggga gcggcgatac cgtaaagcac gaggaagcgg     660
tcagcccatt cgccgccaag ctcttcagca atatcacggg tagccaacgc tatgtcctga     720
tagcggtccg ccacacccag ccggccacag tcgatgaatc cagaaaagcg gccattttcc     780
accatgatat tcggcaagca ggcgtcgccg tgggtcacga cgagatcctc gccgtcgggc     840
atccgcgcct tgagcctggc gaacagttcg gctggcgcga ccccctgatg ctcttcgtcc     900
agatcatcct gatcgacaag accggcttcc atccgagtac gtgctcgctc gatgcggtgt     960
ttcgcttggt ggtcgaatgg gcaggtagcc ggatcaagcg tatgcagccg ccgcattgca    1020
tcagccatga tggatacttt ctcggcagga gcaaggtgag atgacaggag atcctgcccc    1080
ggcacttcgc ccaatagcag ccagtccctt cccgcttcag tgacaacgtc gagcacagct    1140
gcgcaaggaa cgcccgtcgt ggccagccac gatagccgcg ctgcctcgtc ttggagttca    1200
ttcagggcac cggacaggtc ggtcttgaca aaaagaaccg ggcgcccctg cgctgacagc    1260
cggaacacgg cggcatcaga gcagccgatt gtctgttgtg cccagtcata gccgaatagc    1320
ctctccaccc aagcggccgg agaacctgcg tgcaatccat cttgttcaat catgcctcga    1380
tcgagttgag agtgaatatg agactctaat tggataccga ggggaattta tggaacgtca    1440
gtggagcatt tttgacaaga aatatttgct agctgatagt gaccttaggc gacttttgaa    1500
cgcgcaataa tggtttctga cgtatgtgct tagctcatta aactccagaa acccgcggct    1560
gagtggctcc ttcaacgttg cggttctgtc agttccaaac gtaaacggc ttgtcccgcg    1620
tcatcggcgg gggtcataac gtgactccct taattctcat gtatctcctg acagcgaaat    1680
gattgatgaa gaacaatggt ggatgaagaa caaagaagga gggagctttt gttcaagatg    1740
aacaaagaac aatagtggat gaagaacaaa gtgaaaaaaa taaaaaaaaa tgtatggtta    1800
aataaagagt aaagttacca ttgagactcc gtcaggagac tagagccaag ctgatctcct    1860
ttgccccgga gatcaccatg gacgactttc tctatctcta cgatctagga agaaagttcg    1920
acggagaagg tgacgatacc atgttcacca ccgataatga aagattagc ctcttcaatt    1980
tcagaaagaa tgctgaccca cagatggtta gagaggccta cgcggcaggt ctgatcaaga    2040
cgatctaccc gagtaataat ctccaggaga tcaaatacct tcccaagaag gttaaagatg    2100
cagtcaaaag attcaggact aactgcatca agaacacaga gaaagatata tttctcaaga    2160
tcagaagtac tattccagta tggacgattc aaggcttgct tcataaacca aggcaagtaa    2220
tagagattgg agtctctaag aaagtagttc ctactgaatc aaaggccatg gagtcaaaaa    2280
ttcagatcga ggatctaaca gaactcgccg tgaagactgg cgaacagttc atacagagtc    2340
```

```
ttttacgact caatgacaag aagaaaatct tcgtcaacat ggtggagcac gacactctcg    2400
tctactccaa gaatatcaaa gatacagtct cagaagacca aagggctatt gagacttttc    2460
aacaaagggt aatatcggga aacctcctcg gattccattg cccagctatc tgtcacttca    2520
tcaaaaggac agtagaaaag gaaggtggca cctacaaatg ccatcattgc gataaaggaa    2580
aggctatcgt tcaagatgcc tctgccgaca gtggtcccaa agatggaccc ccacccacga    2640
ggagcatcgt ggaaaaagaa gacgttccaa ccacgtcttc aaagcaagtg gattgatgtg    2700
atatctccac tgacgtaagg gatgacgcac aatcccacta tccttcgcaa gacccttcct    2760
ctatataagg aagttcattt catttggaga ggactccggt atttttacaa caataccaca    2820
acaaaacaaa caacaaacaa cattacaatt tactattcta gtcgaaatgg cctcctccga    2880
gaacgtcatc accgagttca tgcgcttcaa ggtgcgcatg gagggcaccg tgaacggcca    2940
cgagttcgag atcgagggcg agggcgaggg ccgcccctac gagggccaca acaccgtgaa    3000
gctgaaggtg accaagggcg cccccctgcc cttcgcctgg gacatcctgt cccccccagtt    3060 ccagtacggc tccaaggtgt acgtgaagca ccccgccgac atccccgact acaagaagct    3120
gtccttcccc gagggcttca gtgggagcg cgtgatgaac ttcgaggacg gcggcgtggc    3180
gaccgtgacc caggactcct ccctgcagga cggctgcttc atctacaagg tgaagttcat    3240
cggcgtgaac ttcccctccg acggccccgt gatgcagaag aagacgatgg gctgggaggc    3300
ctccaccgag cgcctgtacc cccgcgacgg cgtgctgaag ggcgagacac acaaggccct    3360
gaagctgaag gacggcggcc actacctggt ggagttcaag tccatctaca tggccaagaa    3420
gcccgtgcag ctgcccggct actactacgt ggacgccaag ctggacatca cctcccacaa    3480
cgaggactac accatcgtgg agcagtacga gcgcaccgag ggccgccacc acctgttcct    3540
gtaggcttcg gccatgctag agtccgcaaa aatcaccagt ctctctctac aaatctatct    3600
ctctctattt ttctccagaa taatgtgtga gtagttccca gataagggaa ttagggttct    3660
tatagggttt cgctcatgtg ttgagcatat aagaaaccct tagtatgtat ttgtatttgt    3720
aaaatacttc tatcaataaa atttctaatt cctaaaacca aaatccagtg acctcgctgt    3780
caggagtctc aatggtaact ttactcttta tttaaccata catttttttt tattttttc    3840 actttgttct tcatccacta ttgttctttg ttcatcttga acaaaagctc cctccttctt    3900
tgttcttcat ccaccattgt tcttcatcaa tcatttcgct gtcaggagac gggacaagga    3960
tgcgagctag cctgcaggaa ttgttgattt tgtgatgact gatggcagga tatatgcggt    4020
tgtaattcat ttttattgtc taaatttctg tatttgtttg tttgttcggt tgtaaatttt    4080
tttggaagaa caagaaaaga aaaaacaccc gttagggtgt ttttagttag tgtggcgcgc    4140
cgacttgcga catgcggtcc tttgcaatta attattagaa aaattcatcc agcatcagat    4200
gaaattgcag tttgttcata tccggattat caatgccata tttctgaaac agacgttttt    4260
gcaggctcgg gctaaattcg cccaggcagt tccacagaat ggccagatcc tgataacgat    4320
ccgcaatgcc cacacggccc acatcaatgc agccaatcag tttgccttca tcgaaaatca    4380
ggttatccag gctaaaatcg ccgtgggtca ccacgctatc cgggctaaac ggcagcagtt    4440
tatgcatttc tttccacacc tgttccaccg gccagccgtt acgttcatca tcaaaatcgc    4500
tcgcatccac caggccgttg ttcatacggc tctgcgcctg gccagacga aacacacgat    4560 cgctgttaaa cgggcagttg cacaccggaa tgctatgcag acgacgcaga aacacggcca    4620
gcgcatccac aatgttttcg ccgctatccg gatattcttc cagcacctga aacgcggttt    4680
```

```
tgcccggaat cgcggtggtc agcagccacg catcatccgg ggtgcgaata aaatgtttaa    4740
tggtcggcag cggcataaat tcggtcagcc agttcagacg caccatttca tcggtcacat    4800
cgttcgccac gctgcctttg ccatgtttca gaaacagttc cggcgcatcc ggttttgccat   4860 acagacgata aatggtcgcg ccgctctgac ccacgttatc acgcgcccat ttatagccat    4920
acagatccgc atccatgttg ctgttcagac gcggacggct acagctcgtt tcacgctgaa    4980
tatggctcat acaccccttt gtattactgt ttatgtaagc agacagtttt attgttcatg    5040
atgatatatt tttatcttgt gcaatgtaac atcagagatt ttgagacaca agatcggatt   5100
ggcggttatg cggttctacc ggcgcggcag cgttacccgt gtcggcggct ccaacggctc    5160
gccatcgtcc agaaaacacg gctcatcggg catcggcagg cgctgctgcc cgcgccgttc    5220
ccattcctcc gtttcggtca aggctggcag gtctggttcc atgcccggaa tgccgggctg    5280
gctgggcggc tcctcgccgg ggccggtcgg tagttgctgc tcgcccggat acagggtcgg    5340
gatgcggcgc aggtcgccat gccccaacag cgattcgtcc tggtcgtcgt gatcaaccac    5400
cacggcggca ctgaacaccg acaggcgcaa ctggtcgcgg ggctggcccc acgccacgcg    5460
gtcattgacc acgtaggccg cacggtgccg ggggccgttg agcttcacga cggagatcca    5520
gcgctcggcc accaagtcct tgactgcgta ttggaccgtc cgcaaagaac gtccgatgag    5580
cttggaaagt gtcttctggc tgaccaccac ggcgttctgg tggcccatct cgccacgag    5640 gtgatgcagc agcattgccg ccgtgggttt cctcgcaata agcccggccc acgcctcatg    5700
cgctttgcgt tccgtttgca cccagtgacc gggcttgttc ttggcttgaa tgccgatttc    5760
tctggactgc gtggccatgc ttatctccat gcggtagggg tgccgcacgg ttgcggcacc    5820
atgcgcaatc agctgcaact tttcggcagc gcgacaacaa ttatgcgttg cgtaaaagtg    5880
gcagtcaatt acagattttc tttaacctac gcaatgagct attgcggggg gtgccgcaat    5940
gagctgttgc gtacccccct tttttaagtt gttgattttt aagtctttcg catttcgccc    6000
tatatctagt tctttggtgc ccaaagaagg gcacccctgc ggggttcccc cacgccttcg    6060
gcgcggctcc ccctccggca aaaagtggcc cctccggggc ttgttgatcg actgcgcggc    6120
cttcggcctt gcccaaggtg gcgctgcccc cttggaaccc ccgcactcgc cgccgtgagg    6180 ctcgggggc aggcgggcgg gcttcgccct tcgactgccc ccactcgcat aggcttgggt    6240
cgttccaggc gcgtcaaggc caagccgctg cgcggtcgct gcgcgagcct tgacccgcct    6300
tccacttggt gtccaaccgg caagcgaagc gcgcaggccg caggccggag cttttcccc    6360 agagaaaatt aaaaaaattg atggggcaag gccgcaggcc gcgcagttgg agccggtggg    6420
tatgtggtcg aaggctgggt agccggtggg caatccctgt ggtcaagctc gtgggcaggc    6480
gcagcctgtc catcagcttg tccagcaggg ttgtccacgg gccgagcgaa gcagagccagc   6540 cggtggccgc tcgcggccat cgtccacata tccacgggct ggcaagggag cgcagcgacc    6600
gcgcagggcg aagcccggag agcaagcccg taggggg                             6637
```

<210> SEQ ID NO 21
<211> LENGTH: 14938
<212> TYPE: DNA
<213> ORGANISM: Artificial Sequence
<220> FEATURE:
<223> OTHER INFORMATION: pLX-PPV plasmid

<400> SEQUENCE: 21

```
ccatcatcag ttcggtggtc ttccgacgaa caataaggcc gcaaatcgcg gccttttta      60 ttgataacaa aaccggctca gttctgcgta gaaaccaaca tgcaagctcc accgggtgca    120
```

```
aagcggcagc ggcggcagga tatattcaat tgtaaatggc ttcatgtccg ggaaatctac    180
tggtggcagg atatattgtg gtgtaaacaa tggagaaaaa gattaattaa gtactagtcc    240
agtacgcacg attcaaggct tgcttcacaa accaaggcaa gtaatagaga ttggagtctc    300
taaaaaggta gttcccactg aatcaaaggc catggagtca agattcaaa tagaggacct    360 aacagaactc gccgtaaaga ctggcgaaca gttcatacag agtctcttac gactcaatga    420
caagaagaaa tcttcgtca acatggtgga gcacgacaca cttgtctact ccaaaaatat    480
caaagataca gtctcagaag accaaagggc aattgagact tttcaacaaa gggtaatatc    540
cggaaacctc ctcggattcc attgcccagc tatctgtcac tttattgtga agatagtgga    600
aaaggaaggt ggctcctaca atgccatca ttgcgataaa ggaaaggcca tcgttgaaga    660
tgcctctgcc gacagtggtc ccaaagatgg accccaccc acgaggagca tcgtggaaaa    720
agaagacgtt ccaaccacgt cttcaaagca gtggattga tgtgataaca tggtggagca    780
cgacacactt gtctactcca aaatatcaa agatacagtc tcagaagacc aaagggcaat    840
tgagactttt caacaaaggg taatatccgg aaacctcctc ggattccatt gcccagctat    900
ctgtcacttt attgtgaaga gtggaaaaa ggaaggtggc tcctacaaat gccatcattg    960
cgataaagga aaggccatcg ttgaagatcc tctgccgaca gtggtcccaa agatggaccc   1020
ccacccacga ggagcatcgt ggaaaagaa gacgttccaa ccacgtcttc aaagcaagtg   1080
gattgatgtg atatctccac tgacgtaagg gatgacgcac aatcccacta tccttcgcaa   1140
gacccttcct ctatataagg aagttcattt catttggaga ggaaaatata aaaactcaac   1200
acaacataca aaattttatg caatcaaatc aatctcaagc tatcaaaatt tttcaaatct   1260
cacttgaaag atcaaaaatc aacaaagaaa atcccttaat ttctctacca aatttactgc   1320
aagtcaagat gtcaaccatt gtatttggct cattcacttg ccacctcgat gcagctatcc   1380
accaggataa tgcagacaga ttggcaaagg cctggacccg tccagagaac caccaagtca   1440
gtaacgtgca tctactgtgc cgaagagcgg caaaaagtct cataaacaca tatgagagtg   1500
caacagctag tgcttggaaa gggctggaag agaagttgca acctatgttt gctaagcgtg   1560
agtttagcaa aacagtcaca aagagagaag ggcttcggtg cttcaaagaa agctctgaga   1620
agtttattga aaagaagctc aggaaacagt atcaagagga gcgtgagaga ttccaatttc   1680
tcaacggtcc ggatgcaata gtcaaccaaa tcagtgttga caaatgtgaa gcttcagtac   1740
gggtgccatt ccctcatatt attgagaaac ctagctttgc aacaccatca atgaaaaaga   1800
aggtggtgtt tactaaggtt aggatgtccg aggcatcact acaactttt atgaggaggg   1860 ttgctgcaaa cgccaaggca aatggtcaaa aagttgagat catagggcgt aagcgtgtag   1920
tcggtaacta cacaacgaaa agtcgcttga catactttcg cacacatgtt cggcacttgg   1980
atggttcaaa accacgctat gatcttgtgt tggacgaggc aaccaagaag attctgcaac   2040
tgtttgcaaa cacaagcggt ttccaccatg tccacaagaa aggggaggta acaccaggaa   2100
tgagcggatt tgtggtaaat cccatgaatc tatcggaccc aatgcaagtg tatgacacgg   2160
atctttttat agttcgtgga aaacacaact ctattcttgt tgactcacgg tgtaaggttt   2220
ctaaagaaca gagcaatgag ataatccact actctgaccc aggcaaacaa ttttgggatg   2280 gtttccaccaa ttcatttatg cagtgcaagc tacgcgaaac tgatcatcag tgcacatctg   2340
acctggacgt gaaggagtgt ggttatgtcg cagcacttgt gtgccaagcg ataatcccttt   2400 gcggaaaaat cacatgtctg caatgtgctc aaaagtattc ttacatgtca caacaggaaa   2460
```

```
tacgtgatag attttcgaca gtaattgagc agcatgagaa acagtgatg gataactatc    2520 cacaatttc acatgttctc gcttttctaa agagatatcg tgaactaatg cgcgtggaaa    2580
atcagaatta tgaagctttc aaggatatca cgcacatgat aggcgagcgt aaagaagcac   2640
cttttcccca tctcaacaaa atcaatgaat taatcattaa gggtggtatg atgagcgcac   2700
aagactacat agaagcctcg gatcatctgc gcgaactagc gcgatatcag aagaatcgca   2760
cggagaacat taggagcgga tctataaagg ctttcaggaa taaaatctca tcaaaagcac   2820
atgtcaatat gcagcttatg tgtgacaatc aacttgatac taatggcaat tcgtgtggg    2880 gacagagaga gtatcatgct aaacgcttct ttaggaatta cttcgatgtg atcgatgtta   2940
gcgagggcta cagacgtcat attgttcgtg aaaatcctaa aggtatccgc aaattggcca   3000
ttggcaacct tgttatgtca acaaatctgg cagcactacg taagcagctt ttgggtgaag   3060
agtgcattca ttttgaggtc tcaaaggaat gcactagcaa gcgagggaa aactttgtat    3120 accaatgttg ctgtgtcaca cacgaagacg gtacaccact ggagtctgaa ataataagtc   3180
caacaaagaa tcatttagtt gttgggaact caggtgattc gaagtatgtg gatttgccca   3240
cagcaaaagg aggtgcaatg ttcatagcaa aggcaggtta ttgttacatt aacatttcc    3300 ttgctatgct gatcaacata aatgaagatg aagcaaaaag tttcacaaag acagtgcgtg   3360
acactcttgt acctaagctt ggaacatggc catcgatgat ggacttagct acagcttgcc   3420
actttctcgc aattctctac ccagaaactc ggaatgctga acttccacga atactcgttg   3480
atcatgaagc aaaaatcttt catgtagttg actcattcgg atcactgtca actggaatgc   3540
atgttttgaa agcgaacaca atcaatcagc ttattagctt tgcgagtgat acattggatt   3600
caaatatgaa aacatacctg gttggaggtc ttgaagtgga taagtgtgac gaattcaaaa   3660
atgtcaagct cttgatcaga agcatttaca agccacaaat catggagcag gtgcttaagg   3720
aagaaccata tttattgctc atgagcgttt tgtcacctgg cgtcttgatg gcgctgttca   3780
atagtggttc attggagaaa gccacacaat attggatcac acgatctcat agcttggcag   3840
cgatcacatc aatgttatca tcacttgcag ccaaagtttc actcgcaagt acactgaatg   3900
cacagatgag tgtcattgac gaacatgcag cagttctatg tgatagtgtt tttgttggaa   3960
cgaagccata cgcatcctac atgatggcag tgaaaacttt ggaaaggatg aaagcacgga   4020
cggaatccga tcacactta aatgacttag gattctcggt actcagacag gcaacacccc    4080
acttggtgga aaaaagttat ctgcaggtaa gtttctgctt ctacctttga tatatatata   4140
ataattatca ttaattagta gtaatataat atttcaaata ttttttttcaa aataaaagaa   4200 tgtagtatat agcaattgct tttctgtagt ttataagtgt gtatatttta atttataact   4260
tttctaatat atgaccaaaa tttgttgata tgcaggaatt ggagcaagct tggaaagagt   4320
taagctggtc ggaaaaattc tctgcaatct tggaatcgca gcggtggcga aaacatatac   4380
caaaaccttt catcccaaaa gacggcgcag attagggagg caggtacgac atctccgttc   4440
ggtcattact tggcaaccag tacaaacgcc tgagagacgt agtccgacgg aaaagagacg   4500
atgtggtttg ctatacacac cagtcgatgg ggaagctatt ttgcaaagcc atcggaattt   4560
ccacaagttt tcttccaagc actcttaaaa tgtttgacat gctcatcgtg ttcagtctct   4620
tgctttcaat aggagccaca tgcaactcaa tgatcaatga gcataaacat cttaagcaac   4680
ttgccgctga tcgggaagat aagaaaagat tcaaaagatt gcaagtctta cacacgaggt   4740
tatcagagaa agttggttgc acaccaacag cagatgaatt cctggagtat gtgggaggtg   4800
aaaaccctga tttactgaaa catgcagagg atctaattgg ggatggtcaa gttgttgttc   4860
```

```
atcaaagcaa gagagactca caagcaaatt tggaacgggt tgtagcattt gtagctcttg    4920
ttatgatgct gtttgactcg gagcgaagtg acggcgtgta caagattctc aataaactca    4980
aaggcattat ggggagtgtc gaccaggctg ttcagcatca gagcttggac gatatagaag    5040
atatactgga tgagaagaag ctcacagtcg attttgtact gcaaagtaac gaagttgcac    5100
caactgtccc atttgactca acttttgaga atggtggac  gaatcaactt gagacaggaa    5160
atgtgattcc acactacagg actgaaggac atttccttga attcacacga gaaaatgcag    5220
cgcacattgc gaatgaagtc atgcatggct cacatcaaga tatcctaatt cgtggagcag    5280
ttggatcggg caaatcaact ggattgccat tccacttaag caagaagggc cacgtcctgc    5340
taattgaacc caccaggccg ctagctgaga atgtgtgcaa gcagttgcga ggtcaaccat    5400
tcaatgtcaa tcctacactg cgcatgcgtg ggatgagcac ctttggatca actccaatca    5460
ctgtgatgac aagcggttac gcactgcact tcttggcaaa caatccaact tatttggaca    5520
actataagtg catcattttt gacgaatgtc acgtgcatga cgcatcagca atggcattta    5580
gatgtcttct ttcggagtat tcatacccgg gaaagatact gaaggtctca gcgacacccc    5640
ctggacatga agttgatttc aaaacacaga aggaggtgaa ggtcattgtt gaagaatctt    5700
tgtcattcca gcagtttgtc tccaatctcg gcacaggttg caatagcgat attctcaagc    5760
atggggtcaa tgtgttggtc tatgtcgcaa gttacaatga ggttgacaca ctaagcaaat    5820
tgctcacaga caggagcttc aaagtttcaa aagtcgatgg gcgaactatg aaaattggca    5880
atgttgagat accaacgagt ggcactcagg ctaaaccgca tttcgtggtt gcaacaaata    5940
tcattgaaaa tggagtcaca ttggacattg atgtggttgt ggacttcggt ttgaaagtcg    6000
tgcctgtatt ggacattgac aatcgtctcg ttcgatacac gaagaagagc atcagttatg    6060
gagaaaggat tcaaagattg gggcgagttg gtcgaaacaa accaggagca gcacttcgta    6120
ttggatttac agagaaagga ctcactcaaa tacctccaat aatcgcaaca gaagcagctt    6180
ttctatgttt cacttatggt ttgccagtta tgactaacgg tgtgtcaacg agcttactag    6240
cgatgtgcac tgttaagcaa gcacggacga tgcaacaatt tgaattatcc ccgttctaca    6300
cagtggcgtt ggttcgattt gacgggacaa tgcaccagga aatttttcga ttgctcaaga    6360
gctatagact gcgtgactca gaggtaatct taaacaagtt ggctatacca aacagcaacg    6420
tatgtgggtg gatgagtgtt cgtgactaca acgacaagg  ctgcaacttg gacttggatg    6480
agaacattcg tgtaccgttt tacgtgaaag acatccctga aactttgcac gagagaatat    6540
ggcaagtggt agaaacccac aaatctgatg caggatttgg aaggatctgt agttcgagtg    6600
cgtgcaaaat tgcgtatacg ttacagacag acatccactc cattcctcgg acaattaaaa    6660
tcattgacgc actgttggag caagagagaa caaagcaagc acacttcaga gctatgacca    6720
gtcaatcctg ctcaagttca aatttctctc tgtcaagcat caccacaagcc attcgctcaa    6780 aatacgccaa agaccatacg gaagaaaaca ttggtgttct ccaaacggcg aagtctcagt    6840
tgctagaatt caagaacctg aacattgatc caagttatcc tgaacttgtc cgcaactttg    6900
gcgccttaga atgtgtgcac catcaaacaa aggaaggagt ttcaaaggcg ctacaactta    6960
aggggcattg aataagcga ctcatcactc gtgacgcaac attaatgctt ggagttcttg    7020
gtggaggggc atggatgatt ttcagttatt tgagggatag cttcaaagaa gaagttgttc    7080
accaaggctt caatcgtagg caaagacaaa aattgaaatt caggcaagcc cgagataaca    7140
gaatggccag ggaagtgtat ggtgacgatt caactatggc ggactacttt ggttctgcat    7200
```

```
attcaaagaa aggaaagagc aaaggaaaga ctagagggat gggaacgaaa acacgcaaat   7260
ttgtgaacat gtacgggtac gatcccacag actacaactt tgttcgcttt gttgatccat   7320
tgactggtca caccctggac gagaatcctc ttatggacat caacttggtg caggaacact   7380
tctcacagat tcgcaatgat tacatcggag acgacaaaat caccatgcag cacataatgt   7440
caaatccagg tattgtcgca tactatatca aggatgcgac gcagaaagcc ctcaaggtgg   7500
accttactcc acacaaccca ttgcgtgtgt gtgacaaaac tgcaactatt gcaggatttc   7560
cagagagaga gtttgaattg aggcagacag gacacccagt ttttgttgaa cctaatgcaa   7620
tcccaaagat caatgaagag ggggacgaag aagttgacca cgaaagtaaa tcactgttca   7680
gaggcctgag agactataat ccaatcgcaa gctcaatatg ccaattgaat aactcatctg   7740
gtgctagaca aagtgtaatg tttggacttg gctttggggg tttaattgtc acgaatcagc   7800
atttgttcaa aaggaatgac ggagagctaa caatccgatc gcatcatggg gaattcgtag   7860
tgaaggacac aaaaactctc aaactgcttc cttgcaaagg tcgagacata gtgatcatca   7920
gattaccaaa ggatttccct ccttttccga agaggttgca gttccgcacc ccgacgactg   7980
aggacagagt ttgtttaatt ggttcaaatt ccaaacgaa gagcatttca agcaccatgt   8040
cggaaacaag cgcaacatat ccagttgata acagtcattt ctggaaacac tggattagca   8100
cgaaggatgg tcattgcgga ttacccatcg tgagcactcg agatggcagt attcttgggc   8160
tacacagtct tgcaaattca acgaacaccc agaatttcta tgcagctttc cctgacaact   8220
tcgagaccac atacttgtca aatcaagaca atgataactg ataaagcag tggcgataca   8280 acccggatga agtttgctgg ggatccctac aactcaagag ggacattcca cagagtccgt   8340
ttacaatttg taaactgcta acggatcttg atggggaatt tgtttacact cagtccaaaa   8400
ctacacattg gctcagagat agattagaag gaaatttgaa agcagttgga gcctgccctg   8460
ggcagttggt tactaagcat gtcgttaaag gcaaatgtac actctttgaa acatacctgt   8520
tgactcatcc agaggagcac gaattctttc gaccttta at gggagcatac caaaagagtg   8580
ctctaaataa ggacgcatac gtcaaagatc tgatgaagta ttcaaaacca atcgtcgttg   8640
gtgcagttga ctgtgatcaa tttgaacgtg ctgttgatgt ggtcatttcg atgctaattt   8700
ccaaaggttt tgaagaatgt aattacgtca ctgatccaga tgacatattc tcagcactta   8760
acatgaaagc agcagttggc gctttgtaca gtggaaagaa aagagactat tttaagaacg   8820
tgtcagacca ggacaaggaa agtttcgtgc gagctagttg caaacgtttg ttcatgggaa   8880
agaaaggagt gtggaatggc tctttgaagg cagaattgcg ccctaaagag aaggtagagg   8940
ctaataaaac tcgatcattc acagcagcac cgattgatac ccttctgggg ggaaaagtgt   9000
gtgttgatga cttcaataat cagttttaca gcctgaattt acattgtcca tggagcgttg   9060
ggatgacaaa attcagaggt ggttgggaca aactgcttag agcactgcca gaaggatgga   9120
tttactgtga tgccgatggc tctcaatttg acagttccct ctcaccgtac ttaatcaatg   9180
cagttctcaa tattcgtctg gcatttatgg aagaatggga cattggtgaa caaatgcttt   9240
caaacctgta cacggagatt gtatatacac caattgctac accagatggc actattgtta   9300
agaagttcaa gggcaacaat agtggtcaac cctcgacagt tgttgacaat acactcatgg   9360
ttattttggc aatgacatat tcactcctta agcttggata ccatccggat acacacgatt   9420
gcatttgtcg gtacttcgtg aatggtgatg atcttgtcct tgcagtgcac ccagcatacg   9480
agagcattta tgatgagctt caagaacact tttcccaact tggattgaat tacacattcg   9540
ccacaaagac tgaaaacaag gaagagctgt ggtttatgtc acataaaggc gttctctacg   9600
```

```
atgacatgta cattcctaag ctagagcctg agaggattgt atcaatactt gaatgggaca    9660
gatcaaatga gccaatccat cgattggagg caatttgtgc atcaatggtg aagcgtgggg    9720
gttataagga gctgctgagg gagatccgga aattttacag ttgggttctt gaacaagcac    9780
catacaatgc tctttcaaaa gatggaaaag ccccgtacat tgcggagaca gcactgaaga    9840
agctttacac tgacactgaa gcatctgaga cagaaattga gcgatatctt gaagctttt    9900
acgacgactt taacgatgat ggtgagtcca atgtcgtagt acatcaggcc atggtgagca    9960
agggcgagga gctgttcacc ggggtggtgc ccatcctggt cgagctggac ggcgacgtaa   10020
acggccacaa gttcagcgtg tccggcgagg gcgagggcga tgccacctac ggcaagctga   10080
ccctgaagtt catctgcacc accggcaagc tgcccgtgcc ctggcccacc ctcgtgacca   10140
ccttcaccta cggcgtgcag tgcttcagcc gctaccccga ccacatgaag cagcacgact   10200
tcttcaagtc cgccatgccc gaaggctacg tccaggagcg caccatcttc ttcaaggacg   10260
acggcaacta caagacccgc gccgaggtga agttcgaggg cgacaccctg gtgaaccgca   10320
tcgagctgaa gggcatcgac ttcaaggagg acggcaacat cctggggcac aagctggagt   10380
acaactacaa cagccacaac gtctatatca tggccgacaa gcagaagaac ggcatcaagg   10440
tgaacttcaa gatccgccac aacatcgagg acggcagcgt gcagctcgcc gaccactacc   10500
agcagaacac ccccatcggc gacggccccg tgctgctgcc cgacaaccac tacctgagca   10560
cccagtccgc cctgagcaaa gaccccaacg agaagcgcga tcacatggtc ctgctggagt   10620
tcgtgaccgc cgccgggatc actcacggca tggacgagct gtacaagggt accaacgttg   10680
ttgtgcacca agctgacgaa agagaagacg aggaggaagt tgatgcaggc aagccgagtg   10740
tagttactgc accggcagca actagcccaa tacttcaacc acctccagtc atacagcctg   10800
cacccccgga tacggcgtca atgctcaacc ccattttcac gccagcaaca actcaaccag   10860
caacaaaacc agtttcacag gtgtcaggac ctcaactgca aactttggga acatatggta   10920
atgaggatgc atcacctagc aactcaaacg cgctagtcaa cacaaacaga gacagggacg   10980
tcgatgcagg atcagttgga acttttacag tgccacgttt gaaggcaatg acttcgaaac   11040
tatctctgcc aaaggtgaag ggaaaggcta ttatgaactt gaaccatttg gcacattata   11100
gtcctgcaca ggttgacttg tcaaacacga gagctccgca gtcttgtttc caaacttggt   11160
atgaaggagt taagcgagat tatgatgtca cggacgatga aatgagcatc attttaaatg   11220
gtcttatggt ttggtgcata gagaatggaa catccccgaa tatcaatgga atgtgggtga   11280
tgatggatgg ggaaacacaa gtggagtatc caataaagcc attgttggat catgcgaaac   11340
ccacttttag acaaattatg gcacatttca gtaacgtggc tgaagcgtat attgaaaaac   11400
gaaattatga aaaagcatac atgccaaggt atggaattca gcgcaacctg acagactaca   11460
gcctcgccag atatgccttt gatttttacg aaatgacttc aacgacacca gtacgggcac   11520
gtgaagctca tatccagatg aaggcagcag cattgagaaa tgttcaaaat cgtttatttg   11580
gcttggatgg aaacgtcgga acacaagaag aggacacaga gagacacacc gctggtgatg   11640
ttaatcgcaa catgcacaac ctcctcggtg tgaggggagt gtagtggtct cggtatctat   11700
cataaactct acctgggtga gagtctaatc atccagttgt ttttagattc ctgttagcat   11760
ccttttctcc gctttaatag cagtacattc agtgaggttt tacctccata tgttctagtc   11820
tgttattgtc gaacacaggc ccttgtatct gatgtagcga gtgcttcact ccattcgggt   11880
tatagttctt gtgcaagaga caaaaaaaaa aaaaaaaaaa aaaaaaaaaa aaaaaaaaaa   11940
```

-continued

```
aaaaaaaaaa aaaaaaaaa aaaaaaaaaa aaaaaaaaaa aaaaaaaaaa aaaaaaaaaa    12000
atgcatgcct gcagatcgtt caaacatttg gcaataaagt ttcttaagat tgaatcctgt    12060
tgccggtctt gcgatgatta tcatctaatt tctgttgaat tacgttaagc atgtaataat    12120
taacatgtaa tgcatgacgt tatttatgag atgggttttt atgattagag tcccgcaatt    12180
atacatttaa tacgcgatag aaaacaaaat atagcgcgca aactaggata aattatcgcg    12240
cgcggtgtca tctatgttac tagatctcta gcctgcagga attgttgatt ttgtgatgac    12300
tgatggcagg atatatgcgg ttgtaattca ttttttattgt ctaaatttct gtatttgttt    12360
gtttgttcgg ttgtaaattt ttttggaaga acaagaaaag aaaaaacacc cgttagggtg    12420
tttttagtta gtgtggcgcg ccgacttgcg acatgcggtc ctttgcaatc aactattaga    12480
aaaattcatc cagcatcaga tgaaattgca gtttgttcat atccggatta tcaatgccat    12540
atttctgaaa cagacgtttt tgcaggctcg ggctaaattc gcccaggcag ttccacagaa    12600
tggccagatc ctgataacga tccgcaatgc ccacacggcc cacatcaatg cagccaatca    12660
gtttgccttc atcgaaaatc aggttatcca ggctaaaatc gccgtgggtc accacgctat    12720
ccgggctaaa cggcagcagt ttatgcattt cttccacac ctgttccacc ggccagccgt    12780
tacgttcatc atcaaaatcg ctcgcatcca ccaggccgtt gttcatacgg ctctgcgcct    12840
gggccagacg aaacacacga tcgctgttaa acgggcagtt gcacaccgga atgctatgca    12900
gacgacgcag aaacacggcc agcgcatcca caatgttttc gccgctatcc ggatattctt    12960
ccagcacctg aaacgcggtt ttgcccggaa tcgcggtggt cagcagccac gcatcatccg    13020
gggtgcgaat aaaatgttta atggtcggca gcggcataaa ttcggtcagc cagttcagac    13080
gcaccatttc atcggtcaca tcgttcgcca cgctgccttt gccatgtttc agaaacagtt    13140
ccggcgcatc cggtttgcca tacagacgat aaatggtcgc gccgctctga cccacgttat    13200
cacgcgccca tttatagcca tacagatccg catccatgtt gctgttcaga cgcggacggc    13260
tacagctcgt ttcacgctga atatggctca taacaccct tgtattactg tttatgtaag    13320
cagacagttt tattgttcat gatgatatat ttttatcttg tgcaatgtaa catcagagat    13380
tttgagacac aagatcggat tggcggttat gcggttctac cggcgcggca gcgttacccg    13440
tgtcggcggc tccaacggct cgccatcgtc cagaaaacac ggctcatcgg gcatcggcag    13500
gcgctgctgc ccgcgccgtt cccattcctc cgtttcggtc aaggctggca ggtctggttc    13560
catgcccgga atgccgggct ggctgggcgg ctcctcgccg gggccggtcg gtagttgctg    13620
ctcgcccgga tacagggtcg ggatgcggcg caggtcgcca tgccccaaca gcgattcgtc    13680
ctggtcgtcg tgatcaacca ccacggcggc actgaacacc gacaggcgca actggtcgcg    13740
gggctggccc cacgccacgc ggtcattgac cacgtaggcc gacacggtgc cggggccgtt    13800
gagcttcacg acggagatcc agcgctcggc caccaagtcc ttgactgcgt attggaccgt    13860
ccgcaaagaa cgtccgatga gcttggaaag tgtcttctgg ctgaccacca cggcgttctg    13920
gtggcccatc tgcgccacga ggtgatgcag cagcattgcc gccgtgggtt tcctcgcaat    13980
aagcccggcc cacgcctcat gcgctttgcg ttccgtttgc acccagtgac cgggcttgtt    14040
cttggcttga atgccgattt ctctggactg cgtggccatg cttatctcca tgcggtaggg    14100
gtgccgcacg gttgcggcac catgcgcaat cagctgcaac ttttcggcag cgcgacaaca    14160
attatgcgtt gcgtaaaagt ggcagtcaat tacagatttt cttttaaccta cgcaatgagc    14220 tattgcgggg ggtgccgcaa tgagctgttg cgtacccccc tttttttaagt tgttgatttt    14280 taagtctttc gcatttcgcc ctatatctag ttctttggtg cccaaagaag ggcaccctg    14340
```

```
cggggttccc ccacgccttc ggcgcggctc cccctccggc aaaaagtggc ccctccgggg      14400
cttgttgatc gactgcgcgg ccttcggcct tgcccaaggt ggcgctgccc ccttggaacc      14460
cccgcactcg ccgccgtgag gctcgggggg caggcgggcg ggcttcgccc ttcgactgcc      14520
cccactcgca taggcttggg tcgttccagg cgcgtcaagg ccaagccgct gcgcggtcgc      14580
tgcgcgagcc ttgacccgcc ttccacttgg tgtccaaccg gcaagcgaag cgcgcaggcc      14640
gcaggccgga ggcttttccc cagagaaaat taaaaaaatt gatggggcaa ggccgcaggc      14700
cgcgcagttg gagccggtgg gtatgtggtc gaaggctggg tagccggtgg gcaatccctg      14760
tggtcaagct cgtgggcagg cgcagcctgt ccatcagctt gtccagcagg gttgtccacg      14820
ggccgagcga agcgagccag ccggtggccg ctcgcggcca tcgtccacat atccacgggc      14880
tggcaaggga gcgcagcgac cgcgcagggc gaagcccgga gagcaagccc gtaggggg      14938
```

```
<210> SEQ ID NO 22
<211> LENGTH: 13212
<212> TYPE: DNA
<213> ORGANISM: Artificial Sequence
<220> FEATURE:
<223> OTHER INFORMATION: pLX-UCBSV plasmid

<400> SEQUENCE: 22
```

```
ccatcatcag ttcggtggtc ttccgacgaa caataaggcc gcaaatcgcg gccttttta        60 ttgataacaa aaccggctca gttctgcgta gaaaccaaca tgcaagctcc accgggtgca      120
aagcggcagc ggcggcagga tatattcaat tgtaaatggc ttcatgtccg ggaaatctac      180
tggtggcagg atatattgtg gtgtaaacaa tggagaaaaa gattaattaa gtactagtcc      240
agtacgcacg attcaaggct tgcttcacaa accaaggcaa gtaatagaga ttggagtctc      300
taaaaaggta gttcccactg aatcaaaggc catggagtca aagattcaaa tagaggacct      360
aacagaactc gccgtaaaga ctggcgaaca gttcatacag agtctcttac gactcaatga      420
caagaagaaa atcttcgtca acatggtgga gcacgacaca cttgtctact ccaaaaatat      480
caaagataca gtctcagaag accaaggggc aattgagact tttcaacaaa gggtaatatc      540
cggaaacctc ctcggattcc attgcccagc tatctgtcac tttattgtga agatagtgga      600
aaaggaaggt ggctcctaca atgccatca ttgcgataaa ggaaaggcca tcgttgaaga      660
tgcctctgcc gacagtggtc ccaaagatgg acccccaccc acgaggagca tcgtggaaaa      720
agaagacgtt ccaaccacgt cttcaaagca agtggattga tgtgataaca tggtggagca      780
cgacacactt gtctactcca aaaatatcaa agatacagtc tcagaagacc aaagggcaat      840
tgagactttt caacaaaggg taatatccgg aaacctcctc ggattccatt gcccagctat      900
ctgtcacttt attgtgaaga tagtggaaaa ggaaggtggc tcctacaaat gccatcattg      960
cgataaagga aaggccatcg ttgaagatcc tctgccgaca gtggtcccaa agatggaccc     1020
ccacccacga ggagcatcgt ggaaaaagaa gacgttccaa ccacgtcttc aaagcaagtg     1080
gattgatgtg atatctccac tgacgtaagg gatgacgcac aatcccacta tccttcgcaa     1140 gaccettcct ctatataagg aagttcattt catttggaga ggaaaaataa atatgacata     1200
agaatacata aagatacatc gcatacaaac actgtgcatt caaattcgtg agaaagcaag     1260
ctgttacgaa agtttacgat atattcttat atattcatag cactgaatac ctgcagatgt     1320
cgactatcca gctattcaag actatcagat ttggttcctt tgagcctgtt aagctcgatg     1380
aaggaaacaa tattatagag aaggtcccag ttgaccttct ggcaggaaat gatggctctg     1440
```

```
gtcctgagga gcaatcagaa cagaaatacc ataggaaaga agtggtgaa agttggcgga    1500 aagtaaccga cttatattct gtaattggaa attctgttta ctgccgcagt tacgtagcaa    1560
tgaagaactt cctcaatgac acaaagtggg gaggtctttt taaaaataag aagggggcaag   1620 aattaaaggc tgcagcaagg ctcagaaggg ctacaagcta tggattcatg tatgatccag    1680
ttgcttgtgc ctttgaatgt cctgtttgca ggacgaaagc aacagcattg gaagcattca    1740
caagcgattg tgatcattgt tttgaaatca agcacattga cgatgacagg atcgttcaga    1800
ctgaaacaaa gttttatcca ataaatccta ttgaactgga tgttgaggat aacttagtgg    1860
aagctgcatc gcttgaatgg ttgaaaggtg atgtggaaga gagagttgtg gataggtct    1920 tactacttga ggataaggaa atccacgtca cgaagaaagc cctagtcaaa agaagagctg    1980
agacaaaact cgtggcaaat gctgctgatc ttaccaagaa attgactgag atctgttgtg    2040
agtctggaat tcctatcatt gatattgata atagtaagag gaaagccatt ccaatggtca    2100
aactcaagca tatctttggg aaagttgagt gtgatgacat gtttgaagaa gatcggtatt    2160
tcctggagca cagcaatgca gggaaaattt tccgatcatg cgagaaaatt acttatagga    2220
tgattcgtcc tggatggagt ggagcaatca ttttaagaga taatgttcag agtgaggatc    2280
atgataagtt tgatttttatc aatgatattt gtgttgttca agggaagaat ctgattagtt    2340
acaaaattga gaatgccatg cgcgttaaga ctgaaacaga attggattta attgattgt    2400 attccttcaa tctcagttgg gcgaaatcga agataagtt cattaagcat tttgaaagtg    2460
atacaactca attagttaga tcatgttgta ctcctagtac attgtggttg tatgcacgga    2520
aagccaggtt ttacaaattt gtggatcaca tgatcttaaa gggtagtcca ataattgata    2580
ttctagttaa aatggagtat gtaggcaagc atctggacat gttcaatagt gttgaagatg    2640
tgtgtactga gtattctcat tttatgaagg agttgattag cgaaactgtt aatgacaagt    2700
cagatccaga tgtgttgcgt gttagaaatc tgattagagc gcattttgag tcagttttag    2760
aatataataa gtatgagttg atagatagga ttattgaaa aaaaacacag ttagaagcac    2820
aagaaattat gtctcgcgag ctcatcaaac atcagtacgg agagttattt tcttggcgcg    2880 aacgttttgtg tttgaaacta ggtataggtt catcaaatct ctatacgtac tgggtggaac    2940
gagaggaaaa acaatcagag aaatcgaatg taatctcttg catcatttcc aaaccgggaa    3000
tagagatgtt gatcaattgg gtctcagaag tgtgtaagag taaatatcat agtcttgtga    3060
attgtgtcga tagtggtatt ttattcttgt ggtctagaat agttcattta gcgagagttt    3120
cagtttatgg ttattggaat cttttggttta gacaagcaat gtgtgtgttg ttcatttct    3180 tagtttcaaa tttctctggt aaaatagtta gttatcttaa gaaattaatt gtgagtgaga    3240
agaagctagc tataaagaat gaagaaggtt ttgttgaagt gcaaggtcga aaggaagagt    3300
cttttgttct aaagtggtgt gctgctgcaa cttttgtttct tagtttcctt aactatgact    3360
gggcagttgg gtgtgttca gctattggaa agatgaaaac aatattagc gcactaggtc    3420 cagattttat agaaaagcag gatggggatg atgatcttaa attcacaaca tttgaagttg    3480
agattcctgg agattctaga agttcaagtg cacaaacgtt tggggaatgg attgagcatt    3540
gcattaaatt caactttagt tcaattgaac caaccacgag tggacccatg ctaacttgg    3600 agcgtgggaa agcgaatgag ttggctgacc agataaattg tttgaatgca acagacatac    3660
gtgtgcatgg tggtgttgga acgggtaagt caacagctct accatatgag ctaataaggt    3720
atggggcagt tcttgtgtgt gtgcctacga gagttctggc aaatgcattg catgagtcat    3780
tcatgagctt gtttggattt gatgtgtcat tggcttatcg gggtcgagtc agaactggtt    3840
```

```
caaaaccaat tactatcatg acatatggat atgccttgaa tcatttccat cacaatccca    3900
ggaatttagc acagtttcaa ttcataataa tggatgaggt tcacacattc cctgttcatt    3960
taaatccttt attctcattg ttgcgtgagt tgagtcctga caagaaaata atcaagacat    4020
cagcaacaca tgttggccat agtgttgatc tatcaactaa ccacaaagtt gatatacaca    4080
cgcttgagat aatggatgtc aagaaatggg ctgaattaca aggaacatct gtgtttggtg    4140
atgtgacaaa ggaacctgga aatgttttgg tgtttgttgc atcatatagg gatgttgatg    4200
tttgttcaga taagcttaag gataaaggat ttcctgtaat taaagttgat ggaagaaatt    4260
tcaggaagaa tacagaagtt cagaaaatgg tggacggaat gcaaggagag gtgaagttca    4320
ttgtcgcgac taatatcatc gaaaatggtg ttacccttga cgttgatgta gtcgttgatt    4380
ttggcgaacg cataagtcca aatttatgct cagaagatag gtgcatttta atgcagaggc    4440
aaagaatctc acaagctgaa agaaaacaaa gatttgggag agttgggaga atgaagagag    4500
gctcagtgta caaatttgga agggagacgt tgcctgattc aatgagaaat agagtggggt    4560
caacagagag tgcattaatt tgttttgctt acggttaaa accagtagtt gatgatgtgg    4620
atatagggtc agttaggagt gtcacacaga ggcaagcttt gacagcatct atgttgaag    4680 cgaattacat attcacagct cacttagtgg acaaacaagg tttcatgcct aggccggttt    4740
ttgagttgat gaaaagtctt ctgctacata cagatgcggt tggggtcagt agtacatatt    4800
tagctactaa tatgagtggt tggagaaggt tgaaagagta tattagaatt gacgataact    4860
cacgtcacgt gcaagaagtt caaattccat ggtactgttc agacatgagt gacgatttta    4920
ttgttaagtt aactgagtgt gttaaagctg caaagccaaa atcacagtgt ggttacaaag    4980
tagataatgt agattttcat accgtagctc ataaaataag tgtaggagag tcgaatatag    5040
atgagtcaag ggctttagtg gcaacaattt tggatgaagt caaacagtgg agagatggta    5100
ttacatacca ttcaagcaca cctaggaata agagtctgat gagtttgatg gttggatgga    5160
ttccaaggaa agcagagaaa acaaaggaaa ttcttgacaa tcggattcag cgtctcgagt    5220
tactcttgaa ccaattaaat ggagtcagag gaatcgatga ctatgaatct cttgttcggt    5280
ttttcagtga gaatcctcat tcagcggaat atcttgaatc acaatgtgct agtgattata    5340
tcgaagagaa ggttatgagt gtcaaaagaa actacgataa gtcgctaatc cttggtatgg    5400
ttggtttagc tgttgcaaca ggcacgtttg cttactggta tatgaggaga agtgctgcgg    5460
ttgaactcgt tgaaaaacaa gcgaagcaca agtataacag agataagcga acaggaagat    5520
tgatgtttga tatggatgat agagagactt atgagaattt tggtcctgaa tacacagatg    5580
atgtcatatc tgccaagatg acaaaagctc agaaagaaag agactcaaag aagaagggat    5640
ggaaagcagg taaaataaat cgacctatga gggtgtttca tcaattgtat ggagttaatc    5700
ctcttgagtt cgatgaagtt gtcatgagag ttggtaaact tgagactgaa ccgtgggatg    5760
tgaaagaatt aaatgttgat gcaatgatga tcgaattgga tgatgattac cacatttac    5820 gggatgatcg aatgtttggg aagaaagttt ctttagcttt caagaaagaa ggggcagatg    5880
aggaaaccat tgtgaatttg actccacacc gatcaaaaat gacaagtagc atgagcttag    5940
ccccaatggg atttccagaa gagagggta gatggaggca gacaggagca ccgctgataa    6000
ggaagatcga aaaggaagat gaagttgaag ttcaagttgc taagccagag tcaacaaatc    6060
cttacgatca tatcttggtt agacttggca gagcgcatct tgggactcgt gtattgaatt    6120
gtttctttca tgggtcaaaa tgtgttattc catatcattt agctgagaaa ggagatagg    6180
```

```
aagaatcatt ggttattgca accacgagag gacagtttga ttttggacca atgaaaaata    6240
tcaagtgcag gaaggtcaca gactatgata tcactatttg cccactgcca aatgatgttc    6300
aaccattccg ttcaaaaatt gtaatgcgtg aaccaaagct aggagaggaa gtggttattg    6360
tgtgctttac caggatcaat gggaagatcg tgatgaaagt tagtgataag agcaccacat    6420
atcccgctgg tgggcagttt gcgcaccttt gggcgtataa atacgatggc caaccaggag    6480
attgcggagg cccaattgtt gcgacagttg atcaaaaggt ggtggggttc catagtggtg    6540
tgattagaaa tagtagagag gagaaactgc gagctgtgta cactccagta aatcaagagc    6600
ttttgaattg tatcagtggc gatatccaaa tgacggattt ttggacattc aatcctgatc    6660
ttgttgagtg gaattccgta gcaagagtgt caacattttt tcctatgaca aaagcgatta    6720
ataccatcac ggtgcaagcg aatgaaggtg aagaattaat tgatggtaac ttaatgattg    6780
ttggttatgt taaccgcgag gtttatcata atcacgtcat taaagggaaa agagagagtt    6840
tcatgagata ttgtgaacaa ttcccaaatt gtgcttttac caaggaattg cgagaccaat    6900
atcttccaag cattttgagt aagccagctt ttaggaaagg attgttgaag tacaatgagc    6960
cagttcgagt tgggtcagtg aatttctcgt gcttgatacg agcttatttg aaagtggaag    7020
aaatgtttga ggatctagga tttctggagg aagccggacc acagtgggac cctattgaaa    7080
ttttggatga tttgaataag aaagccgcaa tgggcgcatt gtatcaagga agaagcaag    7140 actggttgaa gtccatagag cccgcagatt ttatcacggc agtgcgtgaa agtttcaaac    7200
acttggctgg tggggatgtt ggaatttgga gtggctcact caaagcagaa ttgagacctg    7260
ttgagaaagt gcttgagcag aaaacaagag tgtttactgg agctccaatt gatttgctgt    7320 tgggggaaa gattttagtt gataatttta atcatttctt ttattttaat catttgaagg    7380
ggccttggac tgtaggaatt aataaattta ataaaggttg ggatagatta gctaggtact    7440
ttaatcatag ttggaacttc atagattgtg atggtagtag gtttgatact tctttagctc    7500
ccattttgtt tcaattagtg tgccatatgc gagaaaaatt tggaaatttt gatgatattg    7560
agagggcagc tcttcgtaat ttatacacac agatagtgta tacgccaatt ttaacaattg    7620
acggatacat tactaagaag catcgtggaa ataatagtgg acaaccttct acagttgtcg    7680
acaacactat tatactaatg attgttgtgg aatattgcaa ggctgtcatg gagagtgaag    7740
gaagagtaat gcaattcaag tatatgtgta atggggatga tctgatcctc aatgttcctg    7800
atgatgaggt gagcatagtt cagagtaggt ttagagagtt gttttcagaa tgtggtttag    7860
attataattt tgatgatgtt cataagtcaa tagaaacaat tgagtatatg agccattcat    7920
tcatgctgaa agatggtgtg tatattccaa aattgaagaa agaaagaatc gttgcaattc    7980
ttgaatggga gagaggtgat gagatcatgc gaacgcggag tgctcttaat gctgcttata    8040
ttgagagtta tggatatgac gatctgatgg ttgaaattga gcggtatgca gttttctggg    8100
ctaccgataa aggttgtgag tatccattac tggatagaaa gcgtgtagaa ggactttaca    8160
aagatgatta cacagatatc aatgaagaat ggttgatagg tatttttacca ccatcattcg    8220 aacattgtta tgttgacacg caaactaagg atttgagagg aagagagaag cttgagctga    8280
gaattgagag tcatgacaga acactccaaa tgcaaatgaa gttcccagtt acatttgtga    8340
caggaaattt gggaaaatta gcagaggtga agtctattct tggcattgca aatgatgtta    8400
tggccaagaa cattgattta ccagaagtgc aaggaactcc agaagaaatt gtgagaaaga    8460
aggctcaatt agcagtgaag atgactaata gtcctgtttt agtcgaagat acatgtctct    8520
gttttaatgc tttcaatgga cttcccggac catacatcaa atggtttcta aaagaattgg    8580
```

```
gtcttgatgg tgttgtcaaa atgctgtcag catttggaga taaatcagcg tacgcactat   8640
gtacattcgc atatgtgcac aatgagtcat ctgatccaat tgtgttcaaa ggagttgtga   8700
atggtgaaat tgtgccacca cgaggtaata atggctttgg ctgggatcct atctttaagc   8760
ctgatggatg tggttgtacg ttcgcggaaa tgccaagcag cattaagaat gattttttctc  8820 acagaagaag agctttagag aaagtcaaat tgtttcttga taacttgatg gtgaagcaag   8880
agaagaataa agcaagtgtg gctctaacga ttgacgttca ggccttaaat caggaggaaa   8940
tagaagcaga gatcactgct ttaaagaagc tgtggaaaga caatgggcca acaagaacgc   9000
gtagttcatt tgaggctagg aggttgagag ccccacaagt tgagcgtgta aatgagttac   9060
ttcagaaact gaaagatgaa ggattgcaaa caaagaagag gccatgtgga gaaccagatg   9120
atggggaagt ggtagatgat gacagcaatg atggtgacaa tcagagatct gaaaaggagg   9180
ttgttgacga aagccagaat aatcaacaag ttgatccaag aaagttgaaa ttcaaaatta   9240
ggggagatgg aaatgctatt agacgggatg acattgataa aattccaact aatgctcttg   9300
agatcaagaa gacgttcaag cctccaaagg tatcacagtc agcttacatt tggattccac   9360
gctctcaaag ggataatcta accctgatg ttattcagaa tttcctggca tatataccctc   9420 catctcatgc tatagataac caacttgctt caggaattga agttgaaaat tgggcaattg   9480
aggttgctaa agcatatgga gttaatatac aggaatttta tcgcacagtt ttgccagctt   9540
ggatagtgaa ctgtatagtg aacggcacta gcgatgaaag gaaaaatgag aagtcatggc   9600
gagcagtcga gctgaattct cagggagagg atgttgatga ttttgagtat ccaatggaac   9660
caatgtacaa atttgcattg ccaactatga ggaaggttat gagaaacttt tctagccaag   9720
ctattctcat gtaccagaat agtgtcgctg caggaaaggc gtttgtgata aaagctgcta   9780
gaaatgctgg atacacaagt attgaaaaca aatggctagg tatagacttt ctcgccgaag   9840
ctcaattgtc tcaaagtcaa cttgatatca agcatcagat tctggcagca aatgttggta   9900
ggtcaaagac aaggctgttt gcattagcag ctcctgggga tgatggcaat gtagataaag   9960
aaaggcacac aacacacgat gtcagtgcaa acaggcacag ttatagtggt gccgcaattg  10020
aataaataaa atattagtgt ttctaattag gtttaagtga gattatagct tagttggaaa  10080
gctaagctat atttcaaatt tgaatttaag tacttaaata ttgtatttta ttttcaagct  10140
tggtggagtt ttgatagcc aattatattt tggttgggta agccaaaatg tattttggag   10200
atctttctcc atatccttt gtttggtgta gaaatacacc ttataaaagt acaaaaaaaa   10260
aaaaaaaaaa aaaatgcat gcctgcagat cgttcaaaca tttggcaata aagtttctta   10320
agattgaatc ctgttgccgg tcttgcgatg attatcatat aatttctgtt gaattacgtt   10380
aagcatgtaa taattaacat gtaatgcatg acgttattta tgagatgggt ttttatgatt   10440
agagtcccgc aattatacat ttaatacgcg atagaaaaca aaatatagcg cgcaaactag   10500
gataaattat cgcgcgcggt gtcatctatg ttactagatc tctagcctgc aggaattgtt   10560 gatttttgtga tgactgatgg caggatatat gcggttgtaa ttcattttta ttgtctaaat   10620
ttctgtattt gtttgtttgt tcggttgtaa attttttttgg aagaacaaga aaagaaaaaa  10680 caccccgttag ggtgttttta gttagtgtgg cgcgccgact tgcgacatgc ggtcctttgc  10740
aatcaactat tagaaaaatt catccagcat cagatgaaat tgcagtttgt tcatatccgg   10800
attatcaatg ccatatttct gaaacagacg ttttttgcagg ctcgggctaa attcgcccag  10860
gcagttccac agaatggcca gatcctgata acgatccgca atgcccacac ggcccacatc  10920
```

```
aatgcagcca atcagtttgc cttcatcgaa aatcaggtta tccaggctaa aatcgccgtg    10980
ggtcaccacg ctatccgggc taaacggcag cagtttatgc atttctttcc acacctgttc    11040
caccggccag ccgttacgtt catcatcaaa atcgctcgca tccaccaggc cgttgttcat    11100
acggctctgc gcctgggcca gacgaaacac acgatcgctg ttaaacgggc agttgcacac    11160
cggaatgcta tgcagacgac gcagaaacac ggccagcgca tccacaatgt tttcgccgct    11220
atccggatat tcttccagca cctgaaacgc ggttttgccc ggaatcgcgg tggtcagcag    11280
ccacgcatca tccggggtgc gaataaaatg tttaatggtc ggcagcggca taaattcggt    11340
cagccagttc agacgcacca tttcatcggt cacatcgttc gccacgctgc ctttgccatg    11400
tttcagaaac agttccggcg catccggttt gccatacaga cgataaatgg tcgcgccgct    11460
ctgacccacg ttatcacgcg cccatttata gccatacaga tccgcatcca tgttgctgtt    11520
cagacgcgga cggctacagc tcgtttcacg ctgaatatgg ctcataacac cccttgtatt    11580
actgtttatg taagcagaca gttttattgt tcatgatgat atatttttat cttgtgcaat    11640
gtaacatcag agattttgag acacaagatc ggattggcgg ttatgcggtt ctaccggcgc    11700
ggcagcgtta cccgtgtcgg cggctccaac ggctcgccat cgtccagaaa acacggctca    11760
tcgggcatcg gcaggcgctg ctgcccgcgc cgttcccatt cctccgtttc ggtcaaggct    11820
ggcaggtctg gttccatgcc cggaatgccg ggctggctgg gcggctcctc gccggggccg    11880
gtcggtagtt gctgctcgcc cggatacagg gtcgggatgc ggcgcaggtc gccatgcccc    11940
aacagcgatt cgtcctggtc gtcgtgatca accaccacgg cggcactgaa caccgacagg    12000
cgcaactggt cgcgggggctg gccccacgcc acgcggtcat tgaccacgta ggccgacacg    12060
gtgccggggc cgttgagctt cacgacggag atccagcgct cggccaccaa gtccttgact    12120
gcgtattgga ccgtccgcaa agaacgtccg atgagcttgg aaagtgtctt ctggctgacc    12180
accacggcgt tctggtggcc catctgcgcc acgaggtgat gcagcagcat gccgccgtg    12240
ggtttcctcg caataagccc ggcccacgcc tcatgcgctt tgcgttccgt ttgcacccag    12300
tgaccgggct tgttcttggc ttgaatgccg atttctctgg actgcgtggc catgcttatc    12360
tccatgcggt aggggtgccg cacggttgcg gcaccatgcg caatcagctg caacttttcg    12420
gcagcgcgac aacaattatg cgttgcgtaa aagtggcagt caattacaga tttttcttta    12480
cctacgcaat gagctattgc gggggtgcc gcaatgagct gttgcgtacc ccccttttt    12540
aagttgttga ttttaagtc tttcgcattt cgccctatat ctagttcttt ggtgcccaaa    12600
gaagggcacc cctgcggggt tcccccacgc cttcggcgcg gctcccctc cggcaaaaag    12660
tggcccctcc ggggcttgtt gatcgactgc gcggccttcg gccttgccca aggtggcgct    12720
gccccttgg aaccccgcca ctcgccgccg tgaggctcgg ggggcaggcg ggcgggcttc    12780
gcccttcgac tgcccccact cgcataggct tgggtcgttc caggcgcgtc aaggccaagc    12840
cgctgcgcgg tcgctgcgcg agccttgacc cgccttccac ttggtgtcca accggcaagc    12900
gaagcgcgca ggccgcaggc cggaggcttt tccccagaga aaattaaaaa aattgatggg    12960
gcaaggccgc aggccgcgca gttggagccg gtgggtatgt ggtcgaaggc tgggtagccg    13020
gtgggcaatc cctgtggtca agctcgtggg caggcgcagc ctgtccatca gcttgtccag    13080
cagggttgtc cacgggccga gcgaagcgag ccagccggtg gccgctcgcg gccatcgtcc    13140
acatatccac gggctggcaa gggagcgcag cgaccgcgca gggcgaagcc cggagagcaa    13200
gcccgtaggg gg                                                        13212
```

<210> SEQ ID NO 23
<211> LENGTH: 5929
<212> TYPE: DNA
<213> ORGANISM: Artificial Sequence
<220> FEATURE:
<223> OTHER INFORMATION: pLX-B2-Pcrc:mTFP1 plasmid

<400> SEQUENCE: 23

| | | | | | |
|---|---|---|---|---|---|
| ccatcatcag | ttcggtggtc | ttccgacgaa | caataaggcc | gcaaatcgcg | gccttttta | 60 |
| ttgataacaa | aaccggctca | gttctgcgta | gaaaccaaca | tgcaagctcc | accgggtgca | 120 |
| aagcggcagc | ggcggcagga | tatattcaat | tgtaaatggc | ttcatgtccg | ggaaatctac | 180 |
| tggtggcagg | atatattgtg | gtgtaaacaa | tggagaaaaa | gattaattaa | gtactagtag | 240 |
| cctggtcgaa | accgtctcat | aacgaacgct | catgctaagc | tgcgcaaaat | acttcctaat | 300 |
| caaaacagta | caacgagta | attagcaaaa | tccgagcaga | aaactctcac | ccacctccga | 360 |
| aattcacgtc | ttcactaaaa | ttttcgaaag | gaatcgatca | ataccaaccc | attacacaaa | 420 |
| atacataatc | aaaatggcga | gaatcgtacc | tggaaacttt | gcttcaagtc | gcagagagag | 480 |
| gaaaaggaag | atcgtggaga | aaggggttta | gggtttaagc | tcagacttct | attggagtaa | 540 |
| atgggacggt | gtcacatttt | ccgttttgga | aatgaacttt | gggctcacgt | tatgggctat | 600 |
| tagatatttg | atgggctttc | tagtaaatac | aatataagtt | attgggctta | gtttaaataa | 660 |
| gcccatgttg | gaaatatttg | acacatgtct | tggctactag | tgctaaacat | gcaaccgaac | 720 |
| agttgtcgag | acaagtcgca | gcatatacaa | tggatcaaac | acgcctagtg | tcgccgcgtc | 780 |
| tcgctcatgt | gtcaccttgt | ttcctcgttt | tttttaatt | tttcataagt | tcttttgttt | 840 |
| tatcttcaat | acaaattttt | ggctgtatct | tgcaaactct | tcgatcatat | cgccaatata | 900 |
| cgtgaacact | ggtgatctaa | tttgttgtgt | taattgttaa | atttagattc | tattctccgg | 960 |
| tttaaaagtg | aattatatgt | atcatggtta | aaacattgta | agtaagatga | taataaaaatg | 1020 |
| ataaatttag | ttgatggata | acgtgaagca | aaaaatgaga | tagatacatt | tgattttgtc | 1080 |
| gtattttgac | atatgcggag | agtgagctac | gcgcatgaag | atcaagagac | acttgctcga | 1140 |
| gctcacagag | tgacgtgtaa | aaagcttaga | ctgaagtccc | catgcaaacc | taatcctacg | 1200 |
| tggctcaaac | cacgagctca | cttgacaata | tataaactcc | tcctaagtcc | cgttctcttc | 1260 |
| atccatctct | cacaacaaac | aaaagaaaa | tggtttctaa | aggtgaagag | actacaatgg | 1320 |
| gagtgatcaa | gcctgatatg | aagatcaagc | tcaagatgga | agggaacgtg | aacggacacg | 1380 |
| ctttcgttat | tgaaggagaa | ggggagggca | agccttacga | tggaactaac | accatcaacc | 1440 |
| ttgaagtgaa | agagggtgct | cctctcccctt | tctcttacga | tatcctcact | accgctttcg | 1500 |
| cttacggaaa | cagggctttc | accaagtacc | ctgatgatat | ccctaactac | ttcaagcagt | 1560 |
| ctttcccaga | gggatactct | tgggagagaa | ccatgacctt | cgaggataag | ggaatcgtga | 1620 |
| aagtgaagtc | tgatatctct | atggaagagg | attctttcat | ctacgagatc | catctcaagg | 1680 |
| gcgagaactt | ccctcctaac | ggacctgtga | tgcagaaaaa | gactaccgga | tgggatgctt | 1740 |
| ctaccgagcg | gatgtatgtg | agagatggtg | tgttgaaggg | tgatgtgaag | cacaagctgt | 1800 |
| tgcttgaggg | tggtggacat | cacagagtgg | atttcaagac | catctacagg | gctaagaagg | 1860 |
| ctgttaagct | ccctgattac | cacttcgtgg | atcatcgaat | cgagatcctc | aaccacgata | 1920 |
| aggattacaa | caaagtgacc | gtgtacgagt | ctgctgtggc | tagaaactct | accgatggag | 1980 |
| gctctggtga | ttcaaagac | gatgacgata | agggcagtgg | agactataag | gatgacgacg | 2040 |
| ataaaggagc | ataatgcact | ggaggacaag | gaaggatcca | agtggtcaac | gacaacggac | 2100 |

```
agaacgtgtt ggaccaacag gtgcagaagg gacagctcgt ggtcatccca caagggttcg      2160
catacgttgt ccagtcccac ggaaacaagt tcgagtggga ctctttcaaa actaatgaaa      2220
acgcaatgat cagcactttg gcgggtagaa cctcgctctt gagggcattg ccattggagg      2280
tcatatcaaa tggtttccag atctctcccg aggaagctag gaagatcaag ttcaacacac      2340
ttgagaccac tttgacccgc gctgccggta ggcaacaaca acagttgatc gaggagattg      2400
tcgaggctta aatcaaaacg ttttttcttt tcttaataaa gtatggtcag tttgtaatca      2460
cgtcccttta cctttaacgt acgtgtaaaa tatgtgtctg cggcacctca cttgtaataa      2520
cactttcttc tcataaataa aagggaagtt tcgagttaca tactataata tagcgccagt      2580
tttttcgtct attccacaaa acataagttt gtgtccatct actgtagctt gagcttcgta      2640
tatatacttg gtctttattc tttttttttt caaaatacgg ctttctgctt tctgtgggcc      2700
taaacggagg cccaaacgaa ttaaagttcc gtcacttgga aacgttatcc tagattactc      2760
ttgcggggaa aagtgtagat tagttccaat ttttgaagtg aaaaattgtg ttggattcta      2820
tgtcgtaaca agaaatagca tggcctccaa agattattct ctctttcttt aggctttagc      2880
ttctaaagct aagctacgga aaaactgtat cattcttctc tttttttttgg cttatgatcc      2940 atataagaga gcttggaaga gctgcttttc atctcctgat cactagctca tacagttttt      3000
gtaatttatt aacgaaacta tataaaaaaa gggaagccga aaaacaaaa caaaaaacaa      3060 ccttcatcgg ctgctcaaat gccaatcatc ccaattggtc tccattattg ttttctcgtt      3120
actactcctc catctttgat ttaataattt tttgaaaaaa gttttactat atgaatgata      3180
ttctctgtta gggaaatata aaaattgtaa gcaaatgatt ctatcgagct atgtcaggag      3240
acgggacaag gatgcgagct agcctgcagg aattgttgat tttgtgatga ctgatggcag      3300
gatatatgcg gttgtaattc attttttattg tctaaatttc tgtatttgtt tgtttgttcg      3360
gttgtaaatt ttttttggaag aacaagaaaa gaaaaaacac ccgttagggt gttttttagtt      3420 agtgtggcgc gccgacttgc gacatgcggt cctttgcaat caactattag aaaaattcat      3480
ccagcatcag atgaaattgc agtttgttca tatccggatt atcaatgcca tatttctgaa      3540
acagacgttt ttgcaggctc gggctaaatt cgcccaggca gttccacaga atggccagat      3600
cctgataacg atccgcaatg cccacacggc ccacatcaat gcagccaatc agtttgcctt      3660
catcgaaaat caggttatcc aggctaaaat cgccgtgggt caccacgcta tccgggctaa      3720
acggcagcag tttatgcatt tcttttccaca cctgttccac cggccagccg ttacgttcat      3780
catcaaaatc gctcgcatcc accaggccgt tgttcatacg gctctgcgcc tgggccagac      3840
gaaacacacg atcgctgtta acgggcagt tgcacaccgg aatgctatgc agacgacgca      3900
gaaacacggc cagcgcatcc acaatgtttt cgccgctatc cggatattct tccagcacct      3960
gaaacgcggt tttgcccgga atcgcggtgg tcagcagcca cgcatcatcc ggggtgcgaa      4020
taaaatgttt aatggtcggc agcggcataa attcggtcag ccagttcaga cgcaccattt      4080
catcggtcac atcgttcgcc acgctgcctt tgccatgttt cagaaacagt ccggcgcat      4140 ccggtttgcc atacagacga taaatggtcg cgccgctctg acccacgtta tcacgcgccc      4200
atttatagcc atacagatcc gcatccatgt tgctgttcag acgcggacgg ctacagctcg      4260
tttcacgctg aatatggctc ataacacccc ttgtattact gtttatgtaa gcagacagtt      4320
ttattgttca tgatgatata ttttttatctt gtgcaatgta acatcagaga ttttgagaca      4380
caagatcgga ttggcggtta tgcggttcta ccggcgcggc agcgttaccc gtgtcggcgg      4440
ctccaacggc tcgccatcgt ccagaaaaca cggctcatcg ggcatcggca ggcgctgctg      4500
```

```
cccgcgccgt tcccattcct ccgtttcggt caaggctggc aggtctggtt ccatgcccgg      4560
aatgccgggc tggctgggcg gctcctcgcc ggggccggtc ggtagttgct gctcgcccgg      4620
atacagggtc gggatgcggc gcaggtcgcc atgccccaac agcgattcgt cctggtcgtc      4680
gtgatcaacc accacggcgg cactgaacac cgacaggcgc aactggtcgc ggggctggcc      4740
ccacgccacg cggtcattga ccacgtaggc cgacacggtg ccggggccgt tgagcttcac      4800
gacggagatc cagcgctcgg ccaccaagtc cttgactgcg tattggaccg tccgcaaaga      4860
acgtccgatg agcttggaaa gtgtcttctg gctgaccacc acggcgttct ggtggcccat      4920
ctgcgccacg aggtgatgca gcagcattgc cgccgtgggt ttcctcgcaa taagcccggc      4980
ccacgcctca tgcgctttgc gttccgtttg cacccagtga ccgggcttgt tcttggcttg      5040
aatgccgatt tctctggact gcgtggccat gcttatctcc atgcggtagg ggtgccgcac      5100
ggttgcggca ccatgcgcaa tcagctgcaa cttttcggca gcgcgacaac aattatgcgt      5160
tgcgtaaaag tggcagtcaa ttacagattt tctttaacct acgcaatgag ctattgcggg      5220
gggtgccgca atgagctgtt gcgtaccccc cttttttaag ttgttgattt taagtctttt      5280
cgcatttcgc cctatatcta gttctttggt gcccaaagaa gggcacccct gcggggttcc      5340
cccacgcctt cggcgcggct ccccctccgg caaaaagtgg cccctccggg gcttgttgat      5400
cgactgcgcg gccttcggcc ttgcccaagg tggcgctgcc cccttggaac cccgcactc       5460 gccgccgtga ggctcggggg gcaggcgggc gggcttcgcc cttcgactgc ccccactcgc      5520
ataggcttgg gtcgttccag gcgcgtcaag gccaagccgc tgcgcggtcg ctgcgcgagc      5580
cttgacccgc cttccacttg gtgtccaacc ggcaagcgaa gcgcgcaggc cgcaggccgg      5640
aggcttttcc ccagagaaaa ttaaaaaaat tgatggggca aggccgcagg ccgcgcagtt      5700
ggagccggtg ggtatgtggt cgaaggctgg gtagccggtg ggcaatccct gtggtcaagc      5760
tcgtgggcag gcgcagcctg tccatcagct tgtccagcag ggttgtccac gggccgagcg      5820
aagcgagcca gccggtggcc gctcgcggcc atcgtccaca tatccacggg ctggcaaggg      5880
agcgcagcga ccgcgcaggg cgaagcccgg agagcaagcc cgtaggggg               5929
```

<210> SEQ ID NO 24
<211> LENGTH: 7308
<212> TYPE: DNA
<213> ORGANISM: Artificial Sequence
<220> FEATURE:
<223> OTHER INFORMATION: pLX-Z4-Pmas:RFP-AlcR plasmid

<400> SEQUENCE: 24

```
caagaagatc ctttgatctt ttctacaggc ctgctggtaa tcgcaggcct ttttattttg       60
gcaggatata ttgtggtgta aacacttacc gcacctctgc agcagcggca ggatatatgg      120
cagtgtaaac tccattttcg aacgcgttaa ttaagtagcc tggtcgaaac cgtctcattt      180
ttcaaatcag tgcgcaagac gtgacgtaag tatccgagtc agtttttatt tttctactaa      240
tttggtcgtt tatttcggcg tgtaggacat ggcaaccggg cctgaatttc gcgggtattc      300
tgtttctatt ccaacttttt cttgatccgc agccattaac gacttttgaa tagatacgct      360
gacacgccaa gcctcgctag tcaaaagtgt accaaacaac gctttacagc aagaacggaa      420
tgcgcgtgac gctcgcggtg acgccatttc gccttttcag aaatggataa atagccttgc      480
ttcctattat atcttcccaa attaccaata cattacacta gcatctgaat tcataaccaa      540
atctcgatac accaaatcgg gtaacaacaa tggtttcaaa gggagaagag ctgattaagg      600
```

| | |
|---|---|
| agaacatgca catgaagctg tacatggagg gcaccgtgaa caaccaccac ttcaagtgca | 660 |
| catccgaggg cgaaggcaag ccctacgagg gcacccagac catgagaatc aaggtggtcg | 720 |
| agggcggccc tctcccctc gccttcgaca tcctggctac cagcttcatg tacggcagca | 780 |
| gaaccttcat caaccacacc cagggcatcc ccgacttctt taagcagtcc ttccctgagg | 840 |
| gcttcacatg ggagagagtc accacatacg aagacggggg cgtgctgacc gctacccagg | 900 |
| acaccagcct ccaggacggc tgcctcatct caacgtcaa gatcagaggg gtgaacttcc | 960 |
| catccaacgg ccctgtgatg cagaagaaaa cactcggctg ggaggccaac accgagatgc | 1020 |
| tgtaccccgc tgacggcggc ctggaaggca acagacat ggccctgaag ctcgtgggcg | 1080 |
| ggggccacct gatctgcaac ttcaagacca catacagatc caagaaaccc gctaagaacc | 1140 |
| tcaagatgcc cggcgtctac tatgtggacc acagactgga aagaatcaag gaggccgaca | 1200 |
| aagagaccta cgtcgagcag cacgaggtgg ctgtggccag atactgcgac ctccctagca | 1260 |
| aactggggca caaacttaac ggaggcgag gcgggagagc agaagggaga ggaagcttgc | 1320 |
| taacctgtgg agacgttgag gaaaatccag gccaatggc agatacacgc cgacgccaga | 1380 |
| atcatagctg cgatccctgt cgcaagggca agcgacgctg tgatgccccg gaaaatagaa | 1440 |
| acgaggccaa tgaaacggc tgggtttcgt gttcaaattg caagcgttgg aacaaggatt | 1500 |
| gtaccttcaa ttggctctca tcccaacgct ccaaggcaaa aggggctgca cctagagcga | 1560 |
| gaacaaagaa agccaggacc gcaacaacca ccagtgaacc atcaacttca gctgcaacaa | 1620 |
| tccctacacc ggaaagtgac aatcacgatg cgcctccagt cataaactct cacgacgcgc | 1680 |
| tcccgagctg gactcagggg ctactctccc accccggcga ccttttcgat ttcagccact | 1740 |
| ctgctattcc cgcaaatgca gaagatgcgg ccaacgtgca gtcagacgca ccttttccgt | 1800 |
| gggatctagc catccccggt gatttcagca tgggccaaca gctcgagaaa cctctcagtc | 1860 |
| cgctcagttt tcaagcagtc cttcttccgc cccatagccc gaacacggat gacctcattc | 1920 |
| gcgagctgga agagcagact acagatccgg actcggttac cgatactaat agtgtacaac | 1980 |
| aggtcgctca agatggatcg ctatggtctg atcggcagtc gccgctactg cctgagaaca | 2040 |
| gtctgtgcat ggcctcagac agcacagcac ggcgatatgc ccgttccaca atgacgaaga | 2100 |
| atctgatgcg aatctaccac gatagtatgg agaatgcact gtcctgctgg ctgacagagc | 2160 |
| acaattgtcc atactccgac cagatcagct acctgccgcc caagcagcgg gcggaatggg | 2220 |
| gcccgaactg gtcaaacagg atgtgcatcc gggtgtgccg gctagatcgc gtatctacct | 2280 |
| cattacgcgg gcgcgccctg agtgcggaag aggacaaagc cgcagcccga gccctgcatc | 2340 |
| tggcgatcgt agcttttgcg tcgcaatgga cgcagcatgc gcagaggggg gctgggctaa | 2400 |
| atgttcctgc agacatagcc gccgatgaga ggtccatccg gaggaacgcc tggaatgaag | 2460 |
| cacgccatgc cttgcagcac acgacaggga ttccatcatt ccgggttata tttgcgaata | 2520 |
| tcatcttttc tctcacgcaa tctgtgctgg atgatgatga gcagcacggt atgggtgcac | 2580 |
| gtctagacaa gctactcgaa aatgacggtg cgcccgtgtt cctggaaacc gcgaaccgtc | 2640 |
| agctttatac attccgacat aagtttgcac gaatgcaacg ccgcggtaag gctttcaaca | 2700 |
| ggctcccgga aggatctgtc gcatcgacat tcgccggtat tttcgagaca ccgacgccgt | 2760 |
| cgtctgaaag cccacagctt gacccggttg tggccagtga ggagcatcgc agtacattaa | 2820 |
| gccttatgtt ctggctaggg atcatgttcg atacactaag cgctgcaatg taccagcgac | 2880 |
| cactcgtggt gtcagatgag gatagccaga tatcatcggc atctccacca aggcgcggcg | 2940 |
| ctgaaacgcc gatcaaccta gactgctggg agcccccgag acaggtcccg agcaatcaag | 3000 |

```
aaaagagcga cgtatggggc gacctcttcc tccgcacctc ggactctctc ccagatcacg   3060
aatcccacac acaaatctct cagccagcgg ctcgatggcc ctgcacctac gaacaggccg   3120
ccgccgctct ctcctctgca acgcccgtca aagtcctcct ctaccgccgc gtcacgcagc   3180
tccaaaccct cctctatcgc ggcgccagcc ctgcccgcct tgaagcggcc atccagagaa   3240
cgctctacgt ttataatcac tggacagcga agtaccaacc atttatgcag gactgcgttg   3300
ctaaccacga gctcctccct tcgcgcatcc agtcttggta cgtcattcta gacggtcact   3360
ggcatctagc cgcgatgttg ctagcggacg ttttggagag catcgaccgc gattcgtact   3420
ctgatatcaa ccacatcgac cttgtaacaa agctaaggct cgataatgca ctagcagtta   3480
gtgcccttgc gcgctcttca ctccgaggcc aggagctgga cccgggcaaa gcatctccga   3540
tgtatcgcca tttccatgat tctctgaccg aggtggcatt cctggtagaa ccgtggaccg   3600
tcgttcttat tcactcgttt gccaaagctg cgtatatctt gctggactgt ttagatctgg   3660
acggccaagg aaatgcacta gcggggtacc tgcagctgcg gcaaaattgc aactactgca   3720
ttcgggcgct gcaatttctg ggcaggaagt cggatatggc ggcgctggtt gcgaaggatt   3780
tagagagagg tttgaatggg aaagttgaca gcttcttgta gctcttggac tcccatgttg   3840
gcaaaggcaa ccaaacaaac aatgaatgat ccgctcctgc atatggggcg gtttgagtat   3900
ttcaactgcc atttgggctg aattgaagac atgctcctgt cagaaattcc gtgatcttac   3960
tcaatattca gtaatctcgg ccaatatcct aaatgtgcgt ggctttatct gtctttgtat   4020
tgtttcatca attcatgtaa cgtttgcttt tcttatgaat tttcaaataa attatcgtca   4080
ggagacggga caaggatgcg cctgcaggtt gttgatgatg tgatgactga tggcaggata   4140
tatgtggttg taattcattt ctaccgtgta atttactgta ttttttttgtt tgttcgttcg   4200 tttgtaaaaa tatttttttgg aagcaaaaaa ttagcgcaag aagacaaaaa tcaccttgcg   4260
ctaatgctct gttacaggcg cgccaattta cccaacaact ccgcggccgg gaagccgatc   4320
tcggcttgaa cgaattgtta ggtggcggta cttgggtcga tatcaaagtg catcacttct   4380
tcccgtatgc ccaactttgt atagagagcc actgcgggat cgtcaccgta atctgcttgc   4440
acgtagatca cataagcacc aagcgcgttg gcctcatgct tgaggagatt gatgagcgcg   4500
gtggcaatgc cctgcctccg gtgctctccg gagactgcga gatcatagat atagatctca   4560
ctacgcggct gctcaaactt gggcagaacg taagccgcga gagcgccaac aaccgcttct   4620
tggtcgaagg cagcaagcgc gatgaatgtc ttactacgga gcaagttccc gaggtaatcg   4680
gagtccggct gatgttggga gtaggtggct acatcgccga actcacgacc gaaaagatca   4740
agagcagccc gcatggattt gacttggtca gggccgagcc tacatgtgcg aatgatgccc   4800
atacttgagc cacctaactt tgttttaggg cgactgccct gctgcgtaac atcgttgctg   4860
ctgcgtaaca tcgttgctgc tccataacat caaacatcga cccacggcgt aacgcgcttg   4920
ctgcttggat gcccgaggca taggctgtac aaaaaaacag tcataacaag ccatgaaaac   4980
cgccactgcg ccgttaccac cgctgcgttc ggtcaaggtt ctggaccagt tgcgtgagcg   5040
catacgctac ttgcattaca gtttacgaac cgaacaggct tatgtcaaga tcggattggc   5100
ggttatgcgg ttgcgatgca ggtggctgct gaacccccag ccggaactga ccccacaagg   5160
ccctagcgtt tgcaatgcac caggtcatca ttgacccagg cgtgttccac caggccgctg   5220
cctcgcaact cttcgcaggc ttcgccgacc tgctcgcgcc acttcttcac gcgggtggaa   5280
tccgatccgc acatgaggcg gaaggtttcc agcttgagcg ggtacggctc ccggtgcgag   5340
```

| | |
|---|---|
| ctgaaatagt cgaacatccg tcgggccgtc ggcgacagct tgcggtactt ctcccatatg | 5400 |
| aatttcgtgt agtggtcgcc agcaaacagc acgacgattt cctcgtcgat caggacctgg | 5460 |
| caacgggacg ttttcttgcc acggtccagg acgcggaagc ggtgcagcag cgacaccgat | 5520 |
| tccaggtgcc caacgcggtc ggacgtgaag cccatcgccg tcgcctgtag gcgcgacagg | 5580 |
| cattcctcgg ccttcgtgta ataccggcca ttgatcgacc agcccaggtc ctggcaaagc | 5640 |
| tcgtagaacg tgaaggtgat cggctcgccg atagggggtgc gcttcgcgta ctccaacacc | 5700 |
| tgctgccaca ccagttcgtc atcgtcggcc cgcagctcga cgccggtgta ggtgatcttc | 5760 |
| acgtccttgt tgacgtggaa aatgaccttg ttttgcagcg cctcgcgcgg gattttcttg | 5820 |
| ttgcgcgtgg tgaacagggc agagcgggcc gtgtcgtttg gcatcgctcg catcgtgtcc | 5880 |
| ggccacggcg caatatcgaa caaggaaagc tgcatttcct tgatctgctg cttcgtgtgt | 5940 |
| ttcagcaacg cggcctgctt ggcttcgctg acctgttttg ccaggtcctc gccggcggtt | 6000 |
| tttcgcttct tggtcgtcat agttcctcgc gtgtcgatgg tcatcgactt cgccaaacct | 6060 |
| gccgcctcct gttctagccg acgcgaacgc tccacggcgg ccgatggcgc gggcagggca | 6120 |
| gggggagcca gttgcacgct gtcgcgctcg atcttggccg tagcttgctg gactatcgag | 6180 |
| ccgacgqact ggaaggtttc gcggggcgca cgcatgacgg tgcggcttgc gatggtttcg | 6240 |
| gcatcctcgg cggaaaaccc cgcgtcgatc agttcttgcc tgtatgcctt ccggtcaaac | 6300 |
| gtccgattca ttcaccctcc ttgcgggatt gccccggaat taattcccg gatcgatccg | 6360 |
| tcgatcttga tccctgcgc catcagatcc ttggcggcaa aaagccatc cagtttactt | 6420 |
| tgcagggctt cccaaccta ccagagggcg ccccagctgg caattccggt tcgcttgctg | 6480 |
| tccataaaac cgcccagtct agctatcgcc atgtaagccc actgcaagct acctgctttc | 6540 |
| tctttgcgct tgcgttttcc cttgtccaga tagcccagta gctgacattc atccggggtc | 6600 |
| agcaccgttt ctgcggactg gcttcctacg tggctgccat ttttgggtg aggccgttcg | 6660 |
| cggccgaggg gcgcagcccc tgggggatg ggaggcccgc gttagcgggc cgggagggtt | 6720 |
| cgagaagggg gggcaccccc cttcggcgtg cgcggtcacg cgcacagggc gcagccctgg | 6780 |
| ttaaaaacaa ggtttataaa tattggttta aaagcaggtt aaaagacagg ttagcggtgg | 6840 |
| ccgaaaaacg ggcggaaacc cttgcaaatg ctggattttc tgcctgtgga cagcccctca | 6900 |
| aatgtcaata ggtgcgcccc tcatctgtca gcactctgcc cctcaagtgt caaggatcgc | 6960 |
| gccctcatc tgtcagtagt cgcgcccctc aagtgtcaat accgcagggc acttatcccc | 7020 |
| aggcttgtcc acatcatctg tgggaaactc gcgtaaaatc aggcgttttc gccgatttgc | 7080 |
| gaggctggcc agctccacgt cgccggccga aatcgagcct gcccctcatc tgtcaacgcc | 7140 |
| gcgccgggtg agtcggcccc tcaagtgtca acgtccgccc ctcatctgtc agtgagggcc | 7200 |
| aagttttccg cgaggtatcc acaacgccgg cggccctaca tggctctgct gtagtgagtg | 7260 |
| ggttgcgctc cggcagcggt cctgatcccc cgcagaaaaa aaggatct | 7308 |

<210> SEQ ID NO 25
<211> LENGTH: 5007
<212> TYPE: DNA
<213> ORGANISM: Artificial Sequence
<220> FEATURE:
<223> OTHER INFORMATION: pLX-B2-Petoh:NEON plasmid

<400> SEQUENCE: 25

| | |
|---|---|
| ccatcatcag ttcggtggtc ttccgacgaa caataaggcc gcaaatcgcg gccttttta | 60 |
| ttgataacaa aaccggctca gttctgcgta gaaaccaaca tgcaagctcc accgggtgca | 120 |

| | |
|---|---|
| aagcggcagc ggcggcagga tatattcaat tgtaaatggc ttcatgtccg ggaaatctac | 180 |
| tggtggcagg atatattgtg gtgtaaacaa tggagaaaaa gattaattaa gtactagtag | 240 |
| cctggtcgaa accgtctcaa aatcaccagt ctctctctac aaatctatct ctctctataa | 300 |
| taatgtgtga gtagttccca gataagggaa ttagggttct tatagggttt cgctcatgtg | 360 |
| ttgagcatat aagaaaccct tagtatgtat ttgtatttgt aaaatacttc tatcaataaa | 420 |
| atttctaatt cctaaaacca aaatccagtg acccatgcgg agccgcattg gaggccatgc | 480 |
| ggagccgcac gcgttaacaa gagcggctcc gcttgacctc tcgggatagt tccgacctag | 540 |
| gattggatgc atgcggaacc gcacgagggc ggggcggaaa ttgacacacc actcctctcc | 600 |
| acgcaccgtt caagaggtac gcgtatagag ccgtatagag cagagacgga gcactttctg | 660 |
| gtactgtccg cacgggatgt ccgcacggag agccacaaac gagcggggcc ccgtacgtgc | 720 |
| tctcctaccc caggatcgca tccccgcata gctgaacatc tatataagaa ggcattcatt | 780 |
| cccatttgaa ggatcatcag atactgaacc aatattattt ttacaacaat taccaacaac | 840 |
| aacaaacaac aaacaacatt acaattacta tttacaatta caatggtgag caagggagag | 900 |
| gaggataaca tggcctctct cccagctaca catgagcttc acatctttgg atccatcaac | 960 |
| ggtgtggact ttgacatggt gggtcaggga accggaaatc caaatgatgg atatgaggag | 1020 |
| cttaacctta agtccaccaa gggtgacctc cagttctccc catggattct tgtccctcat | 1080 |
| atcggatatg gattccatca gtaccttcct taccctgatg gaatgtctcc gtttcaagcc | 1140 |
| gcaatggttg atggatccgg ataccaagtc catagaacaa tgcagtttga agatggtgcc | 1200 |
| tcccttactg ttaactacag atacacctac gagggaagcc acatcaaagg agaggcccag | 1260 |
| gtgaagggaa ctggttttcc tgctgacggt cctgtgatga ccaactctct taccgctgct | 1320 |
| gactggtgca ggtctaagaa aacttaccct aacgacaaaa ccatcatcag tacctttaag | 1380 |
| tggagttaca ccactggaaa tggcaagaga tacagaagca ctgctagaac cacctacacc | 1440 |
| tttgccaagc caatggctgc taactatctt aagaaccagc ctatgtacgt gttccgtaag | 1500 |
| actgagctca agcactccaa gaccgagctc aacttcaagg agtggcaaaa ggcctttacc | 1560 |
| gatgtgatgg gaatggacga gctatacaaa taagtgaagc tcatatccag atgaaggcag | 1620 |
| cagcattgag aaatgttcaa aatcgtttat ttggcttgga tggaaacgtc ggaacacaag | 1680 |
| aagaggacac agagagacac accgctggtg atgttaatcg caacatgcac aacctcctcg | 1740 |
| gtgtgagggg agtgtagtgg tctcggtatc tatcataaac tctacctggg tgagagtcta | 1800 |
| atcatccagt tgtttttaga ttcctgttag catcctttc tccgctttaa tagcagtaca | 1860 |
| ttcagtgagg ttttacctcc atatgttcta gtctgttatt gtcgaacaca ggcccttgta | 1920 |
| tctgatgtag cgagtgcttc actccattcg ggttatagtt cttgtgcaag agacaaaaaa | 1980 |
| aaaaaaaaaa aaaaaaaaaa aaaaaaaaaa aaaaaaaaaa aaaaaaaaaa aaaaaaaaaa | 2040 |
| aaatgcatgc ctgcagatcg ttcaaacatt tggcaataaa gtttcttaag attgaatcct | 2100 |
| gttgccggtc ttgcgatgat tatcatctaa tttctgttga attacgttaa gcatgtaata | 2160 |
| attaacatgt aatgcatgac gttatttatg agatgggttt ttatgattag agtcccgcaa | 2220 |
| ttatacattt aatacgcgat agaaaacaaa atatagcgcg caaactagga taaattatcg | 2280 |
| cgcgcggtgt catctatgtt actcgatctc gtcaggagac gggacaagga tgcgagctag | 2340 |
| cctgcaggaa ttgttgattt tgtgatgact gatggcagga tatatgcggt tgtaattcat | 2400 |
| ttttattgtc taaatttctg tatttgtttg tttgttcggt tgtaaatttt tttggaagaa | 2460 |

```
caagaaaaga aaaaacaccc gttagggtgt ttttagttag tgtggcgcgc cgacttgcga   2520
catgcggtcc tttgcaatca actattagaa aaattcatcc agcatcagat gaaattgcag   2580
tttgttcata tccggattat caatgccata tttctgaaac agacgttttt gcaggctcgg   2640
gctaaattcg cccaggcagt tccacagaat ggccagatcc tgataacgat ccgcaatgcc   2700
cacacggccc acatcaatgc agccaatcag tttgccttca tcgaaaatca ggttatccag   2760
gctaaaatcg ccgtgggtca ccacgctatc cgggctaaac ggcagcagtt tatgcatttc   2820
tttccacacc tgttccaccg gccagccgtt acgttcatca tcaaaatcgc tcgcatccac   2880
caggccgttg ttcatacggc tctgcgcctg ggccagacga acacacgat cgctgttaaa    2940 cgggcagttg cacaccggaa tgctatgcag acgacgcaga aacacggcca gcgcatccac   3000
aatgttttcg ccgctatccg gatattcttc cagcacctga aacgcggttt tgcccggaat   3060
cgcggtggtc agcagccacg catcatccgg ggtgcgaata aatgtttaa tggtcggcag    3120 cggcataaat tcggtcagcc agttcagacg caccatttca tcggtcacat cgttcgccac   3180
gctgcctttg ccatgtttca gaaacagttc cggcgcatcc ggtttgccat acagacgata   3240
aatggtcgcg ccgctctgac ccacgttatc acgcgcccat ttatagccat acagatccgc   3300
atccatgttg ctgttcagac gcggacggct acagctcgtt tcacgctgaa tatggctcat   3360
aacacccctt gtattactgt ttatgtaagc agacagtttt attgttcatg atgatatatt   3420
tttatcttgt gcaatgtaac atcagagatt ttgagacaca agatcggatt ggcggttatg   3480
cggttctacc ggcgcggcag cgttacccgt gtcggcggct ccaacggctc gccatcgtcc   3540
agaaaacacg gctcatcggg catcggcagg cgctgctgcc cgcgccgttc ccattcctcc   3600
gtttcggtca aggctggcag gtctggttcc atgcccggaa tgccgggctg ctgggcggc    3660 tcctcgccgg ggccggtcgg tagttgctgc tcgcccggat acagggtcgg gatgcggcgc   3720
aggtcgccat gccccaacag cgattcgtcc tggtcgtcgt gatcaaccac cacggcggca   3780
ctgaacaccg acaggcgcaa ctggtcgcgg ggctggcccc acgccacgcg gtcattgacc   3840
acgtaggccg acacggtgcc ggggccgttg agcttcacga cggagatcca gcgctcggcc   3900
accaagtcct tgactgcgta ttggaccgtc cgcaaagaac gtccgatgag cttggaaagt   3960
gtcttctggc tgaccaccac ggcgttctgg tggcccatct gcgccacgag gtgatgcagc   4020
agcattgccg ccgtgggttt cctcgcaata agcccggccc acgcctcatg cgctttgcgt   4080
tccgtttgca cccagtgacc gggcttgttc ttggcttgaa tgccgatttc tctggactgc   4140
gtggccatgc ttatctccat gcggtagggg tgccgcacgg ttgcggcacc atgcgcaatc   4200
agctgcaact tttcggcagc gcgacaacaa ttatgcgttg cgtaaaagtg gcagtcaatt   4260
acagattttc tttaacctac gcaatgagct attgcggggg gtgccgcaat gagctgttgc   4320 gtaccccct ttttaagtt gttgattttt aagtctttcg catttcgccc tatatctagt     4380
tctttggtgc ccaaagaagg gcaccctgc ggggttcccc cacgccttcg gcgcggctcc     4440
ccctccggca aaaagtggcc cctccggggc ttgttgatcg actgcgcggc cttcggcctt   4500
gcccaaggtg gcgctgcccc cttggaaccc ccgcactcgc cgccgtgagg ctcggggggc   4560
aggcgggcgg gcttcgccct tcgactgccc ccactcgcat aggcttgggt cgttccaggc   4620
gcgtcaaggc caagccgctg cgcggtcgct gcgcgagcct tgacccgcct tccacttggt   4680
gtccaaccgg caagcgaagc gcgcaggccg caggccggag cttttcccc agagaaaatt     4740 aaaaaaattg atggggcaag gccgcaggcc gcgcagttgg agccggtggg tatgtggtcg   4800
aaggctgggt agccggtggg caatccctgt ggtcaagctc gtgggcaggc gcagcctgtc   4860
```

```
catcagcttg tccagcaggg ttgtccacgg gccgagcgaa gcgagccagc cggtggccgc    4920
tcgcggccat cgtccacata tccacgggct ggcaagggag cgcagcgacc gcgcagggcg    4980
aagcccggag agcaagcccg tagggg                                        5007
```

<210> SEQ ID NO 26
<211> LENGTH: 9237
<212> TYPE: DNA
<213> ORGANISM: Artificial Sequence
<220> FEATURE:
<223> OTHER INFORMATION: pSN.5-PPAP85:RFP plasmid

<400> SEQUENCE: 26

```
tggcaggata tattgtggtg taaacaaatt gacgcttaga caacttaata acacattgcg      60
gacgttttta atgtactgaa ttaacgccga attgaattcc tcgagtacgt aggatccatt     120
taaattcctt caagagagca accattgtt tacacgtcaa tttgaattgc gtcaaatatt      180
cgactggaat cctacaacat atttcttcta ttatatcaat aggaagcaac gaacgttcac     240
atgaagccat gcaaaaacaa attgagaaaa aaatcagaa aatttatgac aagtggtctt      300
gcttcttata ctacgtcgtg aatggatggt aataaacaat taaatgttac ctctagtttt     360 tttttttga gagaatggtt tttatccgta tatggcttat tacaagtttc ctccttttc       420 gagtttggtt tgaggtctat attgaagatg agatactaaa aattgaggta aattctttag     480
tgtgaaggaa aattagtaaa tacgatacgt ttggaattgt ttactactaa aaaaaaatt      540 gttttagacc aagccagtcc gacaaaaagg cgtgtgaatc ataagaagta tcacatgatg     600
ctagacataa aagattttc aaacatgaca aaacaaattg tgagtgtctt agtcatgcca      660
tttgaagtag aacgaaactt agtgatgaga cacgtaacat cagtgagaat caagatctaa     720
cttcggactt atcgtacgta ccacgtccac ctaagtgtta tccatatcta ctacatgtct     780
atcttcattc aattttttt ttgcattaac ttgtaaacat agtgcataat aattagaatc      840
aagatttgaa tccaattcgc ttactaaatc ctaaatgtta aaagcataca tgttttcaa      900 atcctacttt taggtgctaa gttttttttc taaggtagtt agagattgtt agattttata     960
tcattgaact gatcatcagt tctctataca acttctagat ctcattgaat gtttactcaa    1020
ttttttttaa tttttttgttt ggataatcgt ctgctcgtgg ttttgatgcg tacgaacact   1080
cgtcaccatg catgtcaagc tctccttcct atataaacta aaaccaccca ttattgtcct    1140
caaaaacaaa cacatcaaca aaacaacaag aaaaaatggt ttcaaaggga gaagagctga    1200
ttaaggagaa catgcacatg aagctgtaca tggagggcac cgtgaacaac caccacttca    1260
agtgcacatc cgagggcgaa ggcaagccct acgagggcac ccagaccatg agaatcaagg    1320
tggtcgaggg cggccctctc cccttcgcct tcgacatcct ggctaccagc ttcatgtacg    1380
gcagcagaac cttcatcaac cacacccagg catccccga cttctttaag cagtccttcc     1440
ctgagggctt cacatgggag agagtcacca catacgaaga cggggcgtg ctgaccgcta     1500 cccaggacac cagcctccag gacggctgcc tcatctacaa cgtcaagatc agaggggtga    1560
acttcccatc caacggccct gtgatgcaga gaaaaacact cggctgggag gccaacaccg    1620
agatgctgta ccccgctgac ggcggcctgg aaggcagaac agacatgcc ctgaagctcg      1680 tgggcggggg ccacctgatc tgcaacttca gaccacata cagatccaag aaacccgcta     1740
agaacctcaa gatgcccggc gtctactatg tggaccacag actggaaaga atcaaggagg    1800
ccgacaaaga gacctacgtc gagcagcacg aggtggctgt ggccagatac tgcgacctcc    1860
```

```
ctagcaaact ggggcacaaa cttaactaat cgatcacgtg aagctcatat ccagatgaag    1920
gcagcagcat tgagaaatgt tcaaaatcgt ttatttggct tggatggaaa cgtcggaaca    1980
caagaagagg acacagagag acacaccgct ggtgatgtta atcgcaacat gcacaacctc    2040
ctcggtgtga ggggagtgta gtggtctcgg tatctatcat aaactctacc tgggtgagag    2100
tctaatcatc cagttgtttt tagattcctg ttagcatcct tttctccgct ttaatagcag    2160
tacattcagt gaggttttac ctccatatgt tctagtctgt tattgtcgaa cacaggccct    2220
tgtatctgat gtagcgagtg cttcactcca ttcgggttat agttcttgtg caagagacaa    2280
aaaaaaaaaa aaaaaaaaaa aaaaaaaaaa aaaaaaaaaa aaaaaaaaaa aaaaaaaaaa    2340
aaaaaaatgc atgcctgcag atcgttcaaa catttggcaa taaagtttct taagattgaa    2400
tcctgttgcc ggtcttgcga tgattatcat ctaatttctg ttgaattacg ttaagcatgt    2460
aataattaac atgtaatgca tgacgttatt tatgagatgg gtttttatga ttagagtccc    2520
gcaattatac atttaatacg cgatagaaaa caaaatatag cgcgcaaact aggataaatt    2580
atcgcgcgcg gtgtcatcta tgttactcga tctctagctt gagcttggat cagattgtcg    2640
tttcctagct tgagcttgga tcagattgtc gtttcccgcc ttcagtttaa actatcagtg    2700
tttgacagga tatattggcg ggtaaaccta agagaaaaga gcgtttatta gaataacgga    2760
tatttaaaag ggcgtgaaaa ggtttatccg ttcgtccatt tgtatgtgca tgccaaccac    2820
agggttcccc tcgggatcaa agtactttga tccaacccct ccgctgctat agtgcagtcg    2880
gcttctgacg ttcagtgcag ccgtcttctg aaaacgacat gtcgcacaag tcctaagtta    2940
cgcgacaggc tgccgccctg ccctttcct ggcgttttct tgtcgcgtgt tttagtcgca    3000
taaagtagaa tacttgcgac tagaaccgga gacattacgc catgaacaag agcgccgccg    3060
ctggcctgct gggctatgcc cgcgtcagca ccgacgacca ggacttgacc aaccaacggg    3120
ccgaactgca cgcggccggc tgcaccaagc tgttttccga aagatcacc ggcaccaggc    3180 gcgaccgccc ggagctggcc aggatgcttg accacctacg ccctggcgac gttgtgacag    3240
tgaccaggct agaccgcctg gcccgcagca cccgcgacct actggacatt gccgagcgca    3300
tccaggaggc cggcgcgggc ctgcgtagcc tggcagagcc gtgggccgac accaccacgc    3360
cggccggccg catggtgttg accgtgttcg ccggcattgc cgagttcgag cgttccctaa    3420
tcatcgaccg cacccggagc gggcgcgagg ccgccaaggc ccgaggcgtg aagtttggcc    3480
cccgccctac cctcaccccg gcacagatcg cgcacgcccg cgagctgatc gaccaggaag    3540
gccgcaccgt gaaagaggcg gctgcactgc ttggcgtgca tcgctcgacc ctgtaccgcg    3600
cacttgagcg cagcgaggaa gtgacgccca ccgaggccag gcggcgcggt gccttccgtg    3660
aggacgcatt gaccgaggcc gacgccctgg cggccgccga gaatgaacgc caagaggaac    3720
aagcatgaaa ccgcaccagg acggccagga cgaaccgttt ttcattaccg aagagatcga    3780
ggcggagatg atcgcggccg ggtacgtgtt cgagccgccc gcgcacgtct caaccgtgcg    3840
gctgcatgaa atcctggccg gtttgtctga tgccaagctg gcggcctggc cggccagctt    3900
ggccgctgaa gaaaccgagc gccgccgtct aaaaaggtga tgtgtatttg agtaaaacag    3960
cttgcgtcat gcggtcgctg cgtatatgat gcgatgagta aataaacaaa tacgcaaggg    4020
gaacgcatga aggttatcgc tgtacttaac cagaaaggcg ggtcaggcaa gacgaccatc    4080
gcaacccatc tagcccgcgc cctgcaactc gccggggccg atgttctgtt agtcgattcc    4140
gatccccagg gcagtgcccg cgattgggcg ccgtgcggg aagatcaacc gctaaccgtt    4200
gtcggcatcg accgcccgac gattgaccgc gacgtgaagg ccatcggccg gcgcgacttc    4260
```

```
gtagtgatcg acggagcgcc ccaggcggcg gacttggctg tgtccgcgat caaggcagcc    4320
gacttcgtgc tgattccggt gcagccaagc ccttacgaca tatgggccac cgccgacctg    4380
gtggagctgg ttaagcagcg cattgaggtc acggatggaa ggctacaagc ggcctttgtc    4440
gtgtcgcggg cgatcaaagg cacgcgcatc ggcggtgagg ttgccgaggc gctggccggg    4500
tacgagctgc ccattcttga gtcccgtatc acgcagcgcg tgagctaccc aggcactgcc    4560
gccgccggca caaccgttct tgaatcagaa cccgagggcg acgctgcccg cgaggtccag    4620
gcgctggccg ctgaaattaa atcaaaactc atttgagtta atgaggtaaa gagaaaatga    4680
gcaaaagcac aaacacgcta agtgccggcc gtccgagcgc acgcagcagc aaggctgcaa    4740
cgttggccag cctggcagac acgccagcca tgaagcgggt caactttcag ttgccggcgg    4800
aggatcacac caagctgaag atgtacgcgg tacgccaagg caagaccatt accgagctgc    4860
tatctgaata catcgcgcag ctaccagagt aaatgagcaa atgaataaat gagtagatga    4920
attttagcgg ctaaaggagg cggcatggaa aatcaagaac aaccaggcac cgacgccgtg    4980
gaatgcccca tgtgtggagg aacgggcggt tggccaggcg taagcggctg ggttgtctgc    5040
cggccctgca atggcactgg aaccccccaag cccgaggaat cggcgtgacg gtcgcaaacc    5100
atccggcccg gtacaaatcg gcgcggcgct gggtgatgac ctggtggaga agttgaaggc    5160
cgcgcaggcc gcccagcggc aacgcatcga ggcagaagca cgccccggtg aatcgtggca    5220
agcggccgct gatcgaatcc gcaaagaatc ccggcaaccg ccggcagccg gtgcgccgtc    5280
gattaggaag ccgcccaagg gcgacgagca accagatttt ttcgttccga tgctctatga    5340
cgtgggcacc cgcgatagtc gcagcatcat ggacgtggcc gttttccgtc tgtcgaagcg    5400
tgaccgacga gctggcgagg tgatccgcta cgagcttcca gacgggcacg tagaggtttc    5460
cgcagggccg ccggcatgg ccagtgtgtg ggattacgac ctggtactga tggcggtttc    5520
ccatctaacc gaatccatga accgataccg ggaagggaag ggagacaagc ccggccgcgt    5580
gttccgtcca cacgttgcgg acgtactcaa gttctgccgg cgagccgatg gcggaaagca    5640
gaaagacgac ctggtagaaa cctgcattcg gttaaacacc acgcacgttg ccatgcagcg    5700
tacgaagaag gccaagaacg gccgcctggt gacggtatcc gagggtgaag ccttgattag    5760
ccgctacaag atcgtaaaga gcgaaaccgg gcggccggag tacatcgaga tcgagctagc    5820
tgattggatg taccgcgaga tcacagaagg caagaacccg gacgtgctga cggttcaccc    5880
cgattacttt ttgatcgatc ccggcatcgg ccgttttctc taccgcctgg cacgccgcgc    5940
cgcaggcaag gcagaagcca gatggttgtt caagacgatc tacgaacgca gtggcagcgc    6000
cggagagttc aagaagttct gtttcaccgt gcgcaagctg atcgggtcaa atgacctgcc    6060
ggagtacgat ttgaaggagg aggcggggca ggctggcccg atcctagtca tgcgctaccg    6120
caacctgatc gagggcgaag catccgccgg ttcctaatgt acggagcaga tgctagggca    6180
aattgcccta gcagggggaaa aaggtcgaaa aggtctcttt cctgtggata gcacgtacat    6240
tgggaaccca aagccgtaca ttgggaaccg gaacccgtac attgggaacc caaagccgta    6300
cattgggaac cggtcacaca tgtaagtgac tgatataaaa gagaaaaaag gcgatttttc    6360
cgcctaaaac tctttaaaac ttattaaaac tcttaaaacc cgcctggcct gtgcataact    6420
gtctggccag cgcacagccg aagagctgca aaaagcgcct acccttcggt cgctgcgctc    6480
cctacgcccc ggcgcttcgc gtcggcctat cgcggccgct ggccgctcaa aaatggctgg    6540
cctacggcca ggcaatctac cagggcgcgg acaagccgcg ccgtcgccac tcgaccgccg    6600
```

```
gcgcccacat caaggcaccc tgcctcgcgc gtttcggtga tgacggtgaa aacctctgac    6660
acatgcagct cccggagacg gtcacagctt gtctgtaagc ggatgccggg agcagacaag    6720
cccgtcaggg cgcgtcagcg ggtgttggcg ggtgtcgggg cgcagccatg acccagtcac    6780
gtagcgatag cggagtgtat actggcttaa ctatgcggca tcagagcaga ttgtactgag    6840
agtgcaccat atgcggtgtg aaataccgca cagatgcgta aggagaaaat accgcatcag    6900
gcgctcttcc gcttcctcgc tcactgactc gctgcgctcg gtcgttcggc tgcggcgagc    6960
ggtatcagct cactcaaagg cggtaatacg gttatccaca gaatcagggg ataacgcagg    7020
aaagaacatg tgagcaaaag gccagcaaaa ggccaggaac cgtaaaaagg ccgcgttgct    7080 ggcgttttc cataggctcc gcccccctga cgagcatcac aaaaatcgac gctcaagtca    7140
gaggtggcga aacccgacag gactataaag ataccaggcg tttccccctg gaagctccct    7200
cgtgcgctct cctgttccga ccctgccgct taccggatac ctgtccgcct ttctcccttc    7260
gggaagcgtg gcgctttctc atagctcacg ctgtaggtat ctcagttcgg tgtaggtcgt    7320
tcgctccaag ctgggctgtg tgcacgaacc ccccgttcag cccgaccgct gcgccttatc    7380
cggtaactat cgtcttgagt ccaacccggt aagacacgac ttatcgccac tggcagcagc    7440
cactggtaac aggattagca gagcgaggta tgtaggcggt gctacagagt tcttgaagtg    7500
gtggcctaac tacggctaca ctagaaggac agtatttggt atctgcgctc tgctgaagcc    7560
agttaccttg gaaaaagag ttggtagctc ttgatccggc aaacaaacca ccgctggtag    7620
cggtggtttt tttgtttgca agcagcagat tacgcgcaga aaaaaggat ctcaagaaga    7680 tcctttgatc ttttctacgg ggtctgacgc tcagtggaac gaaaactcac gttaagggat    7740
tttggtcatg catgatatat ctcccaattt gtgtagggct tattatgcac gcttaaaaat    7800
aataaaagca gacttgacct gatagtttgg ctgtgagcaa ttatgtgctt agtgcatcta    7860
atcgcttgag ttaacgccgg cgaagcggcg tcggcttgaa cgaatttcta gctagacatt    7920
atttgccgac taccttggtg atctcgcctt tcacgtagtg gacaaattct tccaactgat    7980
ctgcgcgcga ggccaagcga tcttcttctt gtccaagata agcctgtcta gcttcaagta    8040
tgacgggctg atactgggcc ggcaggcgct ccattgccca gtcggcagcg acatccttcg    8100
gcgcgatttt gccggttact gcgctgtacc aaatgcggga caacgtaagc actacatttc    8160
gctcatcgcc agcccagtcg gcggcgagt tccatagcgt taaggtttca tttagcgcct    8220
caaatagatc ctgttcagga accggatcaa agagttcctc cgccgctgga cctaccaagg    8280
caacgctatg ttctcttgct tttgtcagca agatagccag atcaatgtcg atcgtggctg    8340
gctcgaagat acctgcaaga atgtcattgc gctgccattc tccaaattgc agttcgcgct    8400
tagctggata acgccacgga atgatgtcgt cgtgcacaac aatggtgact tctacagcgc    8460
ggagaatctc gctctctcca ggggaagccg aagtttccaa aaggtcgttg atcaaagctc    8520
gccgcgttgt ttcatcaagc cttacggtca ccgtaaccag caaatcaata tcactgtgtg    8580
gcttcaggcc gccatccact gcggagccgt acaaatgtac ggccagcaac gtcggttcga    8640
gatggcgctc gatgacgcca actacctctg atagttgagt cgatacttcg gcgatcaccg    8700
cttcccccat gatgtttaac tttgttttag ggcgactgcc ctgctgcgta acatcgttgc    8760
tgctccataa catcaaacat cgacccacgg cgtaacgcgc ttgctgcttg gatgcccgag    8820
gcatagactg taccccaaaa aaacatgtca taacaagaag ccatgaaaac cgccactgcg    8880
ccgttaccac cgctgcgttc ggtcaaggtt ctggaccagt tgcgtgacgg cagttacgct    8940
acttgcatta cagcttacga accgaacgag gcttatgtcc actgggttcg tgcccgaatt    9000
```

```
gatcacaggc agcaacgctc tgtcatcgtt acaatcaaca tgctaccctc cgcgagatca    9060
tccgtgtttc aaacccggca gcttagttgc cgttcttccg aatagcatcg gtaacatgag    9120
caaagtctgc cgccttacaa cggctctccc gctgacgccg tcccggactg atgggctgcc    9180
tgtatcgagt ggtgattttg tgccgagctg ccggtcgggg agctgttggc tggctgg      9237

<210> SEQ ID NO 27
<211> LENGTH: 10048
<212> TYPE: DNA
<213> ORGANISM: Artificial Sequence
<220> FEATURE:
<223> OTHER INFORMATION: GB1686 plasmid

<400> SEQUENCE: 27
ggagagcgat cagcttgcat gccggtcgat ctagtaacat agatgacacc gcgcgcgata      60
atttatccta gtttgcgcgc tatattttgt tttctatcgc gtattaaatg tataattgcg     120
ggactctaat cataaaaacc catctcataa ataacgtcat gcattacatg ttaattatta     180
catgcttaac gtaattcaac agaaattata tgataatcat ggcaagaccg gcaacaggat     240
tcaatcttaa gaaactttat tgccaaatgt ttgaacgatc tgcttgactc tagctagagt     300
ccgaacccca gagtcccgct cagaagaact cgtcaagaag gcgatagaag gctatgcgct     360
gcgaatcggg agcggcgata ccgtaaagca cgaggaagcg gtcagcccat tcgccgccaa     420
gctcttcagc aatatcacgg gtagccaacg ctatgtcctg atagcggtcc gccacaccca     480
gccggccaca gtcgatgaat ccagaaaagc ggccattttc caccatgata ttcggcaagc     540
aggcgtcgcc gtgggtcacg acgagatcct cgccgtcggg catccgcgcc ttgagcctgg     600
cgaacagttc ggctggcgcg agcccctgat gctcttcgtc cagatcatcc tgatcgacaa     660
gaccggcttc catccgagta cgtgctcgct cgatgcggtg tttcgcttgg tggtcgaatg     720
ggcaggtagc cggatcaagc gtatgcagcc gccgcattgc atcagccatg atggatactt     780
tctcggcagg agcaaggtga gatgacagga gatcctgccc cggcacttcg cccaatagca     840
gccagtccct tcccgcttca gtgacaacgt cgagcacagc tgcgcaagga acgcccgtcg     900
tggccagcca cgatagccgc gctgcctcgt cttggagttc attcagggca ccggacaggt     960
cggtcttgac aaaaagaacc gggcgcccct gcgctgacag ccggaacacg gcggcatcag    1020
agcagccgat tgtctgttgt gcccagtcat agccgaatag cctctccacc caagcggccg    1080
gagaacctgc gtgcaatcca tcttgttcaa tcatgcctcg atcgagttga gagtgaatat    1140
gagactctaa ttggataccg aggggaattt atggaacgtc agtggagcat ttttgacaag    1200
aaatatttgc tagctgatag tgaccttagg cgactttga acgcgcaata atggtttctg    1260
acgtatgtgc ttagctcatt aaactccaga aacccgcggc tgagtggctc cttcaacgtt    1320
gcggttctgt cagttccaaa cgtaaacgg cttgtcccgc gtcatcggcg ggggtcataa    1380
cgtgactccc ttaattctca tgtatctcct gacagcgaaa tgattgatga agaacaatgg    1440
tggatgaaga acaaagaagg agggagcttt tgttcaagat gaacaaagaa caatagtgga    1500
tgaagaacaa agtgaaaaaa ataaaaaaaa atgtatggtt aaataaagag taaagttacc    1560
attgagactc cgtcaggaga ctagagccaa gctgatctcc tttgccccgg agatcaccat    1620
ggacgacttt ctctatctct acgatctagg aagaaagttc gacggagaag gtgacgatac    1680
catgttcacc accgataatg agaagattag cctcttcaat ttcagaaaga atgctgaccc    1740
acagatggtt agagaggcct acgcggcagg tctgatcaag acgatctacc cgagtaataa    1800
```

```
tctccaggag atcaaatacc ttcccaagaa ggttaaagat gcagtcaaaa gattcaggac    1860
taactgcatc aagaacacag agaaagatat atttctcaag atcagaagta ctattccagt    1920
atggacgatt caaggcttgc ttcataaacc aaggcaagta atagagattg gagtctctaa    1980
gaaagtagtt cctactgaat caaaggccat ggagtcaaaa attcagatcg aggatctaac    2040
agaactcgcc gtgaagactg gcgaacagtt catacagagt cttttacgac tcaatgacaa    2100
gaagaaaatc ttcgtcaaca tggtggagca cgacactctc gtctactcca agaatatcaa    2160
agatacagtc tcagaagacc aaagggctat tgagactttt caacaaaggg taatatcggg    2220
aaacctcctc ggattccatt gcccagctat ctgtcacttc atcaaaagga cagtagaaaa    2280
ggaaggtggc acctacaaat gccatcattg cgataaagga aaggctatcg ttcaagatgc    2340
ctctgccgac agtggtccca agatggaccc ccacccacg aggagcatcg tggaaaaaga     2400
agacgttcca accacgtctt caaagcaagt ggattgatgt gatatctcca ctgacgtaag    2460
ggatgacgca caatcccact atccttcgca agacccttcc tctatataag gaagttcatt    2520
tcatttggag aggactccgg tatttttaca acaataccac aacaaacaa acaacaaaca     2580
acattacaat ttactattct agtcgaaatg gcctcctccg agaacgtcat caccgagttc    2640
atgcgcttca aggtgcgcat ggagggcacc gtgaacggcc acgagttcga gatcgagggc    2700
gagggcgagg ccgcccccta cgagggccac aacaccgtga agctgaaggt gaccaagggc    2760
ggcccctgc ccttcgcctg gacatcctg tccccccagt ccagtacgg ctccaaggtg       2820
tacgtgaagc accccgccga catccccgac tacaagaagc tgtccttccc cgagggcttc    2880
aagtgggagc gcgtgatgaa cttcgaggac ggcggcgtgg cgaccgtgac ccaggactcc    2940
tccctgcagg acggctgctt catctacaag gtgaagttca tcggcgtgaa cttcccctcc    3000
gacggccccg tgatgcagaa gaagacgatg gctgggagg cctccaccga cgcctgtac     3060
ccccgcgacg gcgtgctgaa gggcgagaca cacaaggccc tgaagctgaa ggacggcggc    3120
cactacctgg tggagttcaa gtccatctac atggccaaga gcccgtgca gctgcccggc    3180
tactactacg tggacgccaa gctggacatc acctcccaca cgaggactac caccatcgtg    3240
gagcagtacg agcgcaccga gggccgccac cacctgttcc tgtaggcttc ggccatgcta    3300
gagtccgcaa aaatcaccag tctctctcta caaatctatc tctctctatt tttctccaga    3360
ataatgtgtg agtagttccc agataaggga attagggttc ttatagggtt tcgctcatgt    3420
gttgagcata taagaaaccc ttagtatgta tttgtatttg taaaatactt ctatcaataa    3480
aatttctaat tcctaaaacc aaaatccagt gacctcgctg tcaggagtct caatggtaac    3540
tttactcttt atttaaccat acatttttt ttattttttt cactttgttc ttcatccact     3600
attgttcttt gttcatcttg aacaaaagct ccctccttct ttgttcttca tccaccattg    3660
ttcttcatca atcatttcgc tgtcatgaga cgaattctga caggatatat tggcgggtaa    3720
acctaagaga aaagagcgtt tattagaata atcggatatt taaaagggcg tgaaaaggtt    3780
tatccgttcg tccatttgta tgtgcatgcc aaccacaggg ttcccctcgg atcaaagta    3840
ctttgatcca accccctccgc tgctatagtg cagtcggctt ctgacgttca gtgcagccgt    3900
catctgaaaa cgacatgtcg cacaagtcct aagttacgcg acaggctgcc gcctgccct    3960
tttcctggcg ttttcttgtc gcgtgtttta gtcgcataaa gtagaatact tgcgactaga    4020
accggagaca ttacgccatg aacaagagcg ccgccgctgg cctgctgggc tatgcccgcg    4080
tcagcaccga cgaccaggac ttgaccaacc aacgggccga actgcacgcg gccggctgca    4140
ccaagctgtt ttccgagaag atcaccggca ccaggcgcga ccgcccggag ctggccagga    4200
```

-continued

```
tgcttgacca cctacgccct ggcgacgttg tgacagtgac caggctagac cgcctggccc    4260
gcagcacccg cgacctactg gacattgccg agcgcatcca ggaggccggc gcgggcctgc    4320
gtagcctggc agagccgtgg gccgacacca ccacgccggc cggccgcatg gtgttgaccg    4380
tgttcgccgg cattgccgag ttcgagcgtt ccctaatcat cgaccgcacc cggagcgggc    4440
gcgaggccgc caaggcccga ggcgtgaagt ttggcccccg ccctacccctc accccggcac    4500 agatcgcgca cgcccgcgag ctgatcgacc aggaaggccg caccgtgaaa gaggcggctg    4560
cactgcttgg cgtgcatcgc tcgaccctgt accgcgcact tgagcgcagc gaggaagtga    4620
cgcccaccga ggccaggcgg cgcggtgcct tccgtgagga cgcattgacc gaggccgacg    4680
ccctggcggc cgccgagaat gaacgccaag aggaacaagc atgaaaccgc accaggacgg    4740
ccaggacgaa ccgttttttca ttaccgaaga gatcgaggcg gagatgatcg cggccgggta    4800
cgtgttcgag ccgcccgcgc acctctcaac cgtgcggctg catgaaatcc tggccggttt    4860
gtctgatgcc aagctggcgg cctggccggc cagcttggcc gctgaagaaa ccgagcgccg    4920
ccgtctaaaa aggtgatgtg tatttgagta aaacagcttg cgtcatgcgg tcgctgcgta    4980
tatgatccga tgagtaaata aacaaatacg caaggggaac gcatgaaggt tatcgctgta    5040
cttaaccaga aaggcgggtc aggcaagacg accatcggaa cccatctagc ccgcgccctg    5100
caactcgccg gggccgatgt tctgttagtc gattccgatc cccagggcag tgcccgcgat    5160
tgggcggccg tgcgggaaga tcaaccgcta accgttgtcg gcatcgaccg cccgacgatt    5220
gaccgcgacg tgaaggccat cggcggcgc gacttcgtag tgatcgacgg agcgccccag    5280
gcggcggact tggctgtgtc cgcgatcaag gcagccgact tcgtgctgat tccggtgcag    5340 ccaagcccctt acgacatatg ggccaccgcc gacctggtgg agctggttaa gcagcgcatt    5400
gaggtcacgg atggaaggct acaagcggcc tttgtcgtgt cgcgggcgat caaaggcacg    5460
cgcatcggcg gtgaggttgc cgaggcgctg gccgggtacg agctgcccat tcttgagtcc    5520
cgtatcacgc agcgcgtgag ctacccaggc actgccgccg ccggcacaac cgttcttgaa    5580
tcagaacccg agggcgacgc tgcccgcgag gtccaggcgc tggccgctga aattaaatca    5640
aaactcattt gagttaatga ggtaaagaga aatgagcaa aagcacaaac acgctaagtg    5700
ccggccgtcc gagcgcacgc agcagcaagg ctgcaacgtt ggccagcctg cagacacgc    5760 cagccatgaa gcgggtcaac tttcagttgc cggcggagga tcacaccaag ctgaagatgt    5820
acgcggtacg ccaaggcaag accattaccg agctgctatc tgaatagatc gcgcagctac    5880
cagagtaaat gagcaaatga ataaatgagt agatgaattt tagcggctaa aggaggcggc    5940
atggaaaatc aagaacaacc aggcaccgac gccgtggaat gccccatgtg tggaggaacg    6000
ggcggttggc caggcgtaag cggctgggtt gtctgccggc cctgcaatgg cactggaacc    6060
cccaagcccg aggaatcggc gtgacggtcg caaaccatcc ggcccggtac aaatcggcgc    6120
ggcgctgggt gatgacctgg tggagaagtt gaaggccgcg caggccgccc agcggcaacg    6180
catcgaggca gaagcacgcc ccggtgaatc gtggcaagcg gccgctgatc gaatccgcaa    6240
agaatcccgg caaccgccgg cagccggtgc gccgtcgatt aggaagccgc ccaagggcga    6300
cgagcaacca gattttttcg ttccgatgct ctatgacgtg gcacccgcg atagtcgcag    6360 catcatggac gtggccgttt tccgtctgtc gaagcgtgac cgacgagctg gcgaggtgat    6420 ccgctacagag cttccagacg ggcacgtaga ggtttccgca gggccggccg gcatggccag    6480
tgtgtgggat tacgacctgg tactgatggc ggtttcccat ctaaccgaat ccatgaaccg    6540
```

```
ataccgggaa gggaagggag acaagcccgg ccgcgtgttc cgtccacacg ttgcggacgt    6600
actcaagttc tgccggcgag ccgatggcgg aaagcagaaa gacgacctgg tagaaacctg    6660
cattcggtta acaccacgc acgttgccat gcagcgtacg aagaaggcca agaacggccg     6720
cctggtgacg gtatccgagg gtgaagcctt gattagccgc tacaagatcg taaagagcga    6780
aaccgggcgg ccggagtaca tcgagatcga gctagctgat tggatgtacc gcgagatcac    6840
agaaggcaag aacccggacg tgctgacggt tcaccccgat tactttttga tcgatcccgg    6900
catcggccgt tttctctacc gcctggcacg ccgcgccgca ggcaaggcag aagccagatg    6960
gttgttcaag acgatctacg aacgcagtgg cagcgccgga gagttcaaga agttctgttt    7020
caccgtgcgc aagctgatcg ggtcaaatga cctgccggag tacgatttga aggaggaggc    7080
ggggcaggct ggcccgatcc tagtcatgcg ctaccgcaac ctgatcgagg gcgaagcatc    7140
cgccggttcc taatgtacgg agcagatgct agggcaaatt gccctagcag gggaaaaagg    7200
tcgaaaagga ctcttttcctg tggatagcac gtacattggg aacccaaagc cgtacattgg    7260
gaaccggaac ccgtacattg ggaacccaaa gccgtacatt gggaaccggt cacacatgta    7320
agtgactgat ataaaagaga aaaaaggcga ttttttccgcc taaaactctt taaaacttat    7380
taaaactctt aaaacccgcc tggcctgtgc ataactgtct ggccagcgca cagccgaaga    7440
gctgcaaaaa gcgcctaccc ttcggtcgct gcgctcccta cgccccgccg cttcgcgtcg    7500
gcctatcgcg gccgctggcc gctcaaaaat ggctggccta cggccaggca atctaccagg    7560
gcgcggacaa gccgcgccgt cgccactcga ccgccggcgc ccacatcaag gcaccctgcc    7620
tcgcgcgttt cggtgatgac ggtgaaaacc tctgacacat gcagctcccg gtgacggtca    7680
cagcttgtct gtaagcggat gccgggagca gacaagcccg tcagggcgcg tcagcgggtg    7740
ttggcgggtg tcggggcgca gccatgaccc agtcacgtag cgatagcgga gtgtatactg    7800
gcttaactat gcggcatcag agcagattgt actgagagtg caccatatgc ggtgtgaaat    7860
accgcacaga tgcgtaagga gaaaataccg catcaggcgc tcttccgctt cctcgctcac    7920
tgactcgctg cgctcggtcg ttcggctgcg gcgagcggta tcagctcact caaaggcggt    7980
aatacggtta tccacagaat cagggggataa cgcaggaaag aacatgtgag caaaaggcca    8040
gcaaaaggcc aggaaccgta aaaaggccgc gttgctggcg tttttccata ggctccgccc    8100
ccctgacgag catcacaaaa atcgacgctc aagtcagagg tggcgaaacc cgacaggact    8160
ataaagatac caggcgtttc cccctggaag ctccctcgtg cgctctcctg ttccgaccct    8220
gccgcttacc ggatacctgt ccgcctttct cccttcggga agcgtggcgc tttctcatag    8280
ctcacgctgt aggtatctca gttcggtgta ggtcgttcgc tccaagctgg gctgtgtgca    8340
cgaaccccc gttcagcccg accgctgcgc cttatccggt aactatcgtc ttgagtccaa    8400
cccggtaaga cacgacttat cgccactggc agcagccact ggtaacagga ttagcagagc    8460
gaggtatgta ggcggtgcta cagagttctt gaagtggtgg cctaactacg gctacactag    8520
aaggacagta tttggtatct gcgctctgct gaagccagtt accttcggaa aaagagttgg    8580
tagctcttga tccggcaaac aaaccaccgc tggtagcggt ggtttttttg tttgcaagca    8640
gcagattacg cgcagaaaaa aaggatctca agaagatcct ttgatctttt ctacgggtc     8700
tgacgctcag tggaacgaaa actcacgtta agggattttg gtcatgcatt ctaggtgatt    8760
agaaaaactc atcgagcatc aaatgaaact gcaatttatt catatcagga ttatcaatac    8820
catatttttg aaaagccgt ttctgtaatg aaggagaaaa ctcaccgagg cagttccata    8880
ggatggcaag atcctggtat cggtctgcga ttccgactcg tccaacatca atacaaccta    8940
```

```
ttaatttccc ctcgtcaaaa ataaggttat caagtgagaa atcaccatga gtgacgactg    9000
aatccggtga gaatggcaaa agtttatgca tttctttcca gacttgttca acaggccagc    9060
cattacgctc gtcatcaaaa tcactcgcat caaccaaacc gttattcatt cgtgattgcg    9120
cctgagcgag tcgaaatacg cgatcgctgt taaaaggaca attacaaaca ggaatcgaat    9180
gcaaccggcg caggaacact gccagcgcat caacaatatt ttcacctgaa tcaggatatt    9240
cttctaatac ctggaatgct gttttccctg ggatcgcagt ggtgagtaac catgcatcat    9300
caggagtacg gataaaatgc ttgatggtcg gaagaggcat aaattccgtc agccagttta    9360
gtctgaccat ctcatctgta acatcattgg caacgctacc tttgccatgt ttcagaaaca    9420
actctggcgc atcgggcttc ccatacaatc ggtagattgt cgcacctgat tgcccgacat    9480
tatcgcgagc ccatttatac ccatataaat cagcatccat gttggaattt aatcgcggcc    9540
ttgagcaaga cgtttcccgt tgaatatggc tcataacaga acttattatt ccttcctct    9600 tttctacagt atttaaagat accccaagaa gctaattata acaagacgaa ctccaattca    9660
ctgttccttg cattctaaaa ccttaaatac cagaaaacag cttttcaaa gttgttttca    9720 aagttggcgt ataacatagt atcgacgag ccgattttga aaccgcggtg atcacaggca    9780
gcaacgctct gtcatcgtta caatcaacat gctaccctcc gcgagatcat ccgtgtttca    9840
aacccggcag cttagttgcc gttcttccga atagcatcgg taacatgagc aaagtctgcc    9900
gccttacaac ggctctcccg ctgacgccgt cccggactga tgggctgcct gtatcgagtg    9960
gtgattttgt gccgagctgc cggtcgggga gctgttggct ggctggtggc aggatatatt   10020
gtggtgtaaa cataacgaat tcgtctca                                       10048

<210> SEQ ID NO 28
<211> LENGTH: 14427
<212> TYPE: DNA
<213> ORGANISM: Artificial Sequence
<220> FEATURE:
<223> OTHER INFORMATION: pLX-TuMV plasmid

<400> SEQUENCE: 28
gaacatggtg gagcacgaca cgctcgtcta ctccaagaat atcaaagata cagtctcaga     60
agaccagagg gctattgaga cttttcaaca aagggtaata tcgggaaacc tcctcggatt    120
ccattgccca gctatctgtc acttcatcga aggacagta gaaaggaag atggcttcta     180 caaatgccat cattgcgata aaggaaaggc tatcgttcaa gatgcctcta ccgacagtgg    240
tcccaaagat ggacccccac ccacgaggaa catcgtggaa aagaagacg ttccaaccac    300 gtcttcaaag caagtggatt gatgtgatat ctccactgac gtaagggatg acgcacaatc    360
ccactatcct tcgcaagacc cttcctctat ataaggaagt tcatttcatt tggagaggaa    420
aaaatataaa aactcaacat aacatacaca aaacgattaa agcaaacaca aatctttcaa    480
agcattcaag caatcaaaga ttctcaaatc tttcatcgtt atcaaagcaa tcaccaacag    540
caaaccaaat ggcagcagtt acattcgcat cagctatcac caacgccatc accagcaaac    600
cagcactcac cggaatggtg cagtttggga gtttccacc aatgccattg cgatccacca    660
ccgtcaccac agtcgccact tcagtggcgc aacctaaact gtacacagtg cagtttggaa    720
gccttgaccc agtagtcgtc aagagtggag cagggtccct tgctaaggca acacgccagc    780
agcctaacgt tgaaatagac gttagcctca gtgaagccgc agctctggag gttgcgaaac    840
ctagatcgaa tgccgtgttg aggatgcacg aggaagcaaa caaggagaga gcactctttt    900
```

```
tggactggga ggctagtttg aagagaagct cgtatggaat tgctgaggac gagaaggttg    960
taatgacaac tcatggcgtc agcaagatag tgcccagaag ttcaagggca atgaagctaa   1020
agcgcgcaag ggagaggcgt agagcgcagc aaccaattat attaaagtgg gagcccaaat   1080
tgagcgggat ctcaatcgga ggagggctct ctgcgagcgt aatcgaagca gaagaggttc   1140
gcacaaagtg gccgcttcat aagacaccgt caatgaagaa gaggacggtg cacagaatat   1200
gcaagatgaa cgaccaagga gttgacatgt tgacacgatc cctggttaag attttcaaga   1260
ctaagagtgc caacattgaa tacatcggaa agaagtcgat taaggtcgat ttcatcagaa   1320
aagaacgaac gaaattcgca agaatccaag tagcacactt actcgggaag agagcacagc   1380
gcgacttgtt aactggaatg gaagaaaacc attttattga cattctcagt aagtactcag   1440
gtaacaaaac aaccataaat cctggagtag tttgcgcagg ttggagtggc atagtcgttg   1500
gaaatggaat tctaacccag aaacgaagca gaagtccatc agaggccttt gtaattagag   1560
gtgagcacga aggcaagttg tacgatgcca ggatcaaagt cacgaggaca atgagtcaca   1620
agattgtgca ctttagtgca gcaggagcca acttctggaa aggcttcgac agatgctttc   1680
tcgcataccg tagtgacaat cgcgagcata catgctattc agggctagat gtcactgagt   1740
gcggcgaggt ggcagcactg atgtgttttgg ctatgttccc atgcggaaag ataacctgcc   1800
ctgactgtgt aacagatagt gagctatccc aaggacaagc aagcggacca tctatgaagc   1860
acaggttgac acagctacgc gatgtcatca agtcaagcta cccacgcttc aagcatgcag   1920
tgcagatact agataggtat gagcaatcac tgagcagtgc aaacgagaac taccaagatt   1980
tcgcagaaat ccagagcata agcgatggag ttgaaaaagc tgcattccca cacgtcaaca   2040
agctaaacgc aatattgatc aaaggggcca cagtaacagg agaggaattc tcgcaggcta   2100
cgaagcactt gctcgagata gcacgatacc tgaagaacag aaccgagaac attgagaagg   2160
gttcactgaa gtcctttcgc aacaagattt cccagaaagc gcacatcaac ccaacactaa   2220
tgtgtgacaa ccagctcgat agaaatggaa atttcatatg gggtgagaga ggataccatg   2280
caaaacgatt cttcagcaac tactttgaaa taatcgatcc aaagaaaggc tacacccaat   2340
acgagacaag agcggtacca aatgggtcac ggaaacttgc aatcggcaaa ctaatagtcc   2400
caacgaactt cgaagtttta agggaacaga tgaaggcga accggtagaa ccatacccag   2460
taacagtcga gtgtgtgagc aagttacagg gtgacttcgt ccatgcatgt tgttgtgtca   2520
caacagaatc aggcgaccca gtcttgtctg agatcaaaat gccaaccaaa caccatctag   2580
tgattggtaa cagcggtgat ccaaagtaca tagatctccc tgagatcgag gagaataaaa   2640
tgtacatagc gaaagaaggt tattgttaca tcaatatctt cctagccatg ttggtaaatg   2700
tcaaggagtc gcaggcaaag gagttcacga aagttgttag ggacaaacta gttggcgaac   2760
ttggcaagtg gcccactctg ttagatgtag caaccgcttg ttatttcctg aaagtatttt   2820
acccagacgt tgctaacgcc gaattgccac gcatgctagt ggaccataag acaaagataa   2880
ttcatgtcgt tgattcatat gggtcactgt caactggata tcatgtcctt aagacaaaca   2940
ctgtggaaca actcatcaaa ttcacgagat gtaatttgga gtcaagcttg aaacactacc   3000
gcgttggagg aacagaatgg gaggacactc atggatccag caacatagat aatccacagt   3060
ggtgcatcaa gaggctcata aaaggagtct acaaaccaaa gcaactgaaa gaagacatgt   3120
tgcaaacccc tttcttacca ctatatgctc tactgtcacc aggtgtcatc ctggcatttt   3180
acaatagtgg ctctctagag tacttgatga accattacat cagggtggac agcaacgtcg   3240
ccgttttgtt ggtcgttttg aaatctctag cgaagaaggt gtcaactagt cagagtgtgt   3300
```

| | |
|---|---|
| tagcccagct tcaaatcatt gaacgaagtc taccagaact catcgaagca aaggctaatg | 3360 |
| ttaatgggcc agatgacgca gccactcgcg cgtgtaacag attcatgggc atgcttctgc | 3420 |
| atatggcaga accaaactgg gagcttgcgg atggtggata cacaattctg agggatcata | 3480 |
| gcatctccat tttggaaaaa agttatctac aaatcttgga cgaagcatgg aacgagttaa | 3540 |
| gttggtcgga gcgctgtgct ataagatact actcgtcaaa gcaagcaatc tttacacaga | 3600 |
| aagatttgcc aatgaaaagc gaagccgatt taggcggcag atacagcgtg tcagtcatgt | 3660 |
| catcttacga acggagtaag caatgtatga aaagcgtgca ctctagtata ggtaatagat | 3720 |
| tacgtagtag tatgtcttgg actagtagca aggtgtcgaa tagtgtgtgt aggactatta | 3780 |
| actatttagt accagatgtg ttcaagttta tgaatgtact cgtttgtatc agcttactaa | 3840 |
| tcaagatgac tgccgaggcg aatcacatcg tcaccacgca aagaaggctc aaactagatg | 3900 |
| tcgaggagac agagcgcagg aaaatagaat gggagcttgc attccaccat gccattctga | 3960 |
| cgcagagtgc aggtcaacac ccaacgatag acgagttcag agcgtacatc gccgacaagg | 4020 |
| caccacatct aagtgagcat atcgagcctg aagaaaggc ggtggttcat caagcgaaga | 4080 |
| gacaatccga gcaagaactc gagcgtataa tagcatttgt tgcattggtg ctcatgatgt | 4140 |
| tcgatgcaga acgaagcgac tgtgtcacaa agattctcaa caagcttaag ggactagtcg | 4200 |
| ccactgtgga acctacagtc taccatcaga ctctcaatga tatagaggat gacttgagtg | 4260 |
| agaggaacct cttcgtcgat tttgagctta gcagcgatgg agatatgctc caacagcttc | 4320 |
| cagccgaaaa gacatttgcc tcatggtgga gtcatcaact aagcagagga ttcacaatcc | 4380 |
| cacactacag gacagaaggg aagttcatga cttttcaccag agcaactgcc acggaagtcg | 4440 |
| cgggtaaaat agcacacgag agtgacaaag acatattact aatgggagca gtaggatcag | 4500 |
| gtaagtcaac tggcttgcca tatcatctct ccagaaaagg gaacgtatta ctccttgagc | 4560 |
| cgactcggcc acttgcagaa aacgtacaca agcagttgtc gcaggcaccg ttccatcaga | 4620 |
| acacaactct taggatgcgc ggactaacag cattcgggtc ggcaccaatc tcagtgatga | 4680 |
| ccagtggttt tgcactcaat tactttgcaa acaacagaat gcgaattgaa gaatttgact | 4740 |
| ttgtcatatt tgatgaatgt cacgttcatg acgccaatgc aatggcgatg agatgtttgc | 4800 |
| tacatgagtg tgactattct ggcaaaatta tcaaagtttc agccacacca ccaggtcgag | 4860 |
| aagttgagtt ctccactcaa taccccgtgt cgataagcac agaagacaca ctatcgtttc | 4920 |
| aggattttgt gaacgcacag ggtagtggaa gcaattgtga tgtgatttca aaaggagaca | 4980 |
| atatcctcgt gtatgtagca agctacaatg aggtagacgc gctttcaaaa cttctaattg | 5040 |
| aaagagactt caaagtcacg aaggttgatg gaagaacgat gaaagttgga aacatcgaga | 5100 |
| tcaccacaag tggaacacct agtaagaagc acttcatagt tgcaaccaac atcatagaga | 5160 |
| acggtgttac tctagacatc gatgtggttg ctgattttgg aacgaaggta ctcccatatc | 5220 |
| ttgatacaga cagcagaatg ctgagcacaa ctaagacaag catcaattat ggggaacgta | 5280 |
| tccaaaggct aggaagagtc ggaaggcaca gccaggtca cgctctgcga ataggtcaca | 5340 |
| cagagaaggg gttgagcgaa gttccaagtt gtattgcaac agaagcagct ttaaagtgct | 5400 |
| tcacttatgg gcttccagtg atcaccaaca acgtctcgac aagtattctt ggtaatgtaa | 5460 |
| cggtaaagca ggcacgaaca atgtctgtat ttgagataac accgttctac acaagccaag | 5520 |
| tggtgagata tgatggctcc atgcatccac aggtgcacgc actcttaaag agattcaaac | 5580 |
| tcagagactc tgagattgtt ttgaataaat tagccatacc tcaccgagga gtgaacgctt | 5640 |

```
ggctcacagc tagtgagtat gcacgacttg gcgcgaatgt tgaagatagg cgtgacgttc    5700
gaattccttt tatgtgtcgc gacatcccag aaaaacttca tctagacatg tgggatgtga    5760
ttgttaaatt caaaggtgat gcaggttttg gtcggctttc aagcgccagt gcgagcaagg    5820
tagcttatac tctacagacg gacgtcaact ccatacagcg aacagtcact atcatagata    5880
cactaatcgc tgaggagaga aggaagcagg aatacttcaa gacggtaacc tccaactgtg    5940
tctcttcttc gaacttctca ctgcagagca taacaaatgc gataaaatct cgtatgatga    6000
aagatcacac gtgcgagaac atatcagtgc ttgaaggagc gaagtcacag ttactcgagt    6060
ttagaaacct gaatgctgat cactcatttg ctacaaaaac cgatggaata tctcggcatt    6120
tcatgagtga gtatggagct cttgaggcag ttcaccatca aaacaccagc gacatgagca    6180
aattcctcaa gcttaagggc aaatggaata aaacgctaat cacgcgagat gtgctggtac    6240
tttgtggagt tcttggaggt ggattgtgga tggttattca gcacctgcgg tcaaagatgt    6300
ccgaacccgt aacccatgaa gcgaaggta agaggcaaag gcagaaacta aaatttcgca    6360
atgcccgaga caacaaaatg ggtagagaag tgtacggaga tgatgatacc atagagcatt    6420
tcttcggtga tgcctacaca aagaaaggga agagcaaggg taggcacgt ggtatcggac    6480 acaaaaacag gaagttcatc aacatgtatg ggtttgatcc tgaagatttc tctgcagttc    6540
gtttcgtgga tccactcaca ggagcgacgt tggacgacaa cccgctcaca gacatcaccc    6600
ttgtgcaaga gcacttcggc aacataagaa tggacttact cggggaggat gagctggact    6660
caaatgaaat acgtgtgaat aagactattc aagcctacta catgaacaat aaaacaggca    6720
aggctttgaa ggtggatctg acaccacaca tacctctcaa ggtgtgtgat cttcacgcaa    6780
ccattgctgg attcccagag cgagaaaacg agctgaggca gactggaaag gctcagccca    6840
tcaacataga cgaagtgcca agagctaaca acgaactcgt cccagtggac cacgagagta    6900
actccatgtt cagagggttg cgtgactaca acccaatatc aaacaacatt tgtcatctca    6960
caaatgtttc agatggagca tcaaactcgt tatatggagt cggtttcgga ccactctat    7020 taacgaaccg acacctcttt gagcggaata acggtgaact cgtaataaaa tcacgacatg    7080
gtgagttcgt gattaaaaac acaactcagc tacacttgct accgattcca gacagagatc    7140
ttctgctaat ccggttacca aaggacgtcc caccctttcc acagaaattg ggtttcaggc    7200
aacctgagaa aggtgaacga atttgcatgg tggggtccaa tttccaaacc aagagcataa    7260
cgagtatagt ctctgagact agtacaataa tgccagtgga gaacagtcag ttttggaaac    7320
actggattag cactaaagac ggccaatgcg gaagtccaat ggtgagcacg aaagacggga    7380
aaatactcgg attacacagc ctagcgaact tccagaactc catcaattac tttgctgctt    7440
tcccagatga ttttgccgag aagtatcttc ataccattga agcacacgag tgggtcaagc    7500
actggaagta taacactagc gccatcagtt ggggctcttt gaatatacaa gcatcgcaac    7560
cgtccggctt gttcaaagta agcaagctaa tctcagacct cgacagcacg gcagtctacg    7620
cacaaaccca gcagaatcgg tggatgttcg agcagctcaa cgggaaccta aaagcgatag    7680
cacactgccc tagccagctt gtgacaaagc acacagttaa aggaaaatgt cagatgtttg    7740
acttgtatct caagttgcat gatgaagcac gagagtattt ccaaccgatg ctgggccagt    7800
atcaaaagag caaactcaat cgagaagcat atgcaaagga tcttctgaaa tatgcaacgc    7860
caatcgaagc aggaaacatc gactgtgatc tgtttgaaaa cacagttgaa atagtcgtat    7920
cagatctgcg aggttatggt ttcgaaacat gcaattatgt cactgatgag aatgacatat    7980
tcgaagctct taacatgaaa tccgcagttg gagcgttgta taaggaaag aagaaggatt    8040
```

```
acttcgctga gttcacaccc gagatgaaag aagaaatact gaaacaaagt tgtgaacggc    8100
tcttcctagg aaagatggga gtgtggaacg gctcgctgaa ggcagagttg cgaccactag    8160
aaaaagtgga agcaaacaaa acacggacgt ttactgccgc accactagac acactgttgg    8220
gtggaaaagt ttgcgtggat gatttcaaca accagttcta tgatcacaac cttagagctc    8280
cttggagcgt tggcatgaca aagttttatt gtggttggga tcgcttgttg gagtcgttgc    8340
cagatggttg ggtgtattgc gatgctgatg gctcacagtt cgacagctcg ctatcgccat    8400
acttgatcaa cgcagtactc aacatccgct taggattcat ggaagagtgg gacataggg     8460 aggtaatgct gagaaatttg tacaccgaaa tcgtgtatac ccctatttct acaccagatg    8520
gtacactcgt caagaagttc aaaggaaaca atagcggaca gccatcgact gttgtggaca    8580
acacgctcat ggtcatattg gcagtcaact attcactcaa gaaaagcgga attccaagtg    8640
agttgcgcga cagcatcatc agattcttcg tcaacggaga tgatttactg ctaagcgtac    8700
acccagagta tgagtatatt cttgacacta tggcagacaa cttcgtgaa ctgggcctga     8760 agtatacttt cgactcaaga accagggaaa aaggagacct ctggtttatg tcgcaccagg    8820
ggcacaaaag agagggaatc tggattccca agctcgagcc agagcgaata gtatcgattc    8880
tagaatggga tcggtcgaaa gagccatgcc atcgactaga ggcaatctgc gcagcgatga    8940
ttgagtcgtg gggatacgac aagttaactc acgagatacg caagttctac gcgtggatga    9000
ttgaacaagc tccatttagc tccctagcac aagaagggaa agctccttac atagcggaaa    9060
cagcgctgag gaagctctac cttgataagg aaccagctca agaggatctc acccattatt    9120
tgcaagcaat ctttgaggat tatgaagatg gtgctgaggc ttgtgtttat caccaggccg    9180
gcatgagtaa aggagaagaa cttttcactg gagttgtccc aattcttgtt gaattagatg    9240
gtgatgttaa tgggcacaaa ttttctgtca gtggagaggg tgaaggtgat gcaacatacg    9300
gaaaacttac ccttaaattt atttgcacta ctggaaaact acctgttcca tggccaacac    9360
ttgtcactac tttctcttat ggtgttcaat gcttttcaag tacccagat catatgaagc      9420 ggcacgactt cttcaagagc gccatgcctg agggatacgt gcaggagagg accatctctt    9480
tcaaggacga cgggaactac aagacacgtg ctgaagtcaa gtttgaggga gacaccctcg    9540
tcaacaggat cgagcttaag ggaatcgatt tcaaggagga cggaaacatc ctcggccaca    9600
agttggaata caactacaac tcccacaacg tatacatcac ggcagacaaa caaagaatg      9660 gaatcaaagc taacttcaaa attagacaca cattgaaga tggaagcgtt caactagcag     9720
accattatca acaaaatact ccaattggcg atggccctgt ccttttacca gacaaccatt    9780
acctgtccac acaatctgcc ctttcgaaag atcccaacga aaagagagac cacatggtcc    9840
ttcttgagtt tgtaacagct gctgggatta cacatggcat ggatgaacta tacaaagcat    9900
gcgtatacca tcaagccggc gaaacgcttg atgcagagtt gacagacgag caaaagcagg    9960
cagagaagga gaagaaggag agagagaagg cagaaaagga acgagagagg caaaagcagt    10020
tggcactcaa gaaaggcaag gatgttgcac aagaagaggg aaaacgcgac aaggaagtaa    10080
acgctggaac ctctggaact ttcagtgtac ccagactcaa gagtctgaca agcaagatgc    10140
gcgtgccaag atacgagaaa agagtggctc taaacctcga tcatctaatc ctatacacgc    10200
cggagcagac ggatctatcc aacacacgtt caacgcgaaa gcagtttgac acatggtttg    10260
aaggtgtaat ggctgattac gaactgacgg aggacaaaat gcgaatcatt ctcaatggtt    10320
taatggtctg gtgcattgag aacggaacct ccccgaacat aaacggaatg tgggtgatga    10380
```

```
tggacggcga cgatcaggtg gaattcccga tcaaaccgct cattgaccac gccaaaccca    10440
catttaggca gataatggcc catttcagtg acgtagctga agcgtacatt gaaaagcgta    10500
accaagaccg accatacatg ccacgatatg gtcttcagcg caatttaacc gacatgagct    10560
tagctcgata cgcatttgat ttctatgaaa tgacttctag gactccaata cgtgcgagag    10620
aggcacacat ccagatgaaa gcagcagcac tgcgtggcgc aaataataat ttgttcggct    10680
tggatggaaa cgttggtaca acggtagaga acacggagag gcatacgacc gaggacgtta    10740
atcggaacat gcataactta ctgggcgttc aggggttgtg aagttgtatg ctggtagact    10800
ataagtattt aagtttactc gttagtattc tcgcttatgg gaaatatgta agtttgttaa    10860
agcagccagt gtgactttgt catgtgtgtt gttgttactt tctgtatttt cgccgaacat    10920
tttattggtg ttagcgcatg tagtgaggat cgtcctcgat tgccttaaca tttgatagga    10980
tgcaagggac aaaaaaaaa aaaaaaaaa aaaaaaaaa aaaaaaaaa aaaaaaaaa          11040
aaaaaatcgg ttcccctag agcagatcgt tcaaacattt ggcaataaag tttcttaaga    11100
ttgaatcctg ttgccggtct tgcgatgatt atcatctaat ttctgttgaa ttacgttaag    11160
catgtaataa ttaacatgta atgcatgacg ttatttatga gatgggtttt tatgattaga    11220
gtcccgcaat tatacattta atacgcgata gaaaacaaaa tatagcgcgc aaactaggat    11280
aaattatcgc gcgcggtgtc atctatgtta ctagatctct agcctgcagg aattgttgat    11340
tttgtgatga ctgatggcag gatatatgcg gttgtaattc attttatttg tctaaatttc    11400
tgtatttgtt tgtttgttcg gttgtaaatt tttttggaag aacaagaaaa gaaaaaacac    11460
ccgttagggt gttttagtt agtgtggcgc gccgacttgc gacatgcggt cctttgcaat    11520
caactattag aaaaattcat ccagcatcag atgaaattgc agtttgttca tatccggatt    11580
atcaatgcca tatttctgaa acagacgttt ttgcaggctc gggctaaatt cgcccaggca    11640
gttccacaga atggccagat cctgataacg atccgcaatg cccacacggc ccacatcaat    11700
gcagccaatc agtttgcctt catcgaaaat caggttatcc aggctaaaat cgccgtgggt    11760
caccacgcta tccgggctaa acggcagcag tttatgcatt tctttccaca cctgttccac    11820
cggccagccg ttacgttcat catcaaaatc gctcgcatcc accaggccgt tgttcatacg    11880
gctctgcgcc tgggccagac gaaacacacg atcgctgtta aacgggcagt tgcacaccgg    11940
aatgctatgc agacgacgca gaaacacggc cagcgcatcc acaatgtttt cgccgctatc    12000
cggatattct tccagcacct gaaacgcggt tttgcccgga atcgcggtgg tcagcagcca    12060
cgcatcatcc ggggtgcgaa taaaatgttt aatggtcggc agcggcataa attcggtcag    12120
ccagttcaga cgcaccattt catcggtcac atcgttcgcc acgctgcctt tgccatgttt    12180
cagaaacagt tccggcgcat ccggtttgcc atacagacga taaatggtcg cgccgctctg    12240
acccacgtta tcacgcgccc atttatagcc atacagatcc gcatccatgt tgctgttcag    12300
acgcggacgg ctacagctcg tttcacgctg aatatggctc ataacacccc ttgtattact    12360
gtttatgtaa gcagacagtt ttattgttca tgatgatata ttttatctt gtgcaatgta     12420
acatcagaga ttttgagaca caagatcgga ttggcggtta tgcggttcta ccggcgcggc    12480
agcgttaccc gtgtcggcgg ctccaacggc tcgccatcgt ccagaaaaca cggctcatcg    12540
ggcatcggca ggcgctgctg cccgcgccgt tcccattcct ccgtttcggt caaggctggc    12600
aggtctggtt ccatgcccgg aatgccgggc tggctgggcg ctcctcgcc ggggccggtc     12660
ggtagttgct gctcgcccgg atacagggtc gggatgcggc gcaggtcgcc atgccccaac    12720
agcgattcgt cctggtcgtc gtgatcaacc accacggcgg cactgaacac cgacaggcgc    12780
```

```
aactggtcgc ggggctggcc ccacgccacg cggtcattga ccacgtaggc cgacacggtg   12840
ccggggccgt tgagcttcac gacggagatc cagcgctcgg ccaccaagtc cttgactgcg   12900
tattggaccg tccgcaaaga acgtccgatg agcttggaaa gtgtcttctg gctgaccacc   12960
acggcgttct ggtggcccat ctgcgccacg aggtgatgca gcagcattgc cgccgtgggt   13020
ttcctcgcaa taagcccggc ccacgcctca tgcgctttgc gttccgtttg cacccagtga   13080
ccgggcttgt tcttggcttg aatgccgatt tctctggact gcgtggccat gcttatctcc   13140
atgcggtagg ggtgccgcac ggttgcggca ccatgcgcaa tcagctgcaa cttttcggca   13200
gcgcgacaac aattatgcgt tgcgtaaaag tggcagtcaa ttacagattt tctttaacct   13260
acgcaatgag ctattgcggg gggtgccgca atgagctgtt gcgtaccccc cttttttaag   13320
ttgttgattt ttaagtcttt cgcatttcgc cctatatcta gttctttggt gcccaaagaa   13380
gggcacccct gcggggttcc cccacgcctt cggcgcggct ccccctccgg caaaaagtgg   13440
cccctccggg gcttgttgat cgactgcgcg gccttcggcc ttgcccaagg tggcgctgcc   13500
cccttggaac ccccgcactc gccgccgtga ggctcggggg gcaggcgggc gggcttcgcc   13560
cttcgactgc ccccactcgc ataggcttgg gtcgttccag gcgcgtcaag gccaagccgc   13620
tgcgcggtcg ctgcgcgagc cttgacccgc cttccacttg gtgtccaacc ggcaagcgaa   13680
gcgcgcaggc cgcaggccgg aggcttttcc ccagagaaaa ttaaaaaaat tgatgggca   13740 aggccgcagg ccgcgcagtt ggagccggtg ggtatgtggt cgaaggctgg gtagccggtg   13800
ggcaatccct gtggtcaagc tcgtgggcag gcgcagcctg tccatcagct tgtccagcag   13860
ggttgtccac gggccgagcg aagcgagcca gccggtggcc gctcgcggcc atcgtccaca   13920
tatccacggg ctggcaaggg agcgcagcga ccgcgcaggg cgaagcccgg agagcaagcc   13980 cgtaggggc catcatcagt tcggtggtct tccgacgaac aataaggccg caaatcgcgg   14040 cctttttat tgataacaaa accggctcag ttctgcgtag aaaccaacat gcaagctcca   14100
ccgggtgcaa agcggcagcg gcggcaggat atattcaatt gtaaatggct tcatgtccgg   14160
gaaatctact ggtggcagga tatattgtgg tgtaaacaat ggagaaaaag attaattaag   14220
tactagtcca gtacgcacga ttcaaggctt gcttcacaaa ccaaggcaag taatagagat   14280
tggagtctct aaaaaggtag ttcccactga atcaaaggcc atggagtcaa agattcaaat   14340
agaggaccta acagaactcg ccgtaaagac tggcgaacag ttcatacaga gtctcttacg   14400
actcaatgac aagaagaaaa tcttcgt                                      14427
```

<210> SEQ ID NO 29
<211> LENGTH: 25
<212> TYPE: DNA
<213> ORGANISM: Artificial Sequence
<220> FEATURE:
<223> OTHER INFORMATION: 1989_F primer

<400> SEQUENCE: 29

```
gattgatgtg atttctccac tgacg                                        25
```

<210> SEQ ID NO 30
<211> LENGTH: 21
<212> TYPE: DNA
<213> ORGANISM: Artificial Sequence
<220> FEATURE:
<223> OTHER INFORMATION: 2050_F primer

<400> SEQUENCE: 30

```
gccattgtcc gaaatctcac g                                              21
```

<210> SEQ ID NO 31
<211> LENGTH: 22
<212> TYPE: DNA
<213> ORGANISM: Artificial Sequence
<220> FEATURE:
<223> OTHER INFORMATION: 2051_R primer

<400> SEQUENCE: 31

```
ctggaaatgc gattctctta gc                                             22
```

<210> SEQ ID NO 32
<211> LENGTH: 16
<212> TYPE: DNA
<213> ORGANISM: Artificial Sequence
<220> FEATURE:
<223> OTHER INFORMATION: X122_R primer

<400> SEQUENCE: 32

```
cgtcaatcgt tagagc                                                    16
```

<210> SEQ ID NO 33
<211> LENGTH: 15
<212> TYPE: DNA
<213> ORGANISM: Artificial Sequence
<220> FEATURE:
<223> OTHER INFORMATION: X123_R primer

<400> SEQUENCE: 33

```
cgaccttgca cttca                                                     15
```

<210> SEQ ID NO 34
<211> LENGTH: 42
<212> TYPE: DNA
<213> ORGANISM: Artificial Sequence
<220> FEATURE:
<223> OTHER INFORMATION: X329_R primer

<400> SEQUENCE: 34

```
cgcatccttg tccggtctcc agcgagagac gtcactcatt ag                       42
```

<210> SEQ ID NO 35
<211> LENGTH: 626
<212> TYPE: DNA
<213> ORGANISM: Artificial Sequence
<220> FEATURE:
<223> OTHER INFORMATION: PEtOH synthetic promoter

<400> SEQUENCE: 35

```
aaatcaccag tctctctcta caaatctatc tctctctata ataatgtgtg agtagttccc    60
agataaggga attagggttc ttatagggtt tcgctcatgt gttgagcata taagaaaccc   120
ttagtatgta tttgtatttg taaaatactt ctatcaataa aatttctaat tcctaaaacc   180
aaaatccagt gacccatgcg gagccgcatt ggaggccatg cggagccgca cgcgttaaca   240
agagcggctc cgcttgacct ctcgggatag ttccgaccta ggattggatg catgcggaac   300
cgcacgaggg cggggcggaa attgacacac cactcctctc cacgcaccgt tcaagaggta   360
cgcgtataga gccgtataga gcagagacgg agcactttct ggtactgtcc gcacgggatg   420
tccgcacgga gagccacaaa cgagcggggc cccgtacgtg ctctcctacc ccaggatcgc   480
atccccgcat agctgaacat ctatataaga aggcattcat tcccatttga aggatcatca   540
gatactgaac caatattatt tttacaacaa ttaccaacaa caacaaacaa caacaacat    600
```
tacaattact atttacaatt acaatg                                          626

<210> SEQ ID NO 36
<211> LENGTH: 50
<212> TYPE: DNA
<213> ORGANISM: Artificial Sequence
<220> FEATURE:
<223> OTHER INFORMATION: X192_F primer

<400> SEQUENCE: 36
cgacttgcga catgcggtcc tttgcaatca actattagaa aaattcatcc                 50

<210> SEQ ID NO 37
<211> LENGTH: 50
<212> TYPE: DNA
<213> ORGANISM: Artificial Sequence
<220> FEATURE:
<223> OTHER INFORMATION: X193_R primer

<400> SEQUENCE: 37
aaccgcataa ccgccaatcc gatcttgtgt ctcaaaatct ctgatgttac                 50

<210> SEQ ID NO 38
<211> LENGTH: 47
<212> TYPE: DNA
<213> ORGANISM: Artificial Sequence
<220> FEATURE:
<223> OTHER INFORMATION: X194_F primer

<400> SEQUENCE: 38
cgacttgcga catgcggtcc tttgttattt gccgactacc ttggtga                   47

<210> SEQ ID NO 39
<211> LENGTH: 44
<212> TYPE: DNA
<213> ORGANISM: Artificial Sequence
<220> FEATURE:
<223> OTHER INFORMATION: X195_R primer

<400> SEQUENCE: 39
aaccgcataa ccgccaatcc gatcgaacct tgaccgaacg cagc                      44

<210> SEQ ID NO 40
<211> LENGTH: 45
<212> TYPE: DNA
<213> ORGANISM: Artificial Sequence
<220> FEATURE:
<223> OTHER INFORMATION: X196_F primer

<400> SEQUENCE: 40
cgacttgcga catgcggtcc tttgcaattt acccaacaac tccgc                     45

<210> SEQ ID NO 41
<211> LENGTH: 46
<212> TYPE: DNA
<213> ORGANISM: Artificial Sequence
<220> FEATURE:
<223> OTHER INFORMATION: X197_R primer

<400> SEQUENCE: 41
aaccgcataa ccgccaatcc gatcttgaca taagcctgtt cggttc                    46

<210> SEQ ID NO 42
<211> LENGTH: 39
<212> TYPE: DNA

```
<213> ORGANISM: Artificial Sequence
<220> FEATURE:
<223> OTHER INFORMATION: X198_F primer

<400> SEQUENCE: 42
gatcggattg cggttatgc ggttctaccg gcgcggcag                          39

<210> SEQ ID NO 43
<211> LENGTH: 44
<212> TYPE: DNA
<213> ORGANISM: Artificial Sequence
<220> FEATURE:
<223> OTHER INFORMATION: X199_R primer

<400> SEQUENCE: 43
ggaagaccac cgaactgatg atggccccct acgggcttgc tctc                   44

<210> SEQ ID NO 44
<211> LENGTH: 44
<212> TYPE: DNA
<213> ORGANISM: Artificial Sequence
<220> FEATURE:
<223> OTHER INFORMATION: X200_F primer

<400> SEQUENCE: 44
gatcggattg cggttatgc ggttgcgatg caggtggctg ctga                    44

<210> SEQ ID NO 45
<211> LENGTH: 50
<212> TYPE: DNA
<213> ORGANISM: Artificial Sequence
<220> FEATURE:
<223> OTHER INFORMATION: X201_R primer

<400> SEQUENCE: 45
ggaagaccac cgaactgatg atgggtagaa aagatcaaag gatcttcttg             50

<210> SEQ ID NO 46
<211> LENGTH: 19
<212> TYPE: DNA
<213> ORGANISM: Artificial Sequence
<220> FEATURE:
<223> OTHER INFORMATION: X210_R primer

<400> SEQUENCE: 46
tgagacggtt tcgaccagg                                               19

<210> SEQ ID NO 47
<211> LENGTH: 20
<212> TYPE: DNA
<213> ORGANISM: Artificial Sequence
<220> FEATURE:
<223> OTHER INFORMATION: X211_F primer

<400> SEQUENCE: 47
gtcaggagac gggacaagga                                              20

<210> SEQ ID NO 48
<211> LENGTH: 23
<212> TYPE: DNA
<213> ORGANISM: Artificial Sequence
<220> FEATURE:
<223> OTHER INFORMATION: X212_F primer

<400> SEQUENCE: 48
atggtttcta aaggtgaaga gac                                          23
```

<210> SEQ ID NO 49
<211> LENGTH: 21
<212> TYPE: DNA
<213> ORGANISM: Artificial Sequence
<220> FEATURE:
<223> OTHER INFORMATION: X213_R primer

<400> SEQUENCE: 49
ttatgctcct ttatcgtcgt c                                         21

<210> SEQ ID NO 50
<211> LENGTH: 21
<212> TYPE: DNA
<213> ORGANISM: Artificial Sequence
<220> FEATURE:
<223> OTHER INFORMATION: X216_F primer

<400> SEQUENCE: 50
atggtttcaa agggagaaga g                                         21

<210> SEQ ID NO 51
<211> LENGTH: 43
<212> TYPE: DNA
<213> ORGANISM: Artificial Sequence
<220> FEATURE:
<223> OTHER INFORMATION: X218_F primer

<400> SEQUENCE: 51
gtagcctggt cgaaaccgtc tcaccagtac gcacgattca agg                 43

<210> SEQ ID NO 52
<211> LENGTH: 49
<212> TYPE: DNA
<213> ORGANISM: Artificial Sequence
<220> FEATURE:
<223> OTHER INFORMATION: X219_R primer

<400> SEQUENCE: 52
cgcatccttg tcccgtctcc tgacgagatc gagtaacata gatgacacc           49

<210> SEQ ID NO 53
<211> LENGTH: 43
<212> TYPE: DNA
<213> ORGANISM: Artificial Sequence
<220> FEATURE:
<223> OTHER INFORMATION: X220_F primer

<400> SEQUENCE: 53
gtagcctggt cgaaaccgtc tcataacgaa cgctcatgct aag                 43

<210> SEQ ID NO 54
<211> LENGTH: 49
<212> TYPE: DNA
<213> ORGANISM: Artificial Sequence
<220> FEATURE:
<223> OTHER INFORMATION: X221_R primer

<400> SEQUENCE: 54
ttgtagtctc ttcaccttta gaaaccattt tcttttttgtt tgttgtgag          49

<210> SEQ ID NO 55
<211> LENGTH: 45
<212> TYPE: DNA
<213> ORGANISM: Artificial Sequence
<220> FEATURE:

<223> OTHER INFORMATION: X222_F primer

<400> SEQUENCE: 55
ggatgacgac gataaaggag cataatgcac tggaggtcaa ggaag        45

<210> SEQ ID NO 56
<211> LENGTH: 47
<212> TYPE: DNA
<213> ORGANISM: Artificial Sequence
<220> FEATURE:
<223> OTHER INFORMATION: X223_R primer

<400> SEQUENCE: 56
cgcatccttg tcccgtctcc tgacatagct cgatagaatc atttgct        47

<210> SEQ ID NO 57
<211> LENGTH: 39
<212> TYPE: DNA
<213> ORGANISM: Artificial Sequence
<220> FEATURE:
<223> OTHER INFORMATION: X238_R primer

<400> SEQUENCE: 57
gtcatattta tttttcctct ccaaatgaaa tgaacttcc        39

<210> SEQ ID NO 58
<211> LENGTH: 50
<212> TYPE: DNA
<213> ORGANISM: Artificial Sequence
<220> FEATURE:
<223> OTHER INFORMATION: X239_F primer

<400> SEQUENCE: 58
gaaatacacc ttataaagt acaaaaaaaa aaaaaaaaa aaaaaaatgc        50

<210> SEQ ID NO 59
<211> LENGTH: 49
<212> TYPE: DNA
<213> ORGANISM: Artificial Sequence
<220> FEATURE:
<223> OTHER INFORMATION: X240_F primer

<400> SEQUENCE: 59
gttcatttca tttggagagg aaaaataaat atgacataag aatacataa        49

<210> SEQ ID NO 60
<211> LENGTH: 25
<212> TYPE: DNA
<213> ORGANISM: Artificial Sequence
<220> FEATURE:
<223> OTHER INFORMATION: X241_R primer

<400> SEQUENCE: 60
ctcttccttt cgaccttgca cttca        25

<210> SEQ ID NO 61
<211> LENGTH: 26
<212> TYPE: DNA
<213> ORGANISM: Artificial Sequence
<220> FEATURE:
<223> OTHER INFORMATION: X242_F primer

<400> SEQUENCE: 61
ttgaagtgca aggtcgaaag gaagag        26

```
<210> SEQ ID NO 62
<211> LENGTH: 32
<212> TYPE: DNA
<213> ORGANISM: Artificial Sequence
<220> FEATURE:
<223> OTHER INFORMATION: X243_R primer

<400> SEQUENCE: 62
aaagaagtat caaacctact accatcacaa tc                                32

<210> SEQ ID NO 63
<211> LENGTH: 31
<212> TYPE: DNA
<213> ORGANISM: Artificial Sequence
<220> FEATURE:
<223> OTHER INFORMATION: X244_F primer

<400> SEQUENCE: 63
gattgtgatg gtagtaggtt tgatacttct t                                 31

<210> SEQ ID NO 64
<211> LENGTH: 57
<212> TYPE: DNA
<213> ORGANISM: Artificial Sequence
<220> FEATURE:
<223> OTHER INFORMATION: X245_R primer

<400> SEQUENCE: 64
tttttttttt tttgtacttt tataaggtgt atttctacac caaacaaaag gatatgg     57

<210> SEQ ID NO 65
<211> LENGTH: 24
<212> TYPE: DNA
<213> ORGANISM: Artificial Sequence
<220> FEATURE:
<223> OTHER INFORMATION: X253_R primer

<400> SEQUENCE: 65
ctttcgtaac agcttgcttt ctca                                         24

<210> SEQ ID NO 66
<211> LENGTH: 25
<212> TYPE: DNA
<213> ORGANISM: Artificial Sequence
<220> FEATURE:
<223> OTHER INFORMATION: X254_F primer

<400> SEQUENCE: 66
ctttggttta gacaagcaat gtgtg                                        25

<210> SEQ ID NO 67
<211> LENGTH: 24
<212> TYPE: DNA
<213> ORGANISM: Artificial Sequence
<220> FEATURE:
<223> OTHER INFORMATION: X255_R primer

<400> SEQUENCE: 67
ccactattat ttccacgatg cttc                                         24

<210> SEQ ID NO 68
<211> LENGTH: 25
<212> TYPE: DNA
<213> ORGANISM: Artificial Sequence
<220> FEATURE:
<223> OTHER INFORMATION: X256_F primer
```

```
<400> SEQUENCE: 68
cagaggtgaa gtctattctt ggcat                                          25

<210> SEQ ID NO 69
<211> LENGTH: 23
<212> TYPE: DNA
<213> ORGANISM: Artificial Sequence
<220> FEATURE:
<223> OTHER INFORMATION: X257_F primer

<400> SEQUENCE: 69
agtttggtgg agttttggat agc                                            23

<210> SEQ ID NO 70
<211> LENGTH: 25
<212> TYPE: DNA
<213> ORGANISM: Artificial Sequence
<220> FEATURE:
<223> OTHER INFORMATION: X258_F primer

<400> SEQUENCE: 70
atacacacgc ttgagataat ggatg                                          25

<210> SEQ ID NO 71
<211> LENGTH: 24
<212> TYPE: DNA
<213> ORGANISM: Artificial Sequence
<220> FEATURE:
<223> OTHER INFORMATION: X259_R primer

<400> SEQUENCE: 71
atcgccactg atacaattca aaag                                           24

<210> SEQ ID NO 72
<211> LENGTH: 27
<212> TYPE: DNA
<213> ORGANISM: Artificial Sequence
<220> FEATURE:
<223> OTHER INFORMATION: X260_R primer

<400> SEQUENCE: 72
aggaccaaaa ttctcataag tctctct                                        27

<210> SEQ ID NO 73
<211> LENGTH: 21
<212> TYPE: DNA
<213> ORGANISM: Artificial Sequence
<220> FEATURE:
<223> OTHER INFORMATION: X295_F primer

<400> SEQUENCE: 73
caatttaccc aacaactccg c                                              21

<210> SEQ ID NO 74
<211> LENGTH: 23
<212> TYPE: DNA
<213> ORGANISM: Artificial Sequence
<220> FEATURE:
<223> OTHER INFORMATION: X296_R primer

<400> SEQUENCE: 74
tgagttcggc gatgtagcca cct                                            23

<210> SEQ ID NO 75
<211> LENGTH: 22
```

```
<212> TYPE: DNA
<213> ORGANISM: Artificial Sequence
<220> FEATURE:
<223> OTHER INFORMATION: X297_F primer

<400> SEQUENCE: 75
ggtggctaca tcgccgaact ca                                              22

<210> SEQ ID NO 76
<211> LENGTH: 24
<212> TYPE: DNA
<213> ORGANISM: Artificial Sequence
<220> FEATURE:
<223> OTHER INFORMATION: X298_R primer

<400> SEQUENCE: 76
cgttcgcgtc ggctagaaca ggag                                            24

<210> SEQ ID NO 77
<211> LENGTH: 22
<212> TYPE: DNA
<213> ORGANISM: Artificial Sequence
<220> FEATURE:
<223> OTHER INFORMATION: X299_F primer

<400> SEQUENCE: 77
tgttctagcc gacgcgaacg ct                                              22

<210> SEQ ID NO 78
<211> LENGTH: 26
<212> TYPE: DNA
<213> ORGANISM: Artificial Sequence
<220> FEATURE:
<223> OTHER INFORMATION: X300_R primer

<400> SEQUENCE: 78
gtagaaaaga tcaaaggatc ttcttg                                          26

<210> SEQ ID NO 79
<211> LENGTH: 45
<212> TYPE: DNA
<213> ORGANISM: Artificial Sequence
<220> FEATURE:
<223> OTHER INFORMATION: X301_F primer

<400> SEQUENCE: 79
gtagcctggt cgaaaccgtc tcattttttca aatcagtgcg caaga                    45

<210> SEQ ID NO 80
<211> LENGTH: 44
<212> TYPE: DNA
<213> ORGANISM: Artificial Sequence
<220> FEATURE:
<223> OTHER INFORMATION: X302_R primer

<400> SEQUENCE: 80
cagctcttct cccttttgaaa ccattgttgt tacccgattt ggtg                     44

<210> SEQ ID NO 81
<211> LENGTH: 20
<212> TYPE: DNA
<213> ORGANISM: Artificial Sequence
<220> FEATURE:
<223> OTHER INFORMATION: X303_R primer

<400> SEQUENCE: 81
```
tggccctgga ttttcctcaa                                                    20

<210> SEQ ID NO 82
<211> LENGTH: 39
<212> TYPE: DNA
<213> ORGANISM: Artificial Sequence
<220> FEATURE:
<223> OTHER INFORMATION: X304_F primer

<400> SEQUENCE: 82
ttgaggaaaa tccagggcca atggcagata cacgccgac                               39

<210> SEQ ID NO 83
<211> LENGTH: 24
<212> TYPE: DNA
<213> ORGANISM: Artificial Sequence
<220> FEATURE:
<223> OTHER INFORMATION: X305_R primer

<400> SEQUENCE: 83
tccagcacag attgcgtgag agaa                                               24

<210> SEQ ID NO 84
<211> LENGTH: 24
<212> TYPE: DNA
<213> ORGANISM: Artificial Sequence
<220> FEATURE:
<223> OTHER INFORMATION: X306_F primer

<400> SEQUENCE: 84
ctctcacgca atctgtgctg gatg                                               24

<210> SEQ ID NO 85
<211> LENGTH: 27
<212> TYPE: DNA
<213> ORGANISM: Artificial Sequence
<220> FEATURE:
<223> OTHER INFORMATION: X307_R primer

<400> SEQUENCE: 85
agctacaaga agctgtcaac tttccca                                            27

<210> SEQ ID NO 86
<211> LENGTH: 43
<212> TYPE: DNA
<213> ORGANISM: Artificial Sequence
<220> FEATURE:
<223> OTHER INFORMATION: X308_F primer

<400> SEQUENCE: 86
ggaaagttga cagcttcttg tagctcttgg actcccatgt tgg                          43

<210> SEQ ID NO 87
<211> LENGTH: 48
<212> TYPE: DNA
<213> ORGANISM: Artificial Sequence
<220> FEATURE:
<223> OTHER INFORMATION: X309_R primer

<400> SEQUENCE: 87
gcatccttgt cccgtctcct gacgataatt tatttgaaaa ttcataag                     48

<210> SEQ ID NO 88
<211> LENGTH: 50
<212> TYPE: DNA
<213> ORGANISM: Artificial Sequence

```
<220> FEATURE:
<223> OTHER INFORMATION: X310_F primer

<400> SEQUENCE: 88
caacattaca attactattt acaattacaa tggtgagcaa gggagaggag            50

<210> SEQ ID NO 89
<211> LENGTH: 19
<212> TYPE: DNA
<213> ORGANISM: Artificial Sequence
<220> FEATURE:
<223> OTHER INFORMATION: X321_F primer

<400> SEQUENCE: 89
gagacgggac aaggatgcg                                              19

<210> SEQ ID NO 90
<211> LENGTH: 46
<212> TYPE: DNA
<213> ORGANISM: Artificial Sequence
<220> FEATURE:
<223> OTHER INFORMATION: X322_F primer

<400> SEQUENCE: 90
cctggtcgaa accgtctcag tcaggagaga gaccaaaagc aaaaac                46

<210> SEQ ID NO 91
<211> LENGTH: 42
<212> TYPE: DNA
<213> ORGANISM: Artificial Sequence
<220> FEATURE:
<223> OTHER INFORMATION: X323_R primer

<400> SEQUENCE: 91
cgcatccttg tcccgtctcc agcgagagac ctcactcatt ag                    42

<210> SEQ ID NO 92
<211> LENGTH: 19
<212> TYPE: DNA
<213> ORGANISM: Artificial Sequence
<220> FEATURE:
<223> OTHER INFORMATION: X324_R primer

<400> SEQUENCE: 92
tgagaccgtt tcgaccagg                                              19

<210> SEQ ID NO 93
<211> LENGTH: 19
<212> TYPE: DNA
<213> ORGANISM: Artificial Sequence
<220> FEATURE:
<223> OTHER INFORMATION: X325_F primer

<400> SEQUENCE: 93
gagaccggac aaggatgcg                                              19

<210> SEQ ID NO 94
<211> LENGTH: 42
<212> TYPE: DNA
<213> ORGANISM: Artificial Sequence
<220> FEATURE:
<223> OTHER INFORMATION: X326_F primer

<400> SEQUENCE: 94
cctggtcgaa acggtctcag gagagagacg aaaagcaaaa ac                    42
```

<210> SEQ ID NO 95
<211> LENGTH: 46
<212> TYPE: DNA
<213> ORGANISM: Artificial Sequence
<220> FEATURE:
<223> OTHER INFORMATION: X327_R primer

<400> SEQUENCE: 95
cgcatccttg tccggtctcc tgacagcgag agacgtcact cattag            46

<210> SEQ ID NO 96
<211> LENGTH: 46
<212> TYPE: DNA
<213> ORGANISM: Artificial Sequence
<220> FEATURE:
<223> OTHER INFORMATION: X328_F primer

<400> SEQUENCE: 96
cctggtcgaa acggtctcag tcaggagaga gacgaaaagc aaaaac            46

<210> SEQ ID NO 97
<211> LENGTH: 37
<212> TYPE: DNA
<213> ORGANISM: Artificial Sequence
<220> FEATURE:
<223> OTHER INFORMATION: X80_R primer

<400> SEQUENCE: 97
ctcaatgctg ctgccttcat ctggatatga gcttcac                      37

<210> SEQ ID NO 98
<211> LENGTH: 49
<212> TYPE: DNA
<213> ORGANISM: Artificial Sequence
<220> FEATURE:
<223> OTHER INFORMATION: X228_F primer

<400> SEQUENCE: 98
cctcgagtac gtaggatcca tttaaattcc ttcaagagag caaaccatt         49

<210> SEQ ID NO 99
<211> LENGTH: 46
<212> TYPE: DNA
<213> ORGANISM: Artificial Sequence
<220> FEATURE:
<223> OTHER INFORMATION: X229_R primer

<400> SEQUENCE: 99
atcagctctt ctccctttga aaccattttt tcttgttgtt ttgttg            46

<210> SEQ ID NO 100
<211> LENGTH: 31
<212> TYPE: DNA
<213> ORGANISM: Artificial Sequence
<220> FEATURE:
<223> OTHER INFORMATION: X333_R primer

<400> SEQUENCE: 100
cgtgtcgtgc tccaccatgt tcacgaagat t                            31

<210> SEQ ID NO 101
<211> LENGTH: 49
<212> TYPE: DNA
<213> ORGANISM: Artificial Sequence
<220> FEATURE:
<223> OTHER INFORMATION: X334_F primer -continued

<400> SEQUENCE: 101
aaaaaaaaaa atcggttccc cctagagcag atcgttcaaa catttggca            49

<210> SEQ ID NO 102
<211> LENGTH: 25
<212> TYPE: DNA
<213> ORGANISM: Artificial Sequence
<220> FEATURE:
<223> OTHER INFORMATION: Right border (pTiA6)

<400> SEQUENCE: 102
tggcaggata tatgcggttg taatt                                      25

<210> SEQ ID NO 103
<211> LENGTH: 25
<212> TYPE: DNA
<213> ORGANISM: Artificial Sequence
<220> FEATURE:
<223> OTHER INFORMATION: Left border (pTiA6)

<400> SEQUENCE: 103
cggcaggata tattcaattg taaat                                      25

<210> SEQ ID NO 104
<211> LENGTH: 25
<212> TYPE: DNA
<213> ORGANISM: Artificial Sequence
<220> FEATURE:
<223> OTHER INFORMATION: Left border (pTiC58)

<400> SEQUENCE: 104
tggcaggata tattgtggtg taaac                                      25

<210> SEQ ID NO 105
<211> LENGTH: 1522
<212> TYPE: DNA
<213> ORGANISM: Artificial Sequence
<220> FEATURE:
<223> OTHER INFORMATION: pBBR1 origin (oriV+rep)
<220> FEATURE:
<221> NAME/KEY: rep_origin
<222> LOCATION: (1)..(663)

<400> SEQUENCE: 105
ctaccggcgc ggcagcgtta cccgtgtcgg cggctccaac ggctcgccat cgtccagaaa    60
acacggctca tcgggcatcg gcaggcgctg ctgcccgcgc cgttcccatt cctccgtttc   120
ggtcaaggct ggcaggtctg gttccatgcc cggaatgccg ggctggctgg gcggctcctc   180
gccggggccg gtcggtagtt gctgctcgcc cggatacagg gtcgggatgc ggcgcaggtc   240
gccatgcccc aacagcgatt cgtcctggtc gtcgtgatca accaccacgg cggcactgaa   300
caccgacagg cgcaactggt cgcggggctg gccccacgcc acgcggtcat tgaccacgta   360
ggccgacacg gtgccggggc cgttgagctt cacgacggag atccagcgct cggccaccaa   420
gtccttgact gcgtattgga ccgtccgcaa agaacgtccg atgagcttgg aaagtgtctt   480
ctggctgacc accacggcgt tctggtggcc catctgcgcc acgaggtgat gcagcagcat   540
tgccgccgtg ggtttcctcg caataagccc ggcccacgcc tcatgcgctt gcgttccgt    600 ttgcacccag tgaccgggct tgttcttggc ttgaatgccg atttctctgg actgcgtggc   660
catgcttatc tccatgcggt aggggtgccg cacggttgcg gcaccatgcg caatcagctg   720 caactttttcg gcagcgcgac aacaattatg cgttgcgtaa aagtggcagt caattacaga   780

```
tttctttaa cctacgcaat gagctattgc ggggggtgcc gcaatgagct gttgcgtacc      840 ccccttttt aagttgttga ttttaagtc tttcgcattt cgccctatat ctagttcttt       900
ggtgcccaaa gaagggcacc cctgcggggt tcccccacgc cttcggcgcg gctcccctc      960 cggcaaaaag tggcccctcc ggggcttgtt gatcgactgc gcggccttcg gccttgccca    1020
aggtggcgct gccccttgg aaccccgca ctcgccgccg tgaggctcgg ggggcaggcg      1080
ggcgggcttc gccttcgac tgcccccact cgcataggct gggtcgttc caggcgcgtc     1140 aaggccaagc cgctgcgcgg tcgctgcgcg agccttgacc cgccttccac ttggtgtcca    1200
accggcaagc gaagcgcgca ggccgcaggc cggaggcttt tccccagaga aaattaaaaa    1260
aattgatggg gcaaggccgc aggccgcgca gttggagccg gtgggtatgt ggtcgaaggc    1320
tgggtagccg gtgggcaatc cctgtggtca agctcgtggg caggcgcagc ctgtccatca    1380
gcttgtccag cagggttgtc cacgggccga gcgaagcgag ccagccggtg ccgctcgcg    1440 gccatcgtcc acatatccac gggctggcaa gggagcgcag cgaccgcgca gggcgaagcc    1500
cggagagcaa gcccgtaggg gg                                              1522

<210> SEQ ID NO 106
<211> LENGTH: 2222
<212> TYPE: DNA
<213> ORGANISM: Artificial Sequence
<220> FEATURE:
<223> OTHER INFORMATION: RK2 origin (oriV+trfA)
<220> FEATURE:
<221> NAME/KEY: rep_origin
<222> LOCATION: (1)..(2222)

<400> SEQUENCE: 106
gcgatgcagg tggctgctga accccagcc ggaactgacc ccacaaggcc ctagcgtttg       60
caatgcacca ggtcatcatt gacccaggcg tgttccacca ggccgctgcc tcgcaactct     120
tcgcaggctt cgccgacctg ctcgcgccac ttcttcacgc gggtggaatc cgatccgcac    180
atgaggcgga aggtttccag cttgagcggg tacggctccc ggtgcgagct gaaatagtcg    240
aacatccgtc gggccgtcgg cgacagcttg cggtacttct cccatatgaa tttcgtgtag    300
tggtcgccag caaacagcac gacgatttcc tcgtcgatca ggacctggca acgggacgtt    360
ttcttgccac ggtccaggac gcggaagcgg tgcagcagcg acaccgattc caggtgccca    420
acgcggtcgg acgtgaagcc catcgccgtc gcctgtaggc gcgacaggca ttcctcggcc    480
ttcgtgtaat accggccatt gatcgaccag cccaggtcct ggcaaagctc gtagaacgtg    540
aaggtgatcg gctcgccgat aggggtgcgc ttcgcgtact ccaacacctg ctgccacacc    600
agttcgtcat cgtcggcccg cagctcgacg ccggtgtagg tgatcttcac gtccttgttg    660
acgtggaaaa tgaccttgtt ttgcagcgcc tcgcgcggga ttttcttgtt gcgcgtggtg    720
aacagggcag agcgggccgt gtcgtttggc atcgctcgca tcgtgtccgg ccacggcgca    780
atatcgaaca aggaaagctg catttccttg atctgctgct tcgtgtgttt cagcaacgcg    840
gcctgcttgg cttcgctgac ctgttttgcc aggtcctcgc cggcggtttt tcgcttcttg    900
gtcgtcatag ttcctcgcgt gtcgatggtc atcgacttcg ccaaacctgc cgcctcctgt    960
tcgagacgac gcgaacgctc cacggcggcc gatgcgcgg gcagggcagg gggagccagt    1020
tgcacgctgt cgcgctcgat cttggccgta gcttgctgga ctatcgagcc gacggactgg    1080
aaggtttcgc ggggcgcacg catgacggtg cggcttgcga tggtttcggc atcctcggcg    1140
gaaaaccccg cgtcgatcag ttcttgcctg tatgccttcc ggtcaaacgt ccgattcatt    1200
```

```
caccctcctt gcgggattgc cccggaatta attccccgga tcgatccgtc gatcttgatc    1260
ccctgcgcca tcagatcctt ggcggcaaga aagccatcca gtttactttg cagggcttcc    1320
caaccttacc agagggcgcc ccagctggca attccggttc gcttgctgtc cataaaaccg    1380
cccagtctag ctatcgccat gtaagcccac tgcaagctac ctgctttctc tttgcgcttg    1440
cgttttccct tgtccagata gcccagtagc tgacattcat ccggggtcag caccgtttct    1500
gcggactggc tttctacgtg gctgccattt ttggggtgag gccgttcgcg gccgaggggc    1560
gcagcccctg gggggatggg aggcccgcgt tagcgggccg ggagggttcg agaagggggg    1620 gcaccccct tcggcgtgcg cggtcacgcg cacagggcgc agccctggtt aaaaacaagg    1680
tttataaata ttggtttaaa agcaggttaa aagacaggtt agcggtggcc gaaaaacggg    1740
cggaaaccct tgcaaatgct ggattttctg cctgtggaca gcccctcaaa tgtcaatagg    1800 tgcgccctc atctgtcagc actctgcccc tcaagtgtca aggatcgcgc ccctcatctg    1860
tcagtagtcg cgcccctcaa gtgtcaatac cgcagggcac ttatcccag gcttgtccac    1920 atcatctgtg ggaaactcgc gtaaaatcag gcgttttcgc cgatttgcga ggctggccag    1980
ctccacgtcg ccgccgaaa tcgagcctgc ccctcatctg tcaacgccgc gccgggtgag    2040
tcggcccctc aagtgtcaac gtccgcccct catctgtcag tgagggccaa gttttccgcg    2100
aggtatccac aacgccggcg gccctacatg gctctgctgt agtgagtggg ttgcgctccg    2160
gcagcggtcc tgatccccg cagaaaaaaa ggatctcaag aagatccttt gatcttttct    2220
ac                                                                    2222

<210> SEQ ID NO 107
<211> LENGTH: 2222
<212> TYPE: DNA
<213> ORGANISM: Artificial Sequence
<220> FEATURE:
<223> OTHER INFORMATION: RK2 origin (oriV+trfA) without BsmBI sites
<220> FEATURE:
<221> NAME/KEY: rep_origin
<222> LOCATION: (1)..(2222)

<400> SEQUENCE: 107
gcgatgcagg tggctgctga accccagcc ggaactgacc ccacaaggcc ctagcgtttg    60
caatgcacca ggtcatcatt gacccaggcg tgttccacca ggccgctgcc tcgcaactct    120
tcgcaggctt cgccgacctg ctcgcgccac ttcttcacgc gggtggaatc cgatccgcac    180
atgaggcgga aggtttccag cttgagcggg tacggctccc ggtgcgagct gaaatagtcg    240
aacatccgtc gggccgtcgg cgacagcttg cggtacttct cccatatgaa tttcgtgtag    300
tggtcgccag caaacagcac gacgatttcc tcgtcgatca ggacctggca acgggacgtt    360
ttcttgccac ggtccaggac gcggaagcgg tgcagcagcg acaccgattc caggtgccca    420
acgcggtcgg acgtgaagcc catcgccgtc gcctgtaggc gcgacaggca ttcctcggcc    480
ttcgtgtaat accggccatt gatcgaccag cccaggtcct ggcaaagctc gtagaacgtg    540
aaggtgatcg gctcgccgat aggggtgcgc ttcgcgtact ccaacacctg ctgccacacc    600
agttcgtcat cgtcggcccg cagctcgacg ccggtgtagg tgatcttcac gtccttgttg    660
acgtggaaaa tgaccttgtt ttgcagcgcc tcgcgcggga ttttcttgtt gcgcgtggtg    720
aacagggcag agcgggccgt gtcgtttggc atcgctcgca tcgtgtccgg ccacggcgca    780
atatcgaaca aggaaagctg catttccttg atctgctgct tcgtgtgttt cagcaacgcg    840
gcctgcttgg cttcgctgac ctgttttgcc aggtcctcgc cggcggtttt tcgcttcttg    900
```

```
gtcgtcatag ttcctcgcgt gtcgatggtc atcgacttcg ccaaacctgc cgcctcctgt      960
tctagccgac gcgaacgctc cacggcggcc gatggcgcgg gcagggcagg gggagccagt     1020
tgcacgctgt cgcgctcgat cttggccgta gcttgctgga ctatcgagcc gacggactgg     1080
aaggtttcgc ggggcgcacg catgacggtg cggcttgcga tggtttcggc atcctcggcg     1140
gaaaaccccg cgtcgatcag ttcttgcctg tatgccttcc ggtcaaacgt ccgattcatt     1200
caccctcctt gcgggattgc cccggaatta attccccgga tcgatccgtc gatcttgatc     1260
ccctgcgcca tcagatcctt ggcggcaaga aagccatcca gtttactttg cagggcttcc     1320
caaccttacc agagggcgcc ccagctggca attccggttc gcttgctgtc cataaaaccg     1380
cccagtctag ctatcgccat gtaagcccac tgcaagctac ctgctttctc tttgcgcttg     1440
cgttttccct tgtccagata gcccagtagc tgacattcat ccggggtcag caccgttttct    1500 gcggactggc tttctacgtg gctgccattt ttggggtgag gccgttcgcg gccgaggggc     1560
gcagcccctg gggggatggg aggcccgcgt tagcgggccg ggagggttcg agaagggggg     1620
gcacccccct tcggcgtgcg cggtcacgcg cacagggcgc agccctggtt aaaaacaagg     1680
tttataaata ttggtttaaa agcaggttaa aagacaggtt agcggtggcc gaaaaacggg     1740
cggaaaccct tgcaaatgct ggattttctg cctgtggaca gcccctcaaa tgtcaatagg     1800
tgcgcccctc atctgtcagc actctgcccc tcaagtgtca aggatcgcgc ccctcatctg     1860
tcagtagtcg cgccctcaa  gtgtcaatac cgcagggcac ttatccccag gcttgtccac     1920
atcatctgtg ggaaactcgc gtaaaatcag gcgttttcgc cgatttgcga ggctggccag     1980
ctccacgtcg ccggccgaaa tcgagcctgc ccctcatctg tcaacgccgc gccgggtgag     2040
tcggcccctc aagtgtcaac gtccgcccct catctgtcag tgaggggccaa gttttccgcg     2100 aggtatccac aacgccggcg gccctacatg gctctgctgt agtgagtggg ttgcgctccg     2160
gcagcggtcc tgatcccccg cagaaaaaaa ggatctcaag aagatccttt gatcttttct     2220
ac                                                                    2222

<210> SEQ ID NO 108
<211> LENGTH: 48
<212> TYPE: DNA
<213> ORGANISM: Artificial Sequence
<220> FEATURE:
<223> OTHER INFORMATION: Bacterial transcription terminator "T1"

<400> SEQUENCE: 108
gacgaacaat aaggccgcaa atcgcggcct tttttattga taacaaaa                    48

<210> SEQ ID NO 109
<211> LENGTH: 41
<212> TYPE: DNA
<213> ORGANISM: Artificial Sequence
<220> FEATURE:
<223> OTHER INFORMATION: Bacterial transcription terminator "T2"

<400> SEQUENCE: 109
caagaaaaga aaaacaccc gttagggtgt ttttagttag t                            41

<210> SEQ ID NO 110
<211> LENGTH: 32
<212> TYPE: DNA
<213> ORGANISM: Artificial Sequence
<220> FEATURE:
<223> OTHER INFORMATION: Bacterial transcription terminator "lambda T1"
```

-continued

```
<400> SEQUENCE: 110
aggcctgctg gtaatcgcag gccttttat tt                                    32

<210> SEQ ID NO 111
<211> LENGTH: 53
<212> TYPE: DNA
<213> ORGANISM: Artificial Sequence
<220> FEATURE:
<223> OTHER INFORMATION: Bacterial transcription terminator "lambda T2"

<400> SEQUENCE: 111
aaaaaattag cgcaagaaga caaaaatcac cttgcgctaa tgctctgtta cag            53

<210> SEQ ID NO 112
<211> LENGTH: 24
<212> TYPE: DNA
<213> ORGANISM: Artificial Sequence
<220> FEATURE:
<223> OTHER INFORMATION: Linker_1

<400> SEQUENCE: 112
ccatcatcag ttcggtggtc ttcc                                            24

<210> SEQ ID NO 113
<211> LENGTH: 24
<212> TYPE: DNA
<213> ORGANISM: Artificial Sequence
<220> FEATURE:
<223> OTHER INFORMATION: Linker_2

<400> SEQUENCE: 113
cgacttgcga catgcggtcc tttg                                            24

<210> SEQ ID NO 114
<211> LENGTH: 24
<212> TYPE: DNA
<213> ORGANISM: Artificial Sequence
<220> FEATURE:
<223> OTHER INFORMATION: Linker_3

<400> SEQUENCE: 114
gatcggattg gcggttatgc ggtt                                            24

<210> SEQ ID NO 115
<211> LENGTH: 25
<212> TYPE: DNA
<213> ORGANISM: Artificial Sequence
<220> FEATURE:
<223> OTHER INFORMATION: Right border (pTiBo542)

<400> SEQUENCE: 115
tggcaggata tatgtggttg taatt                                           25

<210> SEQ ID NO 116
<211> LENGTH: 25
<212> TYPE: DNA
<213> ORGANISM: Artificial Sequence
<220> FEATURE:
<223> OTHER INFORMATION: Left border (pTiBo542)

<400> SEQUENCE: 116
cggcaggata tatggcagtg taaac                                           25
```